US011155841B2

(12) United States Patent
Schwab et al.

(10) Patent No.: US 11,155,841 B2
(45) Date of Patent: *Oct. 26, 2021

(54) METHOD FOR PRODUCING SPHINGOID BASE OR SPHINGOLIPID

(71) Applicants: AJINOMOTO CO., INC., Tokyo (JP); EVOLVA SA, Reinach (CH)

(72) Inventors: Markus Schwab, Loerrach (DE); Corina Daniela Wirdnam, Reinach (CH); Thomas Oestergaard Tange, Riehen (CH); Maud Babau, Copenhagen (DK); Anaelle Hatsch, Hesingue (FR); Fanny Delegrange, Hesingue (FR); David Fischer, Arlesheim (CH); Sabina de Andrade Pereira Tavares, Basel (CH)

(73) Assignees: Ajinomoto Co., Inc., Tokyo (JP); Evolva SA, Reinach (CH)

( * ) Notice: Subject to any disclaimer, the term of this patent is extended or adjusted under 35 U.S.C. 154(b) by 115 days.

This patent is subject to a terminal disclaimer.

(21) Appl. No.: 15/898,358

(22) Filed: Feb. 16, 2018

(65) Prior Publication Data

US 2018/0179563 A1 Jun. 28, 2018

Related U.S. Application Data

(63) Continuation of application No. PCT/JP2016/003865, filed on Aug. 24, 2016.

(60) Provisional application No. 62/208,932, filed on Aug. 24, 2015.

(30) Foreign Application Priority Data

Aug. 24, 2015 (JP) ............................ JP2015-164685

(51) Int. Cl.
*C12P 13/00* (2006.01)
*C12P 13/02* (2006.01)

(52) U.S. Cl.
CPC ............ *C12P 13/02* (2013.01); *C12P 13/001* (2013.01); *C12Y 101/01102* (2013.01); *C12Y 114/18* (2013.01); *C12Y 203/01* (2013.01); *C12Y 203/0105* (2013.01); *C12Y 203/01024* (2013.01); *C12Y 203/01199* (2015.07); *C12Y 204/0108* (2013.01); *C12Y 207/01091* (2013.01); *C12Y 207/11001* (2013.01); *C12Y 305/01023* (2013.01); *C12Y 403/01017* (2013.01); *C12N 2500/05* (2013.01); *C12N 2500/30* (2013.01); *C12Y 114/13169* (2015.07)

(58) Field of Classification Search
CPC .......... A61K 31/43; A61K 31/52; C12N 9/22; C12N 2500/30; C12N 9/93; C12Y 207/04003; C12Y 207/01091; C12P 13/001
USPC ..... 435/184, 196, 97, 252.2, 320.1; 530/321
See application file for complete search history.

(56) References Cited

U.S. PATENT DOCUMENTS

| | | | |
|---|---|---|---|
| 2010/0304467 A1 | 12/2010 | Kodama et al. |
| 2014/0199736 A1 | 7/2014 | Kohler et al. |
| 2016/0304916 A1 | 10/2016 | Kohler et al. |

FOREIGN PATENT DOCUMENTS

| | | | |
|---|---|---|---|
| CN | 102317466 A | 1/2012 |
| CN | 103748218 A | 4/2014 |
| JP | 2014-529400 A | 11/2014 |
| WO | WO94/10131 A1 | 5/1994 |
| WO | WO2007/131720 A1 | 11/2007 |
| WO | WO2013/023878 A1 | 2/2013 |
| WO | WO2015/076423 A1 | 5/2015 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Gould et al. Food and Chem Toxol., 2005, 43, pp. 1451-1459.*
Cowart, L. A., et al., "Yeast sphingolipids: Recent developments in understanding biosynthesis, regulation, and function," Biochimica et Biophysica Acta 2007;1771:421-431.
Pinto, W. J., et al., "Sphingolipid Long-Chain-Base Auxotrophs of *Saccharomyces cerevisiae*: Genetics, Physiology, and a Method for Their Selection," J. Bacteriol. 1992;174(8):2565-2574.
Schorsch, C., et al., "Knockout of the DNA ligase IV homolog gene in the sphingoid base producing yeast *Pichia ciferrii* significantly increases gene targeting efficiency," Curr. Genet. 2009;55:381-389.
Singh, I., et al., "Effect of cyclodextrins on the solubilization of lignoceric acid, ceramide, and cerebroside, and on the enzymatic reactions involving these compounds," J. Lipid Res. 1983;24:662-665.

(Continued)

*Primary Examiner* — Robert B Mondesi
*Assistant Examiner* — Mohammad Y Meah
(74) *Attorney, Agent, or Firm* — Cermak Nakajima & McGowan LLP; Shelly Guest Cermak

(57) ABSTRACT

A method for producing an objective substance such as sphingoid bases and sphingolipids using yeast is provided. An objective substance is produced by cultivating yeast having an ability to produce the objective substance in a culture medium containing an additive that is able to associate with, bind to, solubilize, and/or capture the objective substance, and collecting the objective substance from cells of the yeast and/or the culture medium.

11 Claims, 6 Drawing Sheets

Specification includes a Sequence Listing.

(56) References Cited

OTHER PUBLICATIONS

Veld, F. T., et al., "Production of tetraacetyl phytosphingosine (TAPS) in Wickerhamomyces ciferrii is catalyzed by acetyltransferases Sli1p and Atf2p," Appl. Microbiol. Biotechnol. 2013;97:8537-8546.
International Search Report for PCT Patent App. No. PCT/JP2016/003865 (dated Nov. 18, 2016).
Written Opinion for PCT Patent App. No. PCT/JP2016/003865 (dated Nov. 18, 2016).
Karmelić, I., et al., "Influence of growth phase and zeolite clinoptilolite on the concentration of sphingoid bases in *Saccharomyces uvarum* brewer's yeast," World J. Microbiol. Biotechnol. 2011;27:2969-2979.
Bauman, M., et al., "Natural zeolite clinoptilolite increases the concentration of sphingoid bases in the yeast *Yarrowia lipolytica*," J. Basic Microbiol. 2001;41:7-16.
Communication Pursuant to Article 94(3) EPC for European Patent App. No. 16763597.8 (dated Oct. 24, 2019).
Kobayashi, S. D., et al., "Ceramide/Long-Chain Base Phosphate Rheostat in *Saccharomyces cerevisiae*: Regulation of Ceramide Synthesis by Elo3p and Cka2p," Eukaryotic Cell 2003;2(2):284-294.
Notice of Reasons for Refusal for Japanese Patent App. No. 2018-510904 (dated Aug. 25, 2020) with English language translation thereof.
First Office Action and Search Report dated Feb. 24, 2021 from corresponding Chinese Patent App. No. 201680048761.1 with English language translation.

* cited by examiner

SEQUENCE LISTING

```
<160> NUMBER OF SEQ ID NOS: 83

<210> SEQ ID NO 1
<211> LENGTH: 1677
<212> TYPE: DNA
<213> ORGANISM: Saccharomyces cerevisiae

<400> SEQUENCE: 1

atggcacaca tcccagaggt tttacccaaa tcaataccga ttccggcatt tattgttacc      60

acctcatcgt acctatggta ctacttcaat ctggtgttga ctcaaatccc gggaggccaa     120

ttcatcgttt cgtacatcaa gaaatcgcat catgacgatc catacaggac cacggttgag     180

atagggctta ttttatacgg gatcatctat tacttgtcca agccacaaca gaaaaagagt     240

cttcaagcac agaagcccaa cctatcgccc caggagattg acgcgctaat tgaggactgg     300

gagcccgagc ctctagtcga cccttctgcc accgatgagc aatcgtggag ggtggccaaa     360

acacccgtca ccatggaaat gcccattcag aaccatatta ctatcaccag aaacaacctg     420

caggagaagt ataccaatgt tttcaatttg gcctcgaaca actttttgca attgtccgct     480

acggagcccg tgaaagaagt ggtcaagacc actatcaaga attacggtgt gggcgcctgt     540

ggtcccgccg ggttctacgg taaccaggac gttcattaca cgttggaata tgatttagca     600

cagttctttg gcacccaagg ttccgttctg tacgggcaag acttttgtgc cgcaccctct     660

gttctgcctg ctttcacaaa gcgtggtgat gttatcgtgg cagacgacca ggtgtcatta     720

ccagtgcaaa atgctctgca actaagcaga tccacagtct actacttcaa ccacaacgat     780

atgaattcgc tagaatgttt attaaacgag ttgaccgaac aggagaaact tgagaaactg     840
```

```
cccgccattc caagaaaatt tatcgtcact gagggtattt tccacaactc gggcgattta    900

gctccgttgc ctgagttgac taagctgaag aacaagtaca agttcagact atttgttgac    960

gaaaccttct ccattggtgt tcttggcgct acgggccgtg ggttgtcaga gcacttcaac   1020

atggatcgcg caactgccat tgacattacc gttgggtcca tggccaccgc gttggggtcc   1080

accggtggtt ttgtcctggg tgacagtgtt atgtgtttgc accagcgtat tggttccaat   1140

gcatattgtt tttctgcctg tttgccggct tacaccgtca catccgtctc caaagtcttg   1200

aaattgatgg actccaacaa cgacgccgtc cagacgctgc aaaaactatc caaatctttg   1260

catgattcct ttgcatctga cgactccttg cgttcatacg taatcgtcac gtcctctcca   1320

gtgtctgctg tcctacatct gcaactgact cccgcatata ggtctcgcaa gttcggatac   1380

acctgcgaac agctattcga aaccatgtca gctttgcaaa agaagtccca gacaaacaaa   1440

ttcattgagc catacgaaga ggaggaaaaa tttctgcagt ccatagtaga tcatgctctt   1500

attaactaca acgttctcat cacaagaaac actattgttt taaaacagga gacgctacca   1560

attgtcccta gcttgaaaat ctgctgtaac gccgccatgt ccccagagga actcaaaaat   1620

gcttgcgaaa gtgtcaagca gtccatcctt gcctgttgcc aagaatctaa taaataa      1677
```

<210> SEQ ID NO 2
<211> LENGTH: 558
<212> TYPE: PRT
<213> ORGANISM: Saccharomyces cerevisiae

<400> SEQUENCE: 2

```
Met Ala His Ile Pro Glu Val Leu Pro Lys Ser Ile Pro Ile Pro Ala
1               5                   10                  15

Phe Ile Val Thr Thr Ser Ser Tyr Leu Trp Tyr Tyr Phe Asn Leu Val
            20                  25                  30

Leu Thr Gln Ile Pro Gly Gly Gln Phe Ile Val Ser Tyr Ile Lys Lys
        35                  40                  45

Ser His His Asp Asp Pro Tyr Arg Thr Thr Val Glu Ile Gly Leu Ile
    50                  55                  60

Leu Tyr Gly Ile Ile Tyr Tyr Leu Ser Lys Pro Gln Gln Lys Lys Ser
65                  70                  75                  80

Leu Gln Ala Gln Lys Pro Asn Leu Ser Pro Gln Glu Ile Asp Ala Leu
                85                  90                  95

Ile Glu Asp Trp Glu Pro Glu Pro Leu Val Asp Pro Ser Ala Thr Asp
            100                 105                 110

Glu Gln Ser Trp Arg Val Ala Lys Thr Pro Val Thr Met Glu Met Pro
        115                 120                 125

Ile Gln Asn His Ile Thr Ile Thr Arg Asn Asn Leu Gln Glu Lys Tyr
    130                 135                 140

Thr Asn Val Phe Asn Leu Ala Ser Asn Asn Phe Leu Gln Leu Ser Ala
145                 150                 155                 160

Thr Glu Pro Val Lys Glu Val Val Lys Thr Thr Ile Lys Asn Tyr Gly
                165                 170                 175

Val Gly Ala Cys Gly Pro Ala Gly Phe Tyr Gly Asn Gln Asp Val His
            180                 185                 190

Tyr Thr Leu Glu Tyr Asp Leu Ala Gln Phe Phe Gly Thr Gln Gly Ser
        195                 200                 205

Val Leu Tyr Gly Gln Asp Phe Cys Ala Ala Pro Ser Val Leu Pro Ala
    210                 215                 220
```

```
Phe Thr Lys Arg Gly Asp Val Ile Val Ala Asp Asp Gln Val Ser Leu
225                 230                 235                 240

Pro Val Gln Asn Ala Leu Gln Leu Ser Arg Ser Thr Val Tyr Tyr Phe
                245                 250                 255

Asn His Asn Asp Met Asn Ser Leu Glu Cys Leu Leu Asn Glu Leu Thr
            260                 265                 270

Glu Gln Glu Lys Leu Glu Lys Leu Pro Ala Ile Pro Arg Lys Phe Ile
        275                 280                 285

Val Thr Glu Gly Ile Phe His Asn Ser Gly Asp Leu Ala Pro Leu Pro
    290                 295                 300

Glu Leu Thr Lys Leu Lys Asn Lys Tyr Lys Phe Arg Leu Phe Val Asp
305                 310                 315                 320

Glu Thr Phe Ser Ile Gly Val Leu Gly Ala Thr Gly Arg Gly Leu Ser
                325                 330                 335

Glu His Phe Asn Met Asp Arg Ala Thr Ala Ile Asp Ile Thr Val Gly
            340                 345                 350

Ser Met Ala Thr Ala Leu Gly Ser Thr Gly Gly Phe Val Leu Gly Asp
        355                 360                 365

Ser Val Met Cys Leu His Gln Arg Ile Gly Ser Asn Ala Tyr Cys Phe
    370                 375                 380

Ser Ala Cys Leu Pro Ala Tyr Thr Val Thr Ser Val Ser Lys Val Leu
385                 390                 395                 400

Lys Leu Met Asp Ser Asn Asn Asp Ala Val Gln Thr Leu Gln Lys Leu
                405                 410                 415

Ser Lys Ser Leu His Asp Ser Phe Ala Ser Asp Asp Ser Leu Arg Ser
            420                 425                 430

Tyr Val Ile Val Thr Ser Ser Pro Val Ser Ala Val Leu His Leu Gln
        435                 440                 445

Leu Thr Pro Ala Tyr Arg Ser Arg Lys Phe Gly Tyr Thr Cys Glu Gln
    450                 455                 460

Leu Phe Glu Thr Met Ser Ala Leu Gln Lys Lys Ser Gln Thr Asn Lys
465                 470                 475                 480

Phe Ile Glu Pro Tyr Glu Glu Glu Lys Phe Leu Gln Ser Ile Val
                485                 490                 495

Asp His Ala Leu Ile Asn Tyr Asn Val Leu Ile Thr Arg Asn Thr Ile
            500                 505                 510

Val Leu Lys Gln Glu Thr Leu Pro Ile Val Pro Ser Leu Lys Ile Cys
        515                 520                 525

Cys Asn Ala Ala Met Ser Pro Glu Glu Leu Lys Asn Ala Cys Glu Ser
    530                 535                 540

Val Lys Gln Ser Ile Leu Ala Cys Cys Gln Glu Ser Asn Lys
545                 550                 555
```

<210> SEQ ID NO 3
<211> LENGTH: 1686
<212> TYPE: DNA
<213> ORGANISM: Saccharomyces cerevisiae

<400> SEQUENCE: 3

```
atgagtactc ctgcaaacta tacccgtgtg cccctgtgcg aaccagagga gctgccagac      60

gacatacaaa aagaaaatga atatggtaca ctagattctc cggggcattt gtatcaagtc     120

aagtcacgtc atgggaagcc actacctgag cccgttgtcg acacccctcc ttattacatt     180

tctttgttaa catatctaaa ttatttgatt ctgattatat taggtcatgt tcacgacttc     240
```

```
ttaggtatga ccttccaaaa aaacaaacat ctggatcttt tagagcatga tgggttagca    300

ccttggtttt caaatttcga gagtttttat gtcaggagaa ttaaaatgag aattgatgat    360

tgcttttcta gaccaactac tggtgttcct ggtagattta ttcgttgtat tgatagaatt    420

tctcataata taaatgagta ttttacctac tcaggcgcag tgtatccatg catgaactta    480

tcatcatata actatttagg cttcgcacaa agtaagggtc aatgtaccga tgccgccttg    540

gaatctgtcg ataaatattc tattcaatct ggtggtccaa gagctcaaat cggtaccaca    600

gatttgcaca ttaaagcaga gaaattagtt gctagattta tcggtaagga ggatgccctc    660

gtttttcga tgggttatgg tacaaatgca aacttgttca acgctttcct cgataaaaag    720

tgtttagtta tctctgacga attgaaccac acctctatta gaacaggtgt taggctttct    780

ggtgctgctg tgcgaacttt caagcatggt gatatggtgg gtttagaaaa gcttatcaga    840

gaacagatag tacttggtca accaaaaaca aatcgtccat ggaagaaaat tttaatttgc    900

gcagaagggt tgttttccat ggaaggtact ttgtgtaact tgccaaaatt ggttgaattg    960

aagaagaaat ataaatgtta cttgtttatc gatgaagccc attctatagg cgctatgggc   1020

ccaactggtc gcggtgtttg tgaaatattt ggcgttgatc ccaaggacgt cgacattcta   1080

atgggtactt tcactaagtc gtttggtgct gctggtggtt acattgctgc tgatcaatgg   1140

attatcgata gactgaggtt ggatttaacc actgtgagtt atagtgagtc aatgccggct   1200

cctgttttag ctcaaactat ttcctcatta caaaccatta gtggtgaaat atgtcccgga   1260

caaggtactg aaagattgca acgtatagcc tttaattccc gttatctacg tttagctttg   1320

caaaggttag gatttattgt ctacggtgtg gctgactcac cagttattcc cttactactg   1380

tattgtccct caaagatgcc cgcattttcg agaatgatgt tacaaagacg gattgctgtt   1440

gttgttgttg cttatcctgc tactccgctg atcgaatcaa gagtaagatt ctgtatgtct   1500

gcatctttaa caaaggaaga tatcgattat ttactgcgtc atgttagtga agttggtgac   1560

aaattgaatt tgaaatcaaa ttccggcaaa tccagttacg acggtaaacg tcaaagatgg   1620

gacatcgagg aagttatcag gagaacacct gaagattgta aggacgacaa gtattttgtt   1680

aattga                                                              1686
```

<210> SEQ ID NO 4
<211> LENGTH: 561
<212> TYPE: PRT
<213> ORGANISM: Saccharomyces cerevisiae

<400> SEQUENCE: 4

```
Met Ser Thr Pro Ala Asn Tyr Thr Arg Val Pro Leu Cys Glu Pro Glu
1               5                   10                  15

Glu Leu Pro Asp Asp Ile Gln Lys Glu Asn Glu Tyr Gly Thr Leu Asp
            20                  25                  30

Ser Pro Gly His Leu Tyr Gln Val Lys Ser Arg His Gly Lys Pro Leu
        35                  40                  45

Pro Glu Pro Val Val Asp Thr Pro Pro Tyr Tyr Ile Ser Leu Leu Thr
    50                  55                  60

Tyr Leu Asn Tyr Leu Ile Leu Ile Ile Leu Gly His Val His Asp Phe
65                  70                  75                  80

Leu Gly Met Thr Phe Gln Lys Asn Lys His Leu Asp Leu Leu Glu His
                85                  90                  95

Asp Gly Leu Ala Pro Trp Phe Ser Asn Phe Glu Ser Phe Tyr Val Arg
            100                 105                 110
```

```
Arg Ile Lys Met Arg Ile Asp Asp Cys Phe Ser Arg Pro Thr Thr Gly
        115                 120                 125

Val Pro Gly Arg Phe Ile Arg Cys Ile Asp Arg Ile Ser His Asn Ile
    130                 135                 140

Asn Glu Tyr Phe Thr Tyr Ser Gly Ala Val Tyr Pro Cys Met Asn Leu
145                 150                 155                 160

Ser Ser Tyr Asn Tyr Leu Gly Phe Ala Gln Ser Lys Gly Gln Cys Thr
                165                 170                 175

Asp Ala Ala Leu Glu Ser Val Asp Lys Tyr Ser Ile Gln Ser Gly Gly
            180                 185                 190

Pro Arg Ala Gln Ile Gly Thr Thr Asp Leu His Ile Lys Ala Glu Lys
        195                 200                 205

Leu Val Ala Arg Phe Ile Gly Lys Glu Asp Ala Leu Val Phe Ser Met
    210                 215                 220

Gly Tyr Gly Thr Asn Ala Asn Leu Phe Asn Ala Phe Leu Asp Lys Lys
225                 230                 235                 240

Cys Leu Val Ile Ser Asp Glu Leu Asn His Thr Ser Ile Arg Thr Gly
                245                 250                 255

Val Arg Leu Ser Gly Ala Ala Val Arg Thr Phe Lys His Gly Asp Met
            260                 265                 270

Val Gly Leu Glu Lys Leu Ile Arg Glu Gln Ile Val Leu Gly Gln Pro
        275                 280                 285

Lys Thr Asn Arg Pro Trp Lys Lys Ile Leu Ile Cys Ala Glu Gly Leu
    290                 295                 300

Phe Ser Met Glu Gly Thr Leu Cys Asn Leu Pro Lys Leu Val Glu Leu
305                 310                 315                 320

Lys Lys Lys Tyr Lys Cys Tyr Leu Phe Ile Asp Glu Ala His Ser Ile
                325                 330                 335

Gly Ala Met Gly Pro Thr Gly Arg Gly Val Cys Glu Ile Phe Gly Val
            340                 345                 350

Asp Pro Lys Asp Val Asp Ile Leu Met Gly Thr Phe Thr Lys Ser Phe
        355                 360                 365

Gly Ala Ala Gly Gly Tyr Ile Ala Ala Asp Gln Trp Ile Ile Asp Arg
    370                 375                 380

Leu Arg Leu Asp Leu Thr Thr Val Ser Tyr Ser Glu Ser Met Pro Ala
385                 390                 395                 400

Pro Val Leu Ala Gln Thr Ile Ser Ser Leu Gln Thr Ile Ser Gly Glu
                405                 410                 415

Ile Cys Pro Gly Gln Gly Thr Glu Arg Leu Gln Arg Ile Ala Phe Asn
            420                 425                 430

Ser Arg Tyr Leu Arg Leu Ala Leu Gln Arg Leu Gly Phe Ile Val Tyr
        435                 440                 445

Gly Val Ala Asp Ser Pro Val Ile Pro Leu Leu Leu Tyr Cys Pro Ser
    450                 455                 460

Lys Met Pro Ala Phe Ser Arg Met Met Leu Gln Arg Arg Ile Ala Val
465                 470                 475                 480

Val Val Val Ala Tyr Pro Ala Thr Pro Leu Ile Glu Ser Arg Val Arg
                485                 490                 495

Phe Cys Met Ser Ala Ser Leu Thr Lys Glu Asp Ile Asp Tyr Leu Leu
            500                 505                 510

Arg His Val Ser Glu Val Gly Asp Lys Leu Asn Leu Lys Ser Asn Ser
        515                 520                 525

Gly Lys Ser Ser Tyr Asp Gly Lys Arg Gln Arg Trp Asp Ile Glu Glu
```

```
    530                 535                 540

Val Ile Arg Arg Thr Pro Glu Asp Cys Lys Asp Asp Lys Tyr Phe Val
545                 550                 555                 560

Asn


<210> SEQ ID NO 5
<211> LENGTH: 963
<212> TYPE: DNA
<213> ORGANISM: Saccharomyces cerevisiae

<400> SEQUENCE: 5

atgaagttta cgttagaaga ccaagttgtg ttgatcactg gtggttcaca aggtcttgga     60

aaggaattcg ccaaaaaata ttataatgag gctgaaaaca caaagattat tatcgtcagt    120

aggtcagagg ctagactgct ggacacatgc aacgaaatta ggattgaagc tcacctgaga    180

agggaaacca ctgacgaggg ccaagtgcaa cataagttgg ctgcgccctt ggaccttgag    240

caacggttat tttactaccc atgcgacttg tcctgctacg aatccgtgga atgtttgttc    300

aatgccctga gagacttgga tttactccct acacaaacgt tatgctgtgc agggggggct    360

gttcctaagt tatttcgtgg gctaagcgga catgagttga acttgggtat ggacatcaac    420

tataaaacaa ctttgaacgt ggcacatcag attgcccttg cagagcaaac caaggaacac    480

cacctcatca tcttttctag tgccaccgcg ctttacccat ttgtgggcta ttcccagtat    540

gcgcctgcaa aagctgcaat caaatcactg gtagcaatct taagacaaga actgacgaac    600

ttccgtatca gttgtgttta tcctggtaat tttgaaagcg aaggtttcac tgtagagcag    660

ctaacgaaac ccgaaattac aaagttgatc gaaggcccct cagacgctat cccatgcaaa    720

caagcatgtg atatcattgc caagtcgctg gccagaggtg atgatgacgt ttttacagat    780

tttgtcggat ggatgataat ggggatggac cttgggctca ccgcaaagaa aagccgcttt    840

gttccgttgc aatggatttt tggtgtccta tcaaacattc tggtcgtgcc attctacatg    900

gttggctgtt cctggtatat caggaaatgg tttcgtgaaa atgacggcaa gaaggccaac    960

tga                                                                  963


<210> SEQ ID NO 6
<211> LENGTH: 320
<212> TYPE: PRT
<213> ORGANISM: Saccharomyces cerevisiae

<400> SEQUENCE: 6

Met Lys Phe Thr Leu Glu Asp Gln Val Val Leu Ile Thr Gly Gly Ser
1               5                   10                  15

Gln Gly Leu Gly Lys Glu Phe Ala Lys Lys Tyr Tyr Asn Glu Ala Glu
            20                  25                  30

Asn Thr Lys Ile Ile Ile Val Ser Arg Ser Glu Ala Arg Leu Leu Asp
        35                  40                  45

Thr Cys Asn Glu Ile Arg Ile Glu Ala His Leu Arg Arg Glu Thr Thr
    50                  55                  60

Asp Glu Gly Gln Val Gln His Lys Leu Ala Ala Pro Leu Asp Leu Glu
65                  70                  75                  80

Gln Arg Leu Phe Tyr Tyr Pro Cys Asp Leu Ser Cys Tyr Glu Ser Val
                85                  90                  95

Glu Cys Leu Phe Asn Ala Leu Arg Asp Leu Asp Leu Leu Pro Thr Gln
            100                 105                 110

Thr Leu Cys Cys Ala Gly Gly Ala Val Pro Lys Leu Phe Arg Gly Leu
```

```
        115                 120                 125

Ser Gly His Glu Leu Asn Leu Gly Met Asp Ile Asn Tyr Lys Thr Thr
    130                 135                 140

Leu Asn Val Ala His Gln Ile Ala Leu Ala Glu Gln Thr Lys Glu His
145                 150                 155                 160

His Leu Ile Ile Phe Ser Ser Ala Thr Ala Leu Tyr Pro Phe Val Gly
                165                 170                 175

Tyr Ser Gln Tyr Ala Pro Ala Lys Ala Ala Ile Lys Ser Leu Val Ala
            180                 185                 190

Ile Leu Arg Gln Glu Leu Thr Asn Phe Arg Ile Ser Cys Val Tyr Pro
        195                 200                 205

Gly Asn Phe Glu Ser Glu Gly Phe Thr Val Glu Gln Leu Thr Lys Pro
    210                 215                 220

Glu Ile Thr Lys Leu Ile Glu Gly Pro Ser Asp Ala Ile Pro Cys Lys
225                 230                 235                 240

Gln Ala Cys Asp Ile Ile Ala Lys Ser Leu Ala Arg Gly Asp Asp Asp
                245                 250                 255

Val Phe Thr Asp Phe Val Gly Trp Met Ile Met Gly Met Asp Leu Gly
            260                 265                 270

Leu Thr Ala Lys Lys Ser Arg Phe Val Pro Leu Gln Trp Ile Phe Gly
        275                 280                 285

Val Leu Ser Asn Ile Leu Val Val Pro Phe Tyr Met Val Gly Cys Ser
    290                 295                 300

Trp Tyr Ile Arg Lys Trp Phe Arg Glu Asn Asp Gly Lys Lys Ala Asn
305                 310                 315                 320


<210> SEQ ID NO 7
<211> LENGTH: 1050
<212> TYPE: DNA
<213> ORGANISM: Saccharomyces cerevisiae

<400> SEQUENCE: 7

atgaacgtaa catcgaatgc aactgcagcc ggttcctttc cactagcatt tggtctcaag     60

acctcatttg ggtttatgca ctatgccaag gcccctgcca ttaatttacg ccccaaggaa    120

tccttgctgc cggaaatgag tgatggtgtg ctggccttgg ttgcgccggt tgttgcctac    180

tgggcgttgt ctggtatatt ccatgtaata gacactttcc atctggctga gaagtacaga    240

attcatccga gcgaagaggt tgccaagagg aacaaggcgt cgagaatgca tgttttcctt    300

gaagtgattc tacaacatat catacagacc attgttggcc ttatctttat gcacttcgag    360

ccgatctaca tgactgggtt tgaagaaaat gccatgtgga agcttcgtgc agaccttcct    420

cggattattc cagatgccgc tatttattac ggctatatgt acggaatgtc cgctttgaag    480

atctttgcag gctttttatt cgttgataca tggcaatact tttgcatag attgatgcat    540

atgaataaga ccttatacaa atggttccac tctgttcatc atgaactata cgtgccatat    600

gcttacggtg ctcttttcaa caatcctgtt gagggcttct tgttagatac tttgggaacc    660

ggtattgcca tgacgttaac tcatttgact cacagagagc aaatcattct ttttaccttt    720

gccaccatga agactgtcga tgaccactgt gggtatgctt tgccacttga cccattccaa    780

tggcttttcc ctaataacgc tgtctatcac gatatccacc accagcaatt tggtatcaag    840

acgaactttg ctcaaccatt tttcactttc tgggacaatt tgttccaaac taactttaaa    900

gggtttgaag aatatcaaaa gaagcaaaga cgtgtcacca tcgacaagta caaagagttt    960

ttgcaagaga gagaattgga aaagaaggag aaactcaaaa acttcaaagc tatgaatgct   1020
```

```
gctgaaaatg aagtaaagaa agagaaataa                                   1050


<210> SEQ ID NO 8
<211> LENGTH: 349
<212> TYPE: PRT
<213> ORGANISM: Saccharomyces cerevisiae

<400> SEQUENCE: 8

Met Asn Val Thr Ser Asn Ala Thr Ala Ala Gly Ser Phe Pro Leu Ala
1               5                   10                  15

Phe Gly Leu Lys Thr Ser Phe Gly Phe Met His Tyr Ala Lys Ala Pro
            20                  25                  30

Ala Ile Asn Leu Arg Pro Lys Glu Ser Leu Leu Pro Glu Met Ser Asp
        35                  40                  45

Gly Val Leu Ala Leu Val Ala Pro Val Val Ala Tyr Trp Ala Leu Ser
    50                  55                  60

Gly Ile Phe His Val Ile Asp Thr Phe His Leu Ala Glu Lys Tyr Arg
65                  70                  75                  80

Ile His Pro Ser Glu Glu Val Ala Lys Arg Asn Lys Ala Ser Arg Met
                85                  90                  95

His Val Phe Leu Glu Val Ile Leu Gln His Ile Ile Gln Thr Ile Val
            100                 105                 110

Gly Leu Ile Phe Met His Phe Glu Pro Ile Tyr Met Thr Gly Phe Glu
        115                 120                 125

Glu Asn Ala Met Trp Lys Leu Arg Ala Asp Leu Pro Arg Ile Ile Pro
    130                 135                 140

Asp Ala Ala Ile Tyr Tyr Gly Tyr Met Tyr Gly Met Ser Ala Leu Lys
145                 150                 155                 160

Ile Phe Ala Gly Phe Leu Phe Val Asp Thr Trp Gln Tyr Phe Leu His
                165                 170                 175

Arg Leu Met His Met Asn Lys Thr Leu Tyr Lys Trp Phe His Ser Val
            180                 185                 190

His His Glu Leu Tyr Val Pro Tyr Ala Tyr Gly Ala Leu Phe Asn Asn
        195                 200                 205

Pro Val Glu Gly Phe Leu Leu Asp Thr Leu Gly Thr Gly Ile Ala Met
    210                 215                 220

Thr Leu Thr His Leu Thr His Arg Glu Gln Ile Ile Leu Phe Thr Phe
225                 230                 235                 240

Ala Thr Met Lys Thr Val Asp Asp His Cys Gly Tyr Ala Leu Pro Leu
                245                 250                 255

Asp Pro Phe Gln Trp Leu Phe Pro Asn Asn Ala Val Tyr His Asp Ile
            260                 265                 270

His His Gln Gln Phe Gly Ile Lys Thr Asn Phe Ala Gln Pro Phe Phe
        275                 280                 285

Thr Phe Trp Asp Asn Leu Phe Gln Thr Asn Phe Lys Gly Phe Glu Glu
    290                 295                 300

Tyr Gln Lys Lys Gln Arg Arg Val Thr Ile Asp Lys Tyr Lys Glu Phe
305                 310                 315                 320

Leu Gln Glu Arg Glu Leu Glu Lys Lys Glu Lys Leu Lys Asn Phe Lys
                325                 330                 335

Ala Met Asn Ala Ala Glu Asn Glu Val Lys Lys Glu Lys
            340                 345


<210> SEQ ID NO 9
```

<211> LENGTH: 1407
<212> TYPE: DNA
<213> ORGANISM: Saccharomyces cerevisiae

<400> SEQUENCE: 9

```
atgaatctta aactttctgc tattgaaagt tactttttcc atagaagcag actaaatttg     60

cattcatgtt tttatgtcgg aatcaaactc aacgaattgc ccaaaaaaag tcaactgata    120

gcggctctta agtatactgt aatccaacat gaacgtttga cttgtaatgt attctatgat    180

gaattgaaaa aggaaaactt cctacaaaac attcttgagc cactgaaatt ttgcgatcta    240

gtagaatacc gccacgattg ggaccagtta ggggaaaccg aaattaacca catctttcaa    300

aggtataact tttcatacaa cgagaataaa cctttatgga aaattctgat cctccctaat    360

caaaatcaaa tgctattgct gacagatcat gttctcatgg atgggatgtc cgctattcat    420

gtgtgggaaa cgtttatgga aggcctacag atgcaacagc cggttgaaat tgatgaaaca    480

atatattcac catcattaaa ttcatcaact gaaaaaataa tgtcagcccc actatacgga    540

gattggccca taccttggaa ttggcatata gtgcgacaat tggtcagtag actacattat    600

tggtttccac aaacagtcgt aaaaaacaat agaaatttaa tccaatttgc caactactca    660

tttccaaaag acctgctgga tgataaaccg agcgatggaa ctcaaaaata caaagttaaa    720

aacacgaacc atcaatggga gtttcgatta tcgccgaccc atctcaacga cattttacaa    780

gaatgcaagg ccaataatac ttcgttgact tccctttag gtgccctggt ctgcaccagt    840

ttcgaaaaaa tagctgcaca tgagtatacc ggatcatttt tgaaaattga attaccaatg    900

aatattagaa agccttttga acgagtcttg aaattacctt cagatgataa gctcgccgtg    960

ggaaatttta ttgcggtcat agaattcaac cataaactac atcaaaaccg tggaatatgg   1020

gatatcgctt ctcaaattca aagggccata agaagcagtt ccgaggataa aataatagat   1080

aaagtaaacg aagtaaagtt attggaggtt atttcttctc aacaatacat agaagataaa   1140

attagcttga ataacggacc ttcttccaca tttgaagtaa caaacttagg atttcaaaca   1200

tttaaagatg catgcaacac cagtttaccg ttttatatag tggatgctac attcaacgag   1260

ccgcaaggaa tatcttcaat tttctcacta agcgtaatct ctactcctgg taacggacta   1320

cattgttgta tcagttatcc aaatactctc actaaagtgc tagaacccca ctggcaatat   1380

atgaaagatt acttaaattt atactag                                        1407
```

<210> SEQ ID NO 10
<211> LENGTH: 468
<212> TYPE: PRT
<213> ORGANISM: Saccharomyces cerevisiae

<400> SEQUENCE: 10

```
Met Asn Leu Lys Leu Ser Ala Ile Glu Ser Tyr Phe Phe His Arg Ser
1               5                   10                  15

Arg Leu Asn Leu His Ser Cys Phe Tyr Val Gly Ile Lys Leu Asn Glu
            20                  25                  30

Leu Pro Lys Lys Ser Gln Leu Ile Ala Ala Leu Lys Tyr Thr Val Ile
        35                  40                  45

Gln His Glu Arg Leu Thr Cys Asn Val Phe Tyr Asp Glu Leu Lys Lys
    50                  55                  60

Glu Asn Phe Leu Gln Asn Ile Leu Glu Pro Leu Lys Phe Cys Asp Leu
65                  70                  75                  80

Val Glu Tyr Arg His Asp Trp Asp Gln Leu Gly Glu Thr Glu Ile Asn
                85                  90                  95
```

```
His Ile Phe Gln Arg Tyr Asn Phe Ser Tyr Asn Glu Asn Lys Pro Leu
            100                 105                 110

Trp Lys Ile Leu Ile Leu Pro Asn Gln Asn Gln Met Leu Leu Leu Thr
        115                 120                 125

Asp His Val Leu Met Asp Gly Met Ser Ala Ile His Val Trp Glu Thr
    130                 135                 140

Phe Met Glu Gly Leu Gln Met Gln Gln Pro Val Glu Ile Asp Glu Thr
145                 150                 155                 160

Ile Tyr Ser Pro Ser Leu Asn Ser Ser Thr Glu Lys Ile Met Ser Ala
                165                 170                 175

Pro Leu Tyr Gly Asp Trp Pro Ile Pro Trp Asn Trp His Ile Val Arg
            180                 185                 190

Gln Leu Val Ser Arg Leu His Tyr Trp Phe Pro Gln Thr Val Val Lys
        195                 200                 205

Asn Asn Arg Asn Leu Ile Gln Phe Ala Asn Tyr Ser Phe Pro Lys Asp
    210                 215                 220

Leu Leu Asp Asp Lys Pro Ser Asp Gly Thr Gln Lys Tyr Lys Val Lys
225                 230                 235                 240

Asn Thr Asn His Gln Trp Glu Phe Arg Leu Ser Pro Thr His Leu Asn
                245                 250                 255

Asp Ile Leu Gln Glu Cys Lys Ala Asn Asn Thr Ser Leu Thr Ser Leu
            260                 265                 270

Leu Gly Ala Leu Val Cys Thr Ser Phe Glu Lys Ile Ala Ala His Glu
        275                 280                 285

Tyr Thr Gly Ser Phe Leu Lys Ile Glu Leu Pro Met Asn Ile Arg Lys
    290                 295                 300

Pro Phe Glu Arg Val Leu Lys Leu Pro Ser Asp Asp Lys Leu Ala Val
305                 310                 315                 320

Gly Asn Phe Ile Ala Val Ile Glu Phe Asn His Lys Leu His Gln Asn
                325                 330                 335

Arg Gly Ile Trp Asp Ile Ala Ser Gln Ile Gln Arg Ala Ile Arg Ser
            340                 345                 350

Ser Ser Glu Asp Lys Ile Ile Asp Lys Val Asn Glu Val Lys Leu Leu
        355                 360                 365

Glu Val Ile Ser Ser Gln Gln Tyr Ile Glu Asp Lys Ile Ser Leu Asn
    370                 375                 380

Asn Gly Pro Ser Ser Thr Phe Glu Val Thr Asn Leu Gly Phe Gln Thr
385                 390                 395                 400

Phe Lys Asp Ala Cys Asn Thr Ser Leu Pro Phe Tyr Ile Val Asp Ala
                405                 410                 415

Thr Phe Asn Glu Pro Gln Gly Ile Ser Ser Ile Phe Ser Leu Ser Val
            420                 425                 430

Ile Ser Thr Pro Gly Asn Gly Leu His Cys Cys Ile Ser Tyr Pro Asn
        435                 440                 445

Thr Leu Thr Lys Val Leu Glu Pro His Trp Gln Tyr Met Lys Asp Tyr
    450                 455                 460

Leu Asn Leu Tyr
465
```

<210> SEQ ID NO 11
<211> LENGTH: 1608
<212> TYPE: DNA
<213> ORGANISM: Saccharomyces cerevisiae

<400> SEQUENCE: 11

```
atggaagata tagaaggata cgaaccacat atcactcaag agttgataga ccgtggccat      60
gcaagacgta tgggccactt ggaaaactac tttgctgttt tgagtaggca gaaaatgtac     120
tcgaatttta ctgtttacgc ggaattgaat aaaggtgtta ataagagaca actaatgctt     180
gtcttgaaag tattacttca aaaatactca actcttgcgc atacaatcat tcctaagcat     240
tatcctcatc atgaagcgta ctactctagc gaagagtacc ttagtaaacc ttttccacag     300
catgatttca taaaggtgat ttctcatctt gaattcgatg acttgattat gaataatcaa     360
ccagaataca gagaagtcat ggagaaaatc tcagaacagt tcaaaaagga tgatttcaaa     420
gtcaccaata ggttaatcga attgattagc cctgtaatca tacctctggg taatccgaag     480
aggcctaatt ggagattgat ttgtttacca ggtaaggata ctgatgggtt tgaaacgtgg     540
aaaaacttcg tttatgtcac taaccactgc ggctccgacg gtgtcagtgg atcgaatttt     600
ttcaaagatt tagctctact cttttgtaaa atcgaagaaa aagggtttga ttatgatgaa     660
gagttcatcg aagatcaagt catcattgac tatgatcgag actacactga aatttctaaa     720
ttgccaaaac cgattacgga tcgtattgac tacaagccag cattgacttc attacccaaa     780
ttctttttaa caaccttcat ttatgaacat tgtaatttta aaacctccag cgaatctaca     840
cttacagcta gatatagccc ctctagtaat gctaatgcta gttacaatta cttgttgcat     900
ttcagtacta agcaagtaga acaaatcaga gctcagatca agaaaaatgt tcacgatggg     960
tgcaccctaa cacccttcat tcaagcgtgc tttcttgtag ccctgtatag actggataag    1020
ctgttcacaa aatctcttct cgagtatggg ttcgatgtgg ctattccaag caacgcaaga    1080
aggtttttac caaacgatga agagttaaga gattcttata aatacggctc caacgttgga    1140
ggttcgcatt acgcctatct aatctcctca ttcgacattc ccgaaggtga caatgacaag    1200
ttttggagtc ttgtcgaata ctactatgac cgctttttag aatcgtacga caacggtgac    1260
cacttgattg gtctgggggt cctacaactt gattttatcg ttgaaaacaa gaatatagac    1320
agccttcttg ccaactctta tttgcaccag caaagaggcg gtgcaatcat cagtaataca    1380
ggacttgtct cgcaagatac gaccaagccg tactacgttc gggatttaat cttctcgcag    1440
tctgcaggcg ccttgagatt tgcgttcggc ctaaacgttt gctccacaaa cgtgaatggt    1500
atgaacatgg acatgagcgt ggttcagggc actctacggg atcgtggcga atgggaatcg    1560
ttctgcaagc tcttctacca aaccatcggc gaatttgcgt cgctttaa                 1608
```

<210> SEQ ID NO 12
<211> LENGTH: 535
<212> TYPE: PRT
<213> ORGANISM: Saccharomyces cerevisiae

<400> SEQUENCE: 12

```
Met Glu Asp Ile Glu Gly Tyr Glu Pro His Ile Thr Gln Glu Leu Ile
1               5                   10                  15

Asp Arg Gly His Ala Arg Arg Met Gly His Leu Glu Asn Tyr Phe Ala
            20                  25                  30

Val Leu Ser Arg Gln Lys Met Tyr Ser Asn Phe Thr Val Tyr Ala Glu
        35                  40                  45

Leu Asn Lys Gly Val Asn Lys Arg Gln Leu Met Leu Val Leu Lys Val
    50                  55                  60

Leu Leu Gln Lys Tyr Ser Thr Leu Ala His Thr Ile Ile Pro Lys His
65                  70                  75                  80
```

```
Tyr Pro His His Glu Ala Tyr Tyr Ser Ser Glu Glu Tyr Leu Ser Lys
                85                  90                  95

Pro Phe Pro Gln His Asp Phe Ile Lys Val Ile Ser His Leu Glu Phe
            100                 105                 110

Asp Asp Leu Ile Met Asn Asn Gln Pro Glu Tyr Arg Glu Val Met Glu
        115                 120                 125

Lys Ile Ser Glu Gln Phe Lys Lys Asp Asp Phe Lys Val Thr Asn Arg
    130                 135                 140

Leu Ile Glu Leu Ile Ser Pro Val Ile Ile Pro Leu Gly Asn Pro Lys
145                 150                 155                 160

Arg Pro Asn Trp Arg Leu Ile Cys Leu Pro Gly Lys Asp Thr Asp Gly
                165                 170                 175

Phe Glu Thr Trp Lys Asn Phe Val Tyr Val Thr Asn His Cys Gly Ser
            180                 185                 190

Asp Gly Val Ser Gly Ser Asn Phe Phe Lys Asp Leu Ala Leu Leu Phe
        195                 200                 205

Cys Lys Ile Glu Glu Lys Gly Phe Asp Tyr Asp Glu Glu Phe Ile Glu
    210                 215                 220

Asp Gln Val Ile Ile Asp Tyr Asp Arg Asp Tyr Thr Glu Ile Ser Lys
225                 230                 235                 240

Leu Pro Lys Pro Ile Thr Asp Arg Ile Asp Tyr Lys Pro Ala Leu Thr
                245                 250                 255

Ser Leu Pro Lys Phe Phe Leu Thr Thr Phe Ile Tyr Glu His Cys Asn
            260                 265                 270

Phe Lys Thr Ser Ser Glu Ser Thr Leu Thr Ala Arg Tyr Ser Pro Ser
        275                 280                 285

Ser Asn Ala Asn Ala Ser Tyr Asn Tyr Leu Leu His Phe Ser Thr Lys
    290                 295                 300

Gln Val Glu Gln Ile Arg Ala Gln Ile Lys Lys Asn Val His Asp Gly
305                 310                 315                 320

Cys Thr Leu Thr Pro Phe Ile Gln Ala Cys Phe Leu Val Ala Leu Tyr
                325                 330                 335

Arg Leu Asp Lys Leu Phe Thr Lys Ser Leu Leu Glu Tyr Gly Phe Asp
            340                 345                 350

Val Ala Ile Pro Ser Asn Ala Arg Arg Phe Leu Pro Asn Asp Glu Glu
        355                 360                 365

Leu Arg Asp Ser Tyr Lys Tyr Gly Ser Asn Val Gly Gly Ser His Tyr
    370                 375                 380

Ala Tyr Leu Ile Ser Ser Phe Asp Ile Pro Glu Gly Asp Asn Asp Lys
385                 390                 395                 400

Phe Trp Ser Leu Val Glu Tyr Tyr Tyr Asp Arg Phe Leu Glu Ser Tyr
                405                 410                 415

Asp Asn Gly Asp His Leu Ile Gly Leu Gly Val Leu Gln Leu Asp Phe
            420                 425                 430

Ile Val Glu Asn Lys Asn Ile Asp Ser Leu Leu Ala Asn Ser Tyr Leu
        435                 440                 445

His Gln Gln Arg Gly Gly Ala Ile Ile Ser Asn Thr Gly Leu Val Ser
    450                 455                 460

Gln Asp Thr Thr Lys Pro Tyr Tyr Val Arg Asp Leu Ile Phe Ser Gln
465                 470                 475                 480

Ser Ala Gly Ala Leu Arg Phe Ala Phe Gly Leu Asn Val Cys Ser Thr
                485                 490                 495

Asn Val Asn Gly Met Asn Met Asp Met Ser Val Val Gln Gly Thr Leu
```

```
            500                 505                 510

Arg Asp Arg Gly Glu Trp Glu Ser Phe Cys Lys Leu Phe Tyr Gln Thr
        515                 520                 525

Ile Gly Glu Phe Ala Ser Leu
    530                 535


<210> SEQ ID NO 13
<211> LENGTH: 1236
<212> TYPE: DNA
<213> ORGANISM: Saccharomyces cerevisiae

<400> SEQUENCE: 13

atgacatcag ctacggacaa atctatcgat aggttagttg ttaatgcaaa aacaagaaga      60

cgaaactctt ccgtgggtaa aattgattta ggtgatacag ttcctggctt tgcagccatg     120

cctgaaagtg ctgcctctaa aaatgaggcc aaaaaaagga tgaaagcctt gactggtgac     180

tctaaaaagg atagtgacct actgtggaag gtttggtttt catatagaga aatgaattac     240

cgtcatagtt ggttgacacc attcttcata cttgtatgcg tgtatagcgc gtacttttta     300

tctgggaata gaacagaatc aaacccgctg cacatgttcg tagccatatc atatcaagtt     360

gatggcacag actcatatgc aaaaggtatc aaagatttga gttttgtgtt tttctacatg     420

attttcttca catttttacg tgagtttttg atggatgttg taattcgacc attcacggta     480

tacctaaatg ttacttccga gcatcgtcaa aagcgtatgc tagaacaaat gtatgccata     540

ttttattgcg gagtttcagg gccctttggt ctttatatta tgtaccatag tgatttgtgg     600

ttgttcaaga caaaaccaat gtacagaaca tatcctgtta taaccaatcc gttcttgttt     660

aagatatttt acttgggtca agcggcattt tgggcgcaac aggcttgtgt tcttgttcta     720

caattagaaa agccaagaaa ggattacaag gaattggttt ttcatcacat tgtgacatta     780

ttattaattt ggtcatcata tgttttccat tttaccaaaa tgggattggc tatctatatt     840

actatggatg tgtcagattt tttcctttct ttgtctaaga cattaaacta tctgaattct     900

gtatttactc cctttgtgtt cggcttgttc gtgttctttt ggatctatct gcgccatgtc     960

gtgaatatca gaatattatg gtcagtctta acagaattcc gtcatgaagg taattatgtg    1020

ttgaattttg ccacacaaca atacaaatgt tggatttcgt tgccaattgt atttgtacta    1080

attgctgcgt tacaattagt taacctgtat tggctgtttt taattcttag aatcttgtac    1140

agattgatat ggcaaggtat ccaaaaggac gaaagaagtg acagtgattc tgatgagagc    1200

gctgaaaatg aagaatctaa ggaaaagtgt gaataa                              1236


<210> SEQ ID NO 14
<211> LENGTH: 411
<212> TYPE: PRT
<213> ORGANISM: Saccharomyces cerevisiae

<400> SEQUENCE: 14

Met Thr Ser Ala Thr Asp Lys Ser Ile Asp Arg Leu Val Val Asn Ala
1               5                   10                  15

Lys Thr Arg Arg Arg Asn Ser Ser Val Gly Lys Ile Asp Leu Gly Asp
            20                  25                  30

Thr Val Pro Gly Phe Ala Ala Met Pro Glu Ser Ala Ala Ser Lys Asn
        35                  40                  45

Glu Ala Lys Lys Arg Met Lys Ala Leu Thr Gly Asp Ser Lys Lys Asp
    50                  55                  60

Ser Asp Leu Leu Trp Lys Val Trp Phe Ser Tyr Arg Glu Met Asn Tyr
```

```
65                  70                  75                  80

Arg His Ser Trp Leu Thr Pro Phe Phe Ile Leu Val Cys Val Tyr Ser
                85                  90                  95

Ala Tyr Phe Leu Ser Gly Asn Arg Thr Glu Ser Asn Pro Leu His Met
            100                 105                 110

Phe Val Ala Ile Ser Tyr Gln Val Asp Gly Thr Asp Ser Tyr Ala Lys
        115                 120                 125

Gly Ile Lys Asp Leu Ser Phe Val Phe Phe Tyr Met Ile Phe Phe Thr
    130                 135                 140

Phe Leu Arg Glu Phe Leu Met Asp Val Val Ile Arg Pro Phe Thr Val
145                 150                 155                 160

Tyr Leu Asn Val Thr Ser Glu His Arg Gln Lys Arg Met Leu Glu Gln
                165                 170                 175

Met Tyr Ala Ile Phe Tyr Cys Gly Val Ser Gly Pro Phe Gly Leu Tyr
            180                 185                 190

Ile Met Tyr His Ser Asp Leu Trp Leu Phe Lys Thr Lys Pro Met Tyr
        195                 200                 205

Arg Thr Tyr Pro Val Ile Thr Asn Pro Phe Leu Phe Lys Ile Phe Tyr
    210                 215                 220

Leu Gly Gln Ala Ala Phe Trp Ala Gln Gln Ala Cys Val Leu Val Leu
225                 230                 235                 240

Gln Leu Glu Lys Pro Arg Lys Asp Tyr Lys Glu Leu Val Phe His His
                245                 250                 255

Ile Val Thr Leu Leu Leu Ile Trp Ser Ser Tyr Val Phe His Phe Thr
            260                 265                 270

Lys Met Gly Leu Ala Ile Tyr Ile Thr Met Asp Val Ser Asp Phe Phe
        275                 280                 285

Leu Ser Leu Ser Lys Thr Leu Asn Tyr Leu Asn Ser Val Phe Thr Pro
    290                 295                 300

Phe Val Phe Gly Leu Phe Val Phe Phe Trp Ile Tyr Leu Arg His Val
305                 310                 315                 320

Val Asn Ile Arg Ile Leu Trp Ser Val Leu Thr Glu Phe Arg His Glu
                325                 330                 335

Gly Asn Tyr Val Leu Asn Phe Ala Thr Gln Gln Tyr Lys Cys Trp Ile
            340                 345                 350

Ser Leu Pro Ile Val Phe Val Leu Ile Ala Ala Leu Gln Leu Val Asn
        355                 360                 365

Leu Tyr Trp Leu Phe Leu Ile Leu Arg Ile Leu Tyr Arg Leu Ile Trp
    370                 375                 380

Gln Gly Ile Gln Lys Asp Glu Arg Ser Asp Ser Asp Ser Asp Glu Ser
385                 390                 395                 400

Ala Glu Asn Glu Glu Ser Lys Glu Lys Cys Glu
                405                 410


<210> SEQ ID NO 15
<211> LENGTH: 1257
<212> TYPE: DNA
<213> ORGANISM: Saccharomyces cerevisiae

<400> SEQUENCE: 15

atgtcgacaa taaagccaag cccttcaaac aacaatttga aagtgaggtc aagaccaaga     60

cgcaagtctt ccataggtaa gatcgacctc ggggacactg tacctagttt aggtactatg    120

ttcgagacaa aagaatctaa aacggctgct aaaaggcgta tgcagagatt atctgaagcc    180
```

-continued

```
accaaaaatg atagcgacct ggtcaagaaa atctggtttt cattccgaga gataagttac    240
cgtcatgcct ggatagctcc cttgatgatt ttaatcgcgg tatatagtgc ctatttcact    300
tctggtaaca ctacaaagac aaatgtgtta catagatttg tcgctgtgtc ataccaaata    360
ggtgatacca acgcatatgg taaaggtatt aacgatttgt gctttgtatt ttactatatg    420
atttttttca cattcttacg tgaattccta atggatgttg tcattagacc gttcgctatt    480
aggttacacg tcacttctaa gcacagaata aaaagaatca tggaacaaat gtacgctatt    540
ttctacaccg gtgtttccgg tcctttcggg atatattgta tgtaccattc ggatttatgg    600
tttttcaaca caaaggcaat gtacagaaca tatccagatt tcactaatcc cttcttattc    660
aaggtattct atttgggtca agctgcattt tgggctcaac aagcctgcat tcttgtattg    720
caactagaaa agccaagaaa agatcataac gagttgactt tccatcatat tgttacttta    780
ctattgattt ggtcttccta cgtatttcat ttcactaaaa tgggactgcc aatctatatc    840
acaatggatg tttctgattt tcttttgtca ttctccaaaa ctctaaatta tttggactct    900
ggattggctt ttttttcttt tgctatcttt gttgttgcgt ggatttattt gcgtcattac    960
ataaatttaa agatcctatg gtccgtttta acgcaatttc gcacggaagg taactatgtc   1020
ttgaattttg ccactcagca atataaatgt tggatttcct taccaattgt ctttgtattg   1080
ataggcgctt tgcaattagt gaatctttat tggctgttcc ttatttttag agttctttac   1140
aggattctat ggagaggtat tctcaaggat gacagaagtg atagtgaatc agacgaagaa   1200
agtgatgaaa gttccactac tccaactgac agtactccaa cgaaaaagga tatttga      1257

<210> SEQ ID NO 16
<211> LENGTH: 418
<212> TYPE: PRT
<213> ORGANISM: Saccharomyces cerevisiae

<400> SEQUENCE: 16

Met Ser Thr Ile Lys Pro Ser Pro Ser Asn Asn Asn Leu Lys Val Arg
1               5                   10                  15

Ser Arg Pro Arg Arg Lys Ser Ser Ile Gly Lys Ile Asp Leu Gly Asp
            20                  25                  30

Thr Val Pro Ser Leu Gly Thr Met Phe Glu Thr Lys Glu Ser Lys Thr
        35                  40                  45

Ala Ala Lys Arg Arg Met Gln Arg Leu Ser Glu Ala Thr Lys Asn Asp
    50                  55                  60

Ser Asp Leu Val Lys Lys Ile Trp Phe Ser Phe Arg Glu Ile Ser Tyr
65                  70                  75                  80

Arg His Ala Trp Ile Ala Pro Leu Met Ile Leu Ile Ala Val Tyr Ser
                85                  90                  95

Ala Tyr Phe Thr Ser Gly Asn Thr Thr Lys Thr Asn Val Leu His Arg
            100                 105                 110

Phe Val Ala Val Ser Tyr Gln Ile Gly Asp Thr Asn Ala Tyr Gly Lys
        115                 120                 125

Gly Ile Asn Asp Leu Cys Phe Val Phe Tyr Tyr Met Ile Phe Phe Thr
    130                 135                 140

Phe Leu Arg Glu Phe Leu Met Asp Val Val Ile Arg Pro Phe Ala Ile
145                 150                 155                 160

Arg Leu His Val Thr Ser Lys His Arg Ile Lys Arg Ile Met Glu Gln
                165                 170                 175

Met Tyr Ala Ile Phe Tyr Thr Gly Val Ser Gly Pro Phe Gly Ile Tyr
            180                 185                 190
```

```
Cys Met Tyr His Ser Asp Leu Trp Phe Phe Asn Thr Lys Ala Met Tyr
      195                 200                 205

Arg Thr Tyr Pro Asp Phe Thr Asn Pro Phe Leu Phe Lys Val Phe Tyr
    210                 215                 220

Leu Gly Gln Ala Ala Phe Trp Ala Gln Gln Ala Cys Ile Leu Val Leu
225                 230                 235                 240

Gln Leu Glu Lys Pro Arg Lys Asp His Asn Glu Leu Thr Phe His His
                245                 250                 255

Ile Val Thr Leu Leu Leu Ile Trp Ser Ser Tyr Val Phe His Phe Thr
            260                 265                 270

Lys Met Gly Leu Pro Ile Tyr Ile Thr Met Asp Val Ser Asp Phe Leu
        275                 280                 285

Leu Ser Phe Ser Lys Thr Leu Asn Tyr Leu Asp Ser Gly Leu Ala Phe
    290                 295                 300

Phe Ser Phe Ala Ile Phe Val Val Ala Trp Ile Tyr Leu Arg His Tyr
305                 310                 315                 320

Ile Asn Leu Lys Ile Leu Trp Ser Val Leu Thr Gln Phe Arg Thr Glu
                325                 330                 335

Gly Asn Tyr Val Leu Asn Phe Ala Thr Gln Gln Tyr Lys Cys Trp Ile
            340                 345                 350

Ser Leu Pro Ile Val Phe Val Leu Ile Gly Ala Leu Gln Leu Val Asn
        355                 360                 365

Leu Tyr Trp Leu Phe Leu Ile Phe Arg Val Leu Tyr Arg Ile Leu Trp
    370                 375                 380

Arg Gly Ile Leu Lys Asp Asp Arg Ser Asp Ser Glu Ser Asp Glu Glu
385                 390                 395                 400

Ser Asp Glu Ser Ser Thr Thr Pro Thr Asp Ser Thr Pro Thr Lys Lys
                405                 410                 415

Asp Ile


<210> SEQ ID NO 17
<211> LENGTH: 453
<212> TYPE: DNA
<213> ORGANISM: Saccharomyces cerevisiae

<400> SEQUENCE: 17

atgtctcaac ccactcccat cataactaca aaatcagctg ctaagccaaa accaaaaatt      60

tttaatttat tccgcgtttg cttcatttca ttattgctga tcgctgcggt tgaatacttc     120

aagtatggta caagaattaa ctatgaatgg ttccattgta ccccaatcaa agaaccccag     180

tctggctcag taatcaagct ttgggcacgt ggtgggccaa gttgtgacaa aagaggcgaa     240

tataaaacta tagtaaagag aatcactaga gattatgaac caaatgatga acatctctcg     300

ttctgtatca tcgagaatga taatgttcca cccgtccact acccaattca cgaagataaa     360

ggtgaacctg gctacgtagc ttatgtcggg tacgacacag actctgagct ggttcaagaa     420

ctatgtgctg attccacaat ttatcacatg tga                                  453


<210> SEQ ID NO 18
<211> LENGTH: 150
<212> TYPE: PRT
<213> ORGANISM: Saccharomyces cerevisiae

<400> SEQUENCE: 18

Met Ser Gln Pro Thr Pro Ile Ile Thr Thr Lys Ser Ala Ala Lys Pro
1               5                   10                  15
```

```
Lys Pro Lys Ile Phe Asn Leu Phe Arg Val Cys Phe Ile Ser Leu Leu
            20                  25                  30

Leu Ile Ala Ala Val Glu Tyr Phe Lys Tyr Gly Thr Arg Ile Asn Tyr
        35                  40                  45

Glu Trp Phe His Cys Thr Pro Ile Lys Glu Pro Gln Ser Gly Ser Val
    50                  55                  60

Ile Lys Leu Trp Ala Arg Gly Gly Pro Ser Cys Asp Lys Arg Gly Glu
65                  70                  75                  80

Tyr Lys Thr Ile Val Lys Arg Ile Thr Arg Asp Tyr Glu Pro Asn Asp
                85                  90                  95

Glu His Leu Ser Phe Cys Ile Ile Glu Asn Asp Asn Val Pro Pro Val
            100                 105                 110

His Tyr Pro Ile His Glu Asp Lys Gly Glu Pro Gly Tyr Val Ala Tyr
        115                 120                 125

Val Gly Tyr Asp Thr Asp Ser Glu Leu Val Gln Glu Leu Cys Ala Asp
    130                 135                 140

Ser Thr Ile Tyr His Met
145                 150
```

<210> SEQ ID NO 19
<211> LENGTH: 1640
<212> TYPE: DNA
<213> ORGANISM: Xenopus laevis

<400> SEQUENCE: 19

```
atcgaattcc ccgggagccg cctataccga gcacagatca gattccttct gcttttcgct      60

agtcccctcc cacagcgaca gtccattcaa tcttcctctc tgcgccggcc gctactctac     120

gtctgctggg aggaggatca ctcgtcttcc ccggtcatgg cggtgttgga tctggccctg     180

cagggactcg ccatttttgg ctgtgtctta ttcttcgtct tgtggtttat gcatttcttg     240

tccatcgtct acacaagact acacctgaac aagaagatat ctgacaagca gccatatagc     300

aaactacctg gtgtttcact tcttaaacca ctgaaagggg tcgaccccaa ccttattaat     360

aacttggaga cattctttga attggactat ccaaaatttg aaatccttct ttgtgtgcaa     420

gatcttgatg atccagcagt ggatgtatgt aaaaaattgc ttggcaaata tcctagtgta     480

gatgccaaat tatttatagg tggtaaaaaa gttgggatta acccaaaaat aaacaactta     540

atgccaggat acgaagtggc caaatatgat ctcatatgga tttgtgatag tggaataaaa     600

gtgaaaccag acacattaac agacatggcc aatcaaatga cagagaaagt tggtttggtt     660

cacggactgc catatgtggc tgatcggcaa ggatttgctg ctactttaga acaggtttac     720

tttgggacgt ctcatccaag gtcttacatc tctgctaatg taaccggttt caagtgtgta     780

acaggaatgt cttgtctaat gagaaaagaa gttttggacc aagcgggggg attaatcgcc     840

tttgcacagt atatagctga agattacttt atggctaaag caatagctga ccgcggttgg     900

aaattttcca tggcgacaca agttgcaatg cagaattccg gatgttactc tatatcccag     960

tttcaatcca gaatgatcag atgggcaaag ctacggatta acatgctgcc tgcaaccatc    1020

atttgtgagc ccatttctga atgctttgtt gccagtttaa tcattggttg ggcagcacat    1080

cacatcttcc gatgggacat aatggtgttt ttcatgtgtc attgtttggc ttggttcata    1140

tttgactaca ttcaacttag aggagtacag ggaggtcctc ttaacttttc caaactggac    1200

tatgcagttg cctggttcat ccgggaatcc atgacaatat atattttcct gtctgccttg    1260

tgggatccca ccatcagctg gaggacaggt cgcttccgat tacggtgtgg tggtacagcg    1320
```

```
gaagaaatct tagatgtata gctatggacc tgtggactgt acataacaaa acaaagcaaa   1380

aacgtaaaat taaaaaaaaa agtattataa attatgttta tataaaaatg cttttaaaga   1440

gaagaaacta cctttttgaat agttttatta caatttatgt tttgctatct gatctttatt   1500

tatttgctca tgaaatattg tttttatgaa aagcttttaa taattttatc tgtttgtcat   1560

gctccaatct atccaatggc tattttaaaa aatgaataaa ttaactaact tgttttatta   1620

aaaaaaaaaa aaaaaaaaaa                                                1640


<210> SEQ ID NO 20
<211> LENGTH: 394
<212> TYPE: PRT
<213> ORGANISM: Xenopus laevis

<400> SEQUENCE: 20

Met Ala Val Leu Asp Leu Ala Leu Gln Gly Leu Ala Ile Phe Gly Cys
1               5                   10                  15

Val Leu Phe Phe Val Leu Trp Phe Met His Phe Leu Ser Ile Val Tyr
            20                  25                  30

Thr Arg Leu His Leu Asn Lys Lys Ile Ser Asp Lys Gln Pro Tyr Ser
        35                  40                  45

Lys Leu Pro Gly Val Ser Leu Leu Lys Pro Leu Lys Gly Val Asp Pro
    50                  55                  60

Asn Leu Ile Asn Asn Leu Glu Thr Phe Phe Glu Leu Asp Tyr Pro Lys
65                  70                  75                  80

Phe Glu Ile Leu Leu Cys Val Gln Asp Leu Asp Asp Pro Ala Val Asp
                85                  90                  95

Val Cys Lys Lys Leu Leu Gly Lys Tyr Pro Ser Val Asp Ala Lys Leu
            100                 105                 110

Phe Ile Gly Gly Lys Lys Val Gly Ile Asn Pro Lys Ile Asn Asn Leu
        115                 120                 125

Met Pro Gly Tyr Glu Val Ala Lys Tyr Asp Leu Ile Trp Ile Cys Asp
    130                 135                 140

Ser Gly Ile Lys Val Lys Pro Asp Thr Leu Thr Asp Met Ala Asn Gln
145                 150                 155                 160

Met Thr Glu Lys Val Gly Leu Val His Gly Leu Pro Tyr Val Ala Asp
                165                 170                 175

Arg Gln Gly Phe Ala Ala Thr Leu Glu Gln Val Tyr Phe Gly Thr Ser
            180                 185                 190

His Pro Arg Ser Tyr Ile Ser Ala Asn Val Thr Gly Phe Lys Cys Val
        195                 200                 205

Thr Gly Met Ser Cys Leu Met Arg Lys Glu Val Leu Asp Gln Ala Gly
    210                 215                 220

Gly Leu Ile Ala Phe Ala Gln Tyr Ile Ala Glu Asp Tyr Phe Met Ala
225                 230                 235                 240

Lys Ala Ile Ala Asp Arg Gly Trp Lys Phe Ser Met Ala Thr Gln Val
                245                 250                 255

Ala Met Gln Asn Ser Gly Cys Tyr Ser Ile Ser Gln Phe Gln Ser Arg
            260                 265                 270

Met Ile Arg Trp Ala Lys Leu Arg Ile Asn Met Leu Pro Ala Thr Ile
        275                 280                 285

Ile Cys Glu Pro Ile Ser Glu Cys Phe Val Ala Ser Leu Ile Ile Gly
    290                 295                 300

Trp Ala Ala His His Ile Phe Arg Trp Asp Ile Met Val Phe Phe Met
```

```
305                 310                 315                 320

Cys His Cys Leu Ala Trp Phe Ile Phe Asp Tyr Ile Gln Leu Arg Gly
                325                 330                 335

Val Gln Gly Gly Pro Leu Asn Phe Ser Lys Leu Asp Tyr Ala Val Ala
            340                 345                 350

Trp Phe Ile Arg Glu Ser Met Thr Ile Tyr Ile Phe Leu Ser Ala Leu
        355                 360                 365

Trp Asp Pro Thr Ile Ser Trp Arg Thr Gly Arg Phe Arg Leu Arg Cys
    370                 375                 380

Gly Gly Thr Ala Glu Glu Ile Leu Asp Val
385                 390


<210> SEQ ID NO 21
<211> LENGTH: 4495
<212> TYPE: DNA
<213> ORGANISM: Xenopus laevis

<400> SEQUENCE: 21

attttctgct cagggaagcg gcggcgccag attgaagagg gagtgtttaa ggcgcaggcg     60

gctttgcttt gggggatatt aatagccgcc cataccgagc agtgatccga tcccttctgc    120

tttacgctag tcccctccca cagcgacagt ccattcaatc cccgtttctg ccccggccgc    180

tgctctccgt cttcagtttc tcggggagga gaatctccag tcttcccggt catggcggtg    240

ctggatctgg ccctgcaggg actcgccatc ttcggttgta tcttattttt cgtcctgtgg    300

ttcatgcatt tcttgtccat cgtctacaca aggctacacc tgaacaagaa ggtatctgac    360

aagcagccgt atagcaaact acctggtgtt tcacttctta aaccactgaa aggggtcgac    420

tccaacctta tcaataacct ggagacattt tttgaattgg actatccaaa atttgaaatc    480

ctcctttgtg tgcaagatct tgatgatcca gcagtggatg tatgtaaaaa actgcttggc    540

aaatatccca gtgtagatgc caaattattt ataggtggta aaaaagttgg gattaatcca    600

aagataaaca acctgatgcc aggatatgaa gtggccaaat atgatctcat atggatttgt    660

gatagtggga taaaagtgaa accagacaca ttaacagaca tggccaatca aatgacagag    720

aaagttggct tggttcatgg acttccatat gtggctgatc ggcaaggatt tgctgctact    780

ttagaacagg tttactttgg gacttcccat ccaagatctt acatctctgc caatgtaacg    840

ggtatcaagt gtgtaacagg aatgtcttgt ctaatgagaa aagaagtttt ggaccaagct    900

gggggattaa tcgcctttgc acagtatata gctgaagatt actttatggc taaagcaata    960

gctgaccgcg gttggaaatt ttccatggca acacaagttg caatgcagaa ctccgggtgt   1020

tactctatat cccagtttca atccagaatg atcaggtggg caaagctacg gattaacatg   1080

ctgcctgcaa caatcatttg tgagcccatt tctgaatgct ttgttgccag tttaataatt   1140

ggttgggcag cacatcacat ctttcgatgg gacattatgg tgtttttcat gtgtcattgt   1200

ttggcttggt tcatatttga ctacattcaa cttagaggag ttcagggagg tcctcttaac   1260

ttttccaaac tggactatgc agttgcctgg ttcatccggg aatctatgac aatatatatc   1320

tttctgtctg ccttgtggga tcccaccatc agctggagga caggccgcta ccgattacgg   1380

tgtggtggta cagcagaaga aatcctagac gtatagctgt ggactgtaca taacaaaaca   1440

aaggaaaaac ttaaaattta aaaaaaagta ttataaatta tgtttataca aatgctttta   1500

aagagaagaa actacctttt gaatagtttt attacatgta tgttttgcta tctgatcttt   1560

atttattttg catggcactt gcatctgtga agaagtatgt ttagtaatct gggctaaaat   1620
```

```
ggacagtaca ttttttgtg tgtgtgtgtg tgtaaaatgg gagagaacca taagtcatta   1680
taaatacttt gcattcccac ccagaggaat gggtaaggag acgcaacttg tggatttttg   1740
gctattccca aaccacatct tttaatgcac tcaaataatt gacctaactg tgaatattca   1800
gtgttacagt tcagtcaaca gagtaccggt atttggctat ccctgtaata aaggttccct   1860
gcaatttatg gtaggcagcc ttctttccag atgaaaaata gatcacattc accttgaagg   1920
acaatatttg taccttgaac accggttgtg aaatattcct gcatatttat ttatttacaa   1980
acaaaaactg gatatcatat accttgtcta gctacctcac acagttatta gacacgaggc   2040
aaataaaaag gaaatctcta tatgtgtgat tgtataaatt aaagccagga tgtttaggct   2100
gcagccttcc agctgttcca gaattaactc tcccatcatt ctgtgccagt gactaactga   2160
cggtaatggg gattgcagct cattaactat gaaggtcctt ggttttgcca tccgtcgtgt   2220
tttctttcta tggtggaaaa ctattgttgg tttacagtgt gcgaccttcg ttaattgggt   2280
tttgctagga ttcttcttgc tgatcactgt tctgtatatg gcttcttgct agctttcctc   2340
ctggtgaggt gatttttggt tcaacaaaaa ttacacttgt tctctttttt tgttttctct   2400
ttctacataa aatgaaacac aatttacatg ccatttgaca caaactattt tcttactcca   2460
caccgaattg ttaataagag agtaattttg tgacacacgt atttaatatc tttttaatgc   2520
atgtatacta ttcaaaatga aaaaaacaaa caaaaaaaaa tcagtaaata ttgtaaatag   2580
tatatatatt taaatatata aagaagtttg cgtttgataa aaaaaaaaat cgaaggagct   2640
gtacacagtc ttaatttatt agctatcaaa caaaaaaagg gtactggtgg gttaccctac   2700
accacattta tctagttgtg tttaattctt ttttttaaaa ttcataccga aagagcaaga   2760
tgtaaatgca tgctgtacat tttttcctgc tgcggtaagg aatttgtaat tgttgttttt   2820
tttttgtatc tattttgtct ggtttccctt gaagatgtgg tgagctggag caattttgtt   2880
gatgtgcacg tactgtaaag aaacgagcag gaaatgcaga agcctttaat atgtatataa   2940
gtcttgaata tatttacccg ctcttgcatt aatttgctgg ctagcctcgt tgacatggtc   3000
atgcttgctt gaacatctca gaagatgtta ctatttgatc tttaaactgt ggctgtcaaa   3060
ccattgctga gctacaactc tcagcgtccc attgtctcct gggatttgtt gttcagtcgt   3120
agagctgtca gttgaagatc accgctttag atctggccag agaacttcat cagtgttctt   3180
ataagcaata actacctttt caaattgact gggcaattat tttaaccttg actgagccaa   3240
tagatgtaat tgccccaata gtctctggcc aaagcaaaag cattgtggct agcttgataa   3300
taatatgcct tatgacatca gatgttttgt ttgaagggca tttatattct gcatgggtgg   3360
gtgaggcttt gattgcatgt tttgcattct ttacgtgaat cggggaaact cttccttgag   3420
gaaatgtcac attgcaagcc agtctagttg tgatccacac aagctctcca taaagcgcat   3480
ctgacgtttg ctaatggatg tttgtatata tttttgtttc tcgtgttaag tgaagtttgc   3540
tgccttccgc tatatggcag agatgacagt gacatgtaca gtaccttagt tatagaatgg   3600
tgtataatcg gaacgaagga aaggctggac agaccagttt ttttatgttt tctggatgat   3660
gatttgcact tcttgtacaa atgtttatta aagggaaata tacacccctt tttttaacat   3720
gaactaaatt aaaaatatat atacagtgca taagacctat ctttgataat tgaaatgatt   3780
aagtagctat tttgttagag ttctacatga ttcacccagt ccaaattgtt gaggattaac   3840
catttatata cccaacagca ggcacatata tagacttaag ccagctattc atgtttcttt   3900
gaatttttta actcctaccc tttatgtgcc catttttccc ctgcttctgt tgcccatacc   3960
aatgtctttg cctttgactg cattaacaga gcaaaaagct gctaattgtt tctaggcagg   4020
```

```
ggttgcaagc agcctagaaa tggctactac aaccataatt gccttcttgg gttgggaata   4080

atttgcagaa aaaaatgggc aaaccaacat ggatttatgt tatgagatga ccgggatatc   4140

tgtagctaaa tactcaatca tagcatttat cacagtgtgg gcttatacac cctattaaca   4200

tgagatcaat ttactataat tttataaaaa aaaaaaaaaa ggtgtatact tcacctttaa   4260

agaaaggtta agtttcgctg aagcgcatgg ctgaattaca tcaattgttt ccttggaaat   4320

gttggcttca gtattctaga gggcataaca agtagaatct tttgaattcc aaatactgtt   4380

tatttaaagt ggtcttaaat tacatgcaaa aaagaaaatg tctaggatat tcattgttta   4440

tttcataatt gtcattttga gtttgttcta aaaaaaaaaa aaaaaaaaaa aaaaa        4495
```

<210> SEQ ID NO 22
<211> LENGTH: 394
<212> TYPE: PRT
<213> ORGANISM: Xenopus laevis

<400> SEQUENCE: 22

```
Met Ala Val Leu Asp Leu Ala Leu Gln Gly Leu Ala Ile Phe Gly Cys
1               5                   10                  15

Ile Leu Phe Phe Val Leu Trp Phe Met His Phe Leu Ser Ile Val Tyr
            20                  25                  30

Thr Arg Leu His Leu Asn Lys Lys Val Ser Asp Lys Gln Pro Tyr Ser
        35                  40                  45

Lys Leu Pro Gly Val Ser Leu Leu Lys Pro Leu Lys Gly Val Asp Ser
    50                  55                  60

Asn Leu Ile Asn Asn Leu Glu Thr Phe Phe Glu Leu Asp Tyr Pro Lys
65                  70                  75                  80

Phe Glu Ile Leu Leu Cys Val Gln Asp Leu Asp Asp Pro Ala Val Asp
                85                  90                  95

Val Cys Lys Lys Leu Leu Gly Lys Tyr Pro Ser Val Asp Ala Lys Leu
            100                 105                 110

Phe Ile Gly Gly Lys Lys Val Gly Ile Asn Pro Lys Ile Asn Asn Leu
        115                 120                 125

Met Pro Gly Tyr Glu Val Ala Lys Tyr Asp Leu Ile Trp Ile Cys Asp
    130                 135                 140

Ser Gly Ile Lys Val Lys Pro Asp Thr Leu Thr Asp Met Ala Asn Gln
145                 150                 155                 160

Met Thr Glu Lys Val Gly Leu Val His Gly Leu Pro Tyr Val Ala Asp
                165                 170                 175

Arg Gln Gly Phe Ala Ala Thr Leu Glu Gln Val Tyr Phe Gly Thr Ser
            180                 185                 190

His Pro Arg Ser Tyr Ile Ser Ala Asn Val Thr Gly Ile Lys Cys Val
        195                 200                 205

Thr Gly Met Ser Cys Leu Met Arg Lys Glu Val Leu Asp Gln Ala Gly
    210                 215                 220

Gly Leu Ile Ala Phe Ala Gln Tyr Ile Ala Glu Asp Tyr Phe Met Ala
225                 230                 235                 240

Lys Ala Ile Ala Asp Arg Gly Trp Lys Phe Ser Met Ala Thr Gln Val
                245                 250                 255

Ala Met Gln Asn Ser Gly Cys Tyr Ser Ile Ser Gln Phe Gln Ser Arg
            260                 265                 270

Met Ile Arg Trp Ala Lys Leu Arg Ile Asn Met Leu Pro Ala Thr Ile
        275                 280                 285
```

```
Ile Cys Glu Pro Ile Ser Glu Cys Phe Val Ala Ser Leu Ile Ile Gly
    290                 295                 300

Trp Ala Ala His His Ile Phe Arg Trp Asp Ile Met Val Phe Phe Met
305                 310                 315                 320

Cys His Cys Leu Ala Trp Phe Ile Phe Asp Tyr Ile Gln Leu Arg Gly
                325                 330                 335

Val Gln Gly Gly Pro Leu Asn Phe Ser Lys Leu Asp Tyr Ala Val Ala
            340                 345                 350

Trp Phe Ile Arg Glu Ser Met Thr Ile Tyr Ile Phe Leu Ser Ala Leu
        355                 360                 365

Trp Asp Pro Thr Ile Ser Trp Arg Thr Gly Arg Tyr Arg Leu Arg Cys
    370                 375                 380

Gly Gly Thr Ala Glu Glu Ile Leu Asp Val
385                 390


<210> SEQ ID NO 23
<211> LENGTH: 1875
<212> TYPE: DNA
<213> ORGANISM: Saccharomyces cerevisiae

<400> SEQUENCE: 23

atggtggtgc agaaaaaact tagggctatc ttgaccgatg aaggtgtatt gatcaaatcg     60

caatcacacc atatgttcaa taagcatggt caactcagaa gcggagattc tttatccttg    120

ttgagctgct tgtcctgtct ggatgatgga actttgagct ctgatggagg ttcttttgat    180

gaggatgatt ccctggaact gttgcctctt aatactacca ttccgttcaa cagaattttg    240

aacgcaaaat atgtgaatgt cggtcagaaa ggcttcaata atggcaaaat ttcttcgaat    300

ccttttcaaa cggaaaatct gagttcttcg tctgaaaatg acgacgttga gaatcatagt    360

ttgagcaatg ataaggctcc tgtaagcgaa tcacagtcat ttcccaaaaa agacaagtgg    420

gatacaaaaa cgaacactgt gaaggtgtct cccgatgatt cacaggataa ctcaccatct    480

ttagggataa aagataatca acagttaatt gagttaactt ttgctgtacc caagggccat    540

gatgttatac cacaaaaatt aaccttgtta atagatcacg tttctaggaa atcgagagca    600

aataccggag aggagaacat ttcttctggt actgtggaag aaatcctgga aaaaagttat    660

gaaaattcca agagaaacag atcgatatta gtcattatta atccccacgg tggtaaaggt    720

actgctaaaa atttattcct gacaaaagca aggccaatac tagtggaaag tggctgcaaa    780

atagaaattg catacacaaa atatgcccgt cacgccatcg atattgccaa agatttagat    840

atcagcaaat acgataccat tgcatgtgcc tcgggtgatg gtattccata cgaagtaatt    900

aatgggcttt atagaagacc cgacagagtg gatgcgttca ataaactagc cgtaactcag    960

ctaccttgcg gttcaggaaa tgctatgagc atttcatgtc attggacaaa taacccatcg   1020

tacgccgctc tgtgccttgt caaatccatt gaaacaagaa tagacttaat gtgttgttcc   1080

caaccttctt atatgaacga atggccaaga ttatcctttt tgagtcagac gtacggcgtt   1140

attgcagaat ctgatattaa cactgaattc atcagatgga tgggtcccgt taggtttaat   1200

ttgggtgtag cattcaacat tatccaaggt aagaaatatc cctgcgaagt tttcgtcaaa   1260

tatgctgcca aatctaaaaa ggaattaaaa gttcatttct tagaaaataa agataaaaac   1320

aaaggatgtt taaccttcga accaaatcct agcccaaact cttcgccgga tttactatct   1380

aaaaacaata tcaacaacag tacaaaagat gaactttcac cgaattttct caacgaggac   1440

aactttaaat taaagtatcc gatgacggaa ccagtaccta gagactggga gaaaatggat   1500
```

```
tcagagctaa ctgataactt aacaatcttt tacacaggga aaatgccgta tattgctaag   1560

gacaccaaat tttttcccgc tgctttacca gcggatggta ccattgattt agtcataacg   1620

gatgcaagaa tcccagtgac aagaatgaca ccaattttat tatccttgga taaaggttct   1680

catgtattag agccagaagt tattcactca aaaatattgg cttataagat tataccaaaa   1740

gtggagtcag gtttattttc agtggatggt gaaaagtttc ctttggaacc cttgcaagtg   1800

gaaataatgc ccatgttatg caagacgttg ctaaggaatg gtagatatat cgatacagag   1860

tttgaatcca tgtag                                                    1875


<210> SEQ ID NO 24
<211> LENGTH: 624
<212> TYPE: PRT
<213> ORGANISM: Saccharomyces cerevisiae

<400> SEQUENCE: 24

Met Val Val Gln Lys Lys Leu Arg Ala Ile Leu Thr Asp Glu Gly Val
1               5                   10                  15

Leu Ile Lys Ser Gln Ser His His Met Phe Asn Lys His Gly Gln Leu
            20                  25                  30

Arg Ser Gly Asp Ser Leu Ser Leu Leu Ser Cys Leu Ser Cys Leu Asp
        35                  40                  45

Asp Gly Thr Leu Ser Ser Asp Gly Gly Ser Phe Asp Glu Asp Asp Ser
    50                  55                  60

Leu Glu Leu Leu Pro Leu Asn Thr Thr Ile Pro Phe Asn Arg Ile Leu
65                  70                  75                  80

Asn Ala Lys Tyr Val Asn Val Gly Gln Lys Gly Phe Asn Asn Gly Lys
                85                  90                  95

Ile Ser Ser Asn Pro Phe Gln Thr Glu Asn Leu Ser Ser Ser Ser Glu
            100                 105                 110

Asn Asp Asp Val Glu Asn His Ser Leu Ser Asn Asp Lys Ala Pro Val
        115                 120                 125

Ser Glu Ser Gln Ser Phe Pro Lys Lys Asp Lys Trp Asp Thr Lys Thr
    130                 135                 140

Asn Thr Val Lys Val Ser Pro Asp Asp Ser Gln Asp Asn Ser Pro Ser
145                 150                 155                 160

Leu Gly Ile Lys Asp Asn Gln Gln Leu Ile Glu Leu Thr Phe Ala Val
                165                 170                 175

Pro Lys Gly His Asp Val Ile Pro Gln Lys Leu Thr Leu Leu Ile Asp
            180                 185                 190

His Val Ser Arg Lys Ser Arg Ala Asn Thr Gly Glu Glu Asn Ile Ser
        195                 200                 205

Ser Gly Thr Val Glu Glu Ile Leu Glu Lys Ser Tyr Glu Asn Ser Lys
    210                 215                 220

Arg Asn Arg Ser Ile Leu Val Ile Ile Asn Pro His Gly Gly Lys Gly
225                 230                 235                 240

Thr Ala Lys Asn Leu Phe Leu Thr Lys Ala Arg Pro Ile Leu Val Glu
                245                 250                 255

Ser Gly Cys Lys Ile Glu Ile Ala Tyr Thr Lys Tyr Ala Arg His Ala
            260                 265                 270

Ile Asp Ile Ala Lys Asp Leu Asp Ile Ser Lys Tyr Asp Thr Ile Ala
        275                 280                 285

Cys Ala Ser Gly Asp Gly Ile Pro Tyr Glu Val Ile Asn Gly Leu Tyr
    290                 295                 300
```

```
Arg Arg Pro Asp Arg Val Asp Ala Phe Asn Lys Leu Ala Val Thr Gln
305                 310                 315                 320

Leu Pro Cys Gly Ser Gly Asn Ala Met Ser Ile Ser Cys His Trp Thr
                325                 330                 335

Asn Asn Pro Ser Tyr Ala Ala Leu Cys Leu Val Lys Ser Ile Glu Thr
            340                 345                 350

Arg Ile Asp Leu Met Cys Cys Ser Gln Pro Ser Tyr Met Asn Glu Trp
        355                 360                 365

Pro Arg Leu Ser Phe Leu Ser Gln Thr Tyr Gly Val Ile Ala Glu Ser
    370                 375                 380

Asp Ile Asn Thr Glu Phe Ile Arg Trp Met Gly Pro Val Arg Phe Asn
385                 390                 395                 400

Leu Gly Val Ala Phe Asn Ile Ile Gln Gly Lys Lys Tyr Pro Cys Glu
                405                 410                 415

Val Phe Val Lys Tyr Ala Ala Lys Ser Lys Lys Glu Leu Lys Val His
            420                 425                 430

Phe Leu Glu Asn Lys Asp Lys Asn Lys Gly Cys Leu Thr Phe Glu Pro
        435                 440                 445

Asn Pro Ser Pro Asn Ser Ser Pro Asp Leu Leu Ser Lys Asn Asn Ile
    450                 455                 460

Asn Asn Ser Thr Lys Asp Glu Leu Ser Pro Asn Phe Leu Asn Glu Asp
465                 470                 475                 480

Asn Phe Lys Leu Lys Tyr Pro Met Thr Glu Pro Val Pro Arg Asp Trp
                485                 490                 495

Glu Lys Met Asp Ser Glu Leu Thr Asp Asn Leu Thr Ile Phe Tyr Thr
            500                 505                 510

Gly Lys Met Pro Tyr Ile Ala Lys Asp Thr Lys Phe Phe Pro Ala Ala
        515                 520                 525

Leu Pro Ala Asp Gly Thr Ile Asp Leu Val Ile Thr Asp Ala Arg Ile
    530                 535                 540

Pro Val Thr Arg Met Thr Pro Ile Leu Leu Ser Leu Asp Lys Gly Ser
545                 550                 555                 560

His Val Leu Glu Pro Glu Val Ile His Ser Lys Ile Leu Ala Tyr Lys
                565                 570                 575

Ile Ile Pro Lys Val Glu Ser Gly Leu Phe Ser Val Asp Gly Glu Lys
            580                 585                 590

Phe Pro Leu Glu Pro Leu Gln Val Glu Ile Met Pro Met Leu Cys Lys
        595                 600                 605

Thr Leu Leu Arg Asn Gly Arg Tyr Ile Asp Thr Glu Phe Glu Ser Met
    610                 615                 620
```

<210> SEQ ID NO 25
<211> LENGTH: 2064
<212> TYPE: DNA
<213> ORGANISM: Saccharomyces cerevisiae

<400> SEQUENCE: 25

```
atgactttga aaccttcaaa gagacgtaag ggcaggtctc gccattccag gaagaagcaa      60

ataacgtcag cgatactgac tgaggaagga ataatgatca aggcaaaacc atcaagtcct     120

tacacatacg caaatagaat ggcagataaa cgaagtcgca gcagcattga caacatcagt     180

agaactagct ttcaaagcaa catcagtaga actagctttc aaagcaacag tgataacaac     240

agtatatttg aaacggcttc actaattagc tgtgttacct gtttaagcga tactgataca     300

atagacagat cggaaacatc gacaacggat acaagtaaag atgatctttc tgctaatcca     360
```

```
aaacttcatt atccttcggt gaatggtcaa ttgccagcaa acaccgttat cccctatgga    420

cgaattctgg atgccagata cattgaaaag gaacctctgc attattatga tgccaattca    480

tcacccagtt cacctttaag cagctcaatg agtaacatta gtgaaaagtg tgatcttgat    540

gaattagagt cttcccaaaa aaaagaaagg aagggcaact cgctatcgcg aggaagtaac    600

agtagtagta gcctcctgac ttccagatct ccttttacga aactagtaga ggttatattt    660

gctaggccaa gacggcatga cgttgtaccc aaaagggttt cattgtatat tgactataaa    720

ccccattcat cttctcactt aaaagaagaa gatgacttgg ttgaggagat tttaaagaga    780

agctacaaaa acactagaag gaacaaatcc atatttgtga tcattaatcc gtttggtggt    840

aaaggtaagg cgaaaaaact gtttatgaca aaggcaaagc cgttactatt agcaagtcgg    900

tgttccatag aagtggttta tacaaaatac cctggtcatg ctatagagat cgcgcgggaa    960

atggatattg acaaatatga cactattgct tgcgcttcgg gagatggcat tcctcatgag   1020

gtgatcaatg ggttatacca aaggcctgat catgtcaaag cattcaacaa tatcgccatt   1080

acagaaattc catgcggatc aggtaacgca atgagcgtat cctgccactg gacaaacaat   1140

ccttcgtact caactttatg cttaattaaa tcgatagaga ctagaattga tttgatgtgt   1200

tgttcgcagc cttcttatgc aagagagcac ccaaagttat catttttaag tcaaacatat   1260

ggtctcattg cagaaactga cataaacact gaatttatta gatggatggg acctgcaagg   1320

tttgaattgg gtgtagcctt caatatcata caaaaaaaaa aatatccttg tgagatatat   1380

gtaaagtatg ctgccaaatc aaaaaacgag ttaaaaaatc attacctgga acacaaaaat   1440

aaagggtcgt tagaattcca gcatattact atgaacaaag ataacgagga ttgtgataat   1500

tacaattacg aaaatgaata cgaaaccgaa aacgaagatg aagatgaaga tgcggatgcg   1560

gatgacgaag actcccactt gatatctcgt gatctggcag attctagtgc tgatcaaatt   1620

aaagaggaag atttcaaaat aaaatatcca ttagatgaag gtatccctag tgactgggaa   1680

agattggatc ctaatatttc gaacaaccta ggtatcttct atacgggtaa aatgccatat   1740

gtggctgctg acactaaatt ctttccggca gcgcttcctt cagatggtac aatggatatg   1800

gttatcaccg atgcaagaac ctcgttgacg aggatggcac caatcctgct gggactagat   1860

aagggttccc atgttttaca accggaagtc ttacactcta aaattttggc atacaagata   1920

ataccaaagc tagggaacgg cttgttctct gtcgatggcg agaaatttcc tctagagccc   1980

cttcaagtcg aaattatgcc acgcttatgc aagacgttac tgagaaatgg ccgttatgtg   2040

gacacagatt tcgattctat gtga                                          2064
```

<210> SEQ ID NO 26
<211> LENGTH: 687
<212> TYPE: PRT
<213> ORGANISM: Saccharomyces cerevisiae

<400> SEQUENCE: 26

```
Met Thr Leu Lys Pro Ser Lys Arg Arg Lys Gly Arg Ser Arg His Ser
1               5                   10                  15

Arg Lys Lys Gln Ile Thr Ser Ala Ile Leu Thr Glu Glu Gly Ile Met
            20                  25                  30

Ile Lys Ala Lys Pro Ser Ser Pro Tyr Thr Tyr Ala Asn Arg Met Ala
        35                  40                  45

Asp Lys Arg Ser Arg Ser Ser Ile Asp Asn Ile Ser Arg Thr Ser Phe
    50                  55                  60
```

```
Gln Ser Asn Ile Ser Arg Thr Ser Phe Gln Ser Asn Ser Asp Asn Asn
65                  70                  75                  80

Ser Ile Phe Glu Thr Ala Ser Leu Ile Ser Cys Val Thr Cys Leu Ser
                85                  90                  95

Asp Thr Asp Thr Ile Asp Arg Ser Glu Thr Ser Thr Thr Asp Thr Ser
            100                 105                 110

Lys Asp Asp Leu Ser Ala Asn Pro Lys Leu His Tyr Pro Ser Val Asn
        115                 120                 125

Gly Gln Leu Pro Ala Asn Thr Val Ile Pro Tyr Gly Arg Ile Leu Asp
    130                 135                 140

Ala Arg Tyr Ile Glu Lys Glu Pro Leu His Tyr Tyr Asp Ala Asn Ser
145                 150                 155                 160

Ser Pro Ser Ser Pro Leu Ser Ser Ser Met Ser Asn Ile Ser Glu Lys
                165                 170                 175

Cys Asp Leu Asp Glu Leu Glu Ser Ser Gln Lys Lys Glu Arg Lys Gly
            180                 185                 190

Asn Ser Leu Ser Arg Gly Ser Asn Ser Ser Ser Ser Leu Leu Thr Ser
        195                 200                 205

Arg Ser Pro Phe Thr Lys Leu Val Glu Val Ile Phe Ala Arg Pro Arg
    210                 215                 220

Arg His Asp Val Val Pro Lys Arg Val Ser Leu Tyr Ile Asp Tyr Lys
225                 230                 235                 240

Pro His Ser Ser Ser His Leu Lys Glu Glu Asp Asp Leu Val Glu Glu
                245                 250                 255

Ile Leu Lys Arg Ser Tyr Lys Asn Thr Arg Arg Asn Lys Ser Ile Phe
            260                 265                 270

Val Ile Ile Asn Pro Phe Gly Gly Lys Gly Lys Ala Lys Lys Leu Phe
        275                 280                 285

Met Thr Lys Ala Lys Pro Leu Leu Leu Ala Ser Arg Cys Ser Ile Glu
    290                 295                 300

Val Val Tyr Thr Lys Tyr Pro Gly His Ala Ile Glu Ile Ala Arg Glu
305                 310                 315                 320

Met Asp Ile Asp Lys Tyr Asp Thr Ile Ala Cys Ala Ser Gly Asp Gly
                325                 330                 335

Ile Pro His Glu Val Ile Asn Gly Leu Tyr Gln Arg Pro Asp His Val
            340                 345                 350

Lys Ala Phe Asn Asn Ile Ala Ile Thr Glu Ile Pro Cys Gly Ser Gly
        355                 360                 365

Asn Ala Met Ser Val Ser Cys His Trp Thr Asn Asn Pro Ser Tyr Ser
    370                 375                 380

Thr Leu Cys Leu Ile Lys Ser Ile Glu Thr Arg Ile Asp Leu Met Cys
385                 390                 395                 400

Cys Ser Gln Pro Ser Tyr Ala Arg Glu His Pro Lys Leu Ser Phe Leu
                405                 410                 415

Ser Gln Thr Tyr Gly Leu Ile Ala Glu Thr Asp Ile Asn Thr Glu Phe
            420                 425                 430

Ile Arg Trp Met Gly Pro Ala Arg Phe Glu Leu Gly Val Ala Phe Asn
        435                 440                 445

Ile Ile Gln Lys Lys Lys Tyr Pro Cys Glu Ile Tyr Val Lys Tyr Ala
    450                 455                 460

Ala Lys Ser Lys Asn Glu Leu Lys Asn His Tyr Leu Glu His Lys Asn
465                 470                 475                 480

Lys Gly Ser Leu Glu Phe Gln His Ile Thr Met Asn Lys Asp Asn Glu
```

```
                485                 490                 495

Asp Cys Asp Asn Tyr Asn Tyr Glu Asn Glu Tyr Glu Thr Glu Asn Glu
            500                 505                 510

Asp Glu Asp Glu Asp Ala Asp Ala Asp Asp Glu Asp Ser His Leu Ile
        515                 520                 525

Ser Arg Asp Leu Ala Asp Ser Ser Ala Asp Gln Ile Lys Glu Glu Asp
    530                 535                 540

Phe Lys Ile Lys Tyr Pro Leu Asp Glu Gly Ile Pro Ser Asp Trp Glu
545                 550                 555                 560

Arg Leu Asp Pro Asn Ile Ser Asn Asn Leu Gly Ile Phe Tyr Thr Gly
                565                 570                 575

Lys Met Pro Tyr Val Ala Ala Asp Thr Lys Phe Phe Pro Ala Ala Leu
            580                 585                 590

Pro Ser Asp Gly Thr Met Asp Met Val Ile Thr Asp Ala Arg Thr Ser
        595                 600                 605

Leu Thr Arg Met Ala Pro Ile Leu Leu Gly Leu Asp Lys Gly Ser His
    610                 615                 620

Val Leu Gln Pro Glu Val Leu His Ser Lys Ile Leu Ala Tyr Lys Ile
625                 630                 635                 640

Ile Pro Lys Leu Gly Asn Gly Leu Phe Ser Val Asp Gly Glu Lys Phe
                645                 650                 655

Pro Leu Glu Pro Leu Gln Val Glu Ile Met Pro Arg Leu Cys Lys Thr
            660                 665                 670

Leu Leu Arg Asn Gly Arg Tyr Val Asp Thr Asp Phe Asp Ser Met
        675                 680                 685


<210> SEQ ID NO 27
<211> LENGTH: 1038
<212> TYPE: DNA
<213> ORGANISM: Saccharomyces cerevisiae

<400> SEQUENCE: 27

atgaacacta ccacatctac tgttatagca gcagttgccg accagttcca gtctttgaac     60

tcttcttctt catgtttctt gaaggttcat gttccttcca ttgagaaccc attcggtatt    120

gaattatggc caattttctc caaagtgttt gaatacttta gtggctatcc agctgagcaa    180

ttcgagttta ttcacaataa gactttcttg gctaacgggt atcatgctgt tagtattatt    240

atcgtttatt acattattat ctttggtggc caagctatct tacgcgcctt gaacgcctct    300

ccattaaagt ttaaattgct tttcgagata cacaacttgt tttgacttc tatttctcta     360

gttttatggt tgctgatgtt agaacagttg gttcctatgg tttatcacaa cggtctattc    420

tggtctatct gctctaagga agccttcgca ccaaaattag ttactcttta ctatttgaac    480

tatttgacca aattcgtaga attgattgac actgtgtttt tagttttgag aagaaagaag    540

ttattgtttt tgcacactta ccatcacggt gccaccgctt tgttgtgcta cactcaatta    600

attggtcgta cttctgttga atgggtagtt atcctactaa acttgggtgt tcacgttatc    660

atgtactggt actacttctt gagttcatgt ggtattagag tttggtggaa gcaatgggtc    720

actagattcc aaattattca atttttgatt gacttggtat ttgtttactt tgctacctat    780

acattctatg ctcacaaata cttggacggt attttaccaa acaagggtac ttgttatggt    840

actcaggctg ctgctgctta tgggtatttg attctaacat cttatttgct tttgtttatt    900

tccttctaca tccaatctta caagaaaggt ggtaaaaaga cagtcaagaa ggaatctgaa    960

gtttccggct ccgttgcatc cggttcttct actggtgtca agacctctaa caccaaggtc   1020
```

```
tcttccagga aagcttaa                                                   1038

<210> SEQ ID NO 28
<211> LENGTH: 345
<212> TYPE: PRT
<213> ORGANISM: Saccharomyces cerevisiae

<400> SEQUENCE: 28

Met Asn Thr Thr Thr Ser Thr Val Ile Ala Ala Val Ala Asp Gln Phe
1               5                   10                  15

Gln Ser Leu Asn Ser Ser Ser Ser Cys Phe Leu Lys Val His Val Pro
            20                  25                  30

Ser Ile Glu Asn Pro Phe Gly Ile Glu Leu Trp Pro Ile Phe Ser Lys
        35                  40                  45

Val Phe Glu Tyr Phe Ser Gly Tyr Pro Ala Glu Gln Phe Glu Phe Ile
    50                  55                  60

His Asn Lys Thr Phe Leu Ala Asn Gly Tyr His Ala Val Ser Ile Ile
65                  70                  75                  80

Ile Val Tyr Tyr Ile Ile Ile Phe Gly Gly Gln Ala Ile Leu Arg Ala
                85                  90                  95

Leu Asn Ala Ser Pro Leu Lys Phe Lys Leu Leu Phe Glu Ile His Asn
            100                 105                 110

Leu Phe Leu Thr Ser Ile Ser Leu Val Leu Trp Leu Leu Met Leu Glu
        115                 120                 125

Gln Leu Val Pro Met Val Tyr His Asn Gly Leu Phe Trp Ser Ile Cys
    130                 135                 140

Ser Lys Glu Ala Phe Ala Pro Lys Leu Val Thr Leu Tyr Tyr Leu Asn
145                 150                 155                 160

Tyr Leu Thr Lys Phe Val Glu Leu Ile Asp Thr Val Phe Leu Val Leu
                165                 170                 175

Arg Arg Lys Lys Leu Leu Phe Leu His Thr Tyr His His Gly Ala Thr
            180                 185                 190

Ala Leu Leu Cys Tyr Thr Gln Leu Ile Gly Arg Thr Ser Val Glu Trp
        195                 200                 205

Val Val Ile Leu Leu Asn Leu Gly Val His Val Ile Met Tyr Trp Tyr
    210                 215                 220

Tyr Phe Leu Ser Ser Cys Gly Ile Arg Val Trp Trp Lys Gln Trp Val
225                 230                 235                 240

Thr Arg Phe Gln Ile Ile Gln Phe Leu Ile Asp Leu Val Phe Val Tyr
                245                 250                 255

Phe Ala Thr Tyr Thr Phe Tyr Ala His Lys Tyr Leu Asp Gly Ile Leu
            260                 265                 270

Pro Asn Lys Gly Thr Cys Tyr Gly Thr Gln Ala Ala Ala Ala Tyr Gly
        275                 280                 285

Tyr Leu Ile Leu Thr Ser Tyr Leu Leu Leu Phe Ile Ser Phe Tyr Ile
    290                 295                 300

Gln Ser Tyr Lys Lys Gly Gly Lys Lys Thr Val Lys Lys Glu Ser Glu
305                 310                 315                 320

Val Ser Gly Ser Val Ala Ser Gly Ser Ser Thr Gly Val Lys Thr Ser
                325                 330                 335

Asn Thr Lys Val Ser Ser Arg Lys Ala
            340                 345

<210> SEQ ID NO 29
```

<211> LENGTH: 1020
<212> TYPE: DNA
<213> ORGANISM: Saccharomyces cerevisiae

<400> SEQUENCE: 29

```
atgccattac ctccgtcaac attgaaccag aaatctaata gagtctactc tgtagctagg     60

gtgtacaaga atgcctgcga ggagagacca caagaatact gggactacga acaaggggtg    120

accatcgatt ggggaaagat ttccaattac gaaattatca acaaaattgg aagagggaaa    180

tattccgaag tgttcagcgg tagatgtatt gtaaacaacc agaagtgtgt tattaaagtt    240

ttaaaaccag ttaaaatgaa aaaaatttat agagagttga aattctgac caatctaaca     300

ggcggcccca atgttgttgg cctttatgat atagtacaag acgctgactc caaaatacct    360

gctttgatct ttgaggaaat caaaaatgtt gatttcagaa ctttatatcc tacattcaaa    420

cttcctgaca tccagtatta tttcacgcaa ttattgattg cgttagacta ctgtcactcc    480

atgggcataa tgcacagaga cgtaaagcct cagaatgtca tgattgatcc tacggaacgt    540

aaactaaggc tgatcgattg gggcctggcg gagttctacc atccaggtgt agattacaac    600

gttcgtgtcg cttcgcgtta ccacaaggga ccagaacttt tagtaaactt gaaccaatat    660

gactactccc tagacttatg gtcagtagga tgcatgctag cagctattgt cttcaaaaaa    720

gaaccttttt tcaaagggtc gtctaatcca gatcaactgg taaagattgc cacagtacta    780

ggaaccaagg aactgttagg ctatttgggt aagtacgggt tgcacttacc atctgaatac    840

gacaacatta tgagagactt tacaaaaaaa tcgtggacac actttataac ctccgagacc    900

aaattagctg ttcctgaagt ggttgattta atcgacaatt tattaaggta tgaccatcaa    960

gaaagattaa cagcaaagga ggctatggat cataagtttt tcaaaacgaa gtttgaataa   1020
```

<210> SEQ ID NO 30
<211> LENGTH: 339
<212> TYPE: PRT
<213> ORGANISM: Saccharomyces cerevisiae

<400> SEQUENCE: 30

```
Met Pro Leu Pro Pro Ser Thr Leu Asn Gln Lys Ser Asn Arg Val Tyr
1               5                   10                  15

Ser Val Ala Arg Val Tyr Lys Asn Ala Cys Glu Glu Arg Pro Gln Glu
            20                  25                  30

Tyr Trp Asp Tyr Glu Gln Gly Val Thr Ile Asp Trp Gly Lys Ile Ser
        35                  40                  45

Asn Tyr Glu Ile Ile Asn Lys Ile Gly Arg Gly Lys Tyr Ser Glu Val
    50                  55                  60

Phe Ser Gly Arg Cys Ile Val Asn Asn Gln Lys Cys Val Ile Lys Val
65                  70                  75                  80

Leu Lys Pro Val Lys Met Lys Lys Ile Tyr Arg Glu Leu Lys Ile Leu
                85                  90                  95

Thr Asn Leu Thr Gly Gly Pro Asn Val Val Gly Leu Tyr Asp Ile Val
            100                 105                 110

Gln Asp Ala Asp Ser Lys Ile Pro Ala Leu Ile Phe Glu Glu Ile Lys
        115                 120                 125

Asn Val Asp Phe Arg Thr Leu Tyr Pro Thr Phe Lys Leu Pro Asp Ile
    130                 135                 140

Gln Tyr Tyr Phe Thr Gln Leu Leu Ile Ala Leu Asp Tyr Cys His Ser
145                 150                 155                 160

Met Gly Ile Met His Arg Asp Val Lys Pro Gln Asn Val Met Ile Asp
```

```
                165                 170                 175

Pro Thr Glu Arg Lys Leu Arg Leu Ile Asp Trp Gly Leu Ala Glu Phe
            180                 185                 190

Tyr His Pro Gly Val Asp Tyr Asn Val Arg Val Ala Ser Arg Tyr His
        195                 200                 205

Lys Gly Pro Glu Leu Leu Val Asn Leu Asn Gln Tyr Asp Tyr Ser Leu
    210                 215                 220

Asp Leu Trp Ser Val Gly Cys Met Leu Ala Ala Ile Val Phe Lys Lys
225                 230                 235                 240

Glu Pro Phe Phe Lys Gly Ser Ser Asn Pro Asp Gln Leu Val Lys Ile
                245                 250                 255

Ala Thr Val Leu Gly Thr Lys Glu Leu Leu Gly Tyr Leu Gly Lys Tyr
            260                 265                 270

Gly Leu His Leu Pro Ser Glu Tyr Asp Asn Ile Met Arg Asp Phe Thr
        275                 280                 285

Lys Lys Ser Trp Thr His Phe Ile Thr Ser Glu Thr Lys Leu Ala Val
    290                 295                 300

Pro Glu Val Val Asp Leu Ile Asp Asn Leu Leu Arg Tyr Asp His Gln
305                 310                 315                 320

Glu Arg Leu Thr Ala Lys Glu Ala Met Asp His Lys Phe Phe Lys Thr
                325                 330                 335

Lys Phe Glu


<210> SEQ ID NO 31
<211> LENGTH: 651
<212> TYPE: DNA
<213> ORGANISM: Saccharomyces cerevisiae

<400> SEQUENCE: 31

atgattgacc gcactaaaaa cgaatctcca gcttttgaag agtctccgct tacccccaat      60

gtgtctaacc tgaaaccatt cccttctcaa agcaacaaaa tatccactcc agtgaccgac     120

cataggagaa gacggtcatc cagcgtaata tcacatgtgg aacaggaaac cttcgaagac     180

gaaaatgacc agcagatgct tcccaacatg aacgctacgt gggtcgacca gcgaggcgcg     240

tggttgattc atatcgtcgt aatagtactc ttgaggctct tctactcctt gttcgggtcg     300

acgcccaaat ggacgtggac tttaacaaac atgacctaca tcatcggatt ctatatcatg     360

ttccaccttg tcaaaggtac gcccttcgac tttaacggtg gtgcgtacga caacctgacc     420

atgtgggagc agattaacga tgagactttg tacacaccca ctagaaaatt tctgctgatt     480

gtacccattg tgttgttcct gattagcaac cagtactacc gcaacgacat gacactattc     540

ctctccaacc tcgccgtgac ggtgcttatt ggtgtcgttc ctaagctggg aattacgcat     600

agactaagaa tatccatccc tggtattacg ggccgtgctc aaattagtta g              651


<210> SEQ ID NO 32
<211> LENGTH: 216
<212> TYPE: PRT
<213> ORGANISM: Saccharomyces cerevisiae

<400> SEQUENCE: 32

Met Ile Asp Arg Thr Lys Asn Glu Ser Pro Ala Phe Glu Glu Ser Pro
1               5                   10                  15

Leu Thr Pro Asn Val Ser Asn Leu Lys Pro Phe Pro Ser Gln Ser Asn
            20                  25                  30

Lys Ile Ser Thr Pro Val Thr Asp His Arg Arg Arg Arg Ser Ser Ser
```

```
        35                  40                  45

Val Ile Ser His Val Glu Gln Glu Thr Phe Glu Asp Glu Asn Asp Gln
    50                  55                  60

Gln Met Leu Pro Asn Met Asn Ala Thr Trp Val Asp Gln Arg Gly Ala
65                  70                  75                  80

Trp Leu Ile His Ile Val Val Ile Val Leu Leu Arg Leu Phe Tyr Ser
                85                  90                  95

Leu Phe Gly Ser Thr Pro Lys Trp Thr Trp Thr Leu Thr Asn Met Thr
            100                 105                 110

Tyr Ile Ile Gly Phe Tyr Ile Met Phe His Leu Val Lys Gly Thr Pro
        115                 120                 125

Phe Asp Phe Asn Gly Gly Ala Tyr Asp Asn Leu Thr Met Trp Glu Gln
    130                 135                 140

Ile Asn Asp Glu Thr Leu Tyr Thr Pro Thr Arg Lys Phe Leu Leu Ile
145                 150                 155                 160

Val Pro Ile Val Leu Phe Leu Ile Ser Asn Gln Tyr Tyr Arg Asn Asp
                165                 170                 175

Met Thr Leu Phe Leu Ser Asn Leu Ala Val Thr Val Leu Ile Gly Val
            180                 185                 190

Val Pro Lys Leu Gly Ile Thr His Arg Leu Arg Ile Ser Ile Pro Gly
        195                 200                 205

Ile Thr Gly Arg Ala Gln Ile Ser
    210                 215
```

<210> SEQ ID NO 33
<211> LENGTH: 1083
<212> TYPE: DNA
<213> ORGANISM: Saccharomyces cerevisiae

<400> SEQUENCE: 33

```
atgtcgatag tctacaataa aacaccatta ttacgtcaat tcttccccgg aaaggcttct      60

gcacaatttt tcttgaaata tgaatgcctt caaccaagtg gctccttcaa aagtagagga     120

atcggtaatc tcatcatgaa aagtgccatt cgaattcaaa aggacggtaa aagatctcct     180

caggttttcg ctagttctgg cggtaatgcc ggttttgctg ctgcaacagc atgtcaaaga     240

ctgtctctac catgtacagt cgtggttcct acagcgacaa agaagagaat ggtagataaa     300

atcaggaaca ccggtgccca ggttatcgtg agtggtgcct actggaaaga agcagatact     360

tttttaaaaa caaatgtcat gaataaaata gactctcagg tcattgagcc catttatgtt     420

catcccttcg ataatccgga tatttgggaa ggacattcat ctatgataga tgaaatagta     480

caagatttga aatcgcaaca tatttccgtg aataaggtta aaggcatagt atgcagcgtt     540

ggtggaggtg gtttatacaa tggtattatt caaggtttgg aaaggtatgg tttagctgat     600

aggatcccta ttgtgggggt ggaaacgaat ggatgtcatg ttttcaatac ttctttgaaa     660

ataggccaac cagttcaatt caagaagata acaagtattg ctacttctct aggaacggcc     720

gtgatctcta atcaaacttt cgaatacgct cgcaaataca acaccagatc cgttgtaata     780

gaggacaaag atgttattga aacctgtctt aaatatacac atcaattcaa tatggtgatt     840

gaaccggcat gtggcgccgc attgcatttg ggttacaaca ctaagatcct agaaaatgca     900

ctgggctcaa aattagctgc ggatgacatt gtgataatta ttgcttgtgg cggctcctct     960

aatactataa aggacttgga agaagcgttg gatagcatga gaaaaaaaga cactcctgta    1020

atagaagtcg ctgacaattt catatttcca gaaaaaaata ttgtgaattt aaaaaagtgct    1080
```

tga 1083

<210> SEQ ID NO 34
<211> LENGTH: 360
<212> TYPE: PRT
<213> ORGANISM: Saccharomyces cerevisiae

<400> SEQUENCE: 34

```
Met Ser Ile Val Tyr Asn Lys Thr Pro Leu Leu Arg Gln Phe Phe Pro
1               5                   10                  15

Gly Lys Ala Ser Ala Gln Phe Phe Leu Lys Tyr Glu Cys Leu Gln Pro
            20                  25                  30

Ser Gly Ser Phe Lys Ser Arg Gly Ile Gly Asn Leu Ile Met Lys Ser
        35                  40                  45

Ala Ile Arg Ile Gln Lys Asp Gly Lys Arg Ser Pro Gln Val Phe Ala
    50                  55                  60

Ser Ser Gly Gly Asn Ala Gly Phe Ala Ala Ala Thr Ala Cys Gln Arg
65                  70                  75                  80

Leu Ser Leu Pro Cys Thr Val Val Val Pro Thr Ala Thr Lys Lys Arg
                85                  90                  95

Met Val Asp Lys Ile Arg Asn Thr Gly Ala Gln Val Ile Val Ser Gly
            100                 105                 110

Ala Tyr Trp Lys Glu Ala Asp Thr Phe Leu Lys Thr Asn Val Met Asn
        115                 120                 125

Lys Ile Asp Ser Gln Val Ile Glu Pro Ile Tyr Val His Pro Phe Asp
    130                 135                 140

Asn Pro Asp Ile Trp Glu Gly His Ser Ser Met Ile Asp Glu Ile Val
145                 150                 155                 160

Gln Asp Leu Lys Ser Gln His Ile Ser Val Asn Lys Val Lys Gly Ile
                165                 170                 175

Val Cys Ser Val Gly Gly Gly Gly Leu Tyr Asn Gly Ile Ile Gln Gly
            180                 185                 190

Leu Glu Arg Tyr Gly Leu Ala Asp Arg Ile Pro Ile Val Gly Val Glu
        195                 200                 205

Thr Asn Gly Cys His Val Phe Asn Thr Ser Leu Lys Ile Gly Gln Pro
    210                 215                 220

Val Gln Phe Lys Lys Ile Thr Ser Ile Ala Thr Ser Leu Gly Thr Ala
225                 230                 235                 240

Val Ile Ser Asn Gln Thr Phe Glu Tyr Ala Arg Lys Tyr Asn Thr Arg
                245                 250                 255

Ser Val Val Ile Glu Asp Lys Asp Val Ile Glu Thr Cys Leu Lys Tyr
            260                 265                 270

Thr His Gln Phe Asn Met Val Ile Glu Pro Ala Cys Gly Ala Ala Leu
        275                 280                 285

His Leu Gly Tyr Asn Thr Lys Ile Leu Glu Asn Ala Leu Gly Ser Lys
    290                 295                 300

Leu Ala Ala Asp Asp Ile Val Ile Ile Ile Ala Cys Gly Gly Ser Ser
305                 310                 315                 320

Asn Thr Ile Lys Asp Leu Glu Glu Ala Leu Asp Ser Met Arg Lys Lys
                325                 330                 335

Asp Thr Pro Val Ile Glu Val Ala Asp Asn Phe Ile Phe Pro Glu Lys
            340                 345                 350

Asn Ile Val Asn Leu Lys Ser Ala
        355                 360
```

<210> SEQ ID NO 35
<211> LENGTH: 951
<212> TYPE: DNA
<213> ORGANISM: Saccharomyces cerevisiae

<400> SEQUENCE: 35

```
atgggaatat ttcgttggaa ctatccagag agttctgtcc ccggcgtttg gggagaaaca     60

acttccacta ttgactggtg tgaggagaac tatgtcgttt ctccctatat tgccgagtgg    120

tcaaacactt taactaacag cgtattcata ctgtcagcga tttacacaac ttactctgct    180

tacaagaata aattagaaaa aaggttttta cttattggct tcgggtacgg tttggtcgga    240

gtaggatcat ggctatttca tatgacactg aagtatagat tccaactatt ggatgaactt    300

ccaatgatat acgccatgtg cattccgaca tggagtttag tatgcgaggc caaagaggca    360

ttacttaacg gagataatca caagaaggtt cctctatttg aacagatatt catcggcgta    420

attatcggcc tggccgttac aacagcaagc atactctacg ttatttacaa aaatgtcgat    480

atccatcaaa ttttgtttgg cgtacagatt gtagttgtgg ctgctactgc aggaagtttg    540

acgtacagat acgtccatga tccacttgcc aaaagaaatc tcaaggcttc aatggcgctc    600

ggcgcaattt tgttcttatc tggctacatt tcgtggctac ttgatataca ctattgttcg    660

ttctgggtgc acgttagaag aagtattttg gctttaccac ttggtgtact gcttgaacca    720

cacggatggt ggcatatatt aactggtatg ggatttatt tctacattgt ttctttggaa    780

catttaaggg tcattacgct caacgtcagc tgcaattacc agttcatctg gagatggaaa    840

gtcttccctg aactgatatg gaaagggcgc aaaccctcaa caagatattc acttgaacta    900

tttggcccat acgtagaaga tcaatcaatt gaagttaaaa aggagaagta a             951
```

<210> SEQ ID NO 36
<211> LENGTH: 316
<212> TYPE: PRT
<213> ORGANISM: Saccharomyces cerevisiae

<400> SEQUENCE: 36

```
Met Gly Ile Phe Arg Trp Asn Tyr Pro Glu Ser Ser Val Pro Gly Val
1               5                   10                  15

Trp Gly Glu Thr Thr Ser Thr Ile Asp Trp Cys Glu Glu Asn Tyr Val
            20                  25                  30

Val Ser Pro Tyr Ile Ala Glu Trp Ser Asn Thr Leu Thr Asn Ser Val
        35                  40                  45

Phe Ile Leu Ser Ala Ile Tyr Thr Thr Tyr Ser Ala Tyr Lys Asn Lys
    50                  55                  60

Leu Glu Lys Arg Phe Leu Leu Ile Gly Phe Gly Tyr Gly Leu Val Gly
65                  70                  75                  80

Val Gly Ser Trp Leu Phe His Met Thr Leu Lys Tyr Arg Phe Gln Leu
                85                  90                  95

Leu Asp Glu Leu Pro Met Ile Tyr Ala Met Cys Ile Pro Thr Trp Ser
            100                 105                 110

Leu Val Cys Glu Ala Lys Glu Ala Leu Leu Asn Gly Asp Asn His Lys
        115                 120                 125

Lys Val Pro Leu Phe Glu Gln Ile Phe Ile Gly Val Ile Ile Gly Leu
    130                 135                 140

Ala Val Thr Thr Ala Ser Ile Leu Tyr Val Ile Tyr Lys Asn Val Asp
145                 150                 155                 160

Ile His Gln Ile Leu Phe Gly Val Gln Ile Val Val Val Ala Ala Thr
```

```
                165                 170                 175

Ala Gly Ser Leu Thr Tyr Arg Tyr Val His Asp Pro Leu Ala Lys Arg
            180                 185                 190

Asn Leu Lys Ala Ser Met Ala Leu Gly Ala Ile Leu Phe Leu Ser Gly
        195                 200                 205

Tyr Ile Ser Trp Leu Leu Asp Ile His Tyr Cys Ser Phe Trp Val His
    210                 215                 220

Val Arg Arg Ser Ile Leu Ala Leu Pro Leu Gly Val Leu Leu Glu Pro
225                 230                 235                 240

His Gly Trp Trp His Ile Leu Thr Gly Met Gly Ile Tyr Phe Tyr Ile
                245                 250                 255

Val Ser Leu Glu His Leu Arg Val Ile Thr Leu Asn Val Ser Cys Asn
            260                 265                 270

Tyr Gln Phe Ile Trp Arg Trp Lys Val Phe Pro Glu Leu Ile Trp Lys
        275                 280                 285

Gly Arg Lys Pro Ser Thr Arg Tyr Ser Leu Glu Leu Phe Gly Pro Tyr
    290                 295                 300

Val Glu Asp Gln Ser Ile Glu Val Lys Lys Glu Lys
305                 310                 315
```

```
<210> SEQ ID NO 37
<211> LENGTH: 978
<212> TYPE: DNA
<213> ORGANISM: Pichia ciferrii

<400> SEQUENCE: 37

atgtcctccc atcaattctt gatcaatcaa actactttgg ctgctccacc agttcatttg      60

gttgaaaaac catctttgat caacggtatc ccagataaca ttttggcttt gattgctcca     120

gttatcgcct actattctta ctctggtttc ttctacgtta tcgacacctt ggaaattgcc     180

gaattataca gaattcaccc accagaagaa gtctccagta gaaacaaagc tactaagttc     240

gatgttttga aggacgttgt cttgcaacac ttcatccaat ctgttgttgg ttacatcttc     300

acctacttcg acccaattca atacactggt gatgaagaat atcaagcctg gaagttgcaa     360

caaactttgc catttttgcc tttcgatgtt gcttactact ggaatatgta tggttggtcc     420

tgtttgaaga ttggtttggc cttcttgatt atcgactctt ggcaatattg gttgcacaga     480

atcatgcatt tgaacaagac cttgtacaaa agattccact ccagacacca cagattatat     540

gttccatatg cttttggtgc cttgtataac gatccattcg aaggtttttt gttggatact     600

ttgggtactg gtattgctgc tatcgttact caattgactc caagagaatc cattgtcttg     660

tacactttct ctaccttgaa aaccgttgat gatcattgcg gttattcctt gccatatgat     720

ccattccaaa tcttgttccc aaacaactcc atctaccatg atatccatca tcaacaattc     780

ggtatcaaga ccaacttctc tcaaccattt ttcacccatt gggacgtttt ctctaacacc     840

agatacaaag aaatcgacga atacagagaa aagcaaaagg ctattaccat tgccaagtac     900

aaagaatttt tacacgacag agaaatcgcc aagcaaaaga agaaagctga aatctacaag     960

gacaaaaaga ctgattaa                                                   978

<210> SEQ ID NO 38
<211> LENGTH: 325
<212> TYPE: PRT
<213> ORGANISM: Pichia ciferrii

<400> SEQUENCE: 38
```

```
Met Ser Ser His Gln Phe Leu Ile Asn Gln Thr Thr Leu Ala Ala Pro
1               5                   10                  15

Pro Val His Leu Val Glu Lys Pro Ser Leu Ile Asn Gly Ile Pro Asp
            20                  25                  30

Asn Ile Leu Ala Leu Ile Ala Pro Val Ile Ala Tyr Tyr Ser Tyr Ser
        35                  40                  45

Gly Phe Phe Tyr Val Ile Asp Thr Leu Glu Ile Ala Glu Leu Tyr Arg
    50                  55                  60

Ile His Pro Pro Glu Glu Val Ser Ser Arg Asn Lys Ala Thr Lys Phe
65                  70                  75                  80

Asp Val Leu Lys Asp Val Val Leu Gln His Phe Ile Gln Ser Val Val
                85                  90                  95

Gly Tyr Ile Phe Thr Tyr Phe Asp Pro Ile Gln Tyr Thr Gly Asp Glu
            100                 105                 110

Glu Tyr Gln Ala Trp Lys Leu Gln Gln Thr Leu Pro Phe Leu Pro Phe
        115                 120                 125

Asp Val Ala Tyr Tyr Trp Asn Met Tyr Gly Trp Ser Cys Leu Lys Ile
    130                 135                 140

Gly Leu Ala Phe Leu Ile Ile Asp Ser Trp Gln Tyr Trp Leu His Arg
145                 150                 155                 160

Ile Met His Leu Asn Lys Thr Leu Tyr Lys Arg Phe His Ser Arg His
                165                 170                 175

His Arg Leu Tyr Val Pro Tyr Ala Phe Gly Ala Leu Tyr Asn Asp Pro
            180                 185                 190

Phe Glu Gly Phe Leu Leu Asp Thr Leu Gly Thr Gly Ile Ala Ala Ile
        195                 200                 205

Val Thr Gln Leu Thr Pro Arg Glu Ser Ile Val Leu Tyr Thr Phe Ser
    210                 215                 220

Thr Leu Lys Thr Val Asp Asp His Cys Gly Tyr Ser Leu Pro Tyr Asp
225                 230                 235                 240

Pro Phe Gln Ile Leu Phe Pro Asn Asn Ser Ile Tyr His Asp Ile His
                245                 250                 255

His Gln Gln Phe Gly Ile Lys Thr Asn Phe Ser Gln Pro Phe Phe Thr
            260                 265                 270

His Trp Asp Val Phe Ser Asn Thr Arg Tyr Lys Glu Ile Asp Glu Tyr
        275                 280                 285

Arg Glu Lys Gln Lys Ala Ile Thr Ile Ala Lys Tyr Lys Glu Phe Leu
    290                 295                 300

His Asp Arg Glu Ile Ala Lys Gln Lys Lys Lys Ala Glu Ile Tyr Lys
305                 310                 315                 320

Asp Lys Lys Thr Asp
                325
```

<210> SEQ ID NO 39
<211> LENGTH: 1322
<212> TYPE: DNA
<213> ORGANISM: Pichia ciferrii

<400> SEQUENCE: 39

```
atggtggctg gaccaaacaa agatcttgaa aacctggaac gtatgatgta ctggaagacc      60

actttgaaag cttggtcatg tttccttgtt ggtgctaaat taaacgaaaa attagaaaca     120

gatgatattt taaaaggtat ccacaaatta ttcacgttga gggttcagtt acgtttgaat     180

gttttccaat atcctaaaaa aaggtttgtt accgaagaga taaatggttg gtctgatgat     240
```

```
tttgttgatt ttgtcgatta tccaactgat gattttgata ttattgaagc ttttaaacaa    300

caacataatc aatattttga attgggtgtt caaaagcctt tatggaaatt ggttgtattg    360

aaccatcaat atttagttat tctttgtgat cataccttat atgatgggaa cactgcactt    420

tatatatgtg aggatttgat cacaatattg aatgatcgtg atatcccagt tgatagaatt    480

ccagatatta aaccatatca tgatctatta aaaccaaaac ttggacatac aatcaaaact    540

gtcatccaaa cttttgcacc aaaatgggct tatcctttag ttaatctgat ttatagacca    600

aaaagtgaat ttgaaactgg tgcatatgat gattggggag taactcataa aattgaaaga    660

acaacaaata aattaaagca cttaattaca ataactaatg aagaattttc cataattaaa    720

aaattaacaa aatcacatgg tgtaaatttc acagcatttt gggcatatat caatgttctt    780

gcagttgcac aattgggaaa gtcagctgtt gatttatcaa ttccattcaa tatgagaacc    840

aatttattac caccagaata tttaagatgg tatggtttat tagtttcaca tgttacttta    900

aatgtacata ccaaagttga tcatgattca attgactggg attttgttag atttttaaat    960

ggtagtgttg cacataaata ccaagtaaaa caatcacaaa tgcttggaat gattaaatat   1020

gttagtgctc gtggacttat tgaatcagct ttaaaatcac caagaaaagg tggattagaa   1080

gtttcaaact tgggattgag agtcgatcca gatggtgaat catggaaaaa atatacccct   1140

gaagaatttt tcttttcttt gccaaatgat ctttcaggtt ataatgtttc aaatgctgtg   1200

atttcaagta aaactaaaac aaatattatt ttagacggtg ttccagaatt tgcaaatgaa   1260

tttccaacgt atgcaaataa cgttgaaaca attttgagaa atgcaatcaa tgggtattat   1320

ga                                                                  1322
```

<210> SEQ ID NO 40
<211> LENGTH: 1326
<212> TYPE: DNA
<213> ORGANISM: Pichia ciferrii

<400> SEQUENCE: 40

```
atggttgctg gtccaaacaa ggatttggaa aacttggaaa gaatgatgta ctggaaaacc     60

actttgaagg cttggtcttg ttttttggtt ggtgctaagt tgaacgaaaa gttggaaacc    120

gatgatatct tgaagggtat ccataagttg ttcaccttga gagtccaatt gagattgaac    180

gttttccaat acccaaagaa gagattcgtc accgaagaaa tcaatggttg gtctgatgat    240

ttcgttgact tcgttgatta cccaactgat gacttcgata tcattgaagc ctttaagcaa    300

caacacaatc aatacttcga attgggtgtc caaaaaccat tgtggaagtt ggttgttttg    360

aaccaccaat acttggttat cttgtgcgat cataccttgt acgatggtaa tactgccttg    420

tacatttgcg aagatttgat caccatcttg aacgatagag atatcccagt tgatagaatc    480

ccagatatca agccatacca cgatttgttg aaacctaaat tgggtcatac catcaagacc    540

gttattcaaa cttttgctcc aaaatgggct tacccattgg ttaacttgat ctacagacca    600

aagtctgaat tcgaaactgg tgcttatgat gattggggtg ttacccataa gattgaaaga    660

actaccaaca agttgaagca cttgattacc atcaccaacg aagaattctc catcatcaaa    720

aagttgacca agtcccatgg tgttaacttt actgcttttt gggcctacat taacgttttg    780

gctgttgctc aattgggtaa atctgctgtt gatttgtcca tcccattcaa catgagaact    840

aatttgttgc caccagaata cttgagatgg tacggtttgt tggtttccca tgttactttg    900

aatgttcaca ccaaggttga tcacgattcc attgattggg atttcgtcag atttttgaac    960

ggttcagttg cccataagta ccaagttaag caatctcaaa tgttgggtat gatcaagtac   1020
```

gtttctgcca gaggtttgat tgaatctgct ttgaaatctc caagaaaggg tggtttggaa 1080
gtttctaatt tgggtttgag agttgatcca gatggtgaat cttggaaaaa gtacactcca 1140
gaagaatttt tcttctcctt gccaaacgat ttgtccggtt acaatgtttc caacgccgtt 1200
atttcttcta agaccaagac caacattatc ttggatggtg ttccagaatt tgccaacgaa 1260
tttccaacat acgctaacaa cgttgaaacc attttgagaa acgccatcaa cggttactac 1320
gaatga 1326

<210> SEQ ID NO 41
<211> LENGTH: 441
<212> TYPE: PRT
<213> ORGANISM: Pichia ciferrii

<400> SEQUENCE: 41

Met Val Ala Gly Pro Asn Lys Asp Leu Glu Asn Leu Glu Arg Met Met
1 5 10 15

Tyr Trp Lys Thr Thr Leu Lys Ala Trp Ser Cys Phe Leu Val Gly Ala
20 25 30

Lys Leu Asn Glu Lys Leu Glu Thr Asp Asp Ile Leu Lys Gly Ile His
35 40 45

Lys Leu Phe Thr Leu Arg Val Gln Leu Arg Leu Asn Val Phe Gln Tyr
50 55 60

Pro Lys Lys Arg Phe Val Thr Glu Glu Ile Asn Gly Trp Ser Asp Asp
65 70 75 80

Phe Val Asp Phe Val Asp Tyr Pro Thr Asp Asp Phe Asp Ile Ile Glu
85 90 95

Ala Phe Lys Gln Gln His Asn Gln Tyr Phe Glu Leu Gly Val Gln Lys
100 105 110

Pro Leu Trp Lys Leu Val Val Leu Asn His Gln Tyr Leu Val Ile Leu
115 120 125

Cys Asp His Thr Leu Tyr Asp Gly Asn Thr Ala Leu Tyr Ile Cys Glu
130 135 140

Asp Leu Ile Thr Ile Leu Asn Asp Arg Asp Ile Pro Val Asp Arg Ile
145 150 155 160

Pro Asp Ile Lys Pro Tyr His Asp Leu Leu Lys Pro Lys Leu Gly His
165 170 175

Thr Ile Lys Thr Val Ile Gln Thr Phe Ala Pro Lys Trp Ala Tyr Pro
180 185 190

Leu Val Asn Leu Ile Tyr Arg Pro Lys Ser Glu Phe Glu Thr Gly Ala
195 200 205

Tyr Asp Asp Trp Gly Val Thr His Lys Ile Glu Arg Thr Thr Asn Lys
210 215 220

Leu Lys His Leu Ile Thr Ile Thr Asn Glu Glu Phe Ser Ile Ile Lys
225 230 235 240

Lys Leu Thr Lys Ser His Gly Val Asn Phe Thr Ala Phe Trp Ala Tyr
245 250 255

Ile Asn Val Leu Ala Val Ala Gln Leu Gly Lys Ser Ala Val Asp Leu
260 265 270

Ser Ile Pro Phe Asn Met Arg Thr Asn Leu Leu Pro Pro Glu Tyr Leu
275 280 285

Arg Trp Tyr Gly Leu Leu Val Ser His Val Thr Leu Asn Val His Thr
290 295 300

Lys Val Asp His Asp Ser Ile Asp Trp Asp Phe Val Arg Phe Leu Asn

```
305                 310                 315                 320

Gly Ser Val Ala His Lys Tyr Gln Val Lys Gln Ser Gln Met Leu Gly
                325                 330                 335

Met Ile Lys Tyr Val Ser Ala Arg Gly Leu Ile Glu Ser Ala Leu Lys
            340                 345                 350

Ser Pro Arg Lys Gly Gly Leu Glu Val Ser Asn Leu Gly Leu Arg Val
        355                 360                 365

Asp Pro Asp Gly Glu Ser Trp Lys Lys Tyr Thr Pro Glu Glu Phe Phe
    370                 375                 380

Phe Ser Leu Pro Asn Asp Leu Ser Gly Tyr Asn Val Ser Asn Ala Val
385                 390                 395                 400

Ile Ser Ser Lys Thr Lys Thr Asn Ile Ile Leu Asp Gly Val Pro Glu
                405                 410                 415

Phe Ala Asn Glu Phe Pro Thr Tyr Ala Asn Asn Val Glu Thr Ile Leu
            420                 425                 430

Arg Asn Ala Ile Asn Gly Tyr Tyr Glu
        435                 440


<210> SEQ ID NO 42
<211> LENGTH: 1431
<212> TYPE: DNA
<213> ORGANISM: Pichia ciferrii

<400> SEQUENCE: 42

atgtcattta aatatatcaa tcaaaatgat tcaaaatcat tatcaaattt aaaatataaa     60

ttatcaaaaa atcatgcaag acaaatgggt tttttagaag atttttttgc aattttacaa    120

cgtcaaaaaa tgtataaatc atttttcgtt atgtgtaaat ataatgaaaa aattgatgat    180

tttaaaattt tattccattc attaagatta ttaatattaa aattcccaat attagcttcc    240

acaataatta ctcaaaatgt tccaattaat ataaaacctc gtccttatga ttatattcaa    300

attattgatg aaataaaatt taatgatttg gtttgggatt taagacctga atattcaaat    360

ttattacaag aagatttatt aaataaatta aatgatttaa ttataccata tgaagataat    420

aaattagttt ggagattagg aatcttggat gattatacat taatttttat aacaaatcat    480

gttttacatg atggaatatc tggtaaaaat atttttaatg aattatcatt aatttttaat    540

caattggact tggattcttt aagtgatgat gatgatatcg tgttcaatta ttcacaagat    600

catttgaatt taggtgaatt accaaaacct ataactgatc ttatgaatca tattccatca    660

attaaatctt taccaagata tatttataat tcattaattg aaccaaaact tttttgttca    720

tcaactttaa ttcaaggtca tcttaagaat attcattata gagttaatat aaatccaatg    780

gaattattaa aaattaaatc attattatca aaaaatagtt tcaataatgt taaattaact    840

ttaacacctt tcattcaatc tatttggaat tatactttat atcaagatga atattataaa    900

tcatcaaaat ctttattagg tattgcagtg gattctcgtc aatttattaa taaagatgaa    960

caagatttat ataaatttgg tttaaatgta tcaggtttta gtaaaatttc caaaccaatg   1020

aaattaatta catggaataa aattaatcaa attaatcaag atttaaaaat ttcattaaaa   1080

ttgaaaaaac ctttatattc aatgggtata ttaggttggg ataaaatgat taaaaataaa   1140

catttagatg ttgatttacc aaaaattatg aataaaagaa caggttcaac tttttcaaat   1200

attggtataa tcctaaataa cagtgaatca aatgataaat ttcaaattat tgatgcaatg   1260

tttacacaac attttaatgt tcatttttat gatttctcaa tcactgcaat ttctacaatg   1320

actggtgggt taaatattat aattacatca ccagaatcta ttggaattga aaatttagaa   1380
```

```
agaatttgta aaaaatttca tgaaaattta gttttatgtg atattaaata a            1431


<210> SEQ ID NO 43
<211> LENGTH: 1431
<212> TYPE: DNA
<213> ORGANISM: Pichia ciferrii

<400> SEQUENCE: 43

atgtccttca agtacatcaa tcaaaacgac tccaagtcct tgtccaactt gaagtacaag      60

ttgtctaaga accatgccag acaaatgggt ttcttggaag attttttcgc catcttgcaa     120

agacaaaaga tgtacaagtc cttcttcgtc atgtgcaaat acaacgaaaa gatcgacgac     180

ttcaagattt tgttccactc cttgagatta ttgattttga agttcccaat cttggcctcc     240

accattatta ctcaaaatgt cccaatcaac atcaagccaa gaccatacga ttacatccaa     300

atcatcgacg aaatcaagtt caacgatttg gtctgggact taagaccaga atactctaac     360

ttgttgcaag aagatttgtt gaacaagttg aacgacttga tcatcccata cgaagataac     420

aagttggttt ggagattggg tatcttggat gactacacct tgattttcat taccaaccat     480

gtcttgcacg atggtatttc tggtaagaac atcttcaacg aattgtcctt gatcttcaat     540

caattggact tggactcctt gtccgatgat gatgatatcg ttttcaacta ctcccaagac     600

cacttgaatt tgggtgaatt gccaaagcca attaccgatt tgatgaacca tatcccatcc     660

atcaaatcct tgccaagata tatctacaac tccttgatcg aacctaagtt gttctgttcc     720

tctactttga tccaaggtca cttgaagaac atccactaca gagttaacat caacccaatg     780

gaattattga agattaagtc tttgttgtcc aagaactcct tcaacaacgt taagttgact     840

ttgaccccat tcatccaatc catttggaat tacaccttgt accaagacga atattacaag     900

tcatctaaat ctttgttggg tatcgccgtt gactctagac aattcattaa caaggatgaa     960

caagacttgt ataagttcgg tttgaacgtc agtggtttct ccaaaatttc taagccaatg    1020

aagttgatca cctggaacaa gatcaaccaa atcaatcaag acttgaaaat ctctttgaag    1080

ttgaaaaagc cattatactc catgggtatt ttgggttggg acaagatgat taagaacaag    1140

cacttggatg ttgacttgcc aaagatcatg aacaaaagaa ctggttccac cttctccaac    1200

attggtatta tcttgaacaa ctccgaatcc aacgacaagt tccaaattat tgatgccatg    1260

ttcacccaac acttcaacgt tcatttttac gacttctcca ttaccgccat ttctactatg    1320

actggtggtt tgaacattat catcacctcc ccagaatcta tcggtatcga aaatttggaa    1380

agaatctgca agaagttcca cgaaaacttg gttttgtgcg acatcaagtg a            1431


<210> SEQ ID NO 44
<211> LENGTH: 476
<212> TYPE: PRT
<213> ORGANISM: Pichia ciferrii

<400> SEQUENCE: 44

Met Ser Phe Lys Tyr Ile Asn Gln Asn Asp Ser Lys Ser Leu Ser Asn
1               5                   10                  15

Leu Lys Tyr Lys Leu Ser Lys Asn His Ala Arg Gln Met Gly Phe Leu
            20                  25                  30

Glu Asp Phe Phe Ala Ile Leu Gln Arg Gln Lys Met Tyr Lys Ser Phe
        35                  40                  45

Phe Val Met Cys Lys Tyr Asn Glu Lys Ile Asp Asp Phe Lys Ile Leu
    50                  55                  60
```

```
Phe His Ser Leu Arg Leu Leu Ile Leu Lys Phe Pro Ile Leu Ala Ser
65                  70                  75                  80

Thr Ile Ile Thr Gln Asn Val Pro Ile Asn Ile Lys Pro Arg Pro Tyr
                85                  90                  95

Asp Tyr Ile Gln Ile Ile Asp Glu Ile Lys Phe Asn Asp Leu Val Trp
            100                 105                 110

Asp Leu Arg Pro Glu Tyr Ser Asn Leu Leu Gln Glu Asp Leu Leu Asn
        115                 120                 125

Lys Leu Asn Asp Leu Ile Ile Pro Tyr Glu Asp Asn Lys Leu Val Trp
    130                 135                 140

Arg Leu Gly Ile Leu Asp Asp Tyr Thr Leu Ile Phe Ile Thr Asn His
145                 150                 155                 160

Val Leu His Asp Gly Ile Ser Gly Lys Asn Ile Phe Asn Glu Leu Ser
                165                 170                 175

Leu Ile Phe Asn Gln Leu Asp Leu Asp Ser Leu Ser Asp Asp Asp Asp
            180                 185                 190

Ile Val Phe Asn Tyr Ser Gln Asp His Leu Asn Leu Gly Glu Leu Pro
        195                 200                 205

Lys Pro Ile Thr Asp Leu Met Asn His Ile Pro Ser Ile Lys Ser Leu
    210                 215                 220

Pro Arg Tyr Ile Tyr Asn Ser Leu Ile Glu Pro Lys Leu Phe Cys Ser
225                 230                 235                 240

Ser Thr Leu Ile Gln Gly His Leu Lys Asn Ile His Tyr Arg Val Asn
                245                 250                 255

Ile Asn Pro Met Glu Leu Leu Lys Ile Lys Ser Leu Leu Ser Lys Asn
            260                 265                 270

Ser Phe Asn Asn Val Lys Leu Thr Leu Thr Pro Phe Ile Gln Ser Ile
        275                 280                 285

Trp Asn Tyr Thr Leu Tyr Gln Asp Glu Tyr Tyr Lys Ser Ser Lys Ser
    290                 295                 300

Leu Leu Gly Ile Ala Val Asp Ser Arg Gln Phe Ile Asn Lys Asp Glu
305                 310                 315                 320

Gln Asp Leu Tyr Lys Phe Gly Leu Asn Val Ser Gly Phe Ser Lys Ile
                325                 330                 335

Ser Lys Pro Met Lys Leu Ile Thr Trp Asn Lys Ile Asn Gln Ile Asn
            340                 345                 350

Gln Asp Leu Lys Ile Ser Leu Lys Leu Lys Lys Pro Leu Tyr Ser Met
        355                 360                 365

Gly Ile Leu Gly Trp Asp Lys Met Ile Lys Asn Lys His Leu Asp Val
    370                 375                 380

Asp Leu Pro Lys Ile Met Asn Lys Arg Thr Gly Ser Thr Phe Ser Asn
385                 390                 395                 400

Ile Gly Ile Ile Leu Asn Asn Ser Glu Ser Asn Asp Lys Phe Gln Ile
                405                 410                 415

Ile Asp Ala Met Phe Thr Gln His Phe Asn Val His Phe Tyr Asp Phe
            420                 425                 430

Ser Ile Thr Ala Ile Ser Thr Met Thr Gly Gly Leu Asn Ile Ile Ile
        435                 440                 445

Thr Ser Pro Glu Ser Ile Gly Ile Glu Asn Leu Glu Arg Ile Cys Lys
    450                 455                 460

Lys Phe His Glu Asn Leu Val Leu Cys Asp Ile Lys
465                 470                 475
```

<210> SEQ ID NO 45
<211> LENGTH: 65
<212> TYPE: DNA
<213> ORGANISM: Artificial Sequence
<220> FEATURE:
<223> OTHER INFORMATION: primer

<400> SEQUENCE: 45
aagtctagca gcgaaaagta cgcgaagaat ctactataga taatgccagc tgaagcttcg 60
tacgc 65

<210> SEQ ID NO 46
<211> LENGTH: 67
<212> TYPE: DNA
<213> ORGANISM: Artificial Sequence
<220> FEATURE:
<223> OTHER INFORMATION: primer

<400> SEQUENCE: 46
ttttacaaaa aaatcatttt tgaaggaaaa tataacgtta atctagcata ggccactagt 60
ggatctg 67

<210> SEQ ID NO 47
<211> LENGTH: 65
<212> TYPE: DNA
<213> ORGANISM: Artificial Sequence
<220> FEATURE:
<223> OTHER INFORMATION: primer

<400> SEQUENCE: 47
aaaccacaaa tagtgtaaga tttaaacagt aagccaaaag agatgccagc tgaagcttcg 60
tacgc 65

<210> SEQ ID NO 48
<211> LENGTH: 67
<212> TYPE: DNA
<213> ORGANISM: Artificial Sequence
<220> FEATURE:
<223> OTHER INFORMATION: primer

<400> SEQUENCE: 48
ttgattaatt gttcagtacg aaggaaaaga ttaagtaaag tgtcagcata ggccactagt 60
ggatctg 67

<210> SEQ ID NO 49
<211> LENGTH: 65
<212> TYPE: DNA
<213> ORGANISM: Artificial Sequence
<220> FEATURE:
<223> OTHER INFORMATION: primer

<400> SEQUENCE: 49
taaataaaag cagaaatctt tatttaagaa aatagaagat tgatgccagc tgaagcttcg 60
tacgc 65

<210> SEQ ID NO 50
<211> LENGTH: 67
<212> TYPE: DNA
<213> ORGANISM: Artificial Sequence
<220> FEATURE:
<223> OTHER INFORMATION: primer

<400> SEQUENCE: 50
aaatatgcct atacattatg aatatatatt atgctataat tattagcata ggccactagt 60
ggatctg 67

<210> SEQ ID NO 51
<211> LENGTH: 65
<212> TYPE: DNA
<213> ORGANISM: Artificial Sequence
<220> FEATURE:
<223> OTHER INFORMATION: primer

<400> SEQUENCE: 51
taagtgctgg atagacaaga gacaggaaaa ttaaccagcg agatgccagc tgaagcttcg 60
tacgc 65

<210> SEQ ID NO 52
<211> LENGTH: 67
<212> TYPE: DNA
<213> ORGANISM: Artificial Sequence
<220> FEATURE:
<223> OTHER INFORMATION: primer

<400> SEQUENCE: 52
tcaagggcaa attgatgctt caacgaaaaa gttattggat tttcagcata ggccactagt 60
ggatctg 67

<210> SEQ ID NO 53
<211> LENGTH: 65
<212> TYPE: DNA
<213> ORGANISM: Artificial Sequence
<220> FEATURE:
<223> OTHER INFORMATION: primer

<400> SEQUENCE: 53
aagactatac cattataaaa acgcataaga aacagtttca tcatgccagc tgaagcttcg 60
tacgc 65

<210> SEQ ID NO 54
<211> LENGTH: 67
<212> TYPE: DNA
<213> ORGANISM: Artificial Sequence
<220> FEATURE:
<223> OTHER INFORMATION: primer

<400> SEQUENCE: 54
atatatatat atatatacat atatgcgtat aggcagagcc aactagcata ggccactagt 60
ggatctg 67

<210> SEQ ID NO 55
<211> LENGTH: 68
<212> TYPE: DNA
<213> ORGANISM: Artificial Sequence
<220> FEATURE:
<223> OTHER INFORMATION: primer

<400> SEQUENCE: 55
aaatagaagg aacaataaac ctaaaagaat agaagaaaca gaatgccagc tgaagcttcg 60
tacgctgc 68

<210> SEQ ID NO 56
<211> LENGTH: 69
<212> TYPE: DNA
<213> ORGANISM: Artificial Sequence
<220> FEATURE:
<223> OTHER INFORMATION: primer

<400> SEQUENCE: 56

```
tggtggaaaa agaattgcct tgctaagagt attgttgtcc aattaccgca taggccacta     60

gtggatctg                                                             69
```

<210> SEQ ID NO 57
<211> LENGTH: 4228
<212> TYPE: DNA
<213> ORGANISM: Artificial Sequence
<220> FEATURE:
<223> OTHER INFORMATION: plasmid

<400> SEQUENCE: 57

```
gaacgcggcc gccagctgaa gcttcgtacg ctgcaggtcg acaaccctta atataacttc     60

gtataatgta tgctatacga agttattagg tctagagatc tgtttagctt gccttgtccc    120

cgccgggtca cccggccagc gacatggagg cccagaatac cctccttgac agtcttgacg    180

tgcgcagctc aggggcatga tgtgactgtc gcccgtacat ttagcccata catccccatg    240

tataatcatt tgcatccata cattttgatg gccgcacggc gcgaagcaaa aattacggct    300

cctcgctgca gacctgcgag cagggaaacg ctcccctcac agacgcgttg aattgtcccc    360

acgccgcgcc cctgtagaga aatataaaag gttaggattt gccactgagg ttcttctttc    420

atatacttcc ttttaaaatc ttgctaggat acagttctca catcacatcc gaacataaac    480

aaccatgggt aaaaagcctg aactcaccgc gacgtctgtc gagaagtttc tgatcgaaaa    540

gttcgacagc gtctccgacc tgatgcagct ctcggagggc gaagaatctc gtgctttcag    600

cttcgatgta ggagggcgtg gatatgtcct gcgggtaaat agctgcgccg atggtttcta    660

caaagatcgt tatgtttatc ggcactttgc atcggccgcg ctcccgattc cggaagtgct    720

tgacattggg gaattcagcg agagcctgac ctattgcatc tcccgccgtg cacagggtgt    780

cacgttgcaa gacctgcctg aaaccgaact gcccgctgtt ctgcagccgg tcgcggaggc    840

catggatgcg atcgctgcgg ccgatcttag ccagacgagc gggttcggcc cattcggacc    900

gcaaggaatc ggtcaataca ctacatggcg tgatttcata tgcgcgattg ctgatcccca    960

tgtgtatcac tggcaaactg tgatggacga caccgtcagt gcgtccgtcg cgcaggctct   1020

cgatgagctg atgctttggg ccgaggactg ccccgaagtc cggcacctcg tgcacgcgga   1080

tttcggctcc aacaatgtcc tgacggacaa tggccgcata acagcggtca ttgactggag   1140

cgaggcgatg ttcggggatt cccaatacga ggtcgccaac atcttcttct ggaggccgtg   1200

gttggcttgt atggagcagc agacgcgcta cttcgagcgg aggcatccgg agcttgcagg   1260

atcgccgcgg ctccgggcgt atatgctccg cattggtctt gaccaactct atcagagctt   1320

ggttgacggc aatttcgatg atgcagcttg ggcgcagggt cgatgcgacg caatcgtccg   1380

atccggagcc gggactgtcg ggcgtacaca aatcgcccgc agaagcgcgg ccgtctggac   1440

cgatggctgt gtagaagtac tcgccgatag tggaaaccga cgccccagca ctcgtccgag   1500

ggcaaaggaa taatcagtac tgacaataaa aagattcttg ttttcaagaa cttgtcattt   1560

gtatagtttt tttatattgt agttgttcta ttttaatcaa atgttagcgt gatttatatt   1620

ttttttcgcc tcgacatcat ctgcccagat gcgaagttaa gtgcgcagaa agtaatatca   1680

tgcgtcaatc gtatgtgaat gctggtcgct atactgctgt cgattcgata ctaacgccgc   1740

catccagtgt cgaaaacgag ctctcgagaa cccttaatat aacttcgtat aatgtatgct   1800
```

```
atacgaagtt attaggtgat atcagatcca ctagtggcct atgcggccgc ggatctgccg   1860

gtctccctat agtgagtcgt attaatttcg ataagccagg ttaacctgca ttaatgaatc   1920

ggccaacgcg cggggagagg cggtttgcgt attgggcgct cttccgcttc ctcgctcact   1980

gactcgctgc gctcggtcgt tcggctgcgg cgagcggtat cagctcactc aaaggcggta   2040

atacggttat ccacagaatc aggggataac gcaggaaaga acatgtgagc aaaaggccag   2100

caaaaggcca ggaaccgtaa aaaggccgcg ttgctggcgt ttttccatag gctccgcccc   2160

cctgacgagc atcacaaaaa tcgacgctca agtcagaggt ggcgaaaccc gacaggacta   2220

taaagatacc aggcgtttcc ccctggaagc tccctcgtgc gctctcctgt tccgaccctg   2280

ccgcttaccg gatacctgtc cgcctttctc ccttcgggaa gcgtggcgct ttctcaatgc   2340

tcacgctgta ggtatctcag ttcggtgtag gtcgttcgct ccaagctggg ctgtgtgcac   2400

gaaccccccg ttcagcccga ccgctgcgcc ttatccggta actatcgtct tgagtccaac   2460

ccggtaagac acgacttatc gccactggca gcagccactg gtaacaggat tagcagagcg   2520

aggtatgtag gcggtgctac agagttcttg aagtggtggc ctaactacgg ctacactaga   2580

aggacagtat ttggtatctg cgctctgctg aagccagtta ccttcggaaa aagagttggt   2640

agctcttgat ccggcaaaca aaccaccgct ggtagcggtg gtttttttgt ttgcaagcag   2700

cagattacgc gcagaaaaaa aggatctcaa gaagatcctt tgatcttttc tacggggtct   2760

gacgctcagt ggaacgaaaa ctcacgttaa gggattttgg tcatgagatt atcaaaaagg   2820

atcttcacct agatcctttt aaattaaaaa tgaagtttta aatcaatcta aagtatatat   2880

gagtaaactt ggtctgacag ttaccaatgc ttaatcagtg aggcacctat ctcagcgatc   2940

tgtctatttc gttcatccat agttgcctga ctccccgtcg tgtagataac tacgatacgg   3000

gagggcttac catctggccc cagtgctgca atgataccgc gagacccacg ctcaccggct   3060

ccagatttat cagcaataaa ccagccagcc ggaagggccg agcgcagaag tggtcctgca   3120

actttatccg cctccatcca gtctattaat tgttgccggg aagctagagt aagtagttcg   3180

ccagttaata gtttgcgcaa cgttgttgcc attgctacag gcatcgtggt gtcacgctcg   3240

tcgtttggta tggcttcatt cagctccggt tcccaacgat caaggcgagt tacatgatcc   3300

cccatgttgt gcaaaaaagc ggttagctcc ttcggtcctc cgatcgttgt cagaagtaag   3360

ttggccgcag tgttatcact catggttatg gcagcactgc ataattctct tactgtcatg   3420

ccatccgtaa gatgcttttc tgtgactggt gagtactcaa ccaagtcatt ctgagaatag   3480

tgtatgcggc gaccgagttg ctcttgcccg gcgtcaatac gggataatac cgcgccacat   3540

agcagaactt taaaagtgct catcattgga aaacgttctt cggggcgaaa actctcaagg   3600

atcttaccgc tgttgagatc cagttcgatg taacccactc gtgcacccaa ctgatcttca   3660

gcatctttta ctttcaccag cgtttctggg tgagcaaaaa caggaaggca aaatgccgca   3720

aaaaagggaa taagggcgac acggaaatgt tgaatactca tactcttcct ttttcaatat   3780

tattgaagca tttatcaggg ttattgtctc atgagcggat acatatttga atgtatttag   3840

aaaaataaac aaataggggt tccgcgcaca tttccccgaa aagtgccacc tgacgtctaa   3900

gaaaccatta ttatcatgac attaacctat aaaaataggc gtatcacgag gccctttcgt   3960

ctcgcgcgtt tcggtgatga cggtgaaaac ctctgacaca tgcagctccc ggagacggtc   4020

acagcttgtc tgtaagcgga tgccgggagc agacaagccc gtcagggcgc gtcagcgggt   4080

gttggcgggt gtcggggctg gcttaactat gcggcatcag agcagattgt actgagagtg   4140

caccatatgg acatattgtc gttagaacgc ggctacaatt aatacataac cttatgtatc   4200
```

atacacatac gatttaggtg acactata 4228

<210> SEQ ID NO 58
<211> LENGTH: 4009
<212> TYPE: DNA
<213> ORGANISM: Artificial Sequence
<220> FEATURE:
<223> OTHER INFORMATION: plasmid

<400> SEQUENCE: 58
gaacgcggcc gccagctgaa gcttcgtacg ctgcaggtcg acaaccctta atataacttc 60
gtataatgta tgctatacga agttattagg tctagagatc tgtttagctt gcctcgtccc 120
cgccgggtca cccggccagc gacatggagg cccagaatac cctccttgac agtcttgacg 180
tgcgcagctc aggggcatga tgtgactgtc gcccgtacat ttagcccata catccccatg 240
tataatcatt tgcatccata cattttgatg gccgcacggc gcgaagcaaa aattacggct 300
cctcgctgca gacctgcgag cagggaaacg ctcccctcac agacgcgttg aattgtcccc 360
acgccgcgcc cctgtagaga aatataaaag gttaggattt gccactgagg ttcttctttc 420
atatacttcc ttttaaaatc ttgctaggat acagttctca catcacatcc gaacataaac 480
aaccatgggt aaggaaaaga ctcacgtttc gaggccgcga ttaaattcca acatggatgc 540
tgatttatat gggtataaat gggctcgcga taatgtcggg caatcaggtg cgacaatcta 600
tcgattgtat gggaagcccg atgcgccaga gttgtttctg aaacatggca aaggtagcgt 660
tgccaatgat gttacagatg agatggtcag actaaactgg ctgacggaat ttatgcctct 720
tccgaccatc aagcatttta tccgtactcc tgatgatgca tggttactca ccactgcgat 780
ccccggcaaa acagcattcc aggtattaga agaatatcct gattcaggtg aaaatattgt 840
tgatgcgctg gcagtgttcc tgcgccggtt gcattcgatt cctgtttgta attgtccttt 900
taacagcgat cgcgtatttc gtctcgctca ggcgcaatca cgaatgaata acggtttggt 960
tgatgcgagt gattttgatg acgagcgtaa tggctggcct gttgaacaag tctggaaaga 1020
aatgcataag cttttgccat tctcaccgga ttcagtcgtc actcatggtg atttctcact 1080
tgataacctt atttttgacg aggggaaatt aataggttgt attgatgttg gacgagtcgg 1140
aatcgcagac cgataccagg atcttgccat cctatggaac tgcctcggtg agttttctcc 1200
ttcattacag aaacggcttt ttcaaaaata tggtattgat aatcctgata tgaataaatt 1260
gcagtttcat ttgatgctcg atgagttttt ctaatcagta ctgacaataa aaagattctt 1320
gttttcaaga acttgtcatt tgtatagttt ttttatattg tagttgttct attttaatca 1380
aatgttagcg tgatttatat ttttttttcgc ctcgacatca tctgcccaga tgcgaagtta 1440
agtgcgcaga aagtaatatc atgcgtcaat cgtatgtgaa tgctggtcgc tatactgctg 1500
tcgattcgat actaacgccg ccatccagtg tcgaaaacga gctctcgaga acccttaata 1560
taacttcgta taatgtatgc tatacgaagt tattaggtga tatcagatcc actagtggcc 1620
tatgcggccg cggatctgcc ggtctcccta tagtgagtcg tattaatttc gataagccag 1680
gttaacctgc attaatgaat cggccaacgc gcggggagag gcggtttgcg tattgggcgc 1740
tcttccgctt cctcgctcac tgactcgctg cgctcggtcg ttcggctgcg gcgagcggta 1800
tcagctcact caaaggcggt aatacggtta tccacagaat caggggataa cgcaggaaag 1860
aacatgtgag caaaaggcca gcaaaaggcc aggaaccgta aaaaggccgc gttgctggcg 1920
tttttccata ggctccgccc ccctgacgag catcacaaaa atcgacgctc aagtcagagg 1980

```
tggcgaaacc cgacaggact ataaagatac caggcgtttc cccctggaag ctccctcgtg   2040
cgctctcctg ttccgaccct gccgcttacc ggatacctgt ccgcctttct cccttcggga   2100
agcgtggcgc tttctcaatg ctcacgctgt aggtatctca gttcggtgta ggtcgttcgc   2160
tccaagctgg gctgtgtgca cgaacccccc gttcagcccg accgctgcgc cttatccggt   2220
aactatcgtc ttgagtccaa cccggtaaga cacgacttat cgccactggc agcagccact   2280
ggtaacagga ttagcagagc gaggtatgta ggcggtgcta cagagttctt gaagtggtgg   2340
cctaactacg gctacactag aaggacagta tttggtatct gcgctctgct gaagccagtt   2400
accttcggaa aaagagttgg tagctcttga tccggcaaac aaaccaccgc tggtagcggt   2460
ggtttttttg tttgcaagca gcagattacg cgcagaaaaa aaggatctca agaagatcct   2520
ttgatctttt ctacggggtc tgacgctcag tggaacgaaa actcacgtta agggattttg   2580
gtcatgagat tatcaaaaag gatcttcacc tagatccttt taaattaaaa atgaagtttt   2640
aaatcaatct aaagtatata tgagtaaact tggtctgaca gttaccaatg cttaatcagt   2700
gaggcaccta tctcagcgat ctgtctattt cgttcatcca tagttgcctg actccccgtc   2760
gtgtagataa ctacgatacg ggagggctta ccatctggcc ccagtgctgc aatgataccg   2820
cgagacccac gctcaccggc tccagattta tcagcaataa accagccagc cggaagggcc   2880
gagcgcagaa gtggtcctgc aactttatcc gcctccatcc agtctattaa ttgttgccgg   2940
gaagctagag taagtagttc gccagttaat agtttgcgca acgttgttgc cattgctaca   3000
ggcatcgtgg tgtcacgctc gtcgtttggt atggcttcat tcagctccgg ttcccaacga   3060
tcaaggcgag ttacatgatc ccccatgttg tgcaaaaaag cggttagctc cttcggtcct   3120
ccgatcgttg tcagaagtaa gttggccgca gtgttatcac tcatggttat ggcagcactg   3180
cataattctc ttactgtcat gccatccgta agatgctttt ctgtgactgg tgagtactca   3240
accaagtcat tctgagaata gtgtatgcgg cgaccgagtt gctcttgccc ggcgtcaata   3300
cgggataata ccgcgccaca tagcagaact ttaaaagtgc tcatcattgg aaaacgttct   3360
tcggggcgaa aactctcaag gatcttaccg ctgttgagat ccagttcgat gtaacccact   3420
cgtgcaccca actgatcttc agcatctttt actttcacca gcgtttctgg gtgagcaaaa   3480
acaggaaggc aaaatgccgc aaaaaaggga ataagggcga cacggaaatg ttgaatactc   3540
atactcttcc tttttcaata ttattgaagc atttatcagg gttattgtct catgagcgga   3600
tacatatttg aatgtattta gaaaaataaa caaatagggg ttccgcgcac atttccccga   3660
aaagtgccac ctgacgtcta agaaaccatt attatcatga cattaaccta taaaaatagg   3720
cgtatcacga ggccctttcg tctcgcgcgt ttcggtgatg acggtgaaaa cctctgacac   3780
atgcagctcc cggagacggt cacagcttgt ctgtaagcgg atgccgggag cagacaagcc   3840
cgtcagggcg cgtcagcggg tgttggcggg tgtcggggct ggcttaacta tgcggcatca   3900
gagcagattg tactgagagt gcaccatatg gacatattgt cgttagaacg cggctacaat   3960
taatacataa ccttatgtat catacacata cgatttaggt gacactata              4009
```

<210> SEQ ID NO 59
<211> LENGTH: 6315
<212> TYPE: DNA
<213> ORGANISM: Artificial Sequence
<220> FEATURE:
<223> OTHER INFORMATION: plasmid

<400> SEQUENCE: 59

```
cgcgcctgat gagcctgaac tgcccgggca aatcagctgg cgtaatagcg aagaggcccg     60
```

```
caccgatcgc ccttcccaac agttgcgcag cctgaatggc gaatggcgcg acgcgccctg    120
tagcggcgca ttaagcgcgg cgggtgtggt ggttacgcgc agcgtgaccg ctacacttgc    180
cagcgcccta gcgcccgctc ctttcgcttt cttcccttcc tttctcgcca cgttcgccgg    240
ctttccccgt caagctctaa atcgggggct ccctttaggg ttccgattta gtgctttacg    300
gcacctcgac cccaaaaaac ttgattaggg tgatggttca cgtagtgggc catcgccctg    360
atagacggtt tttcgccctt tgacgttgga gtccacgttc tttaatagtg gactcttgtt    420
ccaaactgga acaacactca accctatctc ggtctattct tttgatttat aagggatttt    480
gccgatttcg gcctattggt taaaaaatga gctgatttaa caaaaattta acgcgaattt    540
taacaaaata ttaacgttta caatttcctg atgcggtatt ttctccttac gcatctgtgc    600
ggtatttcac accgcataga tccgtcgagt tcaagagaaa aaaaaagaaa aagcaaaaag    660
aaaaaaggaa agcgcgcctc gttcagaatg acacgtatag aatgatgcat taccttgtca    720
tcttcagtat catactgttc gtatacatac ttactgacat tcataggtat acatatatac    780
acatgtatat atatcgtatg ctgcagcttt aaataatcgg tgtcactaca taagaacacc    840
tttggtggag ggaacatcgt tggtaccatt gggcgaggtg gcttctctta tggcaaccgc    900
aagagccttg aacgcactct cactacggtg atgatcattc ttgcctcgca gacaatcaac    960
gtggagggta attctgctag cctctgcaaa actttcaaga aaatgcggga tcatctcgca   1020
agagagatct cctactttct ccctttgcaa accaagttcg acaactgcgt acggcctgtt   1080
cgaaagatct accaccgctc tggaaagtgc ctcatccaaa ggcgcaaatc ctgatccaaa   1140
cctttttact ccacgcacgg cccctagggc ctctttaaag gcttgaccga gagcaatccc   1200
gcagtcttca gtggtgtgat ggtcgtctat gtgtaagtca ccaatgcact caacgattag   1260
cgaccagccg gaatgcttgg ccagagcatg tatcatatgg tccagaaacc ctatacctgt   1320
gtggacgtta atcacttgcg attgtgtggc ctgttctgct actgcttctg cctctttttc   1380
tgggaagatc gagtgctcta tcgctagggg accacccttt aaagagatcg caatctgaat   1440
cttggtttca tttgtaatac gctttactag ggctttctgc tctgtcatct ttgccttcgt   1500
ttatcttgcc tgctcatttt ttagtatatt cttcgaagaa atcacattac tttatataat   1560
gtataattca ttatgtgata atgccaatcg ctaagaaaaa aaaagagtca tccgctaggg   1620
gaaaaaaaaa aatgaaaatc attaccgagg cataaaaaaa tatagagtgt actagaggag   1680
gccaagagta atagaaaaag aaaattgcgg gaaaggactg tgttatgact tccctgacta   1740
atgccgtgtt caaacgatac ctggcagtga ctcctagcgc tcaccaagct cttaaaacgg   1800
gaatttatgg tgcactctca gtacaatctg ctctgatgcc gcatagttaa gccagccccg   1860
acacccgcca acacgcgctg acgcgccctg acgggcttgt ctgctcccgg catccgctta   1920
cagacaagct gtgaccgtct ccgggagctg catgtgtcag aggttttcac cgtcatcacc   1980
gaaacgcgcg agacgaaagg gcctcgtgat acgcctattt ttataggtta atgtcatgat   2040
aataatggtt tcttaggacg gatcgcttgc ctgtaactta cacgcgcctc gtatctttta   2100
atgatggaat aatttgggaa tttactctgt gtttatttat ttttatgttt tgtatttgga   2160
ttttagaaag taaataaaga aggtagaaga gttacggaat gaagaaaaaa aaataaacaa   2220
aggtttaaaa aatttcaaca aaaagcgtac tttacatata tatttattag acaagaaaag   2280
cagattaaat agatatacat tcgattaacg ataagtaaaa tgtaaaatca caggattttc   2340
gtgtgtggtc ttctacacag acaagatgaa acaattcggc attaatacct gagagcagga   2400
```

```
agagcaagat aaaaggtagt atttgttggc gatcccccta gagtctttta catcttcgga   2460
aaacaaaaac tatttttttct ttaatttctt tttttacttt ctatttttaa tttatatatt   2520
tatattaaaa aatttaaatt ataattattt ttatagcacg tgatgaaaag gacccaggtg   2580
gcacttttcg gggaaatgtg cgcggaaccc ctatttgttt atttttctaa atacattcaa   2640
atatgtatcc gctcatgaga caataaccct gataaatgct tcaataatat tgaaaaagga   2700
agagtatgag tattcaacat ttccgtgtcg cccttattcc cttttttgcg gcattttgcc   2760
ttcctgtttt tgctcaccca gaaacgctgg tgaaagtaaa agatgctgaa gatcagttgg   2820
gtgcacgagt gggttacatc gaactggatc tcaacagcgg taagatcctt gagagttttc   2880
gccccgaaga acgttttcca atgatgagca cttttaaagt tctgctatgt ggcgcggtat   2940
tatcccgtat tgacgccggg caagagcaac tcggtcgccg catacactat tctcagaatg   3000
acttggttga gtactcacca gtcacagaaa agcatcttac ggatggcatg acagtaagag   3060
aattatgcag tgctgccata accatgagtg ataacactgc ggccaactta cttctgacaa   3120
cgatcggagg accgaaggag ctaaccgctt ttttgcacaa catgggggat catgtaactc   3180
gccttgatcg ttgggaaccg gagctgaatg aagccatacc aaacgacgag cgtgacacca   3240
cgatgcctgt agcaatggca acaacgttgc gcaaactatt aactggcgaa ctacttactc   3300
tagcttcccg gcaacaatta atagactgga tggaggcgga taaagttgca ggaccacttc   3360
tgcgctcggc ccttccggct ggctggttta ttgctgataa atctggagcc ggtgagcgtg   3420
ggtctcgcgg tatcattgca gcactggggc cagatggtaa gccctcccgt atcgtagtta   3480
tctacacgac ggggagtcag gcaactatgg atgaacgaaa tagacagatc gctgagatag   3540
gtgcctcact gattaagcat tggtaactgt cagaccaagt ttactcatat atactttaga   3600
ttgatttaaa acttcatttt taatttaaaa ggatctaggt gaagatcctt tttgataatc   3660
tcatgaccaa aatcccttaa cgtgagtttt cgttccactg agcgtcagac cccgtagaaa   3720
agatcaaagg atcttcttga gatccttttt ttctgcgcgt aatctgctgc ttgcaaacaa   3780
aaaaaccacc gctaccagcg gtggtttgtt tgccggatca agagctacca actctttttc   3840
cgaaggtaac tggcttcagc agagcgcaga taccaaatac tgtccttcta gtgtagccgt   3900
agttaggcca ccacttcaag aactctgtag caccgcctac atacctcgct ctgctaatcc   3960
tgttaccagt ggctgctgcc agtggcgata agtcgtgtct taccgggttg gactcaagac   4020
gatagttacc ggataaggcg cagcggtcgg gctgaacggg gggttcgtgc acacagccca   4080
gcttggagcg aacgacctac accgaactga gatacctaca gcgtgagcta tgagaaagcg   4140
ccacgcttcc cgaagggaga aaggcggaca ggtatccggt aagcggcagg gtcggaacag   4200
gagagcgcac gagggagctt ccagggggaa acgcctggta tctttatagt cctgtcgggt   4260
ttcgccacct ctgacttgag cgtcgatttt tgtgatgctc gtcagggggg cggagcctat   4320
ggaaaaacgc cagcaacgcg gcctttttac ggttcctggc cttttgctgg ccttttgctc   4380
acatgttctt tcctgcgtta tcccctgatt ctgtggataa ccgtattacc gcctttgagt   4440
gagctgatac cgctcgccgc agccgaacga ccgagcgcag cgagtcagtg agcgaggaag   4500
cggaagagcg cccaatacgc aaaccgcctc tccccgcgcg ttggccgatt cattaatgca   4560
gctgatttgc ccgggcagtt caggctcatc aggcgcgccg agcgacctca tgctatacct   4620
gagaaagcaa cctgacctac aggaaagagt tactcaagaa taagaatttt cgttttaaaa   4680
cctaagagtc actttaaaat ttgtatacac ttattttttt tataacttat ttaataataa   4740
aaatcataaa tcataagaaa ttcgcttatt tagaagtgtc aacaacgtat ctaccaacga   4800
```

```
tttgaccctt ttccatcttt tcgtaaattt ctggcaaggt agacaagccg acaaccttga   4860

ttggagactt gaccaaacct ctggcgaaga attgttaatt aagagctcgt ttaaacacct   4920

gcttttagct attttgtaat taaaacttag attagattgc tatgctttct ttctaatgag   4980

caagaagtaa aaaaagttgt aatagaacaa gaaaaatgaa actgaaactt gagaaattga   5040

agaccgttta ttaacttaaa tatcaatggg aggtcatcga aagagaaaaa aatcaaaaaa   5100

aaaaatttc aagaaaaaga aacgtgataa aaattttat tgcctttttc gacgaagaaa   5160

aagaaacgag gcggtctctt ttttcttttc caaaccttta gtacgggtaa ttaacgacac   5220

cctagaggaa gaaagagggg aaatttagta tgctgtgctt gggtgttttg aagtggtacg   5280

gcgatgcgcg gagtccgaga aaatctggaa gagtaaaaaa ggagtagaaa cattttgaag   5340

ctaagatcta cgcacagata ttataacatc tgcataatag gcatttgcaa gaattactcg   5400

tgagtaagga aagagtgagg aactatcgca tacctgcatt taaagatgcc gatttgggcg   5460

cgaatccttt attttggctt caccctcata ctattatcag ggccagaaaa aggaagtgtt   5520

tccctccttc ttgaattgat gttaccctca taaagcacgt ggcctcttat cgagaaagaa   5580

attaccgtcg ctcgtgattt gtttgcaaaa agaacaaaac tgaaaaaacc cagacacgct   5640

cgacttcctg tcttcctatt gattgcagct tccaatttcg tcacacaaca aggtcctagc   5700

gacggctcac aggttttgta acaagcaatc gaaggttctg gaatggcggg aaagggttta   5760

gtaccacatg ctatgatgcc cactgtgatc tccagagcaa agttcgttcg atcgtactgt   5820

tactctctct ctttcaaaca gaattgtccg aatcgtgtga caacaacagc ctgttctcac   5880

acactctttt cttctaacca agggggtggt ttagtttagt agaacctcgt gaaacttaca   5940

tttacatata tataaacttg cataaattgg tcaatgcaag aaatacatat ttggtctttt   6000

ctaattcgta gtttttcaag ttcttagatg ctttctttt ctctttttta cagatcatca   6060

aggaagtaat tatctacttt ttacaacaaa tataaaacaa agcttggtac cgcggctagc   6120

taagatccgc tctaaccgaa aaggaaggag ttagacaacc tgaagtctag gtccctattt   6180

attttttat agttatgtta gtattaagaa cgttatttat atttcaaatt tttctttttt   6240

ttctgtacag acgcgtgtac gcatgtaaca ttatactgaa aaccttgctt gagaaggttt   6300

tgggacgctc gaagg                                                    6315
```

<210> SEQ ID NO 60
<211> LENGTH: 6311
<212> TYPE: DNA
<213> ORGANISM: Artificial Sequence
<220> FEATURE:
<223> OTHER INFORMATION: plasmid

<400> SEQUENCE: 60

```
ctgcattaat gaatcggcca acgcgcgggg agaggcggtt tgcgtattgg gcgctcttcc     60

gcttcctcgc tcactgactc gctgcgctcg gtcgttcggc tgcggcgagc ggtatcagct    120

cactcaaagg cggtaatacg gttatccaca gaatcagggg ataacgcagg aaagaacatg    180

tgagcaaaag gccagcaaaa ggccaggaac cgtaaaaagg ccgcgttgct ggcgtttttc    240

cataggctcc gcccccctga cgagcatcac aaaaatcgac gctcaagtca gaggtggcga    300

aacccgacag gactataaag ataccaggcg tttccccctg gaagctccct cgtgcgctct    360

cctgttccga ccctgccgct taccggatac ctgtccgcct ttctcccttc gggaagcgtg    420

gcgctttctc atagctcacg ctgtaggtat ctcagttcgg tgtaggtcgt tcgctccaag    480
```

```
ctgggctgtg tgcacgaacc ccccgttcag cccgaccgct gcgccttatc cggtaactat    540
cgtcttgagt ccaacccggt aagacacgac ttatcgccac tggcagcagc cactggtaac    600
aggattagca gagcgaggta tgtaggcggt gctacagagt tcttgaagtg gtggcctaac    660
tacggctaca ctagaaggac agtatttggt atctgcgctc tgctgaagcc agttaccttc    720
ggaaaaagag ttggtagctc ttgatccggc aaacaaacca ccgctggtag cggtggtttt    780
tttgtttgca agcagcagat tacgcgcaga aaaaaaggat ctcaagaaga tcctttgatc    840
ttttctacgg ggtctgacgc tcagtggaac gaaaactcac gttaagggat tttggtcatg    900
agattatcaa aaaggatctt cacctagatc cttttaaatt aaaaatgaag ttttaaatca    960
atctaaagta tatatgagta aacttggtct gacagttacc aatgcttaat cagtgaggca   1020
cctatctcag cgatctgtct atttcgttca tccatagttg cctgactccc cgtcgtgtag   1080
ataactacga tacgggaggg cttaccatct ggccccagtg ctgcaatgat accgcgagac   1140
ccacgctcac cggctccaga tttatcagca ataaaccagc cagccggaag ggccgagcgc   1200
agaagtggtc ctgcaacttt atccgcctcc atccagtcta ttaattgttg ccgggaagct   1260
agagtaagta gttcgccagt taatagtttg cgcaacgttg ttgccattgc tacaggcatc   1320
gtggtgtcac gctcgtcgtt tggtatggct tcattcagct ccggttccca acgatcaagg   1380
cgagttacat gatcccccat gttgtgcaaa aaagcggtta gctccttcgg tcctccgatc   1440
gttgtcagaa gtaagttggc cgcagtgtta tcactcatgg ttatggcagc actgcataat   1500
tctcttactg tcatgccatc cgtaagatgc ttttctgtga ctggtgagta ctcaaccaag   1560
tcattctgag aatagtgtat gcggcgaccg agttgctctt gcccggcgtc aatacgggat   1620
aataccgcgc cacatagcag aactttaaaa gtgctcatca ttggaaaacg ttcttcgggg   1680
cgaaaactct caaggatctt accgctgttg agatccagtt cgatgtaacc cactcgtgca   1740
cccaactgat cttcagcatc ttttactttc accagcgttt ctgggtgagc aaaaacagga   1800
aggcaaaatg ccgcaaaaaa gggaataagg gcgacacgga aatgttgaat actcatactc   1860
ttcctttttc aatattattg aagcatttat cagggttatt gtctcatgag cggatacata   1920
tttgaatgta tttagaaaaa taaacaaata ggggttccgc gcacatttcc ccgaaaagtg   1980
ccacctgggt ccttttcatc acgtgctata aaaataatta taatttaaat tttttaatat   2040
aaatatataa attaaaaata gaaagtaaaa aaagaaatta aagaaaaaat agtttttgtt   2100
ttccgaagat gtaaaagact ctagggggat cgccaacaaa tactaccttt tatcttgctc   2160
ttcctgctct caggtattaa tgccgaattg tttcatcttg tctgtgtaga agaccacaca   2220
cgaaaatcct gtgattttac attttactta tcgttaatcg aatgtatatc tatttaatct   2280
gcttttcttg tctaataaat atatatgtaa agtacgcttt ttgttgaaat tttttaaacc   2340
tttgtttatt tttttttctt cattccgtaa ctcttctacc ttctttattt actttctaaa   2400
atccaaatac aaaacataaa aataaataaa cacagagtaa attcccaaat tattccatca   2460
ttaaaagata cgaggcgcgt gtaagttaca ggcaagcgat ccgtcctaag aaaccattat   2520
tatcatgaca ttaacctata aaaataggcg tatcacgagg ccctttcgtc tcgcgcgttt   2580
cggtgatgac ggtgaaaacc tctgacacat gcagctcccg gagacggtca cagcttgtct   2640
gtaagcggat gccgggagca gacaagcccg tcagggcgcg tcagcgggtg ttggcgggtg   2700
tcggggctgg cttaactatg cggcatcaga gcagattgta ctgagagtgc accataccac   2760
agcttttcaa ttcaattcat catttttttt ttattctttt ttttgatttc ggtttctttg   2820
aaattttttt gattcggtaa tctccgaaca gaaggaagaa cgaaggaagg agcacagact   2880
```

```
tagattggta tatatacgca tatgtagtgt tgaagaaaca tgaaattgcc cagtattctt   2940
aacccaactg cacagaacaa aaacctgcag gaaacgaaga taaatcatgt cgaaagctac   3000
atataaggaa cgtgctgcta ctcatcctag tcctgttgct gccaagctat ttaatatcat   3060
gcacgaaaag caaacaaact tgtgtgcttc attggatgtt cgtaccacca aggaattact   3120
ggagttagtt gaagcattag gtcccaaaat ttgtttacta aaaacacatg tggatatctt   3180
gactgatttt tccatggagg gcacagttaa gccgctaaag gcattatccg ccaagtacaa   3240
tttttactc ttcgaagaca gaaaatttgc tgacattggt aatacagtca aattgcagta   3300
ctctgcgggt gtatacagaa tagcagaatg ggcagacatt acgaatgcac acggtgtggt   3360
gggcccaggt attgttagcg gtttgaagca ggcggcagaa gaagtaacaa aggaacctag   3420
aggccttttg atgttagcag aattgtcatg caagggctcc ctatctactg gagaatatac   3480
taagggtact gttgacattg cgaagagcga caaagatttt gttatcggct ttattgctca   3540
aagagacatg ggtggaagag atgaaggtta cgattggttg attatgacac ccggtgtggg   3600
tttagatgac aagggagacg cattgggtca acagtataga accgtggatg atgtggtctc   3660
tacaggatct gacattatta ttgttggaag aggactattt gcaaagggaa gggatgctaa   3720
ggtagagggt gaacgttaca gaaaagcagg ctgggaagca tatttgagaa gatgcggcca   3780
gcaaaactaa aaaactgtat tataagtaaa tgcatgtata ctaaactcac aaattagagc   3840
ttcaatttaa ttatatcagt tattacccta tgcggtgtga aataccgcac agatgcgtaa   3900
ggagaaaata ccgcatcagg aaattgtaaa cgttaatatt ttgttaaaat tcgcgttaaa   3960
tttttgttaa atcagctcat tttttaacca ataggccgaa atcggcaaaa tcccttataa   4020
atcaaaagaa tagaccgaga tagggttgag tgttgttcca gtttggaaca agagtccact   4080
attaaagaac gtggactcca acgtcaaagg gcgaaaaacc gtctatcagg gcgatggccc   4140
actacgtgaa ccatcaccct aatcaagttt tttggggtcg aggtgccgta aagcactaaa   4200
tcggaaccct aaagggagcc cccgatttag agcttgacgg ggaaagccgg cgaacgtggc   4260
gagaaaggaa gggaagaaag cgaaaggagc gggcgctagg gcgctggcaa gtgtagcggt   4320
cacgctgcgc gtaaccacca cacccgccgc gcttaatgcg ccgctacagg gcgcgtcgcg   4380
ccattcgcca ttcaggctgc gcaactgttg ggaagggcga tcggtgcggg cctcttcgct   4440
attacgccag ctgatttgcc cgggcagttc aggctcatca ggcgcgccat gcaggatgca   4500
ttgatcagtt aacccatggg catgcgaagg aaaatgagaa atatcgaggg agacgattca   4560
gaggagcagg acaaactata accgactgtt tgttggagga tgccgtacat aacgaacact   4620
gctgaagcta ccatgtctac agtttagagg aatgggtaca actcacaggc gagggatggt   4680
gttcactcgt gctagcaaac gcggtgggag caaaaagtag aatattatct tttattcgtg   4740
aaacttcgaa cactgtcatc taaagatgct atatactaat ataggcatac ttgataatga   4800
aaactataaa tcgtaaagac ataagagatc cgcggatccc cgggtcgagc ctgaacggcc   4860
tcgaggcctg aacggcctcg acgaattcat tatttgtaga gctcatccat gccatgtgta   4920
atcccagcag cagttacaaa ctcaagaagg accatgtggt cacgcttttc gttgggatct   4980
ttcgaaaggg cagattgtgt cgacaggtaa tggttgtctg gtaaaaggac agggccatcg   5040
ccaattggag tattttgttg ataatggtct gctagttgaa cggatccatc ttcaatgttg   5100
tggcgaattt tgaagttagc tttgattcca ttcttttgtt tgtctgccgt gatgtataca   5160
ttgtgtgagt tatagttgta ctcgagtttg tgtccgagaa tgtttccatc ttctttaaaa   5220
```

```
tcaataccttttaactcgatacgattaacaagggtatcaccttcaaacttgacttcagca   5280
cgcgtcttgtagttcccgtcatctttgaaagatatagtgcgttcctgtacataaccttcg   5340
ggcatggcactcttgaaaaagtcatgccgtttcatatgatccggataacgggaaaagcat   5400
tgaacaccataagagaaagtagtgacaagtgttggccatggaacaggtagttttccagta   5460
gtgcaaataaatttaagggtaagctggccctgcaggccaagctttgttttatatttgttg   5520
taaaaagtagataattacttccttgatgatctgtaaaaaagagaaaaagaaagcatctaa   5580
gaacttgaaaaactacgaattagaaaagaccaaatatgtatttcttgcattgaccaattt   5640
atgcaagtttatatatatgtaaatgtaagtttcacgaggttctactaaactaaaccaccc   5700
ccttggttagaagaaaagagtgtgtgagaacaggctgttgttgtcacacgattcggacaa   5760
ttctgtttgaaagagagagagtaacagtacgatcgaacgaactttgctctggagatcaca   5820
gtgggcatcatagcatgtggtactaaaccctttcccgccattccagaaccttcgattgct   5880
tgttacaaaacctgtgagccgtcgctaggaccttgttgtgtgacgaaattggaagctgca   5940
atcaataggaagacaggaagtcgagcgtgtctgggtttttcagttttgttctttttgca   6000
aacaaatcacgagcgacggtaatttctttctcgataagaggccacgtgctttatgagggt   6060
aacatcaattcaagaaggagggaaacacttcctttttctggccctgataatagtatgagg   6120
gtgaagccaaaataaaggattcgcgcccaaatcggcatctttaaatgcaggtatgcgata   6180
gttcctcactctttccttactcacgagtaattcttgcaaatgcctattatgcagatgtta   6240
taatatctgtgcgtagatctgatatccctgcatggcgcgcctgatgagcctgaactgccc   6300
gggcaaatcag                                                    6311
```

<210> SEQ ID NO 61
<211> LENGTH: 7102
<212> TYPE: DNA
<213> ORGANISM: Artificial Sequence
<220> FEATURE:
<223> OTHER INFORMATION: plasmid

<400> SEQUENCE: 61

```
tcgctattacgccagctgatttgcccgggcagttcaggctcatcaggcgcgccatgcagg     60
atgcattgatcagttaacccatgggcatgcagcttgcaaattaaagccttcgagcgtccc    120
aaaaccttctcaagcaaggttttcagtataatgttacatgcgtacacgcgtctgtacaga    180
aaaaaaagaaaaatttgaaatataaataacgttcttaatactaacataactataaaaaaa    240
taaataggga cctagacttcaggttgtctaactccttcctt ttcggttagagcggatgtg    300
gggggagggcgtgaatgtaagcgtgacataactaattacatgatatcgacaaaggaaaag    360
ggggacggatctccgaggcctcggacccgtcgggccgccgtcggacgtgccgcggtcact    420
tgatgtcgcacaaaaccaagttttcgtggaacttcttgcagattctttccaaattttcga    480
taccgatagattctggggaggtgatgataatgttcaaaccaccagtcatagtagaaatgg    540
cggtaatggagaagtcgtaaaaatgaacgttgaagtgttgggtgaacatggcatcaataa    600
tttggaacttgtcgttggattcggagttgttcaagataataccaatgttggagaaggtgg    660
aaccagttcttttgttcatgatctttggcaagtcaacatccaagtgcttgttcttaatca    720
tcttgtcccaacccaaaatacccatggagtataatggcttttcaacttcaaagagattt    780
tcaagtcttgattgatttggttgatcttgttccaggtgatcaacttcattggcttagaaa    840
ttttggagaaaccactgacgttcaaaccgaacttatacaagtcttgttcatccttgttaa    900
tgaattgtctagagtcaacggcgatacccaacaaagatttagatgacttgtaatattcgt    960
```

```
cttggtacaa ggtgtaattc caaatggatt ggatgaatgg ggtcaaagtc aacttaacgt   1020
tgttgaagga gttcttggac aacaaagact taatcttcaa taattccatt gggttgatgt   1080
taactctgta gtggatgttc ttcaagtgac cttggatcaa agtagaggaa cagaacaact   1140
taggttcgat caaggagttg tagatatatc ttggcaagga tttgatggat gggatatggt   1200
tcatcaaatc ggtaattggc tttggcaatt cacccaaatt caagtggtct tgggagtagt   1260
tgaaaacgat atcatcatca tcggacaagg agtccaagtc caattgattg aagatcaagg   1320
acaattcgtt gaagatgttc ttaccagaaa taccatcgtg caagacatgg ttggtaatga   1380
aaatcaaggt gtagtcatcc aagataccca atctccaaac caacttgtta tcttcgtatg   1440
ggatgatcaa gtcgttcaac ttgttcaaca aatcttcttg caacaagtta gagtattctg   1500
gtcttaagtc ccagaccaaa tcgttgaact tgatttcgtc gatgatttgg atgtaatcgt   1560
atggtcttgg cttgatgttg attgggacat tttgagtaat aatggtggag gccaagattg   1620
ggaacttcaa aatcaataat ctcaaggagt ggaacaaaat cttgaagtcg tcgatctttt   1680
cgttgtattt gcacatgacg aagaaggact tgtacatctt ttgtctttgc aagatggcga   1740
aaaaatcttc caagaaaccc atttgtctgg catggttctt agacaacttg tacttcaagt   1800
tggacaagga cttggagtcg ttttgattga tgtacttgaa ggacatttta agctttttgt   1860
ttgtttatgt gtgtttattc gaaactaagt tcttggtgtt ttaaaactaa aaaaaagact   1920
aactataaaa gtagaattta agaagtttaa gaaatagatt tacagaatta caatcaatac   1980
ctaccgtctt tatatactta ttagtcaagt aggggaataa tttcagggaa ctggtttcaa   2040
ccttttttt cagctttttc caaatcagag agagcagaag gtaatagaag gtgtaagaaa   2100
atgagataga tacatgcgtg ggtcaattgc cttgtgtcat catttactcc aggcaggttg   2160
catcactcca ttgaggttgt gtccgttttt tgcctgtttg tgcccctgtt ctctgtagtt   2220
gcgctaagag aatggaccta tgaactgatg gttggtgaag aaaacaatat tttggtgctg   2280
ggattctttt tttttctgga tgccagctta aaaagcgggc tccattatat ttagtggatg   2340
ccaggaataa actgttcacc cagacaccta cgatgttata tattctgtgt aacccgcccc   2400
ctattttggg catgtacggg ttacagcaga attaaaaggc taattttttg actaaataaa   2460
gttaggaaaa tcactactat taattattta cgtattcttt gaaatggcag tattgataat   2520
gataaactcg aactgagatc tgatatccct gcatggcgcg cctgatgagc ctgaactgcc   2580
cgggcaaatc agctgcatta atgaatcggc caacgcgcgg ggagaggcgg tttgcgtatt   2640
gggcgctctt ccgcttcctc gctcactgac tcgctgcgct cggtcgttcg gctgcggcga   2700
gcggtatcag ctcactcaaa ggcggtaata cggttatcca cagaatcagg ggataacgca   2760
ggaaagaaca tgtgagcaaa aggccagcaa aaggccagga accgtaaaaa ggccgcgttg   2820
ctggcgtttt tccataggct ccgcccccct gacgagcatc acaaaaatcg acgctcaagt   2880
cagaggtggc gaaacccgac aggactataa agataccagg cgtttccccc tggaagctcc   2940
ctcgtgcgct ctcctgttcc gaccctgccg cttaccggat acctgtccgc ctttctccct   3000
tcgggaagcg tggcgctttc tcatagctca cgctgtaggt atctcagttc ggtgtaggtc   3060
gttcgctcca agctgggctg tgtgcacgaa ccccccgttc agcccgaccg ctgcgcctta   3120
tccggtaact atcgtcttga gtccaacccg gtaagacacg acttatcgcc actggcagca   3180
gccactggta acaggattag cagagcgagg tatgtaggcg gtgctacaga gttcttgaag   3240
tggtggccta actacggcta cactagaagg acagtatttg gtatctgcgc tctgctgaag   3300
```

```
ccagttacct tcggaaaaag agttggtagc tcttgatccg gcaaacaaac caccgctggt   3360
agcggtggtt tttttgtttg caagcagcag attacgcgca gaaaaaaagg atctcaagaa   3420
gatcctttga tcttttctac ggggtctgac gctcagtgga acgaaaactc acgttaaggg   3480
attttggtca tgagattatc aaaaaggatc ttcacctaga tccttttaaa ttaaaaatga   3540
agttttaaat caatctaaag tatatatgag taaacttggt ctgacagtta ccaatgctta   3600
atcagtgagg cacctatctc agcgatctgt ctatttcgtt catccatagt tgcctgactc   3660
cccgtcgtgt agataactac gatacgggag ggcttaccat ctggccccag tgctgcaatg   3720
ataccgcgag acccacgctc accggctcca gatttatcag caataaacca gccagccgga   3780
agggccgagc gcagaagtgg tcctgcaact ttatccgcct ccatccagtc tattaattgt   3840
tgccgggaag ctagagtaag tagttcgcca gttaatagtt tgcgcaacgt tgttgccatt   3900
gctacaggca tcgtggtgtc acgctcgtcg tttggtatgg cttcattcag ctccggttcc   3960
caacgatcaa ggcgagttac atgatccccc atgttgtgca aaaaagcggt tagctccttc   4020
ggtcctccga tcgttgtcag aagtaagttg gccgcagtgt tatcactcat ggttatggca   4080
gcactgcata attctcttac tgtcatgcca tccgtaagat gcttttctgt gactggtgag   4140
tactcaacca agtcattctg agaatagtgt atgcggcgac cgagttgctc ttgcccggcg   4200
tcaatacggg ataataccgc gccacatagc agaactttaa aagtgctcat cattggaaaa   4260
cgttcttcgg ggcgaaaact ctcaaggatc ttaccgctgt tgagatccag ttcgatgtaa   4320
cccactcgtg cacccaactg atcttcagca tcttttactt tcaccagcgt ttctgggtga   4380
gcaaaaacag gaaggcaaaa tgccgcaaaa aagggaataa gggcgacacg gaaatgttga   4440
atactcatac tcttcctttt tcaatattat tgaagcattt atcagggtta ttgtctcatg   4500
agcggataca tatttgaatg tatttagaaa aataaacaaa taggggttcc gcgcacattt   4560
ccccgaaaag tgccacctgg gtccttttca tcacgtgcta taaaaataat tataatttaa   4620
atttttaat ataaatatat aaattaaaaa tagaaagtaa aaaaagaaat taaagaaaaa   4680
atagtttttg ttttccgaag atgtaaaaga ctctaggggg atcgccaaca aatactacct   4740
tttatcttgc tcttcctgct ctcaggtatt aatgccgaat tgtttcatct tgtctgtgta   4800
gaagaccaca cacgaaaatc ctgtgatttt acattttact tatcgttaat cgaatgtata   4860
tctatttaat ctgcttttct tgtctaataa atatatatgt aaagtacgct ttttgttgaa   4920
atttttaaa cctttgttta tttttttttc ttcattccgt aactcttcta ccttctttat   4980
ttactttcta aaatccaaat acaaaacata aaaataaata aacacagagt aaattcccaa   5040
attattccat cattaaaaga tacgaggcgc gtgtaagtta caggcaagcg atccgtccta   5100
agaaaccatt attatcatga cattaaccta taaaaatagg cgtatcacga ggccctttcg   5160
tctcgcgcgt ttcggtgatg acggtgaaaa cctctgacac atgcagctcc cggagacggt   5220
cacagcttgt ctgtaagcgg atgccgggag cagacaagcc cgtcagggcg cgtcagcgcg   5280
tgttggcggg tgtcggggct ggcttaacta tgcggcatca gagcagattg tactgagagt   5340
gcaccataaa ttcccgtttt aagagcttgg tgagcgctag gagtcactgc caggtatcgt   5400
ttgaacacgg cattagtcag ggaagtcata acacagtcct ttcccgcaat ttcttttttc   5460
tattactctt ggcctcctct agtacactct atattttttt atgcctcggt aatgattttc   5520
attttttttt ttcccctagc ggatgactct tttttttttct tagcgattgg cattatcaca   5580
taatgaatta tacattatat aaagtaatgt gatttcttcg aagaatatac taaaaaatga   5640
gcaggcaaga taaacgaagg caaagatgac agagcagaaa gccctagtaa agcgtattac   5700
```

```
aaatgaaacc aagattcaga ttgcgatctc tttaaagggt ggtcccctag cgatagagca   5760
ctcgatcttc ccagaaaaag aggcagaagc agtagcagaa caggccacac aatcgcaagt   5820
gattaacgtc cacacaggta tagggtttct ggaccatatg atacatgctc tggccaagca   5880
ttccggctgg tcgctaatcg ttgagtgcat tggtgactta cacatagacg accatcacac   5940
cactgaagac tgcgggattg ctctcggtca agcctttaaa gaggccctag gggccgtgcg   6000
tggagtaaaa aggtttggat caggatttgc gcctttggat gaggcacttt ccagagcggt   6060
ggtagatctt tcgaacaggc cgtacgcagt tgtcgaactt ggtttgcaaa gggagaaagt   6120
aggagatctc tcttgcgaga tgatcccgca ttttcttgaa agttttgcag aggctagcag   6180
aattaccctc cacgttgatt gtctgcgagg caagaatgat catcaccgta gtgagagtgc   6240
gttcaaggct cttgcggttg ccataagaga agccacctcg cccaatggta ccaacgatgt   6300
tccctccacc aaaggtgttc ttatgtagtg acaccgatta tttaaagctg cagcatacga   6360
tatatataca tgtgtatata tgtataccta tgaatgtcag taagtatgta tacgaacagt   6420
atgatactga agatgacaag gtaatgcatc attctatacg tgtcattctg aacgaggcgc   6480
gctttccttt tttctttttg ctttttcttt ttttttctct tgaactcgac ggatctatgc   6540
ggtgtgaaat accgcacaga tgcgtaagga gaaaataccg catcaggaaa ttgtaaacgt   6600
taatattttg ttaaaattcg cgttaaattt ttgttaaatc agctcatttt ttaaccaata   6660
ggccgaaatc ggcaaaatcc cttataaatc aaaagaatag accgagatag ggttgagtgt   6720
tgttccagtt tggaacaaga gtccactatt aaagaacgtg gactccaacg tcaaagggcg   6780
aaaaaccgtc tatcagggcg atggcccact acgtgaacca tcaccctaat caagtttttt   6840
ggggtcgagg tgccgtaaag cactaaatcg gaaccctaaa gggagccccc gatttagagc   6900
ttgacgggga aagccggcga acgtggcgag aaaggaaggg aagaaagcga aaggagcggg   6960
cgctagggcg ctggcaagtg tagcggtcac gctgcgcgta accaccacac ccgccgcgct   7020
taatgcgccg ctacagggcg cgtcgcgcca ttcgccattc aggctgcgca actgttggga   7080
agggcgatcg gtgcgggcct ct                                            7102
```

<210> SEQ ID NO 62
<211> LENGTH: 8045
<212> TYPE: DNA
<213> ORGANISM: Artificial Sequence
<220> FEATURE:
<223> OTHER INFORMATION: plasmid

<400> SEQUENCE: 62

```
catgcccatg ggttaactga tcaatgcatc ctgcatggcg cgcctgatga gcctgaactg     60
cccgggcaaa tcagctgcat taatgaatcg gccaacgcgc ggggagaggc ggtttgcgta    120
ttgggcgctc ttccgcttcc tcgctcactg actcgctgcg ctcggtcgtt cggctgcggc    180
gagcggtatc agctcactca aaggcggtaa tacggttatc cacagaatca ggggataacg    240
caggaaagaa catgtgagca aaaggccagc aaaaggccag gaaccgtaaa aaggccgcgt    300
tgctggcgtt tttccatagg ctccgccccc ctgacgagca tcacaaaaat cgacgctcaa    360
gtcagaggtg gcgaaacccg acaggactat aaagatacca ggcgtttccc cctggaagct    420
ccctcgtgcg ctctcctgtt ccgaccctgc cgcttaccgg atacctgtcc gcctttctcc    480
cttcgggaag cgtggcgctt tctcatagct cacgctgtag gtatctcagt tcggtgtagg    540
tcgttcgctc caagctgggc tgtgtgcacg aaccccccgt tcagcccgac cgctgcgcct    600
```

```
tatccggtaa ctatcgtctt gagtccaacc cggtaagaca cgacttatcg ccactggcag    660
cagccactgg taacaggatt agcagagcga ggtatgtagg cggtgctaca gagttcttga    720
agtggtggcc taactacggc tacactagaa ggacagtatt tggtatctgc gctctgctga    780
agccagttac cttcggaaaa agagttggta gctcttgatc cggcaaacaa accaccgctg    840
gtagcggtgg tttttttgtt tgcaagcagc agattacgcg cagaaaaaaa ggatctcaag    900
aagatccttt gatcttttct acggggtctg acgctcagtg gaacgaaaac tcacgttaag    960
ggattttggt catgagatta tcaaaaagga tcttcaccta gatcctttta aattaaaaat   1020
gaagttttaa atcaatctaa agtatatatg agtaaacttg gtctgacagt taccaatgct   1080
taatcagtga ggcacctatc tcagcgatct gtctatttcg ttcatccata gttgcctgac   1140
tccccgtcgt gtagataact acgatacggg agggcttacc atctggcccc agtgctgcaa   1200
tgataccgcg agacccacgc tcaccggctc cagatttatc agcaataaac cagccagccg   1260
gaagggccga gcgcagaagt ggtcctgcaa ctttatccgc ctccatccag tctattaatt   1320
gttgccggga agctagagta agtagttcgc cagttaatag tttgcgcaac gttgttgcca   1380
ttgctacagg catcgtggtg tcacgctcgt cgtttggtat ggcttcattc agctccggtt   1440
cccaacgatc aaggcgagtt acatgatccc ccatgttgtg caaaaaagcg gttagctcct   1500
tcggtcctcc gatcgttgtc agaagtaagt tggccgcagt gttatcactc atggttatgg   1560
cagcactgca taattctctt actgtcatgc catccgtaag atgcttttct gtgactggtg   1620
agtactcaac caagtcattc tgagaatagt gtatgcggcg accgagttgc tcttgcccgg   1680
cgtcaatacg ggataatacc gcgccacata gcagaacttt aaaagtgctc atcattggaa   1740
aacgttcttc ggggcgaaaa ctctcaagga tcttaccgct gttgagatcc agttcgatgt   1800
aacccactcg tgcacccaac tgatcttcag catcttttac tttcaccagc gtttctgggt   1860
gagcaaaaac aggaaggcaa aatgccgcaa aaaagggaat aagggcgaca cggaaatgtt   1920
gaatactcat actcttcctt tttcaatatt attgaagcat ttatcagggt tattgtctca   1980
tgagcggata catatttgaa tgtatttaga aaaataaaca aataggggtt ccgcgcacat   2040
ttccccgaaa agtgccacct gggtcctttt catcacgtgc tataaaaata attataattt   2100
aaatttttta atataaatat ataaattaaa aatagaaagt aaaaaaagaa attaaagaaa   2160
aaatagtttt tgttttccga agatgtaaaa gactctaggg ggatcgccaa caaatactac   2220
cttttatctt gctcttcctg ctctcaggta ttaatgccga attgtttcat cttgtctgtg   2280
tagaagacca cacacgaaaa tcctgtgatt ttacatttta cttatcgtta atcgaatgta   2340
tatctattta atctgctttt cttgtctaat aaatatatat gtaaagtacg ctttttgttg   2400
aaattttttta aacctttgtt tatttttttt tcttcattcc gtaactcttc taccttcttt   2460
atttactttc taaaatccaa atacaaaaca taaaaataaa taaacacaga gtaaattccc   2520
aaattattcc atcattaaaa gatacgaggc gcgtgtaagt tacaggcaag cgatccgtcc   2580
taagaaacca ttattatcat gacattaacc tataaaaata ggcgtatcac gaggcccttt   2640
cgtctcgcgc gtttcggtga tgacggtgaa aacctctgac acatgcagct cccggagacg   2700
gtcacagctt gtctgtaagc ggatgccggg agcagacaag cccgtcaggg cgcgtcagcg   2760
ggtgttggcg ggtgtcgggg ctggcttaac tatgcggcat cagagcagat tgtactgaga   2820
gtgcaccata tcgactacgt cgtaaggccg tttctgacag agtaaaattc ttgagggaac   2880
tttcaccatt atgggaaatg gttcaagaag gtattgactt aaactccatc aaatggtcag   2940
gtcattgagt gttttttatt tgttgtattt tttttttttt agagaaaatc ctccaatatc   3000
```

```
aaattaggaa tcgtagtttc atgattttct gttacaccta actttttgtg tggtgccctc   3060
ctccttgtca atattaatgt taaagtgcaa ttctttttcc ttatcacgtt gagccattag   3120
tatcaatttg cttacctgta ttcctttact atcctccttt ttctccttct tgataaatgt   3180
atgtagattg cgtatatagt ttcgtctacc ctatgaacat attccatttt gtaatttcgt   3240
gtcgtttcta ttatgaattt catttataaa gtttatgtac aaatatcata aaaaaagaga   3300
atctttttaa gcaaggattt tcttaacttc ttcggcgaca gcatcaccga cttcggtggt   3360
actgttggaa ccacctaaat caccagttct gatacctgca tccaaaacct ttttaactgc   3420
atcttcaatg gccttacctt cttcaggcaa gttcaatgac aatttcaaca tcattgcagc   3480
agacaagata gtggcgatag ggtcaacctt attctttggc aaatctggag cagaaccgtg   3540
gcatggttcg tacaaaccaa atgcggtgtt cttgtctggc aaagaggcca aggacgcaga   3600
tggcaacaaa cccaaggaac ctgggataac ggaggcttca tcggagatga tatcaccaaa   3660
catgttgctg gtgattataa taccatttag gtgggttggg ttcttaacta ggatcatggc   3720
ggcagaatca atcaattgat gttgaacctt caatgtaggg aattcgttct tgatggtttc   3780
ctccacagtt tttctccata atcttgaaga ggccaaaaca ttagctttat ccaaggacca   3840
aataggcaat ggtggctcat gttgtagggc catgaaagcg gccattcttg tgattctttg   3900
cacttctgga acggtgtatt gttcactatc ccaagcgaca ccatcaccat cgtcttcctt   3960
tctcttacca aagtaaatac ctcccactaa ttctctgaca acaacgaagt cagtaccttt   4020
agcaaattgt ggcttgattg gagataagtc taaaagagag tcggatgcaa agttacatgg   4080
tcttaagttg gcgtacaatt gaagttcttt acggattttt agtaaacctt gttcaggtct   4140
aacactaccg gtaccccatt taggaccacc cacagcacct aacaaaacgg catcaacctt   4200
cttggaggct tccagcgcct catctggaag tgggacacct gtagcatcga tagcagcacc   4260
accaattaaa tgattttcga aatcgaactt gacattggaa cgaacatcag aaatagcttt   4320
aagaacctta atggcttcgg ctgtgatttc ttgaccaacg tggtcacctg gcaaaacgac   4380
gatcttctta ggggcagaca taggggcaga cattagaatg gtatatcctt gaaatatata   4440
tatatattgc tgaaatgtaa aaggtaagaa aagttagaaa gtaagacgat tgctaaccac   4500
ctattggaaa aaacaatagg tccttaaata atattgtcaa cttcaagtat tgtgatgcaa   4560
gcatttagtc atgaacgctt ctctattcta tatgaaaagc cggttccggc ctctcacctt   4620
tcctttttct cccaattttt cagttgaaaa aggtatatgc gtcaggcgac ctctgaaatt   4680
aacaaaaaat ttccagtcat cgaatttgat tctgtgcgat agcgcccctg tgtgttctcg   4740
ttatgttgag gaaaaaaata atggttgcta agagattcga actcttgcat cttacgatac   4800
ctgagtattc ccacagttaa ctgcggtcaa gatatttctt gaatcaggcg ccttagaccg   4860
ctcggccaaa caaccaatta cttgttgaga aatagagtat aattatccta taaatataac   4920
gtttttgaac acacatgaac aaggaagtac aggacaattg attttgaaga gaatgtggat   4980
tttgatgtaa ttgttgggat tccatttttta ataaggcaat aatattaggt atgtggatat   5040
actagaagtt ctcctcgacc gtcgatatgc ggtgtgaaat accgcacaga tgcgtaagga   5100
gaaaataccg catcaggaaa ttgtaaacgt taatattttg ttaaaattcg cgttaaattt   5160
ttgttaaatc agctcatttt ttaaccaata ggccgaaatc ggcaaaatcc cttataaatc   5220
aaaagaatag accgagatag ggttgagtgt tgttccagtt tggaacaaga gtccactatt   5280
aaagaacgtg gactccaacg tcaaagggcg aaaaaccgtc tatcagggcg atggcccact   5340
```

acgtgaacca tcaccctaat caagtttttt ggggtcgagg tgccgtaaag cactaaatcg 5400
gaaccctaaa gggagccccc gatttagagc ttgacgggga aagccggcga acgtggcgag 5460
aaaggaaggg aagaaagcga aaggagcggg cgctagggcg ctggcaagtg tagcggtcac 5520
gctgcgcgta accaccacac ccgccgcgct taatgcgccg ctacagggcg cgtcgcgcca 5580
ttcgccattc aggctgcgca actgttggga agggcgatcg gtgcgggcct cttcgctatt 5640
acgccagctg atttgcccgg gcagttcagg ctcatcaggc gcgccatgca gggatatcag 5700
atctcagttc gagtttatca ttatcaatac tgccatttca aagaatacgt aaataattaa 5760
tagtagtgat ttcctaact ttatttagtc aaaaaattag ccttttaatt ctgctgtaac 5820
ccgtacatgc ccaaaatagg gggcgggtta cacagaatat ataacatcgt aggtgtctgg 5880
gtgaacagtt tattcctggc atccactaaa tataatggag cccgcttttt aagctggcat 5940
ccagaaaaaa aaagaatccc agcaccaaaa tattgttttc ttcaccaacc atcagttcat 6000
aggtccattc tcttagcgca actacagaga acaggggcac aaacaggcaa aaaacggaca 6060
caacctcaat ggagtgatgc aacctgcctg gagtaaatga tgacacaagg caattgaccc 6120
acgcatgtat ctatctcatt ttcttacacc ttctattacc ttctgctctc tctgatttgg 6180
aaaaagctga aaaaaaaggt tgaaaccagt tccctgaaat tattccccta cttgactaat 6240
aagtatataa agacggtagg tattgattgt aattctgtaa atctatttct taaacttctt 6300
aaattctact tttatagtta gtcttttttt tagttttaaa acaccaagaa cttagtttcg 6360
aataaacaca cataaacaaa caaaaagctt aaaatggttg ctggtccaaa caaggatttg 6420
gaaaacttgg aaagaatgat gtactggaaa accactttga aggcttggtc ttgtttttttg 6480 gttggtgcta agttgaacga aaagttggaa accgatgata tcttgaaggg tatccataag 6540
ttgttcacct tgagagtcca attgagattg aacgttttcc aatacccaaa gaagagattc 6600
gtcaccgaag aaatcaatgg ttggtctgat gatttcgttg acttcgttga ttacccaact 6660
gatgacttcg atatcattga agcctttaag caacaacaca atcaatactt cgaattgggt 6720
gtccaaaaac cattgtggaa gttggttgtt ttgaaccacc aatacttggt tatcttgtgc 6780
gatcatacct tgtacgatgg taatactgcc ttgtacattt gcgaagattt gatcaccatc 6840
ttgaacgata gagatatccc agttgataga atcccagata tcaagccata ccacgatttg 6900
ttgaaaccta aattgggtca taccatcaag accgttattc aaacttttgc tccaaaatgg 6960
gcttacccat tggttaactt gatctacaga ccaaagtctg aattcgaaac tggtgcttat 7020
gatgattggg gtgttaccca taagattgaa agaactacca acaagttgaa gcacttgatt 7080
accatcacca acgaagaatt ctccatcatc aaaaagttga ccaagtccca tggtgttaac 7140
tttactgctt tttgggccta cattaacgtt ttggctgttg ctcaattggg taaatctgct 7200
gttgatttgt ccatcccatt caacatgaga actaatttgt tgccaccaga atacttgaga 7260
tggtacggtt tgttggtttc ccatgttact ttgaatgttc acaccaaggt tgatcacgat 7320
tccattgatt gggatttcgt cagatttttg aacggttcag ttgcccataa gtaccaagtt 7380
aagcaatctc aaatgttggg tatgatcaag tacgtttctg ccagaggttt gattgaatct 7440
gctttgaaat ctccaagaaa gggtggtttg gaagtttcta atttgggttt gagagttgat 7500
ccagatggtg aatcttggaa aaagtacact ccagaagaat tttcttctc cttgccaaac 7560 gatttgtccg gttacaatgt ttccaacgcc gttatttctt ctaagaccaa gaccaacatt 7620
atcttggatg gtgttccaga atttgccaac gaatttccaa catacgctaa caacgttgaa 7680
accattttga gaaacgccat caacggttac tacgaatgac cgcggcacgt ccgacggcgg 7740

```
cccgacgggt ccgaggcctc ggagatccgt ccccctttc ctttgtcgat atcatgtaat    7800

tagttatgtc acgcttacat tcacgccctc cccccacatc cgctctaacc gaaaaggaag   7860

gagttagaca acctgaagtc taggtcccta tttattttt tatagttatg ttagtattaa    7920

gaacgttatt tatatttcaa atttttcttt tttttctgta cagacgcgtg tacgcatgta   7980

acattatact gaaaaccttg cttgagaagg ttttgggacg ctcgaaggct ttaatttgca   8040

agctg                                                              8045
```

<210> SEQ ID NO 63
<211> LENGTH: 10265
<212> TYPE: DNA
<213> ORGANISM: Artificial Sequence
<220> FEATURE:
<223> OTHER INFORMATION: plasmid

<400> SEQUENCE: 63

```
ccgttaactg tcagaccaag tttactcata tatactttag attgatttaa aacttcattt     60

ttaatttaaa aggatctagg tgaagatcct ttttgataat ctcatgacca aaatccctta    120

acgtgagttt tcgttccact gagcgtcaga ccccgtagaa aagatcaaag gatcttcttg    180

agatcctttt tttctgcgcg taatctgctg cttgcaaaca aaaaaaccac cgctaccagc    240

ggtggtttgt ttgccggatc aagagctacc aactcttttt ccgaaggtaa ctggcttcag    300

cagagcgcag ataccaaata ctgttcttct agtgtagccg tagttaggcc accacttcaa    360

gaactctgta gcaccgccta catacctcgc tctgctaatc ctgttaccag tggctgctgc    420

cagtggcgat aagtcgtgtc ttaccgggtt ggactcaaga cgatagttac cggataaggc    480

gcagcggtcg ggctgaacgg ggggttcgtg cacacagccc agcttggagc gaacgaccta    540

caccgaactg agatacctac agcgtgagct atgagaaagc gccacgcttc ccgaagggag    600

aaaggcggac aggtatccgg taagcggcag ggtcggaaca ggagagcgca cgagggagct    660

tccaggggga aacgcctggt atctttatag tcctgtcggg tttcgccacc tctgacttga    720

gcgtcgattt ttgtgatgct cgtcaggggg gcggagccta tggaaaaacg ccagcaacgc    780

ggccttttta cggttcctgg ccttttgctg gccttttgct cacatgttct ttcctgcgtt    840

atcccctgat tctgtggata accgtattac cgcctttgag tgagctgata ccgctcgccg    900

cagccgaacg accgagcgca gcgagtcagt gagcgaggaa gcggaagagc gcccaatacg    960

catgccacac caaatatggc gatctcggcc ttttcgtttc ttggagctgg gacatgtttg   1020

ccatcgatcc atctaccacc agaacggccg ttagatctgc tgccaccgtt gtttccaccg   1080

aagaaaccac cgttgccgta accaccacga cggttgttgc taaagaagct gccaccgcca   1140

cggccaccgt tgtagccgcc gttgttgtta ttgtagttgc tactgttatt tctggcactt   1200

cttggttttc ctcttaagtg aggaggaaca taaccattct cgttgttgtc gttgatgctt   1260

aaattttgca cttgttcgct cagttcagcc ataatatgaa atgcttttct tgttgttctt   1320

acggaatacc acttgccacc tatcaccaca actaactttt tcccgttcct ccatctcttt   1380

tatatttttt ttctcgatcg agttcaagag aaaaaaaaag aaaaagcaaa aagaaaaaag   1440

gaaagcgcgc ctcgttcaga atgacacgta tagaatgatg cattaccttg tcatcttcag   1500

tatcatactg ttcgtataca tacttactga cattcatagg tatacatata tacacatgta   1560

tatatatcgt atgctgcagc tttaaataat cggtgtcact acataagaac acctttggtg   1620

gagggaacat cgttggtacc attgggcgag gtggcttctc ttatggcaac cgcaagagcc   1680
```

-continued

```
ttgaacgcac tctcactacg gtgatgatca ttcttgcctc gcagacaatc aacgtggagg   1740

gtaattctgc tagcctctgc aaagctttca agaaaatgcg ggatcatctc gcaagagaga   1800

tctcctactt tctccctttg caaaccaagt tcgacaactg cgtacggcct gttcgaaaga   1860

tctaccaccg ctctggaaag tgcctcatcc aaaggcgcaa atcctgatcc aaaccttttt   1920

actccacgca cggcccctag ggcctcttta aaagcttgac cgagagcaat cccgcagtct   1980

tcagtggtgt gatggtcgtc tatgtgtaag tcaccaatgc actcaacgat tagcgaccag   2040

ccggaatgct tggccagagc atgtatcata tggtccagaa accctatacc tgtgtggacg   2100

ttaatcactt gcgattgtgt ggcctgttct gctactgctt ctgcctcttt ttctgggaag   2160

atcgagtgct ctatcgctag ggaccaccc tttaaagaga tcgcaatctg aatcttggtt    2220

tcatttgtaa tacgctttac tagggctttc tgctctgtca tctttgcctt cgtttatctt   2280

gcctgctcat tttttagtat attcttcgaa gaaatcacat tactttatat aatgtataat   2340

tcattatgtg ataatgccaa tcgctaagaa aaaaaaagag tcatccgcta ggtggaaaaa   2400

aaaaaatgaa aatcattacc gaggcataaa aaaatataga gtgtactaga ggaggccaag   2460

agtaatagaa aaagaaaatt gcgggaaagg actgtgttat gacttccctg actaatgccg   2520

tgttcaaacg atacctggca gtgactccta gcgctcacca agctcttaaa acgagaatta   2580

agaaaaagtc gtcatctttc gataagtttt tcccacagca aagcaatagt agaaaaaaac   2640

aatgggaaac gttgaatgaa gacaaagcgt cgtggtttaa aaggaaatac gctcacgtac   2700

atgctaggga acaggaccgt gcagcggatc tgatatccct gcatggcgcg tcatcgtcca   2760

cctccggaga acaggccacc atcacgcatc tgtgtctgaa tttcatcacg acgcgcctta   2820

agggcaccaa taactgcctt aaaaaaatta cgcccgccc tgccactcat cgcagtactg    2880

ttgtaattca ttaagcattc tgccgacatg gaagccatca cagacggcat gatgaacctg   2940

aatcgccagc ggcatcagca ccttgtcgcc ttgcgtataa tatttgccca tggtgaaaac   3000

gggggcgaag aagttgtcca tattggccac gtttaaatca aaactggtga aactcaccca   3060

gggattggct gagacgaaaa acatattctc aataaaccct ttagggaaat aggccaggtt   3120

ttcaccgtaa cacgccacat cttgcgaata tatgtgtaga aactgccgga aatcgtcgtg   3180

gtattcactc cagagcgatg aaaacgtttc agtttgctca tggaaaacgg tgtaacaagg   3240

gtgaacacta tcccatatca ccagctcacc gtctttcatt gccatacgga attccggatg   3300

agcattcatc aggcgggcaa gaatgtgaat aaaggccgga taaaacttgt gcttattttt   3360

ctttacggtc tttaaaaagg ccgtaatatc cagctgaacg gtctggttat aggtacattg   3420

agcaactgac tgaaatgcct caaaatgttc tttacgatgc cattgggata tatcaacggt   3480

ggtatatcca gtgatttttt tctccatttt agcttcctta gctcctgaaa atctcgataa   3540

ctcaaaaaat acgcccggta gtgatcttat ttcattatgg tgaaagttgg aacctcttac   3600

gtgccgatca acgtctcatt ttcgccaaaa gttggcccag ggcttcccgg tatcaacagg   3660

gacaccagga tttatttatt ctgcgaagtg atcttccgtc acaggtattg gaccaccctg   3720

tgggtttata agcgcgctgc tggcgtgtaa ggcggtgacg gcgaaggaag ggtccttttc   3780

atcacgtgct ataaaaataa ttataattta aattttttaa tataaatata taaattaaaa   3840

atagaaagta aaaaaagaaa ttaaagaaaa aatagttttt gttttccgaa gatgtaaaag   3900

actctagggg gatcgccaac aaatactacc ttttatcttg ctcttcctgc tctcaggtat   3960

taatgccgaa ttgtttcatc ttgtctgtgt agaagaccac acacgaaaat cctgtgattt   4020

tacattttac ttatcgttaa tcgaatgtat atctatttaa tctgcttttc ttgtctaata   4080
```

```
aatatatatg taaagtacgc tttttgttga aattttttaa acctttgttt attttttttt   4140
cttcattccg taactcttct accttcttta tttactttct aaaatccaaa tacaaaacat   4200
aaaaataaat aaacacagag taaattccca aattattcca tcattaaaag atacgaggcg   4260
cgtgtaagtt acaggcaagc gatccgtcct aagaaaccat tattatcatg acattaacct   4320
ataaaaatag gcgtatcacg aggccctttc gtctcgcgcg tttcggtgat gacggtgaaa   4380
acctctgaca catgcagctc ccggagacgg tcacagcttg tctgtaagcg gatgccggga   4440
gcagacaagc ccgtcagggc gcgtcagcgg gtgttggcgg gtgtcggggc tggcttaact   4500
atgcggcatc agagcagatt gtactgagag tgcaccacgg cgcgtggcac ccttgcgggc   4560
catgtcatac accgccttca gagcagccgg acctatctgc ccgttacgcg ccagcttgca   4620
aattaaagcc ttcgagcgtc ccaaaacctt ctcaagcaag gttttcagta taatgttaca   4680
tgcgtacacg cgtctgtaca gaaaaaaaag aaaaatttga aatataaata acgttcttaa   4740
tactaacata actataaaaa aataaatagg gacctagact tcaggttgtc taactccttc   4800
cttttcggtt agagcggatg tgggggggagg gcgtgaatgt aagcgtgaca taactaatta   4860
catgatatcg acaaaggaaa agggggacgg atctccgagg cctcggaccc gtcgggccgc   4920
cgtcggacgt gccgcggtta tttattagat tcttggcaac aggcaaggat ggactgcttg   4980
acactttcgc aagcattttt gagttcctct ggggacatgg cggcgttaca gcagattttc   5040
aagctaggga caattggtag cgtctcctgt tttaaaacaa tagtgtttct tgtgatgaga   5100
acgttgtagt taataagagc atgatctact atggactgca gaaatttttc ctcctcttcg   5160
tatggctcaa tgaatttgtt tgtctgggac ttcttttgca aagctgacat ggtttcgaat   5220
agctgttcgc aggtgtatcc gaacttgcga gacctatatg cgggagtcag ttgcagatgt   5280
aggacagcag acactggaga ggacgtgacg attacgtatg aacgcaagga gtcgtcagat   5340
gcaaaggaat catgcaaaga tttggatagt ttttgcagcg tctggacggc gtcgttgttg   5400
gagtccatca atttcaagac tttggagacg gatgtgacgg tgtaagccgg caaacaggca   5460
gaaaaacaat atgcattgga accaatacgc tggtgcaaac acataacact gtcacccagg   5520
acaaaaccac cggtggaccc caacgcggtg gccatggacc caacggtaat gtcaatggca   5580
gttgcgcgat ccatgttgaa gtgctctgac aacccacggc ccgtagcgcc aagaacacca   5640
atggagaagg tttcgtcaac aaatagtctg aacttgtact tgttcttcag cttagtcaac   5700
tcaggcaacg gagctaaatc gcccgagttg tggaaaatac cctcagtgac gataaatttt   5760
cttggaatgg cgggcagttt ctcaagtttc tcctgttcgg tcaactcgtt taataaacat   5820
tctagcgaat tcatatcgtt gtggttgaag tagtagactg tggatctgct tagttgcaga   5880
gcattttgca ctggtaatga cacctggtcg tctgccacga taacatcacc acgctttgtg   5940
aaagcaggca gaacagaggg tgcggcacaa aagtcttgcc cgtacagaac ggaaccttgg   6000
gtgccaaaga actgtgctaa atcatattcc aacgtgtaat gaacgtcctg gttaccgtag   6060
aacccggcgg gaccacaggc gcccacaccg taattcttga tagtggtctt gaccacttct   6120
ttcacgggct ccgtagcgga caattgcaaa aagttgttcg aggccaaatt gaaaacattg   6180
gtatacttct cctgcagatt gtttctggtg atagtaatat ggttctgaat gggcatttcc   6240
atggtgacgg gtgttttggc caccctccac gattgctcat cggtggcaga agggtcgact   6300
agaggctcgg gctcccagtc ctcaattagc gcgtcaatct cctggggcga taggttgggc   6360
ttctgtgctt gaagactctt tttctgttgt ggcttggaca agtaatagat gatcccgtat   6420
```

-continued

```
aaaataagcc ctatctcaac cgtggtcctg tatggatcgt catgatgcga tttcttgatg   6480

tacgaaacga tgaattggcc tcccgggatt tgagtcaaca ccagattgaa gtagtaccat   6540

aggtacgatg aggtggtaac aataaatgcc ggaatcggta ttgatttggg taaaacctct   6600

gggatgtgtg ccattttaag ctttttgttt gtttatgtgt gtttattcga aactaagttc   6660

ttggtgtttt aaaactaaaa aaaagactaa ctataaaagt agaatttaag aagtttaaga   6720

aatagattta cagaattaca atcaatacct accgtcttta tatacttatt agtcaagtag   6780

gggaataatt tcagggaact ggtttcaacc ttttttttca gctttttcca aatcagagag   6840

agcagaaggt aatagaaggt gtaagaaaat gagatagata catgcgtggg tcaattgcct   6900

tgtgtcatca tttactccag gcaggttgca tcactccatt gaggttgtgt ccgttttttg   6960

cctgtttgtg cccctgttct ctgtagttgc gctaagagaa tggacctatg aactgatggt   7020

tggtgaagaa aacaatattt tggtgctggg attctttttt tttctggatg ccagcttaaa   7080

aagcgggctc cattatattt agtggatgcc aggaataaac tgttcaccca gacacctacg   7140

atgttatata ttctgtgtaa cccgcccccct attttgggca tgtacgggtt acagcagaat   7200

taaaaggcta atttttttgac taaataaagt taggaaaatc actactatta attatttacg   7260

tattctttga aatggcagta ttgataatga taaactcgaa ctgggcgcgt cgtgccgtcg   7320

ttgttaatca ccacatggtt attctgctca aacgtcccgg acgcctgcga acgcgccgaa   7380

ggaaaatgag aaatatcgag ggagacgatt cagaggagca ggacaaacta taaccgactg   7440

tttgttggag gatgccgtac ataacgaaca ctgctgaagc taccatgtct acagtttaga   7500

ggaatgggta caactcacag gcgagggatg gtgttcactc gtgctagcaa acgcggtggg   7560

agcaaaaagt agaatattat cttttattcg tgaaacttcg aacactgtca tctaaagatg   7620

ctatatacta atataggcat acttgataat gaaaactata aatcgtaaag acataagaga   7680

tccgcggtca attaacaaaa tacttgtcgt ccttacaatc ttcaggtgtt ctcctgataa   7740

cttcctcgat gtcccatctt tgacgtttac cgtcgtaact ggatttgccg gaatttgatt   7800

tcaaattcaa tttgtcacca acttcactaa catgacgcag taaataatcg atatcttcct   7860

ttgttaaaga tgcagacata cagaatctta ctcttgattc gatcagcgga gtagcaggat   7920

aagcaacaac aacaacagca atccgtcttt gtaacatcat tctcgaaaat gcgggcatct   7980

ttgagggaca atacagtagt aagggaataa ctggtgagtc agccacaccg tagacaataa   8040

atcctaacct ttgcaaagct aaacgtagat aacgggaatt aaaggctata cgttgcaatc   8100

tttcagtacc ttgtccggga catatttcac cactaatggt ttgtaatgag gaaatagttt   8160

gagctaaaac aggagccggc attgactcac tataactcac agtggttaaa tccaacctca   8220

gtctatcgat aatccattga tcagcagcaa tgtaaccacc agcagcacca aacgacttag   8280

tgaaagtacc cattagaatg tcgacgtcct tgggatcaac gccaaatatt tcacaaacac   8340

cgcgaccagt tgggcccata gcgcctatag aatgggcttc atcgataaac aagtaacatt   8400

tatatttctt cttcaattca accaattttg gcaagttaca caaagtacct tccatggaaa   8460

acaacccttc tgcgcaaatt aaaattttct tccatggacg atttgttttt ggttgaccaa   8520

gtactatctg ttctctgatg agcttttcta aacccaccat atcaccatgc ttgaaagttc   8580

gcacagcagc accagaaagc ctaacacctg ttctaataga ggtgtggttc aattcgtcag   8640

agataactaa acacttttta tcgaggaaag cgttgaacaa gtttgcattt gtaccataac   8700

ccatcgaaaa aacgagggca tcctccttac cgataaatct agcaactaat ttctctgctt   8760

taatgtgcaa atctgtggta ccgatttgag ctcttggacc accagattga atagaatatt   8820
```

```
tatcgacaga ttccaaggcg gcatcggtac attgaccctt actttgtgcg aagcctaaat   8880

agttatatga tgataagttc atgcatggat acactgcgcc tgagtaggta aaatactcat   8940

ttatattatg agaaattcta tcaatacaac gaataaatct accaggaaca ccagtagttg   9000

gtctagaaaa gcaatcatca attctcattt taattctcct gacataaaaa ctctcgaaat   9060

ttgaaaacca aggtgctaac ccatcatgct ctaaaagatc cagatgtttg tttttttgga   9120

aggtcatacc taagaagtcg tgaacatgac ctaatataat cagaatcaaa taatttagat   9180

atgttaacaa agaaatgtaa taaggagggg tgtcgacaac gggctcaggt agtggcttcc   9240

catgacgtga cttgacttga tacaaatgcc ccggagaatc tagtgtacca tattcatttt   9300

ctttttgtat gtcgtctggc agctcctctg gttcgcacag ggcacacgg gtatagtttg   9360

caggagtact cattttaagc tttgttttat atttgttgta aaaagtagat aattacttcc   9420

ttgatgatct gtaaaaaaga gaaaaagaaa gcatctaaga acttgaaaaa ctacgaatta   9480

gaaaagacca aatatgtatt tcttgcattg accaatttat gcaagtttat atatatgtaa   9540

atgtaagttt cacgaggttc tactaaacta aaccaccccc ttggttagaa gaaaagagtg   9600

tgtgagaaca ggctgttgtt gtcacacgat tcggacaatt ctgtttgaaa gagagagagt   9660

aacagtacga tcgaacgaac tttgctctgg agatcacagt gggcatcata gcatgtggta   9720

ctaaaccctt tcccgccatt ccagaacctt cgattgcttg ttacaaaacc tgtgagccgt   9780

cgctaggacc ttgttgtgtg acgaaattgg aagctgcaat caataggaag acaggaagtc   9840

gagcgtgtct gggtttttttc agttttgttc tttttgcaaa caaatcacga gcgacggtaa   9900

tttctttctc gataagaggc cacgtgcttt atgagggtaa catcaattca agaaggaggg   9960

aaacacttcc tttttctggc cctgataata gtatgagggt gaagccaaaa taaaggattc  10020

gcgcccaaat cggcatcttt aaatgcaggt atgcgatagt tcctcactct ttccttactc  10080

acgagtaatt cttgcaaatg cctattatgc agatgttata atatctgtgc gtggcgcgtc  10140

cggctgtctg ccatgctgcc cggtgtaccg acataaccgc cggtggcata gccgcgcata  10200

cgcgttttcc cgtctttcag tgccttgttc agttcttcct gacgggcggt atatttctcc  10260

agctt                                                              10265
```

<210> SEQ ID NO 64
<211> LENGTH: 6278
<212> TYPE: DNA
<213> ORGANISM: Artificial Sequence
<220> FEATURE:
<223> OTHER INFORMATION: plasmid

<400> SEQUENCE: 64

```
gcgatccgtc ctaagaaacc attattatca tgacattaac ctataaaaat aggcgtatca     60

cgaggccctt tcgtctcgcg cgtttcggtg atgacggtga aaacctctga cacatgcagc    120

tcccggagac ggtcacagct tgtctgtaag cggatgccgg gagcagacaa gcccgtcagg    180

gcgcgtcagc gggtgttggc gggtgtcggg gctggcttaa ctatgcggca tcagagcaga    240

ttgtactgag agtgcaccat accacagctt ttcaattcaa ttcatcattt ttttttttatt    300

cttttttttg atttcggttt ctttgaaatt tttttgattc ggtaatctcc gaacagaagg    360

aagaacgaag gaaggagcac agacttagat tggtatatat acgcatatgt agtgttgaag    420

aaacatgaaa ttgcccagta ttcttaaccc aactgcacag aacaaaaacc tgcaggaaac    480

gaagataaat catgtcgaaa gctacatata aggaacgtgc tgctactcat cctagtcctg    540
```

```
ttgctgccaa gctatttaat atcatgcacg aaaagcaaac aaacttgtgt gcttcattgg    600
atgttcgtac caccaaggaa ttactggagt tagttgaagc attaggtccc aaaatttgtt    660
tactaaaaac acatgtggat atcttgactg atttttccat ggagggcaca gttaagccgc    720
taaaggcatt atccgccaag tacaattttt tactcttcga agacagaaaa tttgctgaca    780
ttggtaatac agtcaaattg cagtactctg cgggtgtata cagaatagca gaatgggcag    840
acattacgaa tgcacacggt gtggtgggcc caggtattgt tagcggtttg aagcaggcgg    900
cagaagaagt aacaaaggaa cctagaggcc ttttgatgtt agcagaattg tcatgcaagg    960
gctccctatc tactggagaa tatactaagg gtactgttga cattgcgaag agcgacaaag   1020
attttgttat cggctttatt gctcaaagag acatgggtgg aagagatgaa ggttacgatt   1080
ggttgattat gacacccggt gtgggtttag atgacaaggg agacgcattg ggtcaacagt   1140
atagaaccgt ggatgatgtg gtctctacag gatctgacat tattattgtt ggaagaggac   1200
tatttgcaaa gggaagggat gctaaggtag agggtgaacg ttacagaaaa gcaggctggg   1260
aagcatattt gagaagatgc ggccagcaaa actaaaaaac tgtattataa gtaaatgcat   1320
gtatactaaa ctcacaaatt agagcttcaa tttaattata tcagttatta ccctatgcgg   1380
tgtgaaatac cgcacagatg cgtaaggaga aaataccgca tcaggaaatt gtaagcgtta   1440
atattttgtt aaaattcgcg ttaaattttt gttaaatcag ctcatttttt aaccaatagg   1500
ccgaaatcgg caaaatccct tataaatcaa aagaatagac cgagataggg ttgagtgttg   1560
ttccagtttg gaacaagagt ccactattaa agaacgtgga ctccaacgtc aaagggcgaa   1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt   1740
gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tccattcgcc attcaggctg cgcaactgtt gggaagggcg   1920
atcggtgcgg gcctcttcgc tattacgcgg cgcgccagat cttcagcagc tctgatgtag   1980
atacacgcat ctcgatatgt tttattttta ctatatatac ataaaagaaa taaaaaatga   2040
taacgtgtat attattattc atataatcaa tgagggtcat tttctgaaac gcaaaaaacg   2100
gtaaatggaa aaaaaataaa gatagaaaaa gaaaacaaac aaaggaaagg ttagcatatt   2160
aaataactga gctgatactt caacagcatc gctgaagaga acagtattga aaccgaaaca   2220
ttttctaaag gcaaacaagg tactccatat ttgctggacg tgttctttct ctcgtttcat   2280
atgcataatt ctgtcataag cctgttcttt ttcctggctt aaatatcccg ttttgcaaaa   2340
gagaaatcta ttccacatat ttcattcatt cggctaccat actaaggata aactaatccc   2400
gttgtttttt ggcctcatca cataattata aactactaac ccattatcag aagcttaaaa   2460
tgaagtttac gttagaagac caagttgtgt tgatcactgg tggttcacaa ggtcttggaa   2520
aggaattcgc caaaaaatat tataatgagg ctgaaaacac aaagattatt atcgtcagta   2580
ggtcagaggc tagactgctg gacacatgca acgaaattag gattgaagct cacctgagaa   2640
gggaaaccac tgacgagggc caagtgcaac ataagttggc tgcgcccttg gaccttgagc   2700
aacggttatt ttactaccca tgcgacttgt cctgctacga atccgtggaa tgtttgttca   2760
atgccctgag agacttggat ttactcccta cacaaacgtt atgctgtgca ggggggggctg   2820
ttcctaagtt atttcgtggg ctaagcggac atgagttgaa cttgggtatg gacatcaact   2880
ataaaacaac tttgaacgtg gcacatcaga ttgcccttgc agagcaaacc aaggaacacc   2940
```

```
acctcatcat cttttctagt gccaccgcgc tttacccatt tgtgggctat tcccagtatg   3000
cgcctgcaaa agctgcaatc aaatcactgg tagcaatctt aagacaagaa ctgacgaact   3060
tccgtatcag ttgtgtttat cctggtaatt ttgaaagcga aggtttcact gtagagcagc   3120
taacgaaacc cgaaattaca aagttgatcg aaggcccctc agacgctatc ccatgcaaac   3180
aagcatgtga tatcattgcc aagtcgctgg ccagaggtga tgatgacgtt tttacagatt   3240
ttgtcggatg gatgataatg gggatggacc ttgggctcac cgcaaagaaa agccgctttg   3300
ttccgttgca atggattttt ggtgtcctat caaacattct ggtcgtgcca ttctacatgg   3360
ttggctgttc ctggtatatc aggaaatggt ttcgtgaaaa tgacggcaag aaggccaact   3420
gaccgcggcc gcaggcctaa attgatctag agctttggac ttcttcgcca gaggtttggt   3480
caagtctcca atcaaggttg tcggcttgtc taccttgcca gaaatttacg aaaagatgga   3540
aaagggtcaa atcgttggta gatacgttgt tgacacttct aaataagcga atttcttatg   3600
atttatgatt tttattatta aataagttat aaaaaaaata agtgtataca aattttaaag   3660
tgactcttag gttttaaaac gaaaattctt gttcttgagt aactctttcc tgtaggtcag   3720
gttgctttct caggtatagc atgaggtcgc tcttattgac cacacctcta ccggcatgcg   3780
gcgcgccatt aatgaatcgg ccaacgcgcg gggagaggcg gtttgcgtat tgggcgctct   3840
tccgcttcct cgctcactga ctcgctgcgc tcggtcgttc ggctgcggcg agcggtatca   3900
gctcactcaa aggcggtaat acggttatcc acagaatcag gggataacgc aggaaagaac   3960
atgtgagcaa aaggccagca aaaggccagg aaccgtaaaa aggccgcgtt gctggcgttt   4020
ttccataggc tccgcccccc tgacgagcat cacaaaaatc gacgctcaag tcagaggtgg   4080
cgaaacccga caggactata aagataccag gcgtttcccc ctggaagctc cctcgtgcgc   4140
tctcctgttc cgaccctgcc gcttaccgga tacctgtccg cctttctccc ttcgggaagc   4200
gtggcgcttt ctcatagctc acgctgtagg tatctcagtt cggtgtaggt cgttcgctcc   4260
aagctgggct gtgtgcacga accccccgtt cagcccgacc gctgcgcctt atccggtaac   4320
tatcgtcttg agtccaaccc ggtaagacac gacttatcgc cactggcagc agccactggt   4380
aacaggatta gcagagcgag gtatgtaggc ggtgctacag agttcttgaa gtggtggcct   4440
aactacggct acactagaag gacagtattt ggtatctgcg ctctgctgaa gccagttacc   4500
ttcggaaaaa gagttggtag ctcttgatcc ggcaaacaaa ccaccgctgg tagcggtggt   4560
ttttttgttt gcaagcagca gattacgcgc agaaaaaaag gatctcaaga agatcctttg   4620
atcttttcta cggggtctga cgctcagtgg aacgaaaact cacgttaagg gattttggtc   4680
atgagattat caaaaaggat cttcacctag atccttttaa attaaaaatg aagttttaaa   4740
tcaatctaaa gtatatatga gtaaacttgg tctgacagtt accaatgctt aatcagtgag   4800
gcacctatct cagcgatctg tctatttcgt tcatccatag ttgcctgact ccccgtcgtg   4860
tagataacta cgatacggga gggcttacca tctggcccca gtgctgcaat gataccgcga   4920
gacccacgct caccggctcc agatttatca gcaataaacc agccagccgg aagggccgag   4980
cgcagaagtg gtcctgcaac tttatccgcc tccatccagt ctattaattg ttgccgggaa   5040
gctagagtaa gtagttcgcc agttaatagt ttgcgcaacg ttgttgccat tgctacaggc   5100
atcgtggtgt cacgctcgtc gtttggtatg gcttcattca gctccggttc ccaacgatca   5160
aggcgagtta catgatcccc catgttgtgc aaaaaagcgg ttagctcctt cggtcctccg   5220
atcgttgtca gaagtaagtt ggccgcagtg ttatcactca tggttatggc agcactgcat   5280
```

```
aattctctta ctgtcatgcc atccgtaaga tgcttttctg tgactggtga gtactcaacc   5340
aagtcattct gagaatagtg tatgcggcga ccgagttgct cttgcccggc gtcaatacgg   5400
gataataccg cgccacatag cagaacttta aaagtgctca tcattggaaa acgttcttcg   5460
gggcgaaaac tctcaaggat cttaccgctg ttgagatcca gttcgatgta acccactcgt   5520
gcacccaact gatcttcagc atcttttact ttcaccagcg tttctgggtg agcaaaaaca   5580
ggaaggcaaa atgccgcaaa aaagggaata agggcgacac ggaaatgttg aatactcata   5640
ctcttccttt ttcaatatta ttgaagcatt tatcagggtt attgtctcat gagcggatac   5700
atatttgaat gtatttagaa aaataaacaa ataggggttc cgcgcacatt tccccgaaaa   5760
gtgccacctg ggtccttttc atcacgtgct ataaaaataa ttataattta aattttttaa   5820
tataaatata taaattaaaa atagaaagta aaaaaagaaa ttaaagaaaa aatagttttt   5880
gttttccgaa gatgtaaaag actctagggg gatcgccaac aaatactacc ttttatcttg   5940
ctcttcctgc tctcaggtat taatgccgaa ttgtttcatc ttgtctgtgt agaagaccac   6000
acacgaaaat cctgtgattt tacattttac ttatcgttaa tcgaatgtat atctatttaa   6060
tctgcttttc ttgtctaata aatatatatg taaagtacgc tttttgttga aattttttaa   6120
acctttgttt attttttttt cttcattccg taactcttct accttcttta tttactttct   6180
aaaatccaaa tacaaaacat aaaaataaat aaacacagag taaattccca aattattcca   6240
tcattaaaag atacgaggcg cgtgtaagtt acaggcaa                           6278
```

<210> SEQ ID NO 65
<211> LENGTH: 7697
<212> TYPE: DNA
<213> ORGANISM: Artificial Sequence
<220> FEATURE:
<223> OTHER INFORMATION: plasmid

<400> SEQUENCE: 65

```
tcgctattac gccagctgat ttgcccgggc agttcaggct catcaggcgc gccatgcagg     60
atgcattgat cagttaaccc atgggcatgc agcttgcaaa ttaaagcctt cgagcgtccc    120
aaaaccttct caagcaaggt tttcagtata atgttacatg cgtacacgcg tctgtacaga    180
aaaaaaagaa aaatttgaaa tataaataac gttcttaata ctaacataac tataaaaaaa    240
taaataggga cctagacttc aggttgtcta actccttcct tttcggttag agcggatgtg    300
gggggagggc gtgaatgtaa gcgtgacata actaattaca tgatatcgac aaaggaaaag    360
ggggacggat ctccgaggcc tcggacccgt cgggccgccg tcggacgtgc cgcggttaat    420
cagtcttttt gtccttgtag atttcagctt tcttcttttg cttggcgatt tctctgtcgt    480
gtaaaaattc tttgtacttg gcaatggtaa tagccttttg cttttctctg tattcgtcga    540
tttctttgta tctggtgtta gagaaaacgt cccaatgggt gaaaaatggt tgagagaagt    600
tggtcttgat accgaattgt tgatgatgga tatcatggta gatggagttg tttgggaaca    660
agatttggaa tggatcatat ggcaaggaat aaccgcaatg atcatcaacg gttttcaagg    720
tagagaaagt gtacaagaca atggattctc ttggagtcaa ttgagtaacg atagcagcaa    780
taccagtacc caaagtatcc aacaaaaaac cttcgaatgg atcgttatac aaggcaccaa    840
aagcatatgg aacatataat ctgtggtgtc tggagtggaa tcttttgtac aaggtcttgt    900
tcaaatgcat gattctgtgc aaccaatatt gccaagagtc gataatcaag aaggccaaac    960
caatcttcaa acaggaccaa ccatacatat tccagtagta agcaacatcg aaaggcaaaa   1020
atggcaaagt ttgttgcaac ttccaggctt gatattcttc atcaccagtg tattgaattg   1080
```

```
ggtcgaagta ggtgaagatg taaccaacaa cagattggat gaagtgttgc aagacaacgt   1140
ccttcaaaac atcgaactta gtagctttgt ttctactgga gacttcttct ggtgggtgaa   1200
ttctgtataa ttcggcaatt tccaaggtgt cgataacgta gaagaaacca gagtaagaat   1260
agtaggcgat aactggagca atcaaagcca aaatgttatc tgggataccg ttgatcaaag   1320
atggtttttc aaccaaatga actggtggag cagccaaagt agtttgattg atcaagaatt   1380
gatgggagga cattttaagc tttttgtttg tttatgtgtg tttattcgaa actaagttct   1440
tggtgtttta aaactaaaaa aaagactaac tataaaagta gaatttaaga agtttaagaa   1500
atagatttac agaattacaa tcaataccta ccgtctttat atacttatta gtcaagtagg   1560
ggaataattt cagggaactg gtttcaacct ttttttcag ctttttccaa atcagagaga   1620
gcagaaggta atagaaggtg taagaaaatg agatagatac atgcgtgggt caattgcctt   1680
gtgtcatcat ttactccagg caggttgcat cactccattg aggttgtgtc cgtttttttgc   1740
ctgtttgtgc ccctgttctc tgtagttgcg ctaagagaat ggacctatga actgatggtt   1800
ggtgaagaaa acaatatttt ggtgctggga ttcttttttt ttctggatgc cagcttaaaa   1860
agcgggctcc attatattta gtggatgcca ggaataaact gttcacccag acacctacga   1920
tgttatatat tctgtgtaac ccgcccccta ttttgggcat gtacgggtta cagcagaatt   1980
aaaaggctaa ttttttgact aaataaagtt aggaaaatca ctactattaa ttatttacgt   2040
attctttgaa atggcagtat tgataatgat aaactcgaac tgagatctga tatccctgca   2100
tggcgcgcct gatgagcctg aactgcccgg gcaaatcagc tgcattaatg aatcggccaa   2160
cgcgcgggga gaggcggttt gcgtattggg cgctcttccg cttcctcgct cactgactcg   2220
ctgcgctcgg tcgttcggct gcggcgagcg gtatcagctc actcaaaggc ggtaatacgg   2280
ttatccacag aatcagggga taacgcagga aagaacatgt gagcaaaagg ccagcaaaag   2340
gccaggaacc gtaaaaaggc cgcgttgctg gcgtttttcc ataggctccg cccccctgac   2400
gagcatcaca aaaatcgacg ctcaagtcag aggtggcgaa acccgacagg actataaaga   2460
taccaggcgt ttccccctgg aagctccctc gtgcgctctc ctgttccgac cctgccgctt   2520
accggatacc tgtccgcctt tctcccttcg ggaagcgtgg cgctttctca tagctcacgc   2580
tgtaggtatc tcagttcggt gtaggtcgtt cgctccaagc tgggctgtgt gcacgaaccc   2640
cccgttcagc ccgaccgctg cgccttatcc ggtaactatc gtcttgagtc caacccggta   2700
agacacgact tatcgccact ggcagcagcc actggtaaca ggattagcag agcgaggtat   2760
gtaggcggtg ctacagagtt cttgaagtgg tggcctaact acggctacac tagaaggaca   2820
gtatttggta tctgcgctct gctgaagcca gttaccttcg gaaaaagagt tggtagctct   2880
tgatccggca aacaaaccac cgctggtagc ggtggttttt ttgtttgcaa gcagcagatt   2940
acgcgcagaa aaaaaggatc tcaagaagat cctttgatct tttctacggg gtctgacgct   3000
cagtggaacg aaaactcacg ttaagggatt ttggtcatga gattatcaaa aaggatcttc   3060
acctagatcc ttttaaatta aaaatgaagt tttaaatcaa tctaaagtat atatgagtaa   3120
acttggtctg acagttacca atgcttaatc agtgaggcac ctatctcagc gatctgtcta   3180
tttcgttcat ccatagttgc ctgactcccc gtcgtgtaga taactacgat acgggagggc   3240
ttaccatctg gccccagtgc tgcaatgata ccgcgagacc cacgctcacc ggctccagat   3300
ttatcagcaa taaaccagcc agccggaagg gccgagcgca gaagtggtcc tgcaacttta   3360
tccgcctcca tccagtctat taattgttgc cgggaagcta gagtaagtag ttcgccagtt   3420
```

-continued

```
aatagtttgc gcaacgttgt tgccattgct acaggcatcg tggtgtcacg ctcgtcgttt   3480
ggtatggctt cattcagctc cggttcccaa cgatcaaggc gagttacatg atcccccatg   3540
ttgtgcaaaa aagcggttag ctccttcggt cctccgatcg ttgtcagaag taagttggcc   3600
gcagtgttat cactcatggt tatggcagca ctgcataatt ctcttactgt catgccatcc   3660
gtaagatgct tttctgtgac tggtgagtac tcaaccaagt cattctgaga atagtgtatg   3720
cggcgaccga gttgctcttg cccggcgtca atacgggata ataccgcgcc acatagcaga   3780
actttaaaag tgctcatcat tggaaaacgt tcttcggggc gaaaactctc aaggatctta   3840
ccgctgttga gatccagttc gatgtaaccc actcgtgcac ccaactgatc ttcagcatct   3900
tttactttca ccagcgtttc tgggtgagca aaaacaggaa ggcaaaatgc cgcaaaaaag   3960
ggaataaggg cgacacggaa atgttgaata ctcatactct tcctttttca atattattga   4020
agcatttatc agggttattg tctcatgagc ggatacatat ttgaatgtat ttagaaaaat   4080
aaacaaatag gggttccgcg cacatttccc cgaaaagtgc cacctgggtc cttttcatca   4140
cgtgctataa aaataattat aatttaaatt ttttaatata aatatataaa ttaaaaatag   4200
aaagtaaaaa aagaaattaa agaaaaaata gtttttgttt tccgaagatg taaaagactc   4260
taggggggatc gccaacaaat actacctttt atcttgctct tcctgctctc aggtattaat   4320
gccgaattgt ttcatcttgt ctgtgtagaa gaccacacac gaaaatcctg tgattttaca   4380
ttttacttat cgttaatcga atgtatatct atttaatctg cttttcttgt ctaataaata   4440
tatatgtaaa gtacgctttt tgttgaaatt ttttaaacct ttgtttattt ttttttcttc   4500
attccgtaac tcttctacct tctttattta ctttctaaaa tccaaataca aaacataaaa   4560
ataaataaac acagagtaaa ttcccaaatt attccatcat taaaagatac gaggcgcgtg   4620
taagttacag gcaagcgatc cgtcctaaga aaccattatt atcatgacat taacctataa   4680
aaataggcgt atcacgaggc cctttcgtct cgcgcgtttc ggtgatgacg gtgaaaacct   4740
ctgacacatg cagctcccgg agacggtcac agcttgtctg taagcggatg ccgggagcag   4800
acaagcccgt cagggcgcgt cagcgggtgt tggcgggtgt cggggctggc ttaactatgc   4860
ggcatcagag cagattgtac tgagagtgca ccatatcgac tacgtcgtaa ggccgtttct   4920
gacagagtaa aattcttgag ggaactttca ccattatggg aaatggttca agaaggtatt   4980
gacttaaact ccatcaaatg gtcaggtcat tgagtgtttt ttatttgttg tattttttt   5040
tttttagaga aaatcctcca atatcaaatt aggaatcgta gtttcatgat tttctgttac   5100
acctaacttt ttgtgtggtg ccctcctcct tgtcaatatt aatgttaaag tgcaattctt   5160
tttccttatc acgttgagcc attagtatca atttgcttac ctgtattcct ttactatcct   5220
cctttttctc cttcttgata aatgtatgta gattgcgtat atagtttcgt ctaccctatg   5280
aacatattcc attttgtaat ttcgtgtcgt ttctattatg aatttcattt ataaagttta   5340
tgtacaaata tcataaaaaa agagaatctt tttaagcaag gattttctta acttcttcgg   5400
cgacagcatc accgacttcg gtggtactgt tggaaccacc taaatcacca gttctgatac   5460
ctgcatccaa aacctttttta actgcatctt caatggcctt accttcttca ggcaagttca   5520
atgacaattt caacatcatt gcagcagaca agatagtggc gatagggtca accttattct   5580
ttggcaaatc tggagcagaa ccgtggcatg gttcgtacaa accaaatgcg gtgttcttgt   5640
ctggcaaaga ggccaaggac gcagatggca acaaacccaa ggaacctggg ataacggagg   5700
cttcatcgga gatgatatca ccaaacatgt tgctggtgat tataatacca tttaggtggg   5760
ttgggttctt aactaggatc atggcggcag aatcaatcaa ttgatgttga accttcaatg   5820
```

```
tagggaattc gttcttgatg gtttcctcca cagtttttct ccataatctt gaagaggcca   5880
aaagattagc tttatccaag gaccaaatag gcaatggtgg ctcatgttgt agggccatga   5940
aagcggccat tcttgtgatt ctttgcactt ctggaacggt gtattgttca ctatcccaag   6000
cgacaccatc accatcgtct tcctttctct taccaaagta aatacctccc actaattctc   6060
tgacaacaac gaagtcagta cctttagcaa attgtggctt gattggagat aagtctaaaa   6120
gagagtcgga tgcaaagtta catggtctta agttggcgta caattgaagt tctttacgga   6180
tttttagtaa accttgttca ggtctaacac taccggtacc ccatttagga ccagccacag   6240
cacctaacaa aacggcatca accttcttgg aggcttccag cgcctcatct ggaagtggga   6300
cacctgtagc atcgatagca gcaccaccaa ttaaatgatt ttcgaaatcg aacttgacat   6360
tggaacgaac atcagaaata gctttaagaa ccttaatggc ttcggctgtg atttcttgac   6420
caacgtggtc acctggcaaa acgacgatct tcttaggggc agacataggg gcagacatta   6480
gaatggtata tccttgaaat atatatatat attgctgaaa tgtaaaaggt aagaaaagtt   6540
agaaagtaag acgattgcta accacctatt ggaaaaaaca ataggtcctt aaataatatt   6600
gtcaacttca agtattgtga tgcaagcatt tagtcatgaa cgcttctcta ttctatatga   6660
aaagccggtt ccggcctctc acctttcctt tttctcccaa tttttcagtt gaaaaaggta   6720
tatgcgtcag gcgacctctg aaattaacaa aaaatttcca gtcatcgaat ttgattctgt   6780
gcgatagcgc ccctgtgtgt tctcgttatg ttgaggaaaa aaataatggt tgctaagaga   6840
ttcgaactct tgcatcttac gatacctgag tattcccaca gttaactgcg gtcaagatat   6900
ttcttgaatc aggcgcctta gaccgctcgg ccaaacaacc aattacttgt tgagaaatag   6960
agtataatta tcctataaat ataacgtttt tgaacacaca tgaacaagga agtacaggac   7020
aattgatttt gaagagaatg tggattttga tgtaattgtt gggattccat ttttaataag   7080
gcaataatat taggtatgtg gatatactag aagttctcct cgaccgtcga tatgcggtgt   7140
gaaataccgc acagatgcgt aaggagaaaa taccgcatca ggaaattgta aacgttaata   7200
ttttgttaaa attcgcgtta aatttttgtt aaatcagctc attttttaac caataggccg   7260
aaatcggcaa aatcccttat aaatcaaaag aatagaccga gatagggttg agtgttgttc   7320
cagtttggaa caagagtcca ctattaaaga acgtggactc caacgtcaaa gggcgaaaaa   7380
ccgtctatca gggcgatggc ccactacgtg aaccatcacc ctaatcaagt tttttggggt   7440
cgaggtgccg taaagcacta aatcggaacc ctaaagggag cccccgattt agagcttgac   7500
ggggaaagcc ggcgaacgtg gcgagaaagg aagggaagaa agcgaaagga gcgggcgcta   7560
gggcgctggc aagtgtagcg gtcacgctgc gcgtaaccac cacacccgcc gcgcttaatg   7620
cgccgctaca gggcgcgtcg cgccattcgc cattcaggct gcgcaactgt tgggaagggc   7680
gatcggtgcg ggcctct                                                 7697
```

<210> SEQ ID NO 66
<211> LENGTH: 6386
<212> TYPE: DNA
<213> ORGANISM: Artificial Sequence
<220> FEATURE:
<223> OTHER INFORMATION: plasmid

<400> SEQUENCE: 66

```
tcgctattac gccagctgat ttgcccgggc agttcaggct catcaggcgc gccatgcagg     60
atgcattgat cagttaaccc atgggcatgc gaaggaaaat gagaaatatc gagggagacg    120
```

-continued

```
attcagagga gcaggacaaa ctataaccga ctgtttgttg gaggatgccg tacataacga    180
acactgctga agctaccatg tctacagttt agaggaatgg gtacaactca caggcgaggg    240
atggtgttca ctcgtgctag caaacgcggt gggagcaaaa agtagaatat tatcttttat    300
tcgtgaaact tcgaacactg tcatctaaag atgctatata ctaatatagg catacttgat    360
aatgaaaact ataaatcgta aagacataag agatccgcgg atccccgggt cgagcctgaa    420
cggcctcgag gcctgaacgg cctcgacgaa ttcattattt gtagagctca tccatgccat    480
gtgtaatccc agcagcagtt acaaactcaa gaaggaccat gtggtcacgc ttttcgttgg    540
gatctttcga aagggcagat tgtgtcgaca ggtaatggtt gtctggtaaa aggacagggc    600
catcgccaat tggagtattt tgttgataat ggtctgctag ttgaacggat ccatcttcaa    660
tgttgtggcg aattttgaag ttagctttga ttccattctt ttgtttgtct gccgtgatgt    720
atacattgtg tgagttatag ttgtactcga gtttgtgtcc gagaatgttt ccatcttctt    780
taaaatcaat accttttaac tcgatacgat taacaagggt atcaccttca aacttgactt    840
cagcacgcgt cttgtagttc ccgtcatctt tgaaagatat agtgcgttcc tgtacataac    900
cttcgggcat ggcactcttg aaaaagtcat gccgtttcat atgatccgga taacgggaaa    960
agcattgaac accataagag aaagtagtga caagtgttgg ccatggaaca ggtagttttc   1020
cagtagtgca aataaattta agggtaagct ggccctgcag gccaagcttt gttttatatt   1080
tgttgtaaaa agtagataat tacttccttg atgatctgta aaaaagagaa aaagaaagca   1140
tctaagaact tgaaaaacta cgaattagaa aagaccaaat atgtatttct tgcattgacc   1200
aatttatgca agtttatata tatgtaaatg taagtttcac gaggttctac taaactaaac   1260
cacccccttg gttagaagaa aagagtgtgt gagaacaggc tgttgttgtc acacgattcg   1320
gacaattctg tttgaaagag agagagtaac agtacgatcg aacgaacttt gctctggaga   1380
tcacagtggg catcatagca tgtggtacta aacccttttcc cgccattcca gaaccttcga   1440
ttgcttgtta caaaacctgt gagccgtcgc taggaccttg ttgtgtgacg aaattggaag   1500
ctgcaatcaa taggaagaca ggaagtcgag cgtgtctggg ttttttcagt tttgttcttt   1560
ttgcaaacaa atcacgagcg acggtaattt ctttctcgat aagaggccac gtgctttatg   1620
agggtaacat caattcaaga aggagggaaa cacttccttt ttctggccct gataatagta   1680
tgagggtgaa gccaaaataa aggattcgcg cccaaatcgg catctttaaa tgcaggtatg   1740
cgatagttcc tcactctttc cttactcacg agtaattctt gcaaatgcct attatgcaga   1800
tgttataata tctgtgcgta gatctgatat ccctgcatgg cgcgcctgat gagcctgaac   1860
tgcccgggca aatcagctgc attaatgaat cggccaacgc gcggggagag gcggtttgcg   1920
tattgggcgc tcttccgctt cctcgctcac tgactcgctg cgctcggtcg ttcggctgcg   1980
gcgagcggta tcagctcact caaaggcggt aatacggtta tccacagaat caggggataa   2040
cgcaggaaag aacatgtgag caaaaggcca gcaaaaggcc aggaaccgta aaaaggccgc   2100
gttgctggcg tttttccata ggctccgccc ccctgacgag catcacaaaa atcgacgctc   2160
aagtcagagg tggcgaaacc cgacaggact ataaagatac caggcgtttc cccctggaag   2220
ctccctcgtg cgctctcctg ttccgaccct gccgcttacc ggatacctgt ccgcctttct   2280
cccttcggga agcgtggcgc tttctcatag ctcacgctgt aggtatctca gttcggtgta   2340
ggtcgttcgc tccaagctgg gctgtgtgca cgaacccccc gttcagcccg accgctgcgc   2400
cttatccggt aactatcgtc ttgagtccaa cccggtaaga cacgacttat cgccactggc   2460
agcagccact ggtaacagga ttagcagagc gaggtatgta ggcggtgcta cagagttctt   2520
```

```
gaagtggtgg cctaactacg gctacactag aaggacagta tttggtatct gcgctctgct   2580
gaagccagtt accttcggaa aaagagttgg tagctcttga tccggcaaac aaaccaccgc   2640
tggtagcggt ggtttttttg tttgcaagca gcagattacg cgcagaaaaa aaggatctca   2700
agaagatcct ttgatctttt ctacggggtc tgacgctcag tggaacgaaa actcacgtta   2760
agggattttg gtcatgagat tatcaaaaag gatcttcacc tagatccttt taaattaaaa   2820
atgaagtttt aaatcaatct aaagtatata tgagtaaact tggtctgaca gttaccaatg   2880
cttaatcagt gaggcaccta tctcagcgat ctgtctattt cgttcatcca tagttgcctg   2940
actccccgtc gtgtagataa ctacgatacg ggagggctta ccatctggcc ccagtgctgc   3000
aatgataccg cgagacccac gctcaccggc tccagattta tcagcaataa accagccagc   3060
cggaagggcc gagcgcagaa gtggtcctgc aactttatcc gcctccatcc agtctattaa   3120
ttgttgccgg gaagctagag taagtagttc gccagttaat agtttgcgca acgttgttgc   3180
cattgctaca ggcatcgtgg tgtcacgctc gtcgtttggt atggcttcat tcagctccgg   3240
ttcccaacga tcaaggcgag ttacatgatc ccccatgttg tgcaaaaaag cggttagctc   3300
cttcggtcct ccgatcgttg tcagaagtaa gttggccgca gtgttatcac tcatggttat   3360
ggcagcactg cataattctc ttactgtcat gccatccgta agatgctttt ctgtgactgg   3420
tgagtactca accaagtcat tctgagaata gtgtatgcgg cgaccgagtt gctcttgccc   3480
ggcgtcaata cgggataata ccgcgccaca tagcagaact ttaaaagtgc tcatcattgg   3540
aaaacgttct tcggggcgaa aactctcaag gatcttaccg ctgttgagat ccagttcgat   3600
gtaacccact cgtgcaccca actgatcttc agcatctttt actttcacca gcgtttctgg   3660
gtgagcaaaa acaggaaggc aaaatgccgc aaaaaaggga ataagggcga cacggaaatg   3720
ttgaatactc atactcttcc tttttcaata ttattgaagc atttatcagg gttattgtct   3780
catgagcgga tacatatttg aatgtattta gaaaaataaa caaatagggg ttccgcgcac   3840
atttccccga aaagtgccac ctgggtcctt ttcatcacgt gctataaaaa taattataat   3900
ttaaattttt taatataaat atataaatta aaaatagaaa gtaaaaaaag aaattaaaga   3960
aaaaatagtt tttgttttcc gaagatgtaa aagactctag ggggatcgcc aacaaatact   4020
accttttatc ttgctcttcc tgctctcagg tattaatgcc gaattgtttc atcttgtctg   4080
tgtagaagac cacacacgaa aatcctgtga ttttacattt tacttatcgt taatcgaatg   4140
tatatctatt taatctgctt ttcttgtcta ataaatatat atgtaaagta cgctttttgt   4200
tgaaattttt taaacctttg tttatttttt tttcttcatt ccgtaactct tctaccttct   4260
ttatttactt tctaaaatcc aaatacaaaa cataaaaata aataaacaca gagtaaattc   4320
ccaaattatt ccatcattaa aagatacgag gcgcgtgtaa gttacaggca agcgatccgt   4380
cctaagaaac cattattatc atgacattaa cctataaaaa taggcgtatc acgaggccct   4440
ttcgtctcgc gcgtttcggt gatgacggtg aaaacctctg acacatgcag ctcccggaga   4500
cggtcacagc ttgtctgtaa gcggatgccg ggagcagaca agcccgtcag ggcgcgtcag   4560
cgcgtgttgg cgggtgtcgg ggctggctta actatgcggc atcagagcag attgtactga   4620
gagtgcacca taaattcccg ttttaagagc ttggtgagcg ctaggagtca ctgccaggta   4680
tcgtttgaac acggcattag tcagggaagt cataacacag tcctttcccg caattttctt   4740
tttctattac tcttggcctc ctctagtaca ctctatattt ttttatgcct cggtaatgat   4800
tttcattttt ttttttcccc tagcggatga ctcttttttt ttcttagcga ttggcattat   4860
```

```
cacataatga attatacatt atataaagta atgtgatttc ttcgaagaat atactaaaaa   4920
atgagcaggc aagataaacg aaggcaaaga tgacagagca gaaagcccta gtaaagcgta   4980
ttacaaatga aaccaagatt cagattgcga tctctttaaa gggtggtccc ctagcgatag   5040
agcactcgat cttcccagaa aaagaggcag aagcagtagc agaacaggcc acacaatcgc   5100
aagtgattaa cgtccacaca ggtatagggt ttctggacca tatgatacat gctctggcca   5160
agcattccgg ctggtcgcta atcgttgagt gcattggtga cttacacata gacgaccatc   5220
acaccactga agactgcggg attgctctcg gtcaagcctt taaagaggcc ctaggggccg   5280
tgcgtggagt aaaaaggttt ggatcaggat ttgcgccttt ggatgaggca ctttccagag   5340
cggtggtaga tctttcgaac aggccgtacg cagttgtcga acttggtttg caaagggaga   5400
aagtaggaga tctctcttgc gagatgatcc cgcatttttct tgaaagtttt gcagaggcta   5460
gcagaattac cctccacgtt gattgtctgc gaggcaagaa tgatcatcac cgtagtgaga   5520
gtgcgttcaa ggctcttgcg gttgccataa gagaagccac ctcgcccaat ggtaccaacg   5580
atgttccctc caccaaaggt gttcttatgt agtgacaccg attatttaaa gctgcagcat   5640
acgatatata tacatgtgta tatatgtata cctatgaatg tcagtaagta tgtatacgaa   5700
cagtatgata ctgaagatga caaggtaatg catcattcta tacgtgtcat tctgaacgag   5760
gcgcgctttc ctttttcctt tttgcttttt cttttttttt ctcttgaact cgacggatct   5820
atgcggtgtg aaataccgca cagatgcgta aggagaaaat accgcatcag gaaattgtaa   5880
acgttaatat tttgttaaaa ttcgcgttaa atttttgtta aatcagctca ttttttaacc   5940
aataggccga aatcggcaaa atcccttata aatcaaaaga atagaccgag atagggttga   6000
gtgttgttcc agtttggaac aagagtccac tattaaagaa cgtggactcc aacgtcaaag   6060
ggcgaaaaac cgtctatcag ggcgatggcc cactacgtga accatcaccc taatcaagtt   6120
ttttggggtc gaggtgccgt aaagcactaa atcggaaccc taaagggagc ccccgattta   6180
gagcttgacg gggaaagccg gcgaacgtgg cgagaaagga agggaagaaa gcgaaaggag   6240
cgggcgctag ggcgctggca agtgtagcgg tcacgctgcg cgtaaccacc acacccgccg   6300
cgcttaatgc gccgctacag ggcgcgtcgc gccattcgcc attcaggctg cgcaactgtt   6360
gggaagggcg atcggtgcgg gcctct                                         6386
```

```
<210> SEQ ID NO 67
<211> LENGTH: 7434
<212> TYPE: DNA
<213> ORGANISM: Artificial Sequence
<220> FEATURE:
<223> OTHER INFORMATION: plasmid

<400> SEQUENCE: 67

tcgctattac gccagctgat ttgcccgggc agttcaggct catcaggcgc gccatgcagg     60
atgcattgat cagttaaccc atgggcatgc gaaggaaaat gagaaatatc gagggagacg    120
attcagagga gcaggacaaa ctataaccga ctgtttgttg gaggatgccg tacataacga    180
acactgctga agctaccatg tctacagttt agaggaatgg gtacaactca caggcgaggg    240
atggtgttca ctcgtgctag caaacgcggt gggagcaaaa agtagaatat tatcttttat    300
tcgtgaaact tcgaacactg tcatctaaag atgctatata ctaatatagg catacttgat    360
aatgaaaact ataaatcgta aagacataag agatccgcgg atccccgggt cgagcctgaa    420
cggcctcgag gcctgaacgg cctcgacgaa ttcattattt gtagagctca tccatgccat    480
gtgtaatccc agcagcagtt acaaactcaa gaaggaccat gtggtcacgc ttttcgttgg    540
```

```
gatctttcga aagggcagat tgtgtcgaca ggtaatggtt gtctggtaaa aggacagggc    600
catcgccaat tggagtattt tgttgataat ggtctgctag ttgaacggat ccatcttcaa    660
tgttgtggcg aattttgaag ttagctttga ttccattctt ttgtttgtct gccgtgatgt    720
atacattgtg tgagttatag ttgtactcga gtttgtgtcc gagaatgttt ccatcttctt    780
taaaatcaat accttttaac tcgatacgat taacaagggt atcaccttca aacttgactt    840
cagcacgcgt cttgtagttc ccgtcatctt tgaaagatat agtgcgttcc tgtacataac    900
cttcgggcat ggcactcttg aaaaagtcat gccgtttcat atgatccgga taacgggaaa    960
agcattgaac accataagag aaagtagtga caagtgttgg ccatggaaca ggtagttttc   1020
cagtagtgca aataaattta agggtaagct ggccctgcag gccaagcttt gttttatatt   1080
tgttgtaaaa agtagataat tacttccttg atgatctgta aaaaagagaa aaagaaagca   1140
tctaagaact tgaaaaacta cgaattagaa aagaccaaat atgtatttct tgcattgacc   1200
aatttatgca agtttatata tatgtaaatg taagtttcac gaggttctac taaactaaac   1260
cacccccttg gttagaagaa aagagtgtgt gagaacaggc tgttgttgtc acacgattcg   1320
gacaattctg tttgaaagag agagagtaac agtacgatcg aacgaacttt gctctggaga   1380
tcacagtggg catcatagca tgtggtacta aaccctttcc cgccattcca gaaccttcga   1440
ttgcttgtta caaaacctgt gagccgtcgc taggaccttg ttgtgtgacg aaattggaag   1500
ctgcaatcaa taggaagaca ggaagtcgag cgtgtctggg ttttttcagt tttgttcttt   1560
ttgcaaacaa atcacgagcg acggtaattt ctttctcgat aagaggccac gtgctttatg   1620
agggtaacat caattcaaga aggagggaaa cacttccttt ttctggccct gataatagta   1680
tgagggtgaa gccaaaataa aggattcgcg cccaaatcgg catctttaaa tgcaggtatg   1740
cgatagttcc tcactctttc cttactcacg agtaattctt gcaaatgcct attatgcaga   1800
tgttataata tctgtgcgta gatctgatat ccctgcatgg cgcgcctgat gagcctgaac   1860
tgcccgggca aatcagctgc attaatgaat cggccaacgc gcggggagag gcggtttgcg   1920
tattgggcgc tcttccgctt cctcgctcac tgactcgctg cgctcggtcg ttcggctgcg   1980
gcgagcggta tcagctcact caaaggcggt aatacggtta tccacagaat caggggataa   2040
cgcaggaaag aacatgtgag caaaaggcca gcaaaaggcc aggaaccgta aaaaggccgc   2100
gttgctggcg tttttccata ggctccgccc ccctgacgag catcacaaaa atcgacgctc   2160
aagtcagagg tggcgaaacc cgacaggact ataaagatac caggcgtttc cccctggaag   2220
ctccctcgtg cgctctcctg ttccgaccct gccgcttacc ggatacctgt ccgcctttct   2280
cccttcggga agcgtggcgc tttctcatag ctcacgctgt aggtatctca gttcggtgta   2340
ggtcgttcgc tccaagctgg gctgtgtgca cgaacccccc gttcagcccg accgctgcgc   2400
cttatccggt aactatcgtc ttgagtccaa cccggtaaga cacgacttat cgccactggc   2460
agcagccact ggtaacagga ttagcagagc gaggtatgta ggcggtgcta cagagttctt   2520
gaagtggtgg cctaactacg gctacactag aaggacagta tttggtatct gcgctctgct   2580
gaagccagtt accttcggaa aaagagttgg tagctcttga tccggcaaac aaaccaccgc   2640
tggtagcggt ggtttttttg tttgcaagca gcagattacg cgcagaaaaa aaggatctca   2700
agaagatcct ttgatctttt ctacggggtc tgacgctcag tggaacgaaa actcacgtta   2760
agggattttg gtcatgagat tatcaaaaag gatcttcacc tagatccttt taaattaaaa   2820
atgaagtttt aaatcaatct aaagtatata tgagtaaact tggtctgaca gttaccaatg   2880
```

```
cttaatcagt gaggcaccta tctcagcgat ctgtctattt cgttcatcca tagttgcctg   2940
actccccgtc gtgtagataa ctacgatacg ggagggctta ccatctggcc ccagtgctgc   3000
aatgataccg cgagacccac gctcaccggc tccagattta tcagcaataa accagccagc   3060
cggaagggcc gagcgcagaa gtggtcctgc aactttatcc gcctccatcc agtctattaa   3120
ttgttgccgg gaagctagag taagtagttc gccagttaat agtttgcgca acgttgttgc   3180
cattgctaca ggcatcgtgg tgtcacgctc gtcgtttggt atggcttcat tcagctccgg   3240
ttcccaacga tcaaggcgag ttacatgatc ccccatgttg tgcaaaaaag cggttagctc   3300
cttcggtcct ccgatcgttg tcagaagtaa gttggccgca gtgttatcac tcatggttat   3360
ggcagcactg cataattctc ttactgtcat gccatccgta agatgctttt ctgtgactgg   3420
tgagtactca accaagtcat tctgagaata gtgtatgcgg cgaccgagtt gctcttgccc   3480
ggcgtcaata cgggataata ccgcgccaca tagcagaact ttaaaagtgc tcatcattgg   3540
aaaacgttct tcggggcgaa aactctcaag gatcttaccg ctgttgagat ccagttcgat   3600
gtaacccact cgtgcaccca actgatcttc agcatctttt actttcacca gcgtttctgg   3660
gtgagcaaaa acaggaaggc aaaatgccgc aaaaaaggga ataagggcga cacggaaatg   3720
ttgaatactc atactcttcc tttttcaata ttattgaagc atttatcagg gttattgtct   3780
catgagcgga tacatatttg aatgtattta gaaaaataaa caaatagggg ttccgcgcac   3840
atttccccga aaagtgccac ctgggtcctt ttcatcacgt gctataaaaa taattataat   3900
ttaaattttt taatataaat atataaatta aaaatagaaa gtaaaaaaag aaattaaaga   3960
aaaaatagtt tttgttttcc gaagatgtaa aagactctag ggggatcgcc aacaaatact   4020
acctttatc ttgctcttcc tgctctcagg tattaatgcc gaattgtttc atcttgtctg   4080
tgtagaagac cacacacgaa aatcctgtga ttttacattt tacttatcgt taatcgaatg   4140
tatatctatt taatctgctt ttcttgtcta ataaatatat atgtaaagta cgctttttgt   4200
tgaaattttt taaacctttg tttatttttt tttcttcatt ccgtaactct tctaccttct   4260
ttatttactt tctaaaatcc aaatacaaaa cataaaaata aataaacaca gagtaaattc   4320
ccaaattatt ccatcattaa aagatacgag gcgcgtgtaa gttacaggca agcgatccgt   4380
cctaagaaac cattattatc atgacattaa cctataaaaa taggcgtatc acgaggccct   4440
ttcgtctcgc gcgtttcggt gatgacggtg aaaacctctg acacatgcag ctcccggaga   4500
cggtcacagc ttgtctgtaa gcggatgccg ggagcagaca agcccgtcag ggcgcgtcag   4560
cgggtgttgg cgggtgtcgg ggctggctta actatgcggc atcagagcag attgtactga   4620
gagtgcacca tatcgactac gtcgtaaggc cgtttctgac agagtaaaat tcttgaggga   4680
actttcacca ttatgggaaa tggttcaaga aggtattgac ttaaactcca tcaaatggtc   4740
aggtcattga gtgtttttta tttgttgtat tttttttttt ttagagaaaa tcctccaata   4800
tcaaattagg aatcgtagtt tcatgatttt ctgttacacc taactttttg tgtggtgccc   4860
tcctccttgt caatattaat gttaaagtgc aattcttttt ccttatcacg ttgagccatt   4920
agtatcaatt tgcttacctg tattccttta ctatcctcct ttttctcctt cttgataaat   4980
gtatgtagat tgcgtatata gtttcgtcta ccctatgaac atattccatt ttgtaatttc   5040
gtgtcgtttc tattatgaat ttcatttata aagtttatgt acaaatatca taaaaaaaga   5100
gaatcttttt aagcaaggat tttcttaact tcttcggcga cagcatcacc gacttcggtg   5160
gtactgttgg aaccacctaa atcaccagtt ctgatacctg catccaaaac ctttttaact   5220
gcatcttcaa tggccttacc ttcttcaggc aagttcaatg acaatttcaa catcattgca   5280
```

gcagacaaga tagtggcgat agggtcaacc ttattctttg gcaaatctgg agcagaaccg 5340
tggcatggtt cgtacaaacc aaatgcggtg ttcttgtctg gcaaagaggc caaggacgca 5400
gatggcaaca aacccaagga acctgggata acggaggctt catcggagat gatatcacca 5460
aacatgttgc tggtgattat aataccattt aggtgggttg ggttcttaac taggatcatg 5520
gcggcagaat caatcaattg atgttgaacc ttcaatgtag ggaattcgtt cttgatggtt 5580
tcctccacag tttttctcca taatcttgaa gaggccaaaa gattagcttt atccaaggac 5640
caaataggca atggtggctc atgttgtagg gccatgaaag cggccattct tgtgattctt 5700
tgcacttctg gaacggtgta ttgttcacta tcccaagcga caccatcacc atcgtcttcc 5760
tttctcttac caaagtaaat acctcccact aattctctga caacaacgaa gtcagtacct 5820
ttagcaaatt gtggcttgat tggagataag tctaaaagag agtcggatgc aaagttacat 5880
ggtcttaagt tggcgtacaa ttgaagttct ttacggattt ttagtaaacc ttgttcaggt 5940
ctaacactac cggtacccca tttaggacca gccacagcac ctaacaaaac ggcatcaacc 6000
ttcttggagg cttccagcgc ctcatctgga agtgggacac ctgtagcatc gatagcagca 6060
ccaccaatta aatgattttc gaaatcgaac ttgacattgg aacgaacatc agaaatagct 6120
ttaagaacct taatggcttc ggctgtgatt tcttgaccaa cgtggtcacc tggcaaaacg 6180
acgatcttct taggggcaga catagggcca gacattagaa tggtatatcc ttgaaatata 6240
tatatatatt gctgaaatgt aaaaggtaag aaaagttaga aagtaagacg attgctaacc 6300
acctattgga aaaaacaata ggtccttaaa taatattgtc aacttcaagt attgtgatgc 6360
aagcatttag tcatgaacgc ttctctattc tatatgaaaa gccggttccg gcctctcacc 6420
tttccttttt ctcccaattt ttcagttgaa aaaggtatat gcgtcaggcg acctctgaaa 6480
ttaacaaaaa atttccagtc atcgaatttg attctgtgcg atagcgcccc tgtgtgttct 6540
cgttatgttg aggaaaaaaa taatggttgc taagagattc gaactcttgc atcttacgat 6600
acctgagtat tcccacagtt aactgcggtc aagatatttc ttgaatcagg cgccttagac 6660
cgctcggcca aacaaccaat tacttgttga gaaatagagt ataattatcc tataaatata 6720
acgtttttga acacacatga acaaggaagt acaggacaat tgattttgaa gagaatgtgg 6780
attttgatgt aattgttggg attccatttt taataaggca ataatattag gtatgtggat 6840
atactagaag ttctcctcga ccgtcgatat gcggtgtgaa ataccgcaca gatgcgtaag 6900
gagaaaatac cgcatcagga aattgtaaac gttaatattt tgttaaaatt cgcgttaaat 6960
ttttgttaaa tcagctcatt ttttaaccaa taggccgaaa tcggcaaaat cccttataaa 7020
tcaaaagaat agaccgagat agggttgagt gttgttccag tttggaacaa gagtccacta 7080
ttaaagaacg tggactccaa cgtcaaaggg cgaaaaaccg tctatcaggg cgatggccca 7140
ctacgtgaac catcacccta atcaagtttt ttggggtcga ggtgccgtaa agcactaaat 7200
cggaacccta aagggagccc ccgatttaga gcttgacggg gaaagccggc gaacgtggcg 7260
agaaaggaag ggaagaaagc gaaaggagcg ggcgctaggg cgctggcaag tgtagcggtc 7320
acgctgcgcg taaccaccac acccgccgcg cttaatgcgc cgctacaggg cgcgtcgcgc 7380
cattcgccat tcaggctgcg caactgttgg gaagggcgat cggtgcgggc ctct 7434

<210> SEQ ID NO 68
<211> LENGTH: 7904
<212> TYPE: DNA
<213> ORGANISM: Artificial Sequence
<220> FEATURE:

<223> OTHER INFORMATION: plasmid

<400> SEQUENCE: 68

```
tcgctattac gccagctgat ttgcccgggc agttcaggct catcaggcgc gccatgcagg     60
atgcattgat cagttaaccc atgggcatgc agcttgcaaa ttaaagcctt cgagcgtccc    120
aaaaccttct caagcaaggt tttcagtata atgttacatg cgtacacgcg tctgtacaga    180
aaaaaaagaa aaatttgaaa tataaataac gttcttaata ctaacataac tataaaaaaa    240
taaataggga cctagacttc aggttgtcta actccttcct tttcggttag agcggatgtg    300
gggggagggc gtgaatgtaa gcgtgacata actaattaca tgatatcgac aaaggaaaag    360
ggggacggat ctccgaggcc tcggacccgt cgggccgccg tcggacgtgc cgcggctata    420
catctaagat ttcttccgct gtaccaccac accgtaatcg gaagcgacct gtcctccagc    480
tgatggtggg atcccacaag gcagacagga aaatatatat tgtcatggat tcccggatga    540
accaggcaac tgcatagtcc agtttggaaa agttaagagg acctccctgt actcctctaa    600
gttgaatgta gtcaaatatg aaccaagcca aacaatgaca catgaaaaac accattatgt    660
cccatcggaa gatgtgatgt gctgcccaac caatgattaa actggcaaca aagcattcag    720
aaatgggctc acaaatgatg gttgcaggca gcatgttaat ccgtagcttt gcccatctga    780
tcattctgga ttgaaactgg gatatagagt aacatccgga attctgcatt gcaacttgtg    840
tcgccatgga aaatttccaa ccacggtcag ctattgcttt agccataaag taatcttcag    900
ctatatactg tgcaaaggcg attaatcccc ccgcttggtc caaaacttct tttctcatta    960
gacaagacat tcctgttaca cacttgaaac cggttacatt agcagagatg taagaccttg   1020
gatgagacgt cccaaagtaa acctgttcta aagtagcagc aaatccttgc cgatcagcca   1080
catatggcag tccgtgaacc aaaccaactt tctctgtcat ttgattggcc atgtctgtta   1140
atgtgtctgg tttcactttt attccactat cacaaatcca tatgagatca tatttggcca   1200
cttcgtatcc tggcattaag ttgtttattt ttgggttaat cccaactttt ttaccaccta   1260
taaataattt ggcatcatca ctaggatatt tgccaagcaa ttttttacat acatccactg   1320
ctggatcatc aagatcttgc acacaaagaa ggatttcaaa ttttggatag tccaattcaa   1380
agaatgtctc caagttatta ataaggttgg ggtcgacccc tttcagtggt ttaagaagtg   1440
aaacaccagg tagtttgcta tatggctgct tgtcagatat cttcttgttc aggtgtagtc   1500
ttgtgtagac gatggacaag aaatgcataa accacaagac gaagaataag acacagccaa   1560
aaatggcgag tccttgcagg gccagatcca acaccgccat tttaagcttt ttgtttgttt   1620
atgtgtgttt attcgaaact aagttcttgg tgttttaaaa ctaaaaaaaa gactaactat   1680
aaaagtagaa tttaagaagt ttaagaaata gatttacaga attacaatca atacctaccg   1740
tctttatata cttattagtc aagtagggga ataatttcag ggaactggtt tcaacctttt   1800
ttttcagctt tttccaaatc agagagagca gaaggtaata gaaggtgtaa gaaaatgaga   1860
tagatacatg cgtgggtcaa ttgccttgtg tcatcattta ctccaggcag gttgcatcac   1920
tccattgagg ttgtgtccgt tttttgcctg tttgtgcccc tgttctctgt agttgcgcta   1980
agagaatgga cctatgaact gatggttggt gaagaaaaca atattttggt gctgggattc   2040
tttttttttc tggatgccag cttaaaaagc gggctccatt atatttagtg gatgccagga   2100
ataaactgtt cacccagaca cctacgatgt tatatattct gtgtaacccg ccccctattt   2160
tgggcatgta cgggttacag cagaattaaa aggctaattt tttgactaaa taaagttagg   2220
aaaatcacta ctattaatta tttacgtatt ctttgaaatg gcagtattga taatgataaa   2280
```

```
ctcgaactga gatctgatat ccctgcatgg cgcgcctgat gagcctgaac tgcccgggca   2340
aatcagctgc attaatgaat cggccaacgc gcggggagag gcggtttgcg tattgggcgc   2400
tcttccgctt cctcgctcac tgactcgctg cgctcggtcg ttcggctgcg gcgagcggta   2460
tcagctcact caaaggcggt aatacggtta tccacagaat caggggataa cgcaggaaag   2520
aacatgtgag caaaaggcca gcaaaaggcc aggaaccgta aaaaggccgc gttgctggcg   2580
tttttccata ggctccgccc ccctgacgag catcacaaaa atcgacgctc aagtcagagg   2640
tggcgaaacc cgacaggact ataaagatac caggcgtttc cccctggaag ctccctcgtg   2700
cgctctcctg ttccgaccct gccgcttacc ggatacctgt ccgcctttct cccttcggga   2760
agcgtggcgc tttctcatag ctcacgctgt aggtatctca gttcggtgta ggtcgttcgc   2820
tccaagctgg gctgtgtgca cgaacccccc gttcagcccg accgctgcgc cttatccggt   2880
aactatcgtc ttgagtccaa cccggtaaga cacgacttat cgccactggc agcagccact   2940
ggtaacagga ttagcagagc gaggtatgta ggcggtgcta cagagttctt gaagtggtgg   3000
cctaactacg gctacactag aaggacagta tttggtatct gcgctctgct gaagccagtt   3060
accttcggaa aaagagttgg tagctcttga tccggcaaac aaaccaccgc tggtagcggt   3120
ggtttttttg tttgcaagca gcagattacg cgcagaaaaa aaggatctca agaagatcct   3180
ttgatctttt ctacggggtc tgacgctcag tggaacgaaa actcacgtta agggattttg   3240
gtcatgagat tatcaaaaag gatcttcacc tagatccttt taaattaaaa atgaagtttt   3300
aaatcaatct aaagtatata tgagtaaact tggtctgaca gttaccaatg cttaatcagt   3360
gaggcaccta tctcagcgat ctgtctattt cgttcatcca tagttgcctg actccccgtc   3420
gtgtagataa ctacgatacg ggagggctta ccatctggcc ccagtgctgc aatgataccg   3480
cgagacccac gctcaccggc tccagattta tcagcaataa accagccagc cggaagggcc   3540
gagcgcagaa gtggtcctgc aactttatcc gcctccatcc agtctattaa ttgttgccgg   3600
gaagctagag taagtagttc gccagttaat agtttgcgca acgttgttgc cattgctaca   3660
ggcatcgtgg tgtcacgctc gtcgtttggt atggcttcat tcagctccgg ttcccaacga   3720
tcaaggcgag ttacatgatc ccccatgttg tgcaaaaaag cggttagctc cttcggtcct   3780
ccgatcgttg tcagaagtaa gttggccgca gtgttatcac tcatggttat ggcagcactg   3840
cataattctc ttactgtcat gccatccgta agatgctttt ctgtgactgg tgagtactca   3900
accaagtcat tctgagaata gtgtatgcgg cgaccgagtt gctcttgccc ggcgtcaata   3960
cgggataata ccgcgccaca tagcagaact ttaaaagtgc tcatcattgg aaaacgttct   4020
tcggggcgaa aactctcaag gatcttaccg ctgttgagat ccagttcgat gtaacccact   4080
cgtgcaccca actgatcttc agcatctttt actttcacca gcgtttctgg gtgagcaaaa   4140
acaggaaggc aaaatgccgc aaaaaaggga ataagggcga cacggaaatg ttgaatactc   4200
atactcttcc tttttcaata ttattgaagc atttatcagg gttattgtct catgagcgga   4260
tacatatttg aatgtattta gaaaaataaa caaatagggg ttccgcgcac atttccccga   4320
aaagtgccac ctgggtcctt ttcatcacgt gctataaaaa taattataat ttaaattttt   4380
taatataaat atataaatta aaaatagaaa gtaaaaaaag aaattaaaga aaaaatagtt   4440
tttgttttcc gaagatgtaa aagactctag ggggatcgcc aacaaatact accttttatc   4500
ttgctcttcc tgctctcagg tattaatgcc gaattgtttc atcttgtctg tgtagaagac   4560
cacacacgaa aatcctgtga ttttacattt tacttatcgt taatcgaatg tatatctatt   4620
```

```
taatctgctt ttcttgtcta ataaatatat atgtaaagta cgctttttgt tgaaattttt   4680
taaacctttg tttatttttt tttcttcatt ccgtaactct tctaccttct ttatttactt   4740
tctaaaatcc aaatacaaaa cataaaaata aataaacaca gagtaaattc ccaaattatt   4800
ccatcattaa aagatacgag gcgcgtgtaa gttacaggca agcgatccgt cctaagaaac   4860
cattattatc atgacattaa cctataaaaa taggcgtatc acgaggccct ttcgtctcgc   4920
gcgtttcggt gatgacggtg aaaacctctg acacatgcag ctcccggaga cggtcacagc   4980
ttgtctgtaa gcggatgccg ggagcagaca agcccgtcag ggcgcgtcag cgggtgttgg   5040
cgggtgtcgg ggctggctta actatgcggc atcagagcag attgtactga gagtgcacca   5100
tatcgactac gtcgtaaggc cgtttctgac agagtaaaat tcttgaggga actttcacca   5160
ttatgggaaa tggttcaaga aggtattgac ttaaactcca tcaaatggtc aggtcattga   5220
gtgtttttta tttgttgtat tttttttttt ttagagaaaa tcctccaata tcaaattagg   5280
aatcgtagtt tcatgatttt ctgttacacc taactttttg tgtggtgccc tcctccttgt   5340
caatattaat gttaaagtgc aattcttttt ccttatcacg ttgagccatt agtatcaatt   5400
tgcttacctg tattccttta ctatcctcct ttttctcctt cttgataaat gtatgtagat   5460
tgcgtatata gtttcgtcta ccctatgaac atattccatt ttgtaatttc gtgtcgtttc   5520
tattatgaat ttcatttata aagtttatgt acaaatatca taaaaaaaga gaatcttttt   5580
aagcaaggat tttcttaact tcttcggcga cagcatcacc gacttcggtg gtactgttgg   5640
aaccacctaa atcaccagtt ctgatacctg catccaaaac ctttttaact gcatcttcaa   5700
tggccttacc ttcttcaggc aagttcaatg acaatttcaa catcattgca gcagacaaga   5760
tagtggcgat agggtcaacc ttattctttg gcaaatctgg agcagaaccg tggcatggtt   5820
cgtacaaacc aaatgcggtg ttcttgtctg gcaaagaggc caaggacgca gatggcaaca   5880
aacccaagga acctgggata acggaggctt catcggagat gatatcacca aacatgttgc   5940
tggtgattat aataccattt aggtgggttg ggttcttaac taggatcatg gcggcagaat   6000
caatcaattg atgttgaacc ttcaatgtag ggaattcgtt cttgatggtt tcctccacag   6060
tttttctcca taatcttgaa gaggccaaaa gattagcttt atccaaggac caaataggca   6120
atggtggctc atgttgtagg gccatgaaag cggccattct tgtgattctt tgcacttctg   6180
gaacggtgta ttgttcacta tcccaagcga caccatcacc atcgtcttcc tttctcttac   6240
caaagtaaat acctcccact aattctctga caacaacgaa gtcagtacct ttagcaaatt   6300
gtggcttgat tggagataag tctaaaagag agtcggatgc aaagttacat ggtcttaagt   6360
tggcgtacaa ttgaagttct ttacggattt ttagtaaacc ttgttcaggt ctaacactac   6420
cggtacccca tttaggacca gccacagcac ctaacaaaac ggcatcaacc ttcttggagg   6480
cttccagcgc ctcatctgga agtgggacac ctgtagcatc gatagcagca ccaccaatta   6540
aatgatttc gaaatcgaac ttgacattgg aacgaacatc agaaatagct ttaagaacct   6600
taatggcttc ggctgtgatt tcttgaccaa cgtggtcacc tggcaaaacg acgatcttct   6660
taggggcaga catagggca gacattagaa tggtatatcc ttgaaatata tatatatatt   6720
gctgaaatgt aaaaggtaag aaaagttaga aagtaagacg attgctaacc acctattgga   6780
aaaaacaata ggtccttaaa taatattgtc aacttcaagt attgtgatgc aagcatttag   6840
tcatgaacgc ttctctattc tatatgaaaa gccggttccg gcctctcacc tttccttttt   6900
ctcccaattt ttcagttgaa aaaggtatat gcgtcaggcg acctctgaaa ttaacaaaaa   6960
atttccagtc atcgaatttg attctgtgcg atagcgcccc tgtgtgttct cgttatgttg   7020
```

```
aggaaaaaaa taatggttgc taagagattc gaactcttgc atcttacgat acctgagtat   7080
tcccacagtt aactgcggtc aagatatttc ttgaatcagg cgccttagac cgctcggcca   7140
aacaaccaat tacttgttga gaaatagagt ataattatcc tataaatata acgtttttga   7200
acacacatga acaaggaagt acaggacaat tgattttgaa gagaatgtgg attttgatgt   7260
aattgttggg attccatttt taataaggca ataatattag gtatgtggat atactagaag   7320
ttctcctcga ccgtcgatat gcggtgtgaa ataccgcaca gatgcgtaag gagaaaatac   7380
cgcatcagga aattgtaaac gttaatattt tgttaaaatt cgcgttaaat ttttgttaaa   7440
tcagctcatt ttttaaccaa taggccgaaa tcggcaaaat cccttataaa tcaaaagaat   7500
agaccgagat agggttgagt gttgttccag tttggaacaa gagtccacta ttaaagaacg   7560
tggactccaa cgtcaaaggg cgaaaaaccg tctatcaggg cgatggccca ctacgtgaac   7620
catcacccta atcaagtttt ttggggtcga ggtgccgtaa agcactaaat cggaacccta   7680
aagggagccc ccgatttaga gcttgacggg gaaagccggc gaacgtggcg agaaaggaag   7740
ggaagaaagc gaaaggagcg ggcgctaggg cgctggcaag tgtagcggtc acgctgcgcg   7800
taaccaccac acccgccgcg cttaatgcgc cgctacaggg cgcgtcgcgc cattcgccat   7860
tcaggctgcg caactgttgg gaagggcgat cggtgcgggc ctct                    7904
```

```
<210> SEQ ID NO 69
<211> LENGTH: 6979
<212> TYPE: DNA
<213> ORGANISM: Artificial Sequence
<220> FEATURE:
<223> OTHER INFORMATION: plasmid
<220> FEATURE:
<221> NAME/KEY: misc_feature
<222> LOCATION: (2382)..(2382)
<223> OTHER INFORMATION: n is a, c, g, or t

<400> SEQUENCE: 69
```

```
agaaaccatt attatcatga cattaaccta taaaaatagg cgtatcacga ggccctttcg     60
tctcgcgcgt ttcggtgatg acggtgaaaa cctctgacac atgcagctcc cggagacggt    120
cacagcttgt ctgtaagcgg atgccgggag cagacaagcc cgtcagggcg cgtcagcggg    180
tgttggcggg tgtcggggct ggcttaacta tgcggcatca gagcagattg tactgagagt    240
gcaccatacc acagcttttc aattcaattc atcatttttt ttttattctt ttttttgatt    300
tcggtttctt tgaaattttt ttgattcggt aatctccgaa cagaaggaag aacgaaggaa    360
ggagcacaga cttagattgg tatatatacg catatgtagt gttgaagaaa catgaaattg    420
cccagtattc ttaacccaac tgcacagaac aaaaacctgc aggaaacgaa gataaatcat    480
gtcgaaagct acatataagg aacgtgctgc tactcatcct agtcctgttg ctgccaagct    540
atttaatatc atgcacgaaa agcaaacaaa cttgtgtgct tcattggatg ttcgtaccac    600
caaggaatta ctggagttag ttgaagcatt aggtcccaaa atttgtttac taaaaacaca    660
tgtggatatc ttgactgatt tttccatgga gggcacagtt aagccgctaa aggcattatc    720
cgccaagtac aatttttac tcttcgaaga cagaaaattt gctgacattg gtaatacagt     780
caaattgcag tactctgcgg gtgtatacag aatagcagaa tgggcagaca ttacgaatgc    840
acacggtgtg gtgggcccag gtattgttag cggtttgaag caggcggcag aagaagtaac    900
aaaggaacct agaggccttt tgatgttagc agaattgtca tgcaagggct ccctatctac    960
tggagaatat actaagggta ctgttgacat tgcgaagagc gacaaagatt ttgttatcgg   1020
```

```
ctttattgct caaagagaca tgggtggaag agatgaaggt tacgattggt tgattatgac   1080
acccggtgtg ggtttagatg acaagggaga cgcattgggt caacagtata gaaccgtgga   1140
tgatgtggtc tctacaggat ctgacattat tattgttgga agaggactat ttgcaaaggg   1200
aagggatgct aaggtagagg gtgaacgtta cagaaaagca ggctgggaag catatttgag   1260
aagatgcggc cagcaaaact aaaaaactgt attataagta aatgcatgta tactaaactc   1320
acaaattaga gcttcaattt aattatatca gttattaccc tatgcggtgt gaaataccgc   1380
acagatgcgt aaggagaaaa taccgcatca ggaaattgta aacgttaata ttttgttaaa   1440
attcgcgtta aatttttgtt aaatcagctc attttttaac caataggccg aaatcggcaa   1500
aatcccttat aaatcaaaag aatagaccga gatagggttg agtgttgttc cagtttggaa   1560
caagagtcca ctattaaaga acgtggactc caacgtcaaa gggcgaaaaa ccgtctatca   1620
gggcgatggc ccactacgtg aaccatcacc ctaatcaagt tttttggggt cgaggtgccg   1680
taaagcacta aatcggaacc ctaaagggag cccccgattt agagcttgac ggggaaagcc   1740
ggcgaacgtg gcgagaaagg aagggaagaa agcgaaagga gcgggcgcta gggcgctggc   1800
aagtgtagcg gtcacgctgc gcgtaaccac cacacccgcc gcgcttaatg cgccgctaca   1860
gggcgcgtcg cgccattcgc cattcaggct gcgcaactgt tgggaagggc gatcggtgcg   1920
ggcctcttcg ctattacgcc agctggcgaa agggggatgt gctgcaaggc gattaagttg   1980
ggtaacgcca gggttttccc agtcacgacg ttgtaaaacg acggccagtg agcgcgcgta   2040
atacgactca ctatagggcg aattgggtac cggccgcaaa ttaaagcctt cgagcgtccc   2100
aaaaccttct caagcaaggt tttcagtata atgttacatg cgtacacgcg tctgtacaga   2160
aaaaaaagaa aaatttgaaa tataaataac gttcttaata ctaacataac tataaaaaaa   2220
taaataggga cctagacttc aggttgtcta actccttcct tttcggttag agcggatgtg   2280
gggggagggc gtgaatgtaa gcgtgacata actaattaca tgactcgagg tcgacaattc   2340
caaccttacc caagagttcg ccaaactcag acatcacttt angcaaaacc gcgccgtgct   2400
tcttcctcgg tggcattcat cacgaaatgt tcagcactac gcatactttt gacaggaaac   2460
gcaacggata ttgagtcaat atcaggcatt ctatcgctca gctttacagt gacaatgacg   2520
gctggcgact gaatattagt gcttacagac agcactacat attttccgtc gatgttgaaa   2580
tcctttctca tatgtcacca taaatatcaa ataattatag caatcattta cgcgttaatg   2640
gctaatcgcc atcttccagc aggcgcacca ttgcccctgt ttcactatcc agggtacgga   2700
tatagttcat gacaatattt acattggtcc agccaccagc ttgcatgatc tccggtattg   2760
aaactccagc gcgggccata tctcgcgcgg ctccgacacg ggcactgtgt ccagaccagg   2820
ccaggtatct ctgaccagag tcatccttag cgccgtaaat caatcgatga gttgcttcaa   2880
aaatcccttc cagggcgcga gttgatagct ggctggtggc agatggcgcg gcaacaccat   2940
tttttctgac ccggcaaaac aggtagttat tcggatcatc agctacacca gagacggaaa   3000
tccatcgctc gaccagttta gttacccca ggctaagtgc cttctctaca cctgcggtgc    3060
taaccagcgt tttcgttctg ccaatatgga ttaacattct cccaccgtca gtacgtgaga   3120
tatctttaac cctgatcctg gcaatttcgg ctatacgtaa cagggtgtta taagcaatcc   3180
ccagaaatgc cagattacgt atatcctggc agcgatcgct attttccatg agtgaacgaa   3240
cctggtcgaa atcagtgcgt tcgaacgcta gagcctgttt tgcacgttca ccggcatcaa   3300
cgttttcttt tcggatccgc cgcataacca gtgaaacagc attgctgtca cttggtcgtg   3360
gcagcccgga ccgacgatga agcatgttta gctggcccaa atgttgctgg atagttttta   3420
```

```
ctgccagacc gcgcgcctga agatatagaa gataatcgcg aacatcttca ggttctgcgg   3480
gaaaccattt ccggttattc aacttgcacc atgccgccca cgaccggcaa acggacagaa   3540
gcattttcca ggtatgctca gaaaacgcct ggcgatccct gaacatgtcc atcaggttct   3600
tgcgaacctc atcactcgtt gcatcgaccg gtaatgcagg caaattttgg tgtacggtca   3660
gtaaattgga catttaacac tcagataatg gttttaagta aagtgtacag gatcggctct   3720
gcccctcgac ggtatcgata agcttgatat cgaattcctg cagcccgggg gatccactag   3780
ttctagaatc cggggttttt tctccttgac gttaaagtat agaggtatat taacaatttt   3840
ttgttgatac ttttattaca tttgaataag aagtaataca aaccgaaaat gttgaaagta   3900
ttagttaaag tggttatgca gtttttgcat ttatatatct gttaatagat caaaaatcat   3960
cgcttcgctg attaattacc ccagaaataa ggctaaaaaa ctaatcgcat tatcatccta   4020
tggttgttaa tttgattcgt tcatttgaag gtttgtgggg ccaggttact gccaattttt   4080
cctcttcata accataaaag ctagtattgt agaatcttta ttgttcggag cagtgcggcg   4140
cgaggcacat ctgcgtttca ggaacgcgac cggtgaagac gaggacgcac ggaggagagt   4200
cttccttcgg agggctgtca cccgctcggc ggcttctaat ccgtactaga gctccagctt   4260
ttgttccctt tagtgagggt taattgcgcg cttggcgtaa tcatggtcat agctgtttcc   4320
tgtgtgaaat tgttatccgc tcacaattcc acacaacata ggagccggaa gcataaagtg   4380
taaagcctgg ggtgcctaat gagtgaggta actcacatta attgcgttgc gctcactgcc   4440
cgctttccag tcgggaaacc tgtcgtgcca gctgcattaa tgaatcggcc aacgcgcggg   4500
gagaggcggt ttgcgtattg ggcgctcttc cgcttcctcg ctcactgact cgctgcgctc   4560
ggtcgttcgg ctgcggcgag cggtatcagc tcactcaaag gcggtaatac ggttatccac   4620
agaatcaggg gataacgcag gaaagaacat gtgagcaaaa ggccagcaaa aggccaggaa   4680
ccgtaaaaag gccgcgttgc tggcgttttt ccataggctc cgcccccctg acgagcatca   4740
caaaaatcga cgctcaagtc agaggtggcg aaacccgaca ggactataaa gataccaggc   4800
gtttccccct ggaagctccc tcgtgcgctc tcctgttccg accctgccgc ttaccggata   4860
cctgtccgcc tttctccctt cgggaagcgt ggcgctttct catagctcac gctgtaggta   4920
tctcagttcg gtgtaggtcg ttcgctccaa gctgggctgt gtgcacgaac cccccgttca   4980
gcccgaccgc tgcgccttat ccggtaacta tcgtcttgag tccaacccgg taagacacga   5040
cttatcgcca ctggcagcag ccactggtaa caggattagc agagcgaggt atgtaggcgg   5100
tgctacagag ttcttgaagt ggtggcctaa ctacggctac actagaagga cagtatttgg   5160
tatctgcgct ctgctgaagc cagttacctt cggaaaaaga gttggtagct cttgatccgg   5220
caaacaaacc accgctggta gcggtggttt ttttgtttgc aagcagcaga ttacgcgcag   5280
aaaaaaagga tctcaagaag atcctttgat cttttctacg gggtctgacg ctcagtggaa   5340
cgaaaactca cgttaaggga ttttggtcat gagattatca aaaaggatct tcacctagat   5400
ccttttaaat taaaaatgaa gttttaaatc aatctaaagt atatatgagt aaacttggtc   5460
tgacagttac caatgcttaa tcagtgaggc acctatctca gcgatctgtc tatttcgttc   5520
atccatagtt gcctgactcc ccgtcgtgta gataactacg atacgggagg gcttaccatc   5580
tggccccagt gctgcaatga taccgcgaga cccacgctca ccggctccag atttatcagc   5640
aataaaccag ccagccggaa gggccgagcg cagaagtggt cctgcaactt tatccgcctc   5700
catccagtct attaattgtt gccgggaagc tagagtaagt agttcgccag ttaatagttt   5760
```

gcgcaacgtt gttgccattg ctacaggcat cgtggtgtca cgctcgtcgt ttggtatggc 5820
ttcattcagc tccggttccc aacgatcaag gcgagttaca tgatccccca tgttgtgcaa 5880
aaaagcggtt agctccttcg gtcctccgat cgttgtcaga agtaagttgg ccgcagtgtt 5940
atcactcatg gttatggcag cactgcataa ttctcttact gtcatgccat ccgtaagatg 6000
cttttctgtg actggtgagt actcaaccaa gtcattctga gaatagtgta tgcggcgacc 6060
gagttgctct tgcccggcgt caatacggga taataccgcg ccacatagca gaactttaaa 6120
agtgctcatc attggaaaac gttcttcggg gcgaaaactc tcaaggatct taccgctgtt 6180
gagatccagt tcgatgtaac ccactcgtgc acccaactga tcttcagcat cttttacttt 6240
caccagcgtt tctgggtgag caaaaacagg aaggcaaaat gccgcaaaaa agggaataag 6300
ggcgacacgg aaatgttgaa tactcatact cttccttttt caatattatt gaagcattta 6360
tcagggttat tgtctcatga gcggatacat atttgaatgt atttagaaaa ataaacaaat 6420
aggggttccg cgcacatttc cccgaaaagt gccacctggg tccttttcat cacgtgctat 6480
aaaaataatt ataatttaaa tttttttaata taaatatata aattaaaaat agaaagtaaa 6540
aaaagaaatt aaagaaaaaa tagtttttgt tttccgaaga tgtaaaagac tctaggggga 6600
tcgccaacaa atactacctt ttatcttgct cttcctgctc tcaggtatta atgccgaatt 6660
gtttcatctt gtctgtgtag aagaccacac acgaaaatcc tgtgatttta cattttactt 6720
atcgttaatc gaatgtatat ctatttaatc tgcttttctt gtctaataaa tatatatgta 6780
aagtacgctt tttgttgaaa ttttttaaac ctttgtttat ttttttttct tcattccgta 6840
actcttctac cttctttatt tactttctaa aatccaaata caaaacataa aaataaataa 6900
acacagagta aattcccaaa ttattccatc attaaaagat acgaggcgcg tgtaagttac 6960
aggcaagcga tccgtccta 6979

<210> SEQ ID NO 70
<211> LENGTH: 686
<212> TYPE: DNA
<213> ORGANISM: Saccharomyces cerevisiae

<400> SEQUENCE: 70
gatctcagtt cgagtttatc attatcaata ctgccatttc aaagaatacg taaataatta 60
atagtagtga ttttcctaac tttatttagt caaaaaatta gccttttaat tctgctgtaa 120
cccgtacatg cccaaaatag ggggcgggtt acacagaata tataacatcg taggtgtctg 180
ggtgaacagt ttattcctgg catccactaa atataatgga gcccgctttt taagctggca 240
tccagaaaaa aaaagaatcc cagcaccaaa atattgtttt cttcaccaac catcagttca 300
taggtccatt ctcttagcgc aactacagag aacaggggca caaacaggca aaaaacggac 360
acaacctcaa tggagtgatg caacctgcct ggagtaaatg atgacacaag gcaattgacc 420
cacgcatgta tctatctcat tttcttacac cttctattac cttctgctct ctctgatttg 480
gaaaaagctg aaaaaaaagg ttgaaaccag ttccctgaaa ttattcccct acttgactaa 540
taagtatata aagacggtag gtattgattg taattctgta aatctatttc ttaaacttct 600
taaattctac ttttatagtt agtctttttt ttagttttaa aacaccaaga acttagtttc 660
gaataaacac acataaacaa acaaaa 686

<210> SEQ ID NO 71
<211> LENGTH: 750
<212> TYPE: DNA
<213> ORGANISM: Saccharomyces cerevisiae

<400> SEQUENCE: 71

```
acgcacagat attataacat ctgcataata ggcatttgca agaattactc gtgagtaagg     60
aaagagtgag gaactatcgc atacctgcat ttaaagatgc cgatttgggc gcgaatcctt    120
tattttggct tcaccctcat actattatca gggccagaaa aaggaagtgt ttccctcctt    180
cttgaattga tgttaccctc ataaagcacg tggcctctta tcgagaaaga aattaccgtc    240
gctcgtgatt tgtttgcaaa aagaacaaaa ctgaaaaaac ccagacacgc tcgacttcct    300
gtcttcctat tgattgcagc ttccaatttc gtcacacaac aaggtcctag cgacggctca    360
caggttttgt aacaagcaat cgaaggttct ggaatggcgg gaaagggttt agtaccacat    420
gctatgatgc ccactgtgat ctccagagca aagttcgttc gatcgtactg ttactctctc    480
tctttcaaac agaattgtcc gaatcgtgtg acaacaacag cctgttctca cacactcttt    540
tcttctaacc aagggggtgg tttagtttag tagaacctcg tgaaacttac atttacatat    600
atataaactt gcataaattg gtcaatgcaa gaaatacata tttggtcttt tctaattcgt    660
agtttttcaa gttcttagat gctttctttt tctctttttt acagatcatc aaggaagtaa    720
ttatctactt tttacaacaa atataaaaca                                     750
```

<210> SEQ ID NO 72
<211> LENGTH: 326
<212> TYPE: DNA
<213> ORGANISM: Saccharomyces cerevisiae

<400> SEQUENCE: 72

```
ggcacgtccg acggcggccc gacgggtccg aggcctcgga gatccgtccc ccttttcctt     60
tgtcgatatc atgtaattag ttatgtcacg cttacattca cgccctcccc ccacatccgc    120
tctaaccgaa aaggaaggag ttagacaacc tgaagtctag gtccctattt attttttttat    180
agttatgtta gtattaagaa cgttatttat atttcaaatt tttctttttt ttctgtacag    240
acgcgtgtac gcatgtaaca ttatactgaa aaccttgctt gagaaggttt tgggacgctc    300
gaaggcttta atttgcaagc tgcatg                                         326
```

<210> SEQ ID NO 73
<211> LENGTH: 311
<212> TYPE: DNA
<213> ORGANISM: Saccharomyces cerevisiae

<400> SEQUENCE: 73

```
ggatctctta tgtctttacg atttatagtt ttcattatca agtatgccta tattagtata     60
tagcatcttt agatgacagt gttcgaagtt tcacgaataa aagataatat tctacttttt    120
gctcccaccg cgtttgctag cacgagtgaa caccatccct cgcctgtgag ttgtacccat    180
tcctctaaac tgtagacatg gtagcttcag cagtgttcgt tatgtacggc atcctccaac    240
aaacagtcgg ttatagtttg tcctgctcct ctgaatcgtc tccctcgata tttctcattt    300
tccttcgcat g                                                         311
```

<210> SEQ ID NO 74
<211> LENGTH: 34
<212> TYPE: DNA
<213> ORGANISM: Artificial Sequence
<220> FEATURE:
<223> OTHER INFORMATION: LoxP

<400> SEQUENCE: 74
ataacttcgt atagcataca ttatacgaag ttat 34

<210> SEQ ID NO 75
<211> LENGTH: 34
<212> TYPE: DNA
<213> ORGANISM: Artificial Sequence
<220> FEATURE:
<223> OTHER INFORMATION: LoxP
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 75
ataacttcgt atannntann ntatacgaag ttat 34

<210> SEQ ID NO 76
<211> LENGTH: 1704
<212> TYPE: DNA
<213> ORGANISM: Artificial Sequence
<220> FEATURE:
<223> OTHER INFORMATION: Gene deletion construct

<400> SEQUENCE: 76
tcaagggcaa attgatgctt caacgaaaaa gttattggat tttcagcata ggccactagt 60
ggatctgata tcacctaata acttcgtata gcatacatta tacgaagtta tattaagggt 120
tctcgagagc tcgttttcga cactggatgg cggcgttagt atcgaatcga cagcagtata 180
gcgaccagca ttcacatacg attgacgcat gatattactt tctgcgcact taacttcgca 240
tctgggcaga tgatgtcgag gcgaaaaaaa atataaatca cgctaacatt tgattaaaat 300
agaacaacta caatataaaa aaactataca aatgacaagt tcttgaaaac aagaatcttt 360
ttattgtcag tactgattag aaaaactcat cgagcatcaa atgaaactgc aatttattca 420
tatcaggatt atcaatacca tatttttgaa aaagccgttt ctgtaatgaa ggagaaaact 480
caccgaggca gttccatagg atggcaagat cctggtatcg gtctgcgatt ccgactcgtc 540
caacatcaat acaacctatt aatttcccct cgtcaaaaat aaggttatca agtgagaaat 600
caccatgagt gacgactgaa tccggtgaga atggcaaaag cttatgcatt tctttccaga 660
cttgttcaac aggccagcca ttacgctcgt catcaaaatc actcgcatca accaaaccgt 720
tattcattcg tgattgcgcc tgagcgagac gaaatacgcg atcgctgtta aaaggacaat 780
tacaaacagg aatcgaatgc aaccggcgca ggaacactgc cagcgcatca acaatatttt 840
cacctgaatc aggatattct tctaatacct ggaatgctgt tttgccgggg atcgcagtgg 900
tgagtaacca tgcatcatca ggagtacgga taaaatgctt gatggtcgga agaggcataa 960
attccgtcag ccagtttagt ctgaccatct catctgtaac atcattggca acgctacctt 1020
tgccatgttt cagaaacaac tctggcgcat cgggcttccc atacaatcga tagattgtcg 1080
cacctgattg cccgacatta tcgcgagccc atttataccc atataaatca gcatccatgt 1140
tggaatttaa tcgcggcctc gaaacgtgag tcttttcctt acccatggtt gtttatgttc 1200
ggatgtgatg tgagaactgt atcctagcaa gattttaaaa ggaagtatat gaaagaagaa 1260
cctcagtggc aaatcctaac cttttatatt tctctacagg ggcgcggcgt ggggacaatt 1320
caacgcgtct gtgaggggag cgtttccctg ctcgcaggtc tgcagcgagg agccgtaatt 1380
tttgcttcgc gccgtgcggc catcaaaatg tatggatgca aatgattata catggggatg 1440

```
tatgggctaa atgtacgggc gacagtcaca tcatgcccct gagctgcgca cgtcaagact   1500

gtcaaggagg gtattctggg cctccatgtc gctggccggg tgacccggcg gggacgaggc   1560

aagctaaaca gatctctaga cctaataact tcgtatagca tacattatac gaagttatat   1620

taagggttgt cgacctgcag cgtacgaagc ttcagctggc atctcgctgg ttaattttcc   1680

tgtctcttgt ctatccagca ctta                                          1704
```

<210> SEQ ID NO 77
<211> LENGTH: 1467
<212> TYPE: DNA
<213> ORGANISM: Artificial Sequence
<220> FEATURE:
<223> OTHER INFORMATION: Gene deletion construct

<400> SEQUENCE: 77

```
aagtctagca gcgaaaagta cgcgaagaat ctactataga taatgccagc tgaagcttcg     60

tacgctgcag gtcgacaacc cttaatataa cttcgtataa tgtatgctat acgaagttat    120

taggtctaga gatctgttta gcttgccttg tccccgccgg gtcacccggc cagcgacatg    180

gaggcccaga ataccctcct tgacagtctt gacgtgcgca gctcaggggc atgatgtgac    240

tgtcgcccgt acatttagcc catacatccc catgtataat catttgcatc catacatttt    300

gatggccgca cggcgcgaag caaaaattac ggctcctcgc tgcagacctg cgagcaggga    360

aacgctcccc tcacagacgc gttgaattgt ccccacgccg cgcccctgta gagaaatata    420

aaaggttagg atttgccact gaggttcttc tttcatatac ttccttttaa aatcttgcta    480

ggatacagtt ctcacatcac atccgaacat aaacaaccat gggtaccact cttgacgaca    540

cggcttaccg gtaccgcacc agtgtcccgg gggacgccga ggccatcgag gcactggatg    600

ggtccttcac caccgacacc gtcttccgcg tcaccgccac cggggacggc ttcaccctgc    660

gggaggtgcc ggtggacccg cccctgacca aggtgttccc cgacgacgaa tcggacgacg    720

aatcggacga cggggaggac ggcgacccgg actcccggac gttcgtcgcg tacggggacg    780

acggcgacct ggcgggcttc gtggtcgtct cgtactccgg ctggaaccgc cggctgaccg    840

tcgaggacat cgaggtcgcc ccggagcacc gggggcacgg ggtcgggcgc gcgttgatgg    900

ggctcgcgac ggagttcgcc cgcgagcggg gcgccgggca cctctggctg gaggtcacca    960

acgtcaacgc accggcgatc cacgcgtacc ggcggatggg gttcaccctc tgcggcctgg   1020

acaccgccct gtacgacggc accgcctcgg acggcgagca ggcgctctac atgagcatgc   1080

cctgccccta atcagtactg acaataaaaa gattcttgtt ttcaagaact tgtcatttgt   1140

atagtttttt tatattgtag ttgttctatt ttaatcaaat gttagcgtga tttatatttt   1200

ttttcgcctc gacatcatct gcccagatgc gaagttaagt gcgcagaaag taatatcatg   1260

cgtcaatcgt atgtgaatgc tggtcgctat actgctgtcg attcgatact aacgccgcca   1320

tccagtgtcg aaaacgagct ctcgagaacc cttaatataa cttcgtataa tgtatgctat   1380

acgaagttat taggtgatat cagatccact agtggcctat gctagattaa cgttatattt   1440

tccttcaaaa atgatttttt tgtaaaa                                       1467
```

<210> SEQ ID NO 78
<211> LENGTH: 1467
<212> TYPE: DNA
<213> ORGANISM: Artificial Sequence
<220> FEATURE:
<223> OTHER INFORMATION: Gene deletion construct

<400> SEQUENCE: 78

```
aagactatac cattataaaa acgcataaga aacagtttca tcatgccagc tgaagcttcg      60
tacgctgcag gtcgacaacc cttaatataa cttcgtataa tgtatgctat acgaagttat     120
taggtctaga gatctgttta gcttgccttg tccccgccgg gtcacccggc cagcgacatg     180
gaggcccaga ataccctcct tgacagtctt gacgtgcgca gctcaggggc atgatgtgac     240
tgtcgcccgt acatttagcc catacatccc catgtataat catttgcatc catacatttt     300
gatggccgca cggcgcgaag caaaaattac ggctcctcgc tgcagacctg cgagcaggga     360
aacgctcccc tcacagacgc gttgaattgt ccccacgccg cgcccctgta gagaaatata     420
aaaggttagg atttgccact gaggttcttc tttcatatac ttccttttaa aatcttgcta     480
ggatacagtt ctcacatcac atccgaacat aaacaaccat gggtaccact cttgacgaca     540
cggcttaccg gtaccgcacc agtgtcccgg gggacgccga ggccatcgag gcactggatg     600
ggtccttcac caccgacacc gtcttccgcg tcaccgccac cggggacggc ttcaccctgc     660
gggaggtgcc ggtggacccg cccctgacca aggtgttccc cgacgacgaa tcggacgacg     720
aatcggacga cggggaggac ggcgacccgg actcccggac gttcgtcgcg tacggggacg     780
acggcgacct ggcgggcttc gtggtcgtct cgtactccgg ctggaaccgc cggctgaccg     840
tcgaggacat cgaggtcgcc ccggagcacc gggggcacgg ggtcgggcgc gcgttgatgg     900
ggctcgcgac ggagttcgcc cgcgagcggg gcgccgggca cctctggctg gaggtcacca     960
acgtcaacgc accggcgatc cacgcgtacc ggcggatggg gttcaccctc tgcggcctgg    1020
acaccgccct gtacgacggc accgcctcgg acggcgagca ggcgctctac atgagcatgc    1080
cctgccccta atcagtactg acaataaaaa gattcttgtt ttcaagaact tgtcatttgt    1140
atagtttttt tatattgtag ttgttctatt ttaatcaaat gttagcgtga tttatatttt    1200
ttttcgcctc gacatcatct gcccagatgc gaagttaagt gcgcagaaag taatatcatg    1260
cgtcaatcgt atgtgaatgc tggtcgctat actgctgtcg attcgatact aacgccgcca    1320
tccagtgtcg aaaacgagct ctcgagaacc cttaatataa cttcgtataa tgtatgctat    1380
acgaagttat taggtgatat cagatccact agtggcctat gctagttggc tctgcctata    1440
cgcatatatg tatatatata tatatat                                       1467
```

<210> SEQ ID NO 79
<211> LENGTH: 1706
<212> TYPE: DNA
<213> ORGANISM: Artificial Sequence
<220> FEATURE:
<223> OTHER INFORMATION: Gene deletion construct

<400> SEQUENCE: 79

```
tggtggaaaa agaattgcct tgctaagagt attgttgtcc aattaccgca taggccacta      60
gtggatctga tatcacctaa taacttcgta tagcatacat tatacgaagt tatattaagg     120
gttctcgaga gctcgttttc gacactggat ggcggcgtta gtatcgaatc gacagcagta     180
tagcgaccag cattcacata cgattgacgc atgatattac tttctgcgca cttaacttcg     240
catctgggca gatgatgtcg aggcgaaaaa aaatataaat cacgctaaca tttgattaaa     300
atagaacaac tacaatataa aaaaactata caaatgacaa gttcttgaaa acaagaatct     360
tttattgtc agtactgatt agaaaaactc atcgagcatc aaatgaaact gcaatttatt     420
catatcagga ttatcaatac catatttttg aaaaagccgt ttctgtaatg aaggagaaaa     480
ctcaccgagg cagttccata ggatggcaag atcctggtat cggtctgcga ttccgactcg     540
```

```
tccaacatca atacaaccta ttaatttccc ctcgtcaaaa ataaggttat caagtgagaa    600

atcaccatga gtgacgactg aatccggtga gaatggcaaa agcttatgca tttctttcca    660

gacttgttca acaggccagc cattacgctc gtcatcaaaa tcactcgcat caaccaaacc    720

gttattcatt cgtgattgcg cctgagcgag acgaaatacg cgatcgctgt taaaaggaca    780

attacaaaca ggaatcgaat gcaaccggcg caggaacact gccagcgcat caacaatatt    840

ttcacctgaa tcaggatatt cttctaatac ctggaatgct gttttgccgg ggatcgcagt    900

ggtgagtaac catgcatcat caggagtacg gataaaatgc ttgatggtcg gaagaggcat    960

aaattccgtc agccagttta gtctgaccat ctcatctgta acatcattgg caacgctacc   1020

tttgccatgt ttcagaaaca actctggcgc atcgggcttc ccatacaatc gatagattgt   1080

cgcacctgat tgcccgacat tatcgcgagc ccatttatac ccatataaat cagcatccat   1140

gttggaattt aatcgcggcc tcgaaacgtg agtcttttcc ttacccatgg ttgtttatgt   1200

tcggatgtga tgtgagaact gtatcctagc aagattttaa aaggaagtat atgaaagaag   1260

aacctcagtg gcaaatccta accttttata tttctctaca ggggcgcggc gtggggacaa   1320

ttcaacgcgt ctgtgagggg agcgtttccc tgctcgcagg tctgcagcga ggagccgtaa   1380

tttttgcttc gcgccgtgcg gccatcaaaa tgtatggatg caaatgatta tacatgggga   1440

tgtatgggct aaatgtacgg gcgacagtca catcatgccc ctgagctgcg cacgtcaaga   1500

ctgtcaagga gggtattctg ggcctccatg tcgctggccg ggtgacccgg cggggacgag   1560

gcaagctaaa cagatctcta gacctaataa cttcgtatag catacattat acgaagttat   1620

attaagggtt gtcgacctgc agcgtacgaa gcttcagctg gcattctgtt tcttctattc   1680

ttttaggttt attgttcctt ctattt                                        1706
```

<210> SEQ ID NO 80
<211> LENGTH: 413
<212> TYPE: DNA
<213> ORGANISM: Saccharomyces cerevisiae

<400> SEQUENCE: 80

```
ttagcttcaa aatgtttcta ctcctttttt actcttccag attttctcgg actccgcgca     60

tcgccgtacc acttcaaaac acccaagcac agcatactaa atttcccctc tttcttcctc    120

tagggtgtcg ttaattaccc gtactaaagg tttggaaaag aaaaaagaga ccgcctcgtt    180

tctttttctt cgtcgaaaaa ggcaataaaa atttttatca cgtttctttt tcttgaaaat    240

tttttttttt gatttttttc tctttcgatg acctcccatt gatatttaag ttaataaacg    300

gtcttcaatt tctcaagttt cagtttcatt tttcttgttc tattacaact ttttttactt    360

cttgctcatt agaaagaaag catagcaatc taatctaagt tttaattaca aaa           413
```

<210> SEQ ID NO 81
<211> LENGTH: 488
<212> TYPE: DNA
<213> ORGANISM: Saccharomyces cerevisiae

<400> SEQUENCE: 81

```
tcagcagctc tgatgtagat acacgcatct cgatatgttt tatttttact atatatacat     60

aaaagaaata aaaaatgata acgtgtatat tattattcat ataatcaatg agggtcattt    120

tctgaaacgc aaaaaacggt aaatggaaaa aaaataaaga tagaaaaaga aaacaaacaa    180

aggaaaggtt agcatattaa ataactgagc tgatacttca acagcatcgc tgaagagaac    240
```

-continued

```
agtattgaaa ccgaaacatt ttctaaaggc aaacaaggta ctccatattt gctggacgtg    300

ttctttctct cgtttcatat gcataattct gtcataagcc tgttcttttt cctggcttaa    360

atatcccgtt ttgcaaaaga gaaatctatt ccacatattt cattcattcg gctaccatac    420

taaggataaa ctaatcccgt tgttttttgg cctcatcaca taattataaa ctactaaccc    480

attatcag                                                             488


<210> SEQ ID NO 82
<211> LENGTH: 165
<212> TYPE: DNA
<213> ORGANISM: Saccharomyces cerevisiae

<400> SEQUENCE: 82

cgaatttctt atgatttatg atttttatta ttaaataagt tataaaaaaa ataagtgtat     60

acaaatttta aagtgactct taggttttaa aacgaaaatt cttattcttg agtaactctt    120

tcctgtaggt caggttgctt tctcaggtat agcatgaggt cgctc                    165


<210> SEQ ID NO 83
<211> LENGTH: 351
<212> TYPE: DNA
<213> ORGANISM: Saccharomyces cerevisiae

<400> SEQUENCE: 83

agtgctttta actaagaatt attagtcttt tctgcttatt ttttcatcat agtttagaac     60

actttatatt aacgaatagt ttatgaatct atttaggttt aaaaattgat acagttttat    120

aagttacttt ttcaaagact cgtgctgtct attgcataat gcactggaag gggaaaaaaa    180

aggtgcacac gcgtggcttt ttcttgaatt tgcagtttga aaaataacta catggatgat    240

aagaaaacat ggagtacagt cactttgaga accttcaatc agctggtaac gtcttcgtta    300

attggatact caaaaaagat ggatagcatg aatcacaaga tggaaggaaa t             351
```

METHOD FOR PRODUCING SPHINGOID BASE OR SPHINGOLIPID

This application is a Continuation of, and claims priority under 35 U.S.C. § 120 to, International Application No. PCT/JP2016/003865, filed Aug. 24, 2016, and claims priority therethrough under 35 U.S.C. § 119 to Japanese Patent Application No. 2015-164685, filed Aug. 24, 2015 and U.S. Provisional Application 62/208,932, filed Aug. 24, 2015, the entireties of which are incorporated by reference herein. Also, the Sequence Listing filed electronically herewith is hereby incorporated by reference (File name: 2018-02-16T_US-540_Seq_List; File size: 240 KB; Date recorded: Feb. 16, 2018).

BACKGROUND OF THE INVENTION

Field of the Invention

The present invention relates to a method for producing an objective substance such as sphingoid bases and sphingolipids using yeast. Sphingoid bases and sphingolipids are industrially useful as ingredients for pharmaceuticals, cosmetics, and so forth.

Brief Description of the Related Art

There has been attempted to produce sphingoid bases and sphingolipids with bioengineering techniques. As methods for producing sphingoid bases and sphingolipids with bioengineering techniques, there have been reported methods of using yeast (JP2014-529400).

Cyclodextrins are used to improve the solubilities of non-polar molecules such as lipid-soluble vitamins and hormones into aqueous media. Also, zeolites are microporous, aluminosilicate minerals, and are commonly used as commercial adsorbents and catalysts.

SUMMARY OF THE INVENTION

An object of the present invention is to develop a novel technique for improving production of an objective substance such as sphingoid bases and sphingolipids by yeast, and thereby to provide a method for efficiently producing the objective substance.

The inventor of the present invention conducted research in order to achieve the aforementioned object. As a result, the inventor found that production of an objective substance such as sphingoid bases and sphingolipids by yeast could be improved by using a culture medium containing an additive that is able to associate with, bind to, solubilize, and/or capture the objective substance upon cultivation of the yeast, and thereby accomplished the present invention.

That is, the present invention can be embodied, for example, as follows.

A method for producing an objective substance, the method comprising:

cultivating yeast having an ability to produce the objective substance in a culture medium containing an additive that is able to associate with, bind to, solubilize, and/or capture the objective substance; and collecting the objective substance from cells of the yeast and/or the culture medium, wherein the objective substance is selected from the group consisting of sphingoid bases and sphingolipids.

The aforementioned method, wherein the additive is selected from the group consisting of cyclodextrin and zeolite.

The aforementioned method, wherein the cyclodextrin is selected from the group consisting of alpha-cyclodextrin, beta-cyclodextrin, gamma-cyclodextrin, and derivatives thereof.

The aforementioned method, wherein the derivatives are selected from the group consisting of methyl-alpha-cyclodextrin, methyl-beta-cyclodextrin, hydroxypropyl-alpha-cyclodextrin, and hydroxypropyl-beta-cyclodextrin.

The aforementioned method, wherein the objective substance is selected from the group consisting of phytosphingosine (PHS), sphingosine, 6-hydroxysphingosine, sphinganine (DHS), tetraacetylphytosphingosine (TAPS), triacetylphytosphingosine, diacetylphytosphingosine, phytoceramides, dihydroceramides, 6-hydroxyceramides, and glucosylceramides.

The aforementioned method, wherein the objective substance is selected from the group consisting of phytosphingosine (PHS), sphinganine (DHS), tetraacetylphytosphingosine (TAPS), phytoceramides, and glucosylceramides.

The aforementioned method, wherein the phytosphingosine is selected from the group consisting of C16 PHS, C18 PHS, C20 PHS, C18:1 PHS, C20:1 PHS, 4-(hydroxymethyl)-2-methyl-6-tetradecanyl-1,3-oxazinan-5-ol, and 4-(hydroxymethyl)-2-methyl-6-hexadecanyl-1,3-oxazinan-5-ol.

The aforementioned method, wherein the yeast has been modified so that the expression and/or activity or activities of one or more proteins selected from proteins encoded by LCB1, LCB2, TSC10, SUR2, SLI1, ATF2, LAG1, LAC1, LIP1, and UGCG genes are increased.

The aforementioned method, wherein the activity or activities of the one or more proteins are increased by increasing the expression of the respective genes encoding the one or more proteins.

The aforementioned method, wherein the yeast has been modified so that the expression and/or activity or activities of one or more proteins selected from proteins encoded by LCB4, LCB5, ELO3, CKA2, ORM2, CHA1, and YPC1 genes are reduced.

The aforementioned method, wherein the activity or activities of the one or more proteins are reduced by attenuating the expression of the respective genes encoding the one or more proteins, or by disrupting the respective genes encoding the one or more proteins.

The aforementioned method, wherein the yeast belongs to the genus *Saccharomyces* or *Pichia*.

The aforementioned method, wherein the yeast is *Saccharomyces cerevisiae* or *Pichia ciferrii* (*Wickerhamomyces ciferrii*).

The aforementioned method, wherein the amount produced of the objective substance by the yeast is increased in the presence of the additive as compared with in the absence of the additive.

DETAILED DESCRIPTION OF THE PREFERRED EMBODIMENTS

Figure 1:
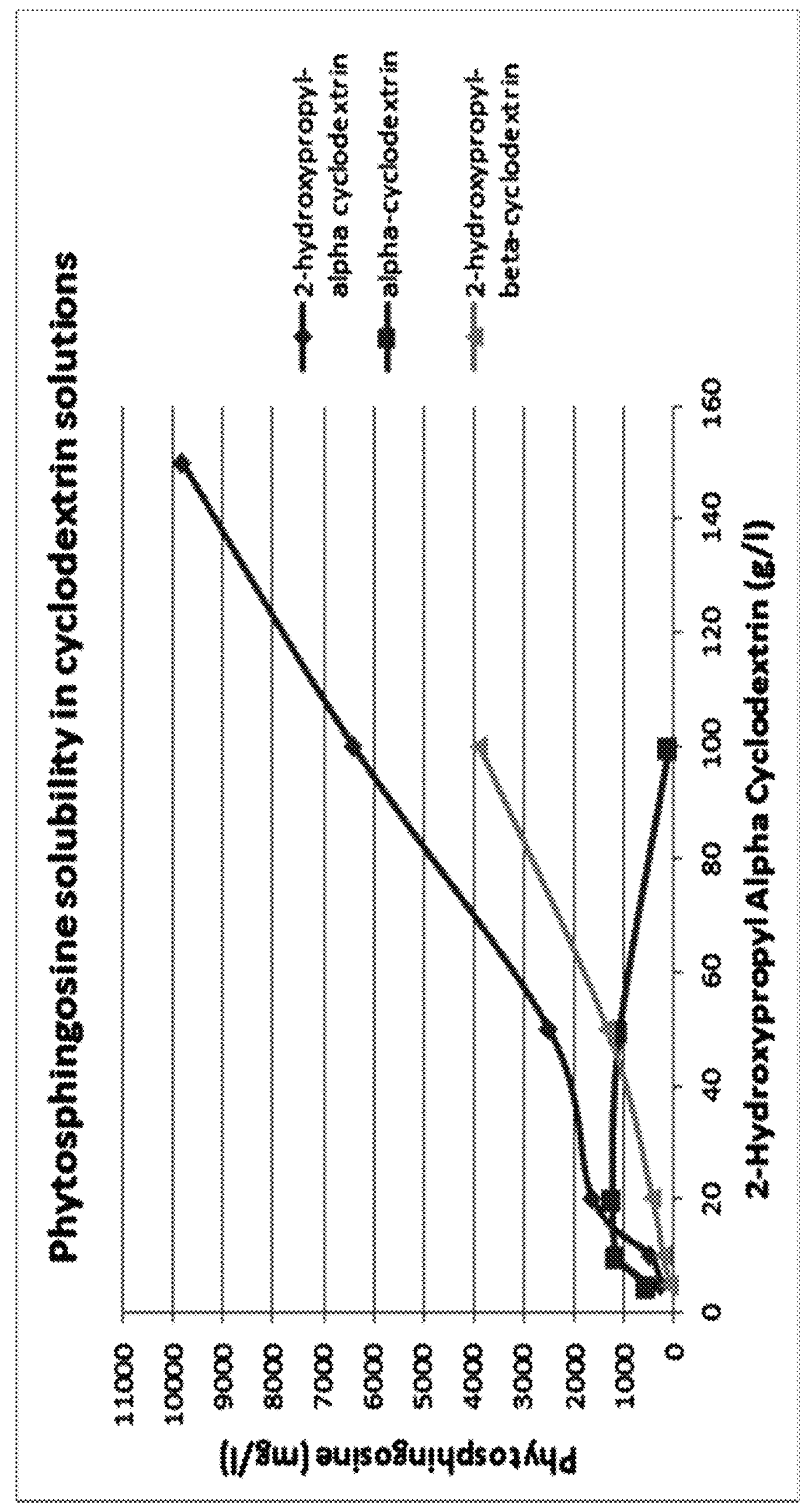
FIG. 1: The Figure shows data regarding phytosphingosine solubility with various cyclodextrins. Phytosphingosine amounts (mg/l) measured in supernatants after incubation of an excess of pure phytosphingosine (20 g/l) with each of the three types of cyclodextrin at various concentrations.

Hereafter, the present invention will be explained in detail.

The method of the present invention is a method for producing an objective substance comprising cultivating yeast having an ability to produce the objective substance in a culture medium containing an additive that is able to associate with, bind to, solubilize, and/or capture the objective substance, and collecting the objective substance from cells of the yeast and/or the culture medium. The yeast used for method of the present invention is also referred to as "the yeast of the present invention".

<1> Yeast of the Present Invention

The yeast of the present invention is yeast having an ability to produce an objective substance. The "ability to produce an objective substance" may also be referred to as "objective substance-producing ability".

<1-1> Yeast Having Objective Substance-Producing Ability

In the present invention, the term "yeast having an objective substance-producing ability" refers to yeast that is able to produce and accumulate an objective substance in a culture medium or cells of the yeast in such a degree that the objective substance can be collected, when the yeast is cultivated in the culture medium. The culture medium may be a medium that can be used in the method of the present invention, and may specifically be a medium containing an additive that is able to associate with, bind to, solubilize, and/or capture the objective substance. The yeast having an objective substance-producing ability may also be yeast that is able to produce and accumulate an objective substance in a culture medium or cells of the yeast in an amount larger than that obtainable with a non-modified strain. The term "non-modified strain" may refer to a reference strain that has not been modified so that an objective substance-producing ability is imparted or enhanced. Examples of the non-modified strain include a wild-type strain and parent strain, such as *Saccharomyces cerevisiae* strains BY4742 (ATCC 201389; EUROSCARF Y10000), S288C (ATCC 26108), and NCYC 3608. The yeast having an objective substance-producing ability may also be yeast that is able to produce and accumulate an objective substance in a culture medium in an amount of preferably 5 mg/L or more, more preferably 10 mg/L or more.

In the present invention, the objective substance is selected from the group consisting of sphingoid bases and sphingolipids.

The term "sphingoid base" refers to a compound comprising a long alkyl chain having an amino group at C2 and one or more hydroxyl groups usually at C1 and/or C3, wherein one or more of the amino group and hydroxyl groups may be acetylated. Examples of sphingoid bases include phytosphingosine (PHS), sphingosine, sphingadienine, 6-hydroxysphingosine, sphinganine (dihydrosphingosine; DHS), and acetylated derivatives thereof. Examples of acetylated derivatives include tetraacetylphytosphingosine (TAPS), triacetylphytosphingosine, diacetylphytosphingosine, O-acetylphytosphingosine, N-acetylphytosphingosine, triacetylsphinganine, diacetylsphinganine, O-acetylsphinganine, N-acetylsphinganine, triacetylsphingosine, diacetylsphingosine, O-acetylsphingosine, N-acetylsphingosine, tetraacetyl-6-hydroxysphingosine, triacetyl-6-hydroxysphingosine, diacetyl-6-hydroxysphingosine, O-acetyl-6-hydroxysphingosine, N-acetyl-6-hydroxysphingosine, triacetylsphingadienine, diacetylsphingadienine, and O-acetylsphingadienine. The length and the unsaturation degree of the alkyl chain constituting the sphingoid base may vary. The alkyl chain may have a length of, for example, C16, C18, or C20. The alkyl chain may have one or more unsaturated double bonds. That is, examples of sphingoid bases also include such variant species of the sphingoid bases exemplified above, which variant species have different lengths and/or different unsaturation degrees. The term "phytosphingosine (PHS)" may refer to C18 PHS, which is a typical species of PHS, or may collectively refer to such variant species of PHS, such as C16 PHS, which has a saturated C16 alkyl chain; C18 PHS, which has a saturated C18 alkyl chain; C20 PHS, which has a saturated C20 alkyl chain; C18:1 PHS, which has a C18 alkyl chain having one unsaturated double bond; and C20:1 PHS, which has a C20 alkyl chain having one unsaturated double bond. The term "phytosphingosine (PHS)" may also include adducts of PHS, such as 4-(hydroxymethyl)-2-methyl-6-tetradecanyl-1,3-oxazinan-5-ol and 4-(hydroxymethyl)-2-methyl-6-hexadecanyl-1,3-oxazinan-5-ol, which may be generated via reaction of C18 PHS and C20 PHS with acetaldehyde, respectively. Similarly, the term "sphinganine (DHS)" may refer to C18 DHS, which is a typical species of DHS and has a saturated C18 alkyl chain, or may collectively refer to such variant species of DHS. Such description regarding variant species may also be applied to other sphingoid bases.

The term "sphingolipid" refers to a compound that comprises an N-acyl sphingoid base moiety, i.e. a compound that comprises a sphingoid base moiety covalently linked via an amide bond to a fatty acid. Examples of sphingolipids include ceramides, glucosylceramides (cerebrosides), inositol phosphorylceramides, mannosylinositol phosphorylceramides, and mannosyldiinositol phosphorylceramides. Examples of ceramides include phytoceramides, which correspond to ceramides of PHS; dihydroceramides, which correspond to ceramides of DHS; and 6-hydroxyceramides, which correspond to ceramides of 6-hydroxysphingosine. The length and the unsaturation degree of the acyl chain constituting the sphingolipid may vary. The acyl chain may have a length of, for example, C14 to C26, such as C14, C16, C18, C20, C22, C24, and C26. The acyl chain may have one or more unsaturated double bonds. The acyl chain may have one or more functional groups such as hydroxy group.

In cases where the objective substance is a compound that can form a salt, the objective substance to be produced may be a free compound, a salt thereof, or a mixture thereof. That is, in the present invention, the term "objective substance" may refer to an objective substance in a free form, a salt thereof, or a mixture thereof. Examples of the salt include, for example, inorganic acid salts such as sulfate salt, hydrochloride salt, and carbonate salt, and organic acid salts such as lactic acid salt and glycolic acid salt (Acta Derm Venereol. 2002; 82(3):170-3.). As the salt of the objective substance, one kind of salt may be employed, or two or more kinds of salts may be employed.

The yeast is not particularly limited so long as it can be used for the method of the present invention. The yeast may be budding yeast, or may be fission yeast. The yeast may be haploid yeast, or may be diploid or more polyploid yeast.

Examples of the yeast include yeast belonging to the genus *Saccharomyces* such as *Saccharomyces cerevisiae*, the genus *Pichia* (also referred to as the genus *Wickerhamomyces*) such as *Pichia ciferrii, Pichia sydowiorum*, and *Pichia pastoris*, the genus *Candida* such as *Candida utilis*, the genus *Hansenula* such as *Hansenula polymorpha*, the genus *Schizosaccharomyces* such as *Schizosaccharomyces pombe*. Some species of the genus *Pichia* has been reclassified into the genus *Wickerhamomyces* (Int J Syst Evol Microbiol. 2014 March; 64(Pt 3):1057-61). Therefore, for example, *Pichia ciferrii* and *Pichia sydowiorum* are also called *Wickerhamomyces ciferrii* and *Wickerhamomyces sydowiorum*, respectively. In the present invention, the term "*Pichia*" should include such species that had been classified into the genus *Pichia* but have been reclassified into another genus such as *Wickerhamomyces*.

Specific examples of *Saccharomyces cerevisiae* include strains BY4742 (ATCC 201389; EUROSCARF Y10000), S288C (ATCC 26108), Y006 (FERM BP-11299), NCYC 3608, and derivative strains thereof. Specific examples of *Pichia ciferrii* (*Wickerhamomyces ciferrii*) include strain NRRL Y-1031 (ATCC 14091), strain CS.PCΔPro2 (Schorsch et al., 2009, Curr Genet. 55, 381-9.), strains disclosed in WO 95/12683, and derivative strains thereof. Specific examples of *Pichia sydowiorum* (*Wickerhamomyces sydowiorum*) include strain NRRL Y-7130 (ATCC 58369) and derivative strains thereof.

These strains are available from, for example, the American Type Culture Collection (ATCC, Address: P.O. Box 1549, Manassas, Va. 20108, United States of America), EUROpean *Saccharomyces Cerevisiae* ARchive for Functional Analysis (EUROSCARF, Address: Institute for Molecular Biosciences, Johann Wolfgang Goethe-University Frankfurt, Max-von-Laue Str. 9; Building N250, D-60438 Frankfurt, Germany), the National Collection of Yeast Cultures (NCYC, Address: Institute of Food Research, Norwich Research Park, Norwich, NR4 7UA, UK), or depositary institutions corresponding to deposited strains. That is, for example, in cases of ATCC strains, registration numbers are assigned to the respective strains, and the strains can be ordered by using these registration numbers (refer to atcc.org). The registration numbers of the strains are listed in the catalogue of the American Type Culture Collection (ATCC).

The yeast of the present invention may be yeast inherently having an objective substance-producing ability, or may be yeast modified so that it has an objective substance-producing ability. The yeast having an objective substance-producing ability can be obtained by imparting an objective substance-producing ability to yeast such as those mentioned above, or by enhancing an objective substance-producing ability of yeast such as those mentioned above.

Hereafter, methods for imparting or enhancing an objective substance-producing ability are specifically exemplified. All the modifications for imparting or enhancing an objective substance-producing ability may be used independently or in any appropriate combination. Modifications for constructing the yeast of the present invention can be performed in an arbitrary order.

An objective substance-producing ability may be imparted or enhanced by modifying yeast so that the expression and/or activity or activities of one or more kinds of proteins involved in production of the objective substance are increased or reduced. That is, the yeast of the present invention may have been modified so that the expression and/or activity or activities of one or more kinds of proteins involved in production of the objective substance are increased or reduced. The term "protein" also includes so-called peptides such as polypeptides. Examples of the proteins involved in production of the objective substance include enzymes that catalyze the synthesis of the objective substance (also referred to as "biosynthetic enzyme of objective substance"), enzymes that catalyze a reaction branching away from the biosynthetic pathway of the objective substance to generate a compound other than the objective substance (also referred to as "biosynthetic enzyme of byproduct"), enzymes that catalyze decomposition of the objective substance (also referred to as "decomposition enzyme of objective substance"), and proteins that affect, e.g. increase or reduce, the activity of an enzyme such as those described above.

The protein of which the expression and/or activity is to be increased or reduced can be appropriately chosen depending on the type of the objective substance and on the types and activities of the proteins involved in production of the objective substance and inherently possessed by the yeast of the present invention. For example, the expression and/or activity or activities of one or more kinds of proteins selected from biosynthetic enzymes of the objective substance may preferably be increased. Also, for example, the expression and/or activity or activities of one or more kinds of proteins selected from biosynthetic enzymes of a byproduct and decomposition enzymes of the objective substance may preferably be reduced.

Methods for increasing or reducing the expression and/or activity of a protein will be described in detail later. The activity of a protein can be increased by, for example, increasing the expression of a gene encoding the protein. The activity of a protein can be reduced by, for example, attenuating the expression of a gene encoding the protein or disrupting a gene encoding the protein. The expression of a gene is also referred to as "the expression of a protein (i.e. the protein encoded by the gene)". Such methods of increasing or reducing the expression and/or activity of a protein are well known in the art.

Specific examples of the proteins involved in production of the objective substance include proteins encoded by LCB1, LCB2, TSC10, SUR2, SLI1, ATF2, LAG1, LAC1, LIP1, UGCG, LCB4, LCB5, ELO3, CKA2, ORM2, CHA1, and YPC1 genes. These genes may be collectively referred to as "target gene", and proteins encoded thereby may be collectively referred to as "target protein".

For example, the yeast of the present invention may have been modified so that the expression and/or activity or activities of one or more proteins selected from proteins encoded by LCB1, LCB2, TSC10, SUR2, SLI1, ATF2, LAG1, LAC1, LIP1, and UGCG genes are increased, and/or that the expression and/or activity or activities of one or more proteins selected from proteins encoded by LCB4, LCB5, ELO3, CKA2, ORM2, CHA1, and YPC1 genes are reduced. The expression "the activity or activities of one or more proteins selected from proteins encoded by LCB1, LCB2, TSC10, SUR2, SLI1, ATF2, LAG1, LAC1, LIP1, and UGCG genes are increased" may specifically mean that the expression of one or more genes selected from LCB1, LCB2, TSC10, SUR2, SLI1, ATF2, LAG1, LAC1, LIP1, and UGCG genes is increased. The expression "the activity or activities of one or more proteins selected from proteins encoded by LCB4, LCB5, ELO3, CKA2, ORM2, CHA1, and YPC1 genes are reduced" may specifically mean that the expression of one or more genes selected from LCB4, LCB5, ELO3, CKA2, ORM2, CHA1, and YPC1 genes is attenuated, or one or more genes selected from LCB4, LCB5, ELO3, CKA2, ORM2, CHA1, and YPC1 genes are disrupted.

LCB1 and LCB2 genes encode serine palmitoyltransferase. The term "serine palmitoyltransferase" refers to a protein having an activity of catalyzing the synthesis of 3-ketosphinganine from serine and palmitoyl-CoA (EC 2.3.1.50). This activity may be referred to as "serine palmitoyltransferase activity". Proteins encoded by LCB1 and LCB2 genes may be referred to as "Lcb1p" and "Lcb2p", respectively. Examples of LCB1 and LCB2 genes include those of yeast such as *S. cerevisiae* and *Pichia ciferrii*. The nucleotide sequences of LCB1 and LCB2 genes of *S. cerevisiae* S288C are shown as SEQ ID NOS: 1 and 3, and the amino acid sequences of Lcb1p and Lcb2p encoded thereby are shown as SEQ ID NOS: 2 and 4. Lcb1p and Lcb2p may form a heterodimer to function as serine palmitoyltransferase (Plant Cell. 2006 December; 18(12):3576-93.). The activity or activities of either one or both of Lcb1p and Lcb2p may be increased, for example, in cases of producing any objective substance, and specifically in cases of producing sphingoid bases such as PHS and TAPS. An increased activity or activities of either one or both of Lcb1p and Lcb2p may specifically mean an increased serine palmitoyltransferase activity. Serine palmitoyltransferase activity can be measured by, for example, a known method (J Biol Chem. 2000 Mar. 17; 275(11):7597-603.).

TSC10 gene encodes 3-dehydrosphinganine reductase. The term "3-dehydrosphinganine reductase" refers to a protein having an activity of catalyzing the conversion of 3-ketosphinganine to dihydrosphingosine (sphinganine) in the presence of an electron donor such as NADPH (EC 1.1.1.102). This activity may be referred to as "3-dehydrosphinganine reductase activity". A protein encoded by TSC10 gene may be referred to as "Tsc10p". Examples of TSC10 gene include those of yeast such as *S. cerevisiae* and *Pichia ciferrii*. The nucleotide sequence of TSC10 gene of *S. cerevisiae* S288C is shown as SEQ ID NO: 5, and the amino acid sequence of Tsc10p encoded thereby is shown as SEQ ID NO: 6. The activity of Tsc10p may be increased, for example, in cases of producing any objective substance, and specifically in cases of producing sphingoid bases such as PHS and TAPS. An increased activity of Tsc10p may specifically mean an increased 3-dehydrosphinganine reductase activity. 3-dehydrosphinganine reductase activity can be measured by, for example, a known method (Biochim Biophys Acta. 2006 January; 1761(1):52-63.).

SUR2 (SYR2) gene encodes sphingosine hydroxylase. The term "sphingosine hydroxylase" refers to a protein having an activity of catalyzing the hydroxylation of a sphingoid base or the hydroxylation of sphingoid base moiety of a ceramide (EC 1.-.-.-). This activity may be referred to as "sphingosine hydroxylase activity". Sphingosine hydroxylase may catalyze, for example, the hydroxylation of dihydrosphingosine (DHS; sphinganine) to form phytosphingosine (PHS), or the hydroxylation of a ceramide containing DHS (dihydroceramide) to form a ceramide containing PHS (phytoceramide). A protein encoded by SUR2 gene may be referred to as "Sur2p". Examples of SUR2 gene include those of yeast such as *S. cerevisiae* and *Pichia ciferrii*. The nucleotide sequence of SUR2 gene of *S. cerevisiae* S288C is shown as SEQ ID NO: 7, and the amino acid sequence of Sur2p encoded thereby is shown as SEQ ID NO: 8. The nucleotide sequence of SUR2 gene of *Pichia ciferrii* is shown as SEQ ID NO: 37, and the amino acid sequence of Sur2p encoded thereby is shown as SEQ ID NO: 38. The activity of Sur2p may be increased, for example, in cases of producing PHS and phytoceramides. An increased activity of Sur2p may specifically mean an increased sphingosine hydroxylase activity. Sphingosine hydroxylase activity can be measured by, for example, incubating the enzyme with DHS or a dihydroceramide and determining an enzyme-dependent production of PHS or a phytoceramide.

SLI1 and ATF2 genes encode acetyltransferases. The term "acetyltransferase" refers to a protein having an activity of catalyzing the acetylation of a sphingoid base in the presence of an acetyl donor such as acetyl-CoA (EC 2.3.1.-). This activity may be referred to as "acetyltransferase activity". Proteins encoded by SLI1 and ATF2 genes may be referred to as "Sli1p" and "Atf2p", respectively. Examples of SLI1 and ATF2 genes include those of yeast such as *S. cerevisiae* and *Pichia ciferrii*. The nucleotide sequences of SLI1 and ATF2 genes of *S. cerevisiae* S288C are shown as SEQ ID NOS: 9 and 11, and the amino acid sequences of Sli1p and Atf2p encoded thereby are shown as SEQ ID NOS: 10 and 12. The nucleotide sequences of SLI1 (partial) and ATF2 genes of *Pichia ciferrii* are shown as SEQ ID NOS: 39 and 42, the nucleotide sequences of SLI1 and ATF2 genes of *Pichia ciferrii* used in the Examples section, which are optimized for *S. cerevisiae* codon usage, are shown as SEQ ID NOS: 40 and 43, and the amino acid sequences of Sli1p and Atf2p encoded thereby are shown as SEQ ID NOS: 41 and 44. The activity or activities of either one or both of Sli1p and Atf2p may be increased, for example, in cases of producing an acetylated derivative according to the type of acetylation. For example, tetraacetyl phytosphingosine (TAPS) can be synthesized from PHS by combination of Sli1p and Atf2p (Appl Microbiol Biotechnol. 2013 October; 97(19):8537-46.). Specifically, Sli1p may catalyze initial O- and N-acetylation of PHS to yield triacetyl phytosphingosine, and Atf2p may catalyze final O-acetylation to yield TAPS (Appl Microbiol Biotechnol. 2013 October; 97(19):8537-46.). Hence, for example, when the objective substance is TAPS, the activities of both of Sli1p and Atf2p may preferably be increased. By contrast, for example, when the objective substance is triacetyl phytosphingosine, the activity of Sli1p may preferably be increased. An increased activity or activities of either one or both of Sli1p and Atf2p may specifically mean an increased acetyltransferase activity. Acetyltransferase activity can be measured by, for example, incubating the enzyme with a sphingoid base and determining an enzyme-dependent production of an acetylated sphingoid base.

LAG1, LAC1, and LIP1 genes encode ceramide synthase. The term "ceramide synthase" refers to a protein having an activity of catalyzing the synthesis of a ceramide from a sphingoid base and an acyl-coenzyme A (EC 2.3.1.24). This activity may be referred to as "ceramide synthase activity". Proteins encoded by LAG1, LAC1, and LIP1 genes may be referred to as "Lag1p", "Lac1p", and "Lip1p", respectively. Examples of LAG1, LAC1, and LIP1 genes include those of yeast such as *S. cerevisiae* and *Pichia ciferrii*. The nucleotide sequences of LAG1, LAC1, and LIP1 genes of *S. cerevisiae* S288C are shown as SEQ ID NOS: 13, 15, and 17, and the amino acid sequences of Lag1p, Lac1p, and Lip1p encoded thereby are shown as SEQ ID NOS: 14, 16, and 18. LAG1 and LAC1 genes specifically encode functionally equivalent catalytic subunits of ceramide synthase. LIP1 gene specifically encodes a non-catalytic subunit of ceramide synthase. The non-catalytic subunit Lip1p is associated with each of the catalytic subunits Lag1p and Lac1p, and is required for ceramide synthase activity. The activity of any one of Lag1p, Lac1p, and Lip1p may be increased alone, the activity of either one of Lag1p and Lac1p may be increased in combination with Lip1p, the activities of both of Lag1p and Lac1p may be increased, or the activities of all of Lag1p, Lac1p, and Lip1p may be increased. The activity or activities of one or more of Lag1p, Lac1p, and Lip1p may be increased, for example, in cases of producing sphingolipids such as phytoceramides and glucosylceramides. An increased activity or activities of one or more of Lag1p, Lac1p, and Lip1p may specifically mean an increased ceramide synthase activity. Ceramide synthase activity can be measured by, for example, a known method (Guillas, Kirchman, Chuard, Pfefferli, Jiang, Jazwinski and Conzelman (2001) EMBO J. 20, 2655-2665; Schorling, Vallee, Barz, Reizman and Oesterhelt (2001) Mol. Biol. Cell 12, 3417-3427; Vallee and Riezman (2005) EMBO J. 24, 730-741).

UGCG gene encodes ceramide UDP-glucose ceramide glucosyltransferase. The term "UDP-glucose ceramide glucosyltransferase" refers to a protein having an activity of catalyzing the reaction of glycosylating a ceramide to form a glucosylceramide (EC 2.4.1.80). This activity may be referred to as "UDP-glucose ceramide glucosyltransferase activity". A protein encoded by UGCG gene may be referred to as "Ugcg protein". Examples of UGCG gene include ugcg-a and ugcg-b genes. Proteins encoded by ugcg-a and ugcg-b genes may be referred to as "Ugcg-a protein" and "Ugcg-b protein", respectively. Examples of the ugcg-a and ugcg-b genes include those of *Xenopus laevis* (African clawed frog) (Dev Dyn. 2008 January; 237(1):112-23.). The nucleotide sequences of ugcg-a and ugcg-b mRNAs of *Xenopus laevis* are shown as SEQ ID NOS: 19 and 21, and the amino acid sequences of Ugcg-a and Ugcg-b proteins encoded thereby are shown as SEQ ID NOS: 20 and 22. The activity or activities of either one or both of Ugcg-a and Ugcg-b proteins may be increased, for example, in cases of producing glucosylceramides. An increased activity or activities of either one or both of Ugcg-a and Ugcg-b proteins may specifically mean an increased UDP-glucose ceramide glucosyltransferase activity. UDP-glucose ceramide glucosyltransferase activity can be measured by, for example, a known method (Dev Dyn. 2008 January; 237 (1):112-23.).

LCB4 and LCB5 genes encode sphingoid base kinases. The term "sphingoid base kinase" refers to a protein having an activity of catalyzing the phosphorylation a sphingoid base to form a sphingoid base phosphate (EC 2.7.1.91). This activity may be referred to as "sphingoid base kinase activity". Proteins encoded by LCB4 and LCB5 genes may be referred to as "Lcb4p" and "Lcb5p", respectively. The nucleotide sequences of LCB4 and LCB5 genes of *S. cerevisiae* S288C are shown as SEQ ID NOS: 23 and 25, and the amino acid sequences of Lcb4p and Lcb5p encoded thereby are shown as SEQ ID NOS: 24 and 26. Of these, Lcb4p is the major sphingoid base kinase in *S. cerevisiae* (J Biol Chem. 2003 Feb. 28; 278(9):7325-34.). At least the activity of Lcb4p may preferably be reduced. The activity or activities of either one or both of Lcb4p and Lcb5p may be reduced, for example, in cases of producing any objective substance, and specifically in cases of producing sphingoid bases such as PHS and TAPS and sphingolipids such as phytoceramides and glucosylceramides. A reduced activity or activities of either one or both of Lcb4p and Lcb5p may specifically mean a reduced sphingoid base kinase activity. Sphingoid base kinase activity can be measured by, for example, a known method (Plant Physiol. 2005 February; 137(2):724-37.).

ELO3 gene encodes fatty acid elongase III. The term "fatty acid elongase III" refers to a protein having an activity of catalyzing the elongation of C18-CoA to form C20-C26-CoA (EC 2.3.1.199). This activity may be referred to as "fatty acid elongase III activity". C26-CoA may preferably be used for the synthesis of ceramides catalyzed by ceramide synthase. A protein encoded by ELO3 gene may be referred to as "Elo3p". The nucleotide sequence of ELO3 gene of *S. cerevisiae* S288C is shown as SEQ ID NO: 27, and the amino acid sequence of Elo3p encoded thereby is shown as SEQ ID NO: 28. The activity of Elo3p may be reduced, for example, in cases of producing sphingoid bases such as PHS. A reduced activity of Elo3p may specifically mean a reduced fatty acid elongase III activity. Fatty acid elongase III activity can be measured by, for example, a known method (J Biol Chem. 1997 Jul. 11; 272(28):17376-84.).

CKA2 gene encodes an alpha' subunit of casein kinase 2. The term "casein kinase 2" refers to a protein having an activity of catalyzing the serine/threonine-selective phosphorylation of proteins (EC 2.7.11.1). This activity may be referred to as "casein kinase 2 activity". A protein encoded by CKA2 gene may be referred to as "Cka2p". The nucleotide sequence of CKA2 gene of *S. cerevisiae* S288C is shown as SEQ ID NO: 29, and the amino acid sequence of Cka2p encoded thereby is shown as SEQ ID NO: 30. Cka2p may form a heterotetramer in combination with CKA1, CKB1, and CKB2 gene products, i.e. Cka1p, Ckb1p, and Ckb2p, to function as casein kinase 2. Cka2p may be required for full activation of ceramide synthase (Eukaryot Cell. 2003 April; 2(2):284-94.). The activity of Cka2p may be reduced, for example, in cases of producing sphingoid bases such as PHS. A reduced activity of Cka2p may specifically mean a reduced casein kinase 2 activity. Also, a reduced activity of Cka2p may specifically mean a reduced ceramide synthase activity. Casein kinase 2 activity can be measured by, for example, a known method (Gene. 1997 Jun. 19; 192(2):245-50.).

ORM2 gene encodes a membrane protein that regulates serine palmitoyltransferase activity. A protein encoded by ORM2 gene may be referred to as "Orm2p". The nucleotide sequence of ORM2 gene of *S. cerevisiae* S288C is shown as SEQ ID NO: 31, and the amino acid sequence of Orm2p encoded thereby is shown as SEQ ID NO: 32. The activity of Orm2p may be reduced, for example, in cases of producing any objective substance, and specifically in cases of producing sphingoid bases such as PHS. A reduced activity of Orm2p may specifically mean an increased serine palmitoyltransferase activity.

CHA1 gene encodes L-serine/L-threonine ammonia-lyase. The term "L-serine/L-threonine ammonia-lyase" refers to a protein having an activity of catalyzing the reaction of degrading of L-serine and L-threonine (EC 4.3.1.17 and EC 4.3.1.19). This activity may be referred to as "L-serine/L-threonine ammonia-lyase activity". A protein encoded by CHA1 gene may be referred to as "Cha1p". The nucleotide sequence of CHA1 gene of *S. cerevisiae* S288C is shown as SEQ ID NO: 33, and the amino acid sequence of Cha1p encoded thereby is shown as SEQ ID NO: 34. The activity of Cha1p may be reduced, for example, in cases of producing any objective substance, and specifically in cases of producing sphingoid bases such as PHS and sphingolipids such as phytoceramides and glucosylceramides. A reduced activity of Cha1p may specifically mean a reduced L-serine/L-threonine ammonia-lyase activity. L-serine/L-threonine ammonia-lyase activity can be measured by, for example, a known method (Eur J Biochem. 1982 April; 123(3):571-6.).

YPC1 gene encodes phytoceramidase. The term "phytoceramidase" refers to a protein having an activity of catalyzing the decomposition of phytoceramides (EC 3.5.1.-). This activity may be referred to as "phytoceramidase activity". A protein encoded by YPC1 gene may be referred to as "Ypc1p". The nucleotide sequence of YPC1 gene of *S. cerevisiae* S288C is shown as SEQ ID NO: 35, and the amino acid sequence of Ypc1p encoded thereby is shown as SEQ ID NO: 36. The activity of Ypc1p may be reduced, for example, in cases of producing sphingolipids such as phytoceramides and glucosylceramides. A reduced activity of Ypc1p may specifically mean a reduced phytoceramidase activity. Phytoceramidase activity can be measured by, for example, a known method (J Biol Chem. 2000 Mar. 10; 275(10):6876-84.).

The target genes and proteins, i.e. LCB1, LCB2, TSC10, SUR2, SLI1, ATF2, LAG1, LAC1, LIP1, UGCG, LCB4, LCB5, ELO3, CKA2, ORM2, CHA1, and YPC1 genes, and proteins encoded thereby, may have the aforementioned nucleotide and amino acid sequences. The expression "a gene or protein has a nucleotide or amino acid sequence" encompasses cases where a gene or protein comprises the nucleotide or amino acid sequence and cases where a gene or protein consists of the nucleotide or amino acid sequence.

The target genes may be variants of the respective genes exemplified above, so long as the original function thereof is maintained. Similarly, the target proteins may be variants of the respective proteins exemplified above, so long as the original function thereof is maintained. Such variants that maintain the original function thereof may also be referred to as "conservative variant". The term "LCB1", "LCB2", "TSC10", "SUR2", "SLI1", "ATF2", "LAG1", "LAC1", "LIP1", "UGCG", "LCB4", "LCB5", "ELO3", "CKA2", "ORM2", "CHA1", and "YPC1" genes include, in addition to the respective genes exemplified above, conservative variants thereof. Similarly, the term "Lcb1p", "Lcb2p", "Tsc10p", "Sur2p", "Sli1p", "Atf2p", "Lag1p", "Lac1p", "Lip1p", "Ugcg protein", "Lcb4p", "Lcb5p", "Elo3p", "Cka2p", "Orm2p", "Cha1p", and "Ypc1p" include, in addition to the respective proteins exemplified above, conservative variants thereof. That is, for example, the term "LCB1 gene" includes the LCB1 gene exemplified above, e.g. LCB1 gene of *S. cerevisiae*, and further includes variants thereof. Similarly, for example, the term "Lcb1 protein" includes the Lcb1 protein exemplified above, e.g. the protein encoded by LCB1 gene of *S. cerevisiae*, and further includes variants thereof. Examples of the conservative variants include, for example, homologues and artificially modified versions of the target genes and proteins exemplified above. Methods of generating variants of a gene or a protein are well known in the art.

The expression "the original function is maintained" means that a variant of a gene or protein has a function (such as activity and property) corresponding to the function (such as activity and property) of the original gene or protein. The expression "the original function is maintained" regarding a gene means that a variant of the gene encodes a protein of which the original function is maintained. The expression "the original function is maintained" regarding a protein means that a variant of the protein has the corresponding function such as activity and property exemplified above. That is, the expression "the original function is maintained" regarding the target proteins may mean that a variant protein has serine palmitoyltransferase activity as for Lcb1p and Lcb2p; 3-dehydrosphinganine reductase activity as for Tsc10p; sphingosine hydroxylase activity as for Sur2p; acetyltransferase activity as for Atf2p and Sli1p; ceramide synthase activity as for Lag1p, Lac1p, and Lip1p; UDP-glucose ceramide glucosyltransferase as for Ugcg proteins; sphingoid base kinase activity as for Lcb4p and Lcb5p; fatty acid elongase III activity as for Elo3p; casein kinase 2 activity as for Cka2p; property of regulating serine palmitoyltransferase activity as for Orm2p; L-serine/L-threonine ammonia-lyase activity as for Cha1p; and phytoceramidase activity as for Ypc1p. In addition, the expression "the original function is maintained" regarding Cka2p may also mean that a variant of the protein has a property that a reduced activity thereof results in a reduced ceramide synthase activity. In addition, the expression "the original function is maintained" regarding Orm2p may also mean that a variant of the protein has a property that a reduced activity thereof results in an increased serine palmitoyltransferase activity. In cases where a target protein functions as a complex consisting of a plurality of subunits, the expression "the original function is maintained" regarding the target protein may also mean that a variant of the protein exhibits the corresponding function such as activity and property exemplified above in combination with other appropriate subunit(s). That is, for example, the expression "the original function is maintained" regarding Lcb1p may also mean that a variant protein has serine palmitoyltransferase activity in combination with an appropriate Lcb2p, and the expression "the original function is maintained" regarding Lcb2p may also mean that a variant protein has serine palmitoyltransferase activity in combination with an appropriate Lcb1p. Also, the expression "the original function is maintained" regarding Lag1p or Lac1p may also mean that a variant protein has ceramide synthase activity in combination with an appropriate Lip1p, and the expression "the original function is maintained" regarding Lip1p may also mean that a variant protein has ceramide synthase activity in combination with an appropriate Lag1p or Lac1p.

Hereafter, conservative variants will be exemplified.

Homologues of the genes exemplified above or homologues of the proteins exemplified above can easily be obtained from a public database by, for example, BLAST search or FASTA search using the nucleotide sequence of any of the genes exemplified above or the amino acid sequence of any of the proteins exemplified above as a query sequence. Furthermore, homologues of the genes exemplified above can be obtained by, for example, PCR using the chromosome of an organism such as yeast as the template, and oligonucleotides prepared on the basis of the nucleotide sequence of any of the genes exemplified above as primers.

The target genes each may be a gene encoding a protein having any of the aforementioned amino acid sequences but including substitution, deletion, insertion, and/or addition of one or several amino acid residues at one or several positions, so long as the original function is maintained. For example, the encoded protein may have an extended or deleted N-terminus and/or C-terminus. Although the number meant by the term "one or several" used above may differ depending on the positions of amino acid residues in the three-dimensional structure of the protein or the types of amino acid residues, specifically, it is, for example, 1 to 50, 1 to 40, or 1 to 30, preferably 1 to 20, more preferably 1 to 10, still more preferably 1 to 5, particularly preferably 1 to 3.

The aforementioned substitution, deletion, insertion, and/or addition of one or several amino acid residues is a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gin, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as mentioned above includes a naturally occurring mutation due to an individual difference, or a difference of species of the organism from which the gene is derived (mutant or variant).

Furthermore, the target genes each may be a gene encoding a protein showing a homology of 80% or more, preferably 90% or more, more preferably 95% or more, still more preferably 97% or more, particularly preferably 99% or more, to any of the total amino acid sequence mentioned above, so long as the original function is maintained. In addition, in this specification, "homology" means "identity".

Furthermore, the target genes each may be a DNA that is able to hybridize under stringent conditions with a probe that can be prepared from any of the aforementioned nucleotide sequences, such as a sequence complementary to the whole sequence or a partial sequence of any of the aforementioned nucleotide sequences, so long as the original function is maintained. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, preferably not less than 90% homologous, more preferably not less than 95% homologous, still more preferably not less than 97% homologous, particularly preferably not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., preferably 0.1×SSC, 0.1% SDS at 60° C., more preferably 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing the nucleotide sequence as a template. As the probe, for example, a DNA fragment having a length of about 300 bp can be used. When a DNA fragment having a length of about 300 bp is used as the probe, in particular, the washing conditions of the hybridization may be, for example, 50° C., 2×SSC and 0.1% SDS.

Further, the target genes each may be a gene having any of the aforementioned nucleotide sequences in which an arbitrary codon is replaced with an equivalent codon. For example, the target genes each may be a gene modified so that it has optimal codons according to codon frequencies in a host to be used.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244, Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

<1-2> Methods for Increasing Activity of Protein

Hereafter, methods for increasing the activity of a protein will be explained.

The expression "the activity of a protein is increased" means that the activity of the protein per cell is increased as compared with that of a non-modified strain. The term "non-modified strain" may refer to a reference strain that has not been modified so that the activity of an objective protein is increased. Examples of the non-modified strain include a wild-type strain and parent strain. The state that "the activity of a protein is increased" may also be expressed as "the activity of a protein is enhanced". Specifically, the expression "the activity of a protein is increased" means that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) coding for the protein, or the translation amount of the protein (i.e. the amount of the protein). Although the degree of the increase in the activity of a protein is not particularly limited so long as the activity of the protein is increased as compared with that of a non-modified strain, the activity of the protein may be increased 1.5 times or more, 2 times or more, or 3 times or more, as compared with that of a non-modified strain. Further, the state that "the activity of a protein is increased" includes not only a state that the activity of an objective protein is increased in a strain inherently having the activity of the objective protein, but also a state that the activity of an objective protein is imparted to a strain not inherently having the activity of the objective protein. Further, so long as the activity of the protein is eventually increased, the activity of an objective protein inherently contained in a host may be attenuated and/or eliminated, and then an appropriate type of the objective protein may be introduced thereto.

The modification for increasing the activity of a protein is attained by, for example, increasing the expression of a gene coding for the protein. The expression "the expression of a gene is increased" means that the expression amount of the gene per cell is increased as compared with that of a non-modified strain such as a wild-type strain and parent strain. The expression "the expression of a gene is increased" may specifically mean that the transcription amount of the gene (i.e. the amount of mRNA) is increased, and/or the translation amount of the gene (i.e. the amount of the protein expressed from the gene) is increased. The state that "the expression of a gene is increased" may also be referred to as "the expression of a gene is enhanced". The expression of a gene may be increased 1.5 times or more, 2 times or more, or 3 times or more, as compared with that observed in a non-modified strain. Further, the state that "the expression of a gene is increased" includes not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include autonomously replicating sequences (ARS) consisting of a specific short repeated sequence, and rDNA sequences present in about 150 copies on the chromosome. WO95/32289 discloses an example where gene recombination was performed in yeast by using homologous recombination. In addition, a gene can also be introduced into a chromosome by, for example, integrating the gene into a transposon and transferring the transposon to the chromosome.

Introduction of an objective gene into a chromosome can be confirmed by Southern hybridization using a probe having a sequence complementary to the whole or a part of the gene, PCR using primers prepared on the basis of the sequence of the gene, or the like.

Further, the copy number of an objective gene can also be increased by introducing a vector including the gene into a host. For example, the copy number of an objective gene can be increased by ligating a DNA fragment including the objective gene with a vector that functions in a host to construct an expression vector of the gene, and by transforming the host with the expression vector. The DNA fragment including the objective gene can be obtained by, for example, PCR using the genomic DNA of a microorganism having the objective gene as the template. As the vector, a vector autonomously replicable in the cell of the host can be used. The vector may be a single copy vector or may be a multi-copy vector. Further, the vector preferably includes a marker for selection of transformant. Examples of the marker include antibiotic resistance genes such as KanMX, NatMX(nat1), and HygMX (hph) genes, and genes complimenting auxotrophy such as LEU2, HIS3, and URA3 genes. Examples of vector autonomously replicable in yeast include plasmids having a CEN4 replication origin and plasmids having a 2 μm DNA replication origin. Specific examples of vector autonomously replicable in yeast include pAUR123 (TAKARA BIO) and pYES2 (Invitrogen).

When a gene is introduced, it is sufficient that the gene is expressibly harbored by the yeast of the present invention. Specifically, it is sufficient that the gene is introduced so that it is expressed under the control of a promoter sequence that functions in the yeast of the present invention. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator can be located downstream the gene. The terminator is not particularly limited as long as a terminator that functions in the yeast of the present invention is chosen. The terminator may be a terminator derived from the host, or a heterogenous terminator. The terminator may be the native terminator of the gene to be introduced, or a terminator of another gene. Examples of the terminator that functions in the yeast of the present invention include CYC1, ADH1, ADH2, ENO2, PG/1, and TDH1 terminators.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Further, when two or more kinds of genes are introduced, it is sufficient that the genes each are expressibly harbored by the yeast of the present invention. For example, all the genes may be carried by a single expression vector or a chromosome. Alternatively, the genes may be separately carried by two or more expression vectors, or separately carried by a single or two or more expression vectors and a chromosome. An operon constituted by two or more genes may also be introduced.

The gene to be introduced is not particularly limited so long as it codes for a protein that functions in the host. The gene to be introduced may be a gene derived from the host, or may be a heterogenous gene. The gene to be introduced can be obtained by, for example, PCR using primers designed on the basis of the nucleotide sequence of the gene and the genomic DNA of an organism having the gene or a plasmid carrying the gene as a template. The gene to be introduced may also be totally synthesized, for example, on the basis of the nucleotide sequence of the gene (Gene, 60(1), 115-127 (1987)). The obtained gene can be used as it is, or after being modified as required.

Further, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively refers to sites that affect the expression of a gene, such as a promoter. Expression control sequences can be identified by using a promoter search vector or gene analysis software such as GENETYX.

The transcription efficiency of a gene can be improved by, for example, replacing the promoter of the gene on a chromosome with a stronger promoter. The "stronger promoter" means a promoter providing an improved transcription of a gene as compared with an inherently existing wild-type promoter of the gene. Examples of stronger promoters usable in yeast include PGK1, PGK2, PDC1, TDH3, TEF1, TEF2, TPI1, HXT7, ADH1, GPD1, and KEX2 promoters. Further, as the stronger promoter, a highly-active type of an existing promoter may also be obtained by using various reporter genes.

The translation efficiency of a gene can also be improved by, for example, modifying codons. For example, in the case of heterogenous expression of a gene or the like, the translation efficiency of the gene can be improved by replacing a rare codon present in the gene with a more frequently used synonymous codon. That is, a gene to be introduced may have been modified, for example, so that it has optimal codons according to codon frequencies observed in the host to be used. Codons can be replaced by, for example, the site-specific mutation method for introducing an objective mutation into an objective site of DNA. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Further, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Further, the modification that increases the activity of an enzyme can also be attained by, for example, enhancing the specific activity of the enzyme. An enzyme showing an enhanced specific activity can be obtained by, for example, searching various organisms. Further, a highly-active type of an existing enzyme may also be obtained by introducing a mutation into the existing enzyme. Enhancement of the specific activity may be independently used, or may be used in an arbitrary combination with such methods for enhancing the gene expression as mentioned above.

The method for transformation is not particularly limited, and methods conventionally used for transformation of yeast can be used. Examples of such methods include protoplast method, KU method (H. Ito et al., J. Bateriol., 153-163 (1983)), KUR method (Fermentation and industry, vol. 43, p. 630-637 (1985)), electroporation method (Luis et al., FEMS Micro biology Letters 165 (1998) 335-340), and a method using a carrier DNA (Gietz R. D. and Schiestl R. H., Methods Mol. Cell. Biol. 5:255-269 (1995)). Methods for manipulating yeast such as methods for spore-forming and methods for isolating haploid yeast are disclosed in Chemistry and Biology, Experimental Line 31, Experimental Techniques for Yeast, 1st Edition, Hirokawa-Shoten; Bio-Manual Series 10, Genetic Experimental Methods for Yeast, 1st Edition, Yodosha; and so forth.

An increase in the activity of a protein can be confirmed by measuring the activity of the protein.

An increase in the activity of a protein can also be confirmed by confirming an increase in the expression of a gene coding for the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that observed in a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

<1-3> Method for Reducing Activity of Protein

Hereafter, methods for reducing the activity of a protein will be explained.

The expression "the activity of a protein is reduced" means that the activity of the protein per cell is reduced as compared with that of a non-modified strain. The term "non-modified strain" may refer to a reference strain that has not been modified so that the activity of an objective protein is reduced. Examples of the non-modified strain include a wild-type strain or parent strain. The state that "the activity of a protein is reduced" also includes a state that the activity of the protein has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) coding for the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule completely disappears. Although the degree of the reduction in the activity of a protein is not particularly limited so long as the activity is reduced as compared with that of a non-modified strain, it may be reduced to, for example, 50% or less, 20% or less, 10% or less, 5% or less, or 0% of that of a non-modified strain.

The modification for reducing the activity of a protein can be attained by, for example, reducing the expression of a gene coding for the protein. The expression "the expression of a gene is reduced" means that the expression of the gene per cell is reduced as compared with that of a non-modified strain such as a wild-type strain and parent strain. The expression "the expression of a gene is reduced" may specifically mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter. When an expression control sequence is modified, preferably one or more nucleotides, more preferably two or more nucleotides, particularly preferably three or more nucleotides, of the expression control sequence are modified. Further, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Further, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Further, for example, the gene expression may be reduced due to disruption of a gene as described later.

The modification for reducing the activity of a protein can also be attained by, for example, disrupting a gene coding for the protein. The expression "a gene is disrupted" means that a gene is modified so that a protein that can normally function is not produced. The expression "a protein that can normally function is not produced" encompasses cases where no protein is expressed from the gene at all and cases where a protein of which the function (such as activity and property) has been reduced or completely eliminated is expressed from the gene.

Disruption of a gene can be attained by, for example, deleting a part or the whole of the coding region of the gene on a chromosome. Furthermore, the whole of a gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Further, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an objective substance.

Such modification of a gene on a chromosome as described above can be attained by, for example, using a recombinant DNA. The structure of the recombinant DNA to be used for homologous recombination is not particularly limited as long as it causes homologous recombination in a desired manner. For example, a host can be transformed with a linear DNA comprising an arbitrary sequence such as a deficient type gene or any appropriate insertion sequence, which arbitrary sequence is flanked with upstream and downstream sequences of the homologous recombination target region on the chromosome, so that homologous recombination can occur at upstream and downstream sides of the target region, to thereby replace the target region with the arbitrary sequence. Specifically, such modification of a gene on a chromosome as described above can be attained by, for example, preparing a deficient type gene modified so that it cannot produce a protein that can normally function, and transforming a host with a recombinant DNA including the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easy. Examples of the deficient type gene include a gene in which a part or whole of the gene is deleted, a gene introduced with missense mutation, a gene introduced with an insertion sequence such as a transposon and a marker gene, a gene introduced with nonsense mutation, and a gene introduced with frameshift mutation. The protein encoded by the deficient type gene has a conformation different from that of the wild-type protein, even if it is produced, and thus the function thereof is reduced or eliminated.

The modification for reducing the activity of a protein can also be attained by, for example, a mutagenesis treatment. Examples of the mutagenesis treatment include usual mutation treatments such as irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

A reduction in the activity of a protein can be confirmed by measuring the activity of the protein.

A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that observed in a non-modified strain. Examples of the method for evaluating the amount of mRNA include Northern hybridization, RT-PCR, and so forth (Molecular Cloning, Cold spring Harbor Laboratory Press, Cold Spring Harbor (USA), 2001). The amount of mRNA is preferably reduced to, for example, 50% or less, 20% or less, 10% or less, 5% or less, or 0%, of that observed in a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein is preferably reduced to, for example, 50% or less, 20% or less, 10% or less, 5% or less, or 0%, of that observed in a non-modified strain.

Disruption of a gene can be confirmed by determining nucleotide sequence of a part or the whole of the gene, restriction enzyme map, full length, or the like of the gene depending on the means used for the disruption.

<2> Method for Producing Objective Substance of the Present Invention

The method of the present invention is a method for producing an objective substance comprising cultivating the yeast of the present invention in a culture medium containing an additive that is able to associate with, bind to, solubilize, and/or capture the objective substance, and collecting the objective substance from cells of the yeast and/or the culture medium. In the method of the present invention, a single kind of objective substance may be produced, or two or more kinds of objective substances may be produced.

The medium to be used is not particularly limited, so long as it contains the additive that is able to associate with, bind to, solubilize, and/or capture the objective substance, the yeast of the present invention can proliferate in it, and an objective substance can be produced. As the medium, for example, a usual medium used for cultivating yeast can be used, except that it contains the additive. Examples of such a medium include SD medium, SG medium, SDTE medium, and YPD medium, supplemented with the additive. The medium may contain carbon source, nitrogen source, phosphorus source, and sulfur source, as well as components selected from other various organic components and inorganic components as required, in addition to the additive. The types and concentrations of the medium components can be appropriately determined according to various conditions such as the type of the yeast to be used and the type of the objective substance to be produced.

The culture medium contains an additive that is able to associate with, bind to, solubilize, and/or capture the objective substance. Use of the additive results in an increased production of the objective substance. That is, the amount produced of the objective substance by the yeast of the present invention is increased in the presence of the additive as compared with in the absence of the additive. Use of the additive may specifically result in an increased production of the objective substance in the culture medium. The production of the objective substance in the culture medium may also be referred to as "excretion of the objective substance". The expression "associating with, binding to, solubilizing, and/or capturing an objective substance" may specifically mean increasing the solubility of the objective substance into the culture medium. Examples of the additive include cyclodextrins and zeolites. The number of glucose residues constituting cyclodextrins is not particularly limited, and it may be, for example, 5, 6, 7, or 8. That is, examples of cyclodextrins include cyclodextrin consisting of 5 glucose residues, alpha-cyclodextrin, beta-cyclodextrin, gamma-cyclodextrin, and derivatives thereof. Examples of cyclodextrin derivatives include cyclodextrins into which one or more functional groups have been introduced. The type, number, and amount of the functional group, and the position to which the functional group is introduced are not particularly limited as long as the derivative is able to associate with, bind to, solubilize, and/or capture the objective substance. The functional group may be introduced to, for example, hydroxyl group of C2, C3, C6, or a combination thereof, which may result in an increased solubility of cyclodextrin itself. Examples of the functional group include alkyl groups and hydroxyalkyl groups. The alkyl groups and hydroxyalkyl groups each may have a linear alkyl chain or may have a branched alkyl chain. The alkyl groups and hydroxyalkyl groups each may have a carbon number of, for example, 1, 2, 3, 4, or 5. Specific examples of the alkyl groups include methyl, ethyl, propyl, butyl, pentyl, isopropyl, and isobutyl groups. Specific examples of the hydroxyalkyl groups include hydroxymethyl, hydroxyethyl, hydroxypropyl, hydroxybutyl, hydroxypentyl, hydroxyisopropyl, and hydroxyisobutyl groups. Specific examples of cyclodextrin derivatives include methyl-alpha-cyclodextrin, methyl-beta-cyclodextrin, hydroxypropyl-alpha-cyclodextrin such as 2-hydroxypropyl-alpha-cyclodextrin, and hydroxypropyl-beta-cyclodextrin such as 2-hydroxypropyl-beta-cyclodextrin. The types of zeolites are not particularly limited. As the additive, a single kind of additive may be used, or two or more kinds of additives may be used in combination.

The additive may be contained in the medium during the whole period of the culture, or may be contained in the medium during only a part of the culture period. For example, the additive may be or may not be contained in the medium from the start of the culture. When the additive is not contained in the medium at the time of the start of the culture, the additive is supplied to the medium after the start of the culture. Timing of the supply can be appropriately determined according to various conditions such as the length of culture period. For example, the additive may be supplied to the medium after the yeast of the present invention fully grows. Further, in any case, the additive may be additionally supplied to the medium as required. Means for supplying the additive to the medium is not particularly limited. For example, the additive can be supplied to the medium by feeding a feed medium containing the additive to the medium. The concentration of the additive in the medium is not particularly limited so long as production of the objective substance can be improved. For example, the concentration of the additive in the medium may be 0.1 g/L or higher, 1 g/L or higher, 2 g/L or higher, 5 g/L or higher, or 10 g/L or higher, may be 200 g/L or lower, 100 g/L or lower, 50 g/L or lower, or 20 g/L or lower, or may be within a range defined with a combination thereof. The concentration of the additive in the medium may be, for example, 0.1 g/L to 200 g/L, 1 g/L to 100 g/L, or 5 g/L to 50 g/L. The additive may be or may not be contained in the medium at a concentration within the range exemplified above during the whole period of the culture. For example, the additive may be contained in the medium at a concentration within the range exemplified above at the start of the culture, or it may be supplied to the medium so that a concentration within the range exemplified above is attained after the start of the culture.

Specific examples of the carbon source include, for example, saccharides such as glucose, fructose, sucrose, lactose, galactose, xylose, arabinose, blackstrap molasses, starch hydrolysates, and hydrolysates of biomass, organic acids such as acetic acid, fumaric acid, citric acid, and succinic acid, alcohols such as glycerol, crude glycerol, and ethanol, and aliphatic acids. As the carbon source, a single kind of carbon source may be used, or two or more kinds of carbon sources may be used in combination.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Further, when an auxotrophic mutant that requires an amino acid, a nucleic acid, or the like for growth thereof is used, it is preferable to supplement a required nutrient to the medium.

The culture conditions are not particularly limited so long as the yeast of the present invention can proliferate, and the objective substance can be produced. The culture can be performed, for example, under usual conditions used for cultivating yeast. The culture conditions can be appropriately determined according to various conditions such as the type of yeast to be used and the type of objective substance to be produced.

The culture can be performed by using a liquid medium under an aerobic condition, a microaerobic condition, or an anaerobic condition. The culture can preferably be performed under an aerobic condition. The term "aerobic condition" may refer to a condition where the dissolved oxygen concentration in the liquid medium is 0.33 ppm or higher, or preferably 1.5 ppm or higher. In cases of the aerobic condition, the oxygen concentration can be controlled to be, for example, 5 to 50%, preferably about 10 to 20%, of the saturated oxygen concentration. Specifically, the aerobic culture can be performed with aeration or shaking. The term "microaerobic condition" may refer to a condition where oxygen is supplied to the culture system but the dissolved oxygen concentration in the liquid medium is lower than 0.33 ppm. The term "anaerobic condition" may refer to a condition where oxygen is not supplied to the culture system. The culture temperature may be, for example, 25 to 35° C., preferably 27 to 33° C., more preferably 28 to 32° C. pH of the medium may be, for example, 3 to 10, or 4 to 8. pH of the medium may be adjusted as required during the culture. For adjusting pH, inorganic or organic acidic or alkaline substances, such as ammonia gas and so forth, can be used. The culture period may be, for example, 10 to 200 hours, or 15 to 120 hours. The culture condition may be constant during the whole period of the culture, or may be changed during the culture. The culture can be performed as batch culture, fed-batch culture, continuous culture, or a combination of these. Further, the culture may be performed as two steps of a seed culture and a main culture. In such a case, the culture conditions of the seed culture and the main culture may or may not be the same. For example, both the seed culture and the main culture may be performed as batch culture. Alternatively, for example, the seed culture may be performed as batch culture, and the main culture may be performed as fed-batch culture or continuous culture.

By culturing the yeast of the present invention under such conditions, the objective substance is accumulated in the medium and/or cells of the yeast.

Production of the objective substance can be confirmed by known methods used for detection or identification of compounds. Examples of such methods include, for example, HPLC, UPLC, LC/MS, GC/MS, and NMR. These methods may be used independently or in any appropriate combination.

The produced objective substance can be collected by known methods used for separation and purification of compounds. Examples of such methods include, for example, ion-exchange resin method, membrane treatment, precipitation, and crystallization. These methods may be used independently or in any appropriate combination. When the objective substance accumulates in cells, the cells can be disrupted with, for example, ultrasonic waves or the like, and then the objective substance can be collected from the supernatant obtained by removing the cells from the cell-disrupted suspension by centrifugation. The objective substance to be collected may be a free compound, a salt thereof, or a mixture thereof.

Further, when the objective substance deposits in the medium, it can be collected by centrifugation, filtration, or the like. The objective substance deposited in the medium may also be isolated together with the objective substance dissolved in the medium after the objective substance dissolved in the medium is crystallized.

The objective substance collected may contain yeast cells, medium components, moisture, and by-product metabolites of the yeast, in addition to the objective substance. The purity of the objective substance collected may be, for example, 50% (w/w) or higher, preferably 85% (w/w) or higher, particularly preferably 95% (w/w) or higher.

When a sphingoid base such as phytosphingosine (PHS) and sphinganine (DHS) is obtained as the objective substance, the sphingoid base obtained may be converted to a corresponding sphingolipid such as phytoceramides (PHC) and dihydroceramides (DHC) by chemical reaction of mixture of the sphingoid base and a fatty acid (J. Biol. Chem. July 2002 277 (29): 25847-5).

EXAMPLES

The present invention will be more specifically explained with reference to the following examples. However, these examples should not be construed to limit the present invention in any meanings.

Example 1: Construction of Strains

*S. cerevisiae* strain EYS3762 was constructed from strain BY4742 (MATalpha his3Δ1 leu2Δ0 lys2Δ0 ura3Δ0, EUROSCARF Y10000) by sequential deletion of the LCB4 and LCB5 genes. This was done by first transforming the strain with a deletion construct containing the hygromycin resistance gene HygMX (hph) flanked by loxP sites that was PCR amplified from a plasmid template pEVE698 using primers EV4024 and EV4025, which introduced in the deletion construct sequences homologous to the native promoter and terminator of the LCB4 gene. Upon transformation, the recombination fragment replaced the complete native LCB4 open reading frame. Transformants were selected on YPD-agarose plates (10 g/l yeast extract, 20 g/L bacto-peptone, 20 g/L glucose, 20 g/L agar) containing 300 mg/L hygromycin. Clones were verified by PCR testing for proper insertion of the deletion construct.

In a second step, the LCB4 gene deletion strain was transformed with a deletion construct containing the KanMX gene that confers resistance to the aminoglycoside antibiotic G418 flanked by loxP sites, that was PCR amplified from a plasmid template pEVE73 using primers EV4030 and EV4031, which introduced in the deletion construct sequences homologous to the native promoter and terminator of the LCB5 gene. Upon transformation, the recombination fragment replaced the complete native LCB5 open reading frame. Transformants were selected on YPD-agarose plates containing 100 mg/L G418. Clones were verified by PCR testing for proper insertion of the deletion construct.

*S. cerevisiae* strain EYS4061 was constructed from the previously described strain EYS3762 by insertion into the YNRCΔ9 locus of a triple expression construct consisting of the GPD1 promoter followed by the open reading frame of the LCB1 gene and a CYC1 terminator, the PGK1 promoter followed by the open reading frame of the LCB2 gene and the ADH2 terminator and the PGK1 promoter followed by the open reading frame of the TSC10 gene and the ADH2 terminator. All promoters, open reading frames and terminators were from *S. cerevisiae*. The integration construct also contained an expression cassette for the NatMX (nat1) gene that confers resistance to the antibiotic nourseothricin flanked by loxP sequences.

*S. cerevisiae* strain EYS4299 was constructed from the previously described strain EYS4061 by transformation with 2 plasmids (pEVE2785 and pEVE2120) to render the strain prototrophic for histidine and uracil. Plasmid pEVE2785 expressed a HIS3 selection marker and contained a double expression cassette with TEF1 promoter and ADH1 terminator, and PGK1 promoter and CYC1 terminator. Both expression cassettes lacked an open reading frame. Plasmid pEVE2120 expressed a URA3 selection marker contained an expression cassette with PGK1 promoter and ADH2 terminator lacking an open reading frame.

*S. cerevisiae* strain EYS4300 was constructed from the previously described strain EYS4061 by transformation with 2 plasmids, pEVE3910 and pEVE3908. Plasmid pEVE3910 contained an expression cassette for expression of *Pichia ciferrii* acetyltransferase gene ATF2 under the *S. cerevisiae* GPD1 promoter and CYC1 terminator. The plasmid also had a HIS3 selection marker. Plasmid pEVE3908 contained an expression cassette for expression of *Pichia ciferrii* acetyltransferase gene SLI1 under the *S. cerevisiae* GPD1 promoter and CYC1 terminator. The nucleotide sequences of SLI1 and ATF2 genes used were those optimized for *S. cerevisiae* codon usage. The plasmid also had a LEU2 selection marker. The presence of the two plasmids was verified by growth on EYS4300 on selective SC plates lacking the amino acids histidine and leucine (1.546 g/L SC-mix without histidine and leucine, 6.7 g/L yeast nitrogen base, 20 g/L glucose, pH 5.8) (for SC mix see Table 11).

*Saccharomyces cerevisiae* strain EYS3805 was constructed from the previously described strain BY4742 by deletion of the YPC1 gene and by insertion of the LAG1, LAC1, and LIP1 genes. Lag1p and Lac1p are functionally equivalent catalytic ceramide synthase component, involved in synthesis of ceramide from C26(acyl)-coenzyme A and dihydrosphingosine or phytosphingosine. Lip1p is a non-catalytic ceramide synthase subunit associated with Lag1p and Lac1p and required for ceramide synthase activity. Deletion of the YPC1 gene was done through a PCR-based gene deletion strategy which generated a start-to-stop-codon deletion of the open reading frame. A deletion construct containing the hygromycin resistance gene HygMX (hph) flanked by loxP sites was PCR amplified from a plasmid template pEVE698 using primers EV4018 and EV4019, which introduced in the deletion construct sequences homologous to the native promoter and terminator of the YPC1 gene. Upon transformation the recombination fragment replaced the complete native YPC1 open reading frame. Transformants were selected on YPD-agarose plates containing 300 mg/L hygromycin. Clones were verified by PCR testing for correct insertion of the deletion construct. Insertion of the LAG1, LAC1, and LIP1 genes was done by insertion of a triple expression construct into the integration locus YORW22Δ (chrXV:969221-969906). The construct consisted of (1) Nourseothricin resistance gene NatMX (nat1) flanked by loxP sites; (2) *S. cerevisiae* GPD1 promoter, followed by the *S. cerevisiae* LAG1 open reading frame and *S. cerevisiae* CYC1 terminator; (3) *S. cerevisiae* PGK1 promoter followed by *S. cerevisiae* LAC1 open reading frame and *S. cerevisiae* ADH2 terminator; (4) *S. cerevisiae* TEF1 promoter followed by *S. cerevisiae* LIP1 open reading frame and *S. cerevisiae* ENO2 terminator; (5) sequences homologous to the integration locus YORWΔ22 upstream of the selection marker and downstream of the LIP1 expression cassette. Transformants were selected on SC-agar plates (6.7 g/L yeast nitrogen base w/o amino acids, 2.0 g/L complete SC mixture, 20 g/L glucose, 20 g/L agar) containing 100 mg/L nourseothricin. Clones were verified by PCR for correct insertion of the expression construct. Strain EYS3805 was constructed by removal of the previously inserted selection markers for nourseothricin and hygromycin, nat1 and hph. This was done by transformation with a URA3 selectable plasmid pEVE0078 containing an expression cassette for the Cre recombinase. Cre recombinase catalyzed site specific recombination between two loxP sites which led to removal of the selection marker flanked by loxP sites. Clones expressing the Cre recombinase were picked and tested for the loss of the loxP flanked selection markers by plating on the respective selective plates. The Cre recombinase bearing plasmid pEVE0078 that was under URA3 selection was removed by growing strains in presence of 5'-fluoroorotic acid which is turned into a toxic compound by the activity of the URA3 gene encoded enzyme. Only clones that have lost the plasmid were able to grow on selective medium.

*S. cerevisiae* strain EYS4423 was constructed from the previously described strain BY4742 by deletion of CHA1, LCB4, ORM2, and CKA2 genes and by overexpression of LCB1, LCB2 TSC10 and SUR2 genes. Deletion of the CHA1 gene was done by a PCR-based gene deletion strategy generating a start-to-stop-codon deletion of the open reading frame. CHA1 gene was replaced by a deletion construct of SEQ ID NO: 76, which was comprised of the KanMX gene flanked by loxP sites, and sequences homologous to the native promoter and terminator of the CHA1 gene that were added by PCR using primers EV3782 and EV3783. Transformants were selected on YPD-agar plates containing 100 mg/L G418. Clones were verified by PCR testing for proper insertion of the deletion construct. Deletion of the LCB4 gene was done by a PCR-based gene deletion strategy generating a start-to-stop-codon deletion of the open reading frame. LCB4 gene was replaced by a deletion construct of SEQ ID NO: 77, which was comprised of the NatMX gene flanked by loxP sites, and sequences homologous to the native promoter and terminator of the LCB4 gene that were added by PCR using primers EV4024 and EV4025. Transformants were selected on SC-agar plates containing 100 mg/L nourseothricin. Clones were verified by PCR testing for proper insertion of the deletion construct. Deletion of the ORM2 gene was done by a PCR-based gene deletion strategy generating a start-to-stop-codon deletion of the open reading frame. ORM2 gene was replaced by a deletion construct of SEQ ID NO: 78, which was comprised of the NatMX gene flanked by loxP sites, and sequences homologous to the native promoter and terminator of the ORM2 gene that were added by PCR using primers EV4215 and EV4216. Transformants were selected on SC-agar plates containing 100 mg/L nourseothricin. Clones were verified by PCR testing for proper insertion of the deletion construct. Deletion of the CKA2 gene was done by a PCR-based gene deletion strategy generating a start-to-stop-codon deletion of the open reading frame. CKA2 gene was replaced by a deletion construct of SEQ ID NO: 79, which was comprised of the KanMX gene flanked by loxP sites, and sequences homologous to the native promoter and terminator of the CKA2 gene that were added by PCR using primers EV4740 and EV4741. Transformants were selected on SC-agar plates containing 100 mg/L G418. Clones were verified by PCR testing for proper insertion of the deletion construct. Overexpression of LCB1, LCB2, TSC10, and SUR2 genes were from plasmids pEVE3105, pEVE2932 and pEVE4321. Plasmid pEVE3105 contained the HIS3 selection marker and cassettes for expression of LCB1 gene under the GPD1 promoter and a CYC1 terminator, as well as cassette for expression of LCB2 gene under the PGK1 promoter and the ADH2 terminator. Plasmid pEVE2932 contained an expression cassette for expression of *S. cerevisiae* TSC10 gene under the KEX2 promoter and ADH1 terminator. The plasmid also had a URA3 selection marker. Plasmid pEVE4321 contained an expression cassette for expression of *Pichia ciferrii* SUR2 gene under the GPD1 promoter and a CYC1 terminator. The plasmid also contained a LEU2 selection marker. The presence of the three plasmids was verified by growth of EYS4423 on selective plates lacking the amino acids histidine and leucine and the nucleobase uracil (1.47 g/L SC-mix without histidine and leucine, 6.7 g/L yeast nitrogen base, 20 g/L glucose, pH 5.8).

*S. cerevisiae* strain EYS4022 was constructed from the previously described strain BY4742 by deletion of the LCB4 gene, CHA1 gene, and YPC1 gene and by insertion of LAG1, LAC1, and LIP1 genes. Deletion of the LCB4 gene was done by a PCR-based gene deletion strategy generating a start-to-stop-codon deletion of the open reading frame. LCB4 gene was replaced by a deletion construct of SEQ ID NO: 77, which was comprised of the Nourseothricin resistance gene NatMX (nat1) flanked by loxP sites, and sequences homologous to the native promoter and terminator of the LCB4 gene that were added by PCR using primers EV4024 and EV4025. Transformants were selected on SC-agar plates containing nourseothricin. Clones were verified by PCR testing for proper insertion of the deletion construct. Deletion of the CHA1 gene was done by a PCR-based gene deletion strategy generating a start-to-stop-codon deletion of the open reading frame. CHA1 gene was replaced by a deletion construct of SEQ ID NO: 76, which was comprised of the KanMX gene flanked by loxP sites, and sequences homologous to the native promoter and terminator of the CHA1 gene that were added by PCR using primers EV3782 and EV3783. Transformants were selected on YPD-agar plates containing 100 mg/L G418. Deletion of the YPC1 gene was done by a PCR-based gene deletion strategy generating a start-to-stop-codon deletion of the open reading frame. YPC1 gene was replaced by a deletion construct PCR amplified from a plasmid template pEVE698, which construct was comprised of the hygromycin resistance gene HygMX (hph) flanked by loxP sites, and sequences homologous to the native promoter and terminator of the YPC1 gene that were added by PCR using primers EV4018 and EV4019. Transformants were selected on SC-agar plates containing hygromycin. Clones were verified by PCR testing for proper insertion of the deletion construct. Insertion of LAG1, LAC1, and LIP1 genes was done by insertion of a triple expression construct into the integration locus YORW22Δ. The construct consisted of (1) Nourseothricin resistance gene NatMX (nat1) flanked by loxP sites; (2) *S. cerevisiae* GPD1 promoter, followed by the *S. cerevisiae* LAG1 open reading frame and *S. cerevisiae* CYC1 terminator; (3) *S. cerevisiae* PGK1 promoter followed by *S. cerevisiae* LAC1 open reading frame and *S. cerevisiae* ADH2 terminator; (4) *S. cerevisiae* TEF1 promoter followed by *S. cerevisiae* LIP1 open reading frame and *S. cerevisiae* ENO2 terminator; (5) sequences homologous to the integration locus YORWΔ22 upstream of the selection marker and downstream of the LIP1 expression cassette. Transformants were selected on SC-agar plates containing nourseothricin. Clones were verified by PCR for correct insertion of the expression construct. In a second step, the previously inserted selection markers were removed by transformation with a URA3 selectable plasmid pEVE0078 containing an expression cassette for the Cre recombinase enzyme. Cre recombinase catalyzed site specific recombination between two loxP sites flanking the hph selection marker with concomitant removal of the same. Clones expressing the Cre recombinase were selected on SC-agar plates without uracil. A few clones were picked and tested for the loss of the selection marker by plating on the respective selective plates. The Cre recombinase bearing plasmid pEVE0078 was removed by growing strains in the presence of 5'-fluoroorotic acid which is converted into a toxic compound by the activity of the URA3 gene encoded enzyme. Only clones that have lost the plasmid were able to grow on selective medium.

*S. cerevisiae* strain EYS4798 was constructed from the previously described EYS4022 by transformation with plasmid pEVE4782 containing an expression cassette for *Xenopus laevis* UDP-glucose ceramide glucosyltransferase gene Ugcg-a (GenBank Accession No. AY112732), which encodes a protein belonging to UGT family 21, under the *S. cerevisiae* GPD1 promoter and CYC1 terminator. The *Xenopus laevis* Ugcg-a gene used is also referred to as "*Xenopus laevis* UGT21-M". The plasmid also had a LEU2 selection maker. The presence of the plasmid was verified by growth of EYS4798 on selective plates lacking the amino acids leucine.

Example 2: Cyclodextrins Solubilize Sphingoid Bases in Aqueous Solution

These experiments were conducted to determine if and to what extent cyclodextrins solubilized sphingoid bases. To that end, an excess of phytosphingosine was incubated with increasing concentrations of solutions of three different types of cyclodextrin species—α-cyclodextrin, 2-hydroxypropyl-α-cyclodextrin, 2-hydroxypropyl-β-cyclodextrin. Solubilized phytosphingosine in the supernatants were quantified by liquid chromatography-mass spectrometry (LC-MS) using standards prepared in the same cyclodextrin solutions. The results showed that the tested cyclodextrins solubilized phytosphingosine to different concentrations depending on the cyclodextrin concentration, in a dose-dependent fashion (FIG. 1). Impressively, more than 9 g/L phytosphingosine were shown to be solubilized with 2-hydroxypropyl-α-cyclodextrin.

Figure 2:
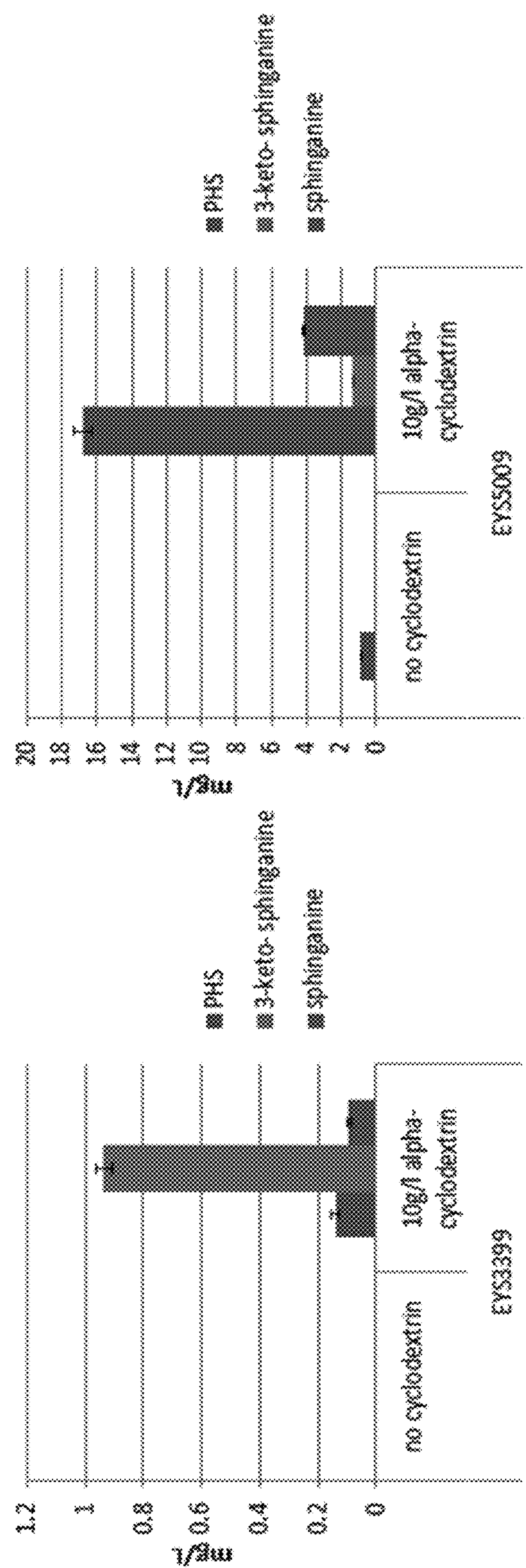
FIG. 2: The Figure shows data regarding excretion of sphingoid bases in shake flask cultures with or without α-cyclodextrin.

Example 3: Cyclodextrin Enhances Excretion of Sphingoid Bases in Shake Flask Cultures The *S. cerevisiae* strain EYS3399 was used as basic strain to improve sphingoid base production. Strain EYS3399 is the Applicant's nomenclature identical to strain NCYC 3608 of the National Collection of Yeast Cultures (genotype MATalpha gal2 ho::HygMX ura3::KanMX), which is a Mat a derivative of S288C. As described previously, deletion of LCB4 and CKA2 genes encoding long-chain base kinase and the alpha subunit of casein kinase 2 in the strain EYS3399, resulted in the generation of another strain, EYS5009. Strain EYS5009 showed increased sphingoid base biosynthesis as compared with the strain EYS3399 (FIG. 2). Both strains, EYS3399 and EYS5009, were grown in shake flask cultures in synthetic complete (SC)-medium (2.0 g/L SC-mix, 6.7 g/L YNB, 20 g/L glucose, pH 5.8) with or without 20 g/L α-cyclodextrin for 24 h at 30° C. Supernatants were analyzed by LC-MS and the 3-keto sphinganine, sphinganine and phytosphingosine were quantified (FIG. 2). Samples without cyclodextrin (CD) were not diluted, samples with CD were diluted 50-fold in methanol. These results showed that in both strains EYS3399 and EYS5009, cyclodextrin exposure resulted in enhanced production of sphingoid bases. This effect of cyclodextrin was more pronounced for phytosphingosine than for 3-keto sphinganine or for sphinganine. Further, this effect of cyclodextrin was more pronounced in strain EYS5009 as compared to strain EYS3399. Similar effects were observed when other cyclodextrin species were examined on these and other yeast strains.

Example 4: Cyclodextrin Enhances Excretion of Sphingoid Base in Bioreactors

Strain EYS4928 was constructed in several steps from EYS3399, identical to NCYC 3608 (genotype MATalpha gal2 ho::HygMX ura3::KanMX), which is a Mat α derivative of S288C. The selection marker HygMX was removed by initially inserting a loxP flanked URA3 gene into the ho locus (Chromosome IV 46271 . . . 48031) of EYS3399, followed by removal of the URA3 gene via expression of Cre recombinase using pEVE0078. Then, the selection marker KanMX was removed from the URA3 locus by a similar approach. In order to allow further genetic manipulations, the thus-obtained strain was made auxotrophic for LEU2 and HIS3 by removal of the whole open reading frames of these genes. For growth in a bioreactor, the thus-obtained auxotrophic strain was rendered prototrophic by transformation with two expression plasmids: the first plasmid carrying the HIS3 and LEU2 genes, and the second plasmid carrying the URA3 gene, to thereby obtain strain EYS4928.

A fed-batch fermentation was performed with the following parameters: temperature kept at 30° C., pH controlled at 5.85 (regulated by 0.5 M HCl and 5 M $NH_4OH$), and $pO_2$ was maintained above 20% of the maximum oxygen saturation by a cascade on stirrer and aeration. As for the fermentation media, selective SC medium was used in the batch phase and a 30-fold concentrated selective SC medium was added to the fed-batch phase, both supplemented with 15 g/L α-cyclodextrin (Sigma-Aldrich). The batch phase ended latest after 11 hours, after which the feeding was initiated following an exponential profile calculated on an hourly rate. Over a period of about 100 h, samples were taken and analyzed either for both, biomass production and production of phytosphingosine. Phytosphingosine was quantified by LC-MS. LC-MS analysis was performed using Waters Ultra Performance Liquid Chromatography (UPLC) coupled with a Bruker Micro Q-TOF II mass spectrometer. Typically 5 μl samples were injected into an Acquity BEH UPLC C8 2.1×100 mm 1.7 μm column (Waters). 2 mM ammonium formate in water with 0.2% formic acid (mobile phase A) and a mixture of acetonitrile and methanol 1:1 containing 1 mM ammonium formate and 0.2% formic acid (mobile phase B) were used as mobile phases. The gradient was from 50% mobile phase B to 85% mobile phase B in 1 minute and then went to 100% B in 3 minutes. Mobile phase B was kept at 100% for 1 minute followed by a reconditioning step of 50% mobile phase B for 1 minute. The column temperature was kept at 50° C. and the flow was 0.4 ml/min. The mass spectrometry analysis was performed in electrospray positive mode with a capillary voltage of 4.5 kV, a source temperature of 180° C. and nebulizer pressure of 1.6 bar. The mass spectrum was acquired from a mass-to-charge ratio (m/z) of 100-1400. Concentration of phytosphingosine was determined according to a calibration curve of phytosphingosine (Santa Cruz Biotechnology) (4 mg/L, 2 mg/L, 1 mg/L, 500 μg/L, 250 μg/L, 125 μg/L, 62.5

μg/L, 31.25 μg/L) in the matrix corresponding to the samples (for example medium containing cyclodextrin diluted 10-fold in methanol).

Results are shown in Tables 1 and 2. In presence of α-cyclodextrin, phytosphingosine was detected in cell culture supernatants in concentrations of up to 2.03 mg/L, whereas in absence of α-cyclodextrin the concentration was below limit of quantification. Total phytosphingosine concentration in biomass and supernatant reached as high as 1.54 mg/L in presence of α-cyclodextrin, and 0.35 mg/L in the absence of α-cyclodextrin, representing a more than 4-fold increase in phytosphingosine in the presence of cyclodextrin. These studies provide further support that cyclodextrin enhances production and excretion of sphingoid bases.

TABLE 1

Fermentation with strain EYS4928 in absence of cyclodextrin WITHOUT CYCLODEXTRIN

| time (h) | Biomass g/L | PHS supernatant mg/L | PHS broth mg/L | PHS broth std deviation mg/L |
|---|---|---|---|---|
| 0 | 0.112 | | | |
| 69.75 | 63 | none detectable | 0.42 | 0.15 |
| 73.83 | 77 | none detectable | 0.42 | 0.18 |
| 75.75 | 63 | none detectable | 0.37 | 0.18 |
| 94 | 117.25 | none detectable | 0.46 | 0.14 |
| 98.25 | 120.75 | none detectable | 0.35 | 0.07 |

Genotype: MATalpha gal2 ho his3Δ0 leu2Δ0 ura3Δ0 CAT5-I91M MIP1-A661T SAL1-1 [HIS3][LEU2 URA3]
Media: Synthetic complete dropout minus His, Leu, Ura; fermentation mode: fed batch

TABLE 2

Fermentation with strain EYS4928 in presence of cyclodextrin WITH CYCLODEXTRIN (15 g/L alpha-cyclodextrin)

| time (h) | Biomass g/L | PHS supernatant mg/L | PHS Supernatant std deviation mg/L | PHS broth mg/L | PHS broth std deviation mg/L | PHS pellet mg/L | PHS wash with 15 g/L alpha-CD medium containing azide mg/L |
|---|---|---|---|---|---|---|---|
| 0 | 0.0735 | | | | | | |
| 69.75 | 112 | 1.25 | 0.12 | 1.15 | 0.10 | | |
| 73.83 | 147 | 2.03 | 0.22 | 1.54 | 0.10 | 0.57 | 0.36 |

Genotype: MATalpha gal2 ho his3Δ0 leu2Δ0 uro3Δ0 CAT5-I91M MIP1-A661T- SAL1-1 [HIS3][LEU2 URA3]
Media: Synthetic complete dropout minus His, Leu, Ura; fermentation mode: fed batch

Example 5: Cyclodextrin Improves Excretion of Tetra-Acetyl Phytosphingosine (TAPS)

The *S. cerevisiae* strain EYS4061, which overexpresses acetyltransferase genes ATF2 and SLI1 from *Wickerhamomyces ciferrii* (*Pichia ciferrii*), was subject to further genetic modifications: deletions of the long-chain base kinase genes, LCB4 and LCB5, and overexpression of the *S. cerevisiae* LCB1, LCB2 and TSC10 genes, thereby giving rise to strain EYS4300. A similar control strain EYS4299 was also generated that contained plasmids pEVE2152 and pEVE2159 with the selection markers HIS3 and LEU2, respectively, but no acetyltransferase genes. Both strains were grown in shake flask cultures with selective SC-media for 48 h at 30° C., and biomass and culture supernatant was subject to analysis and quantification for long-chain bases phytosphingosine, sphinganine, and tetra-acetylated-phytosphingosine levels. LC-MS analysis was performed as described in Example 4 with the exception that the samples were not diluted. Concentration of tetraacetyl-phytosphingosine (TAPS) was determined according to a calibration curve with purified TAPS in the matrix corresponding to the samples (for example medium containing cyclodextrin diluted in methanol).

Figure 3:
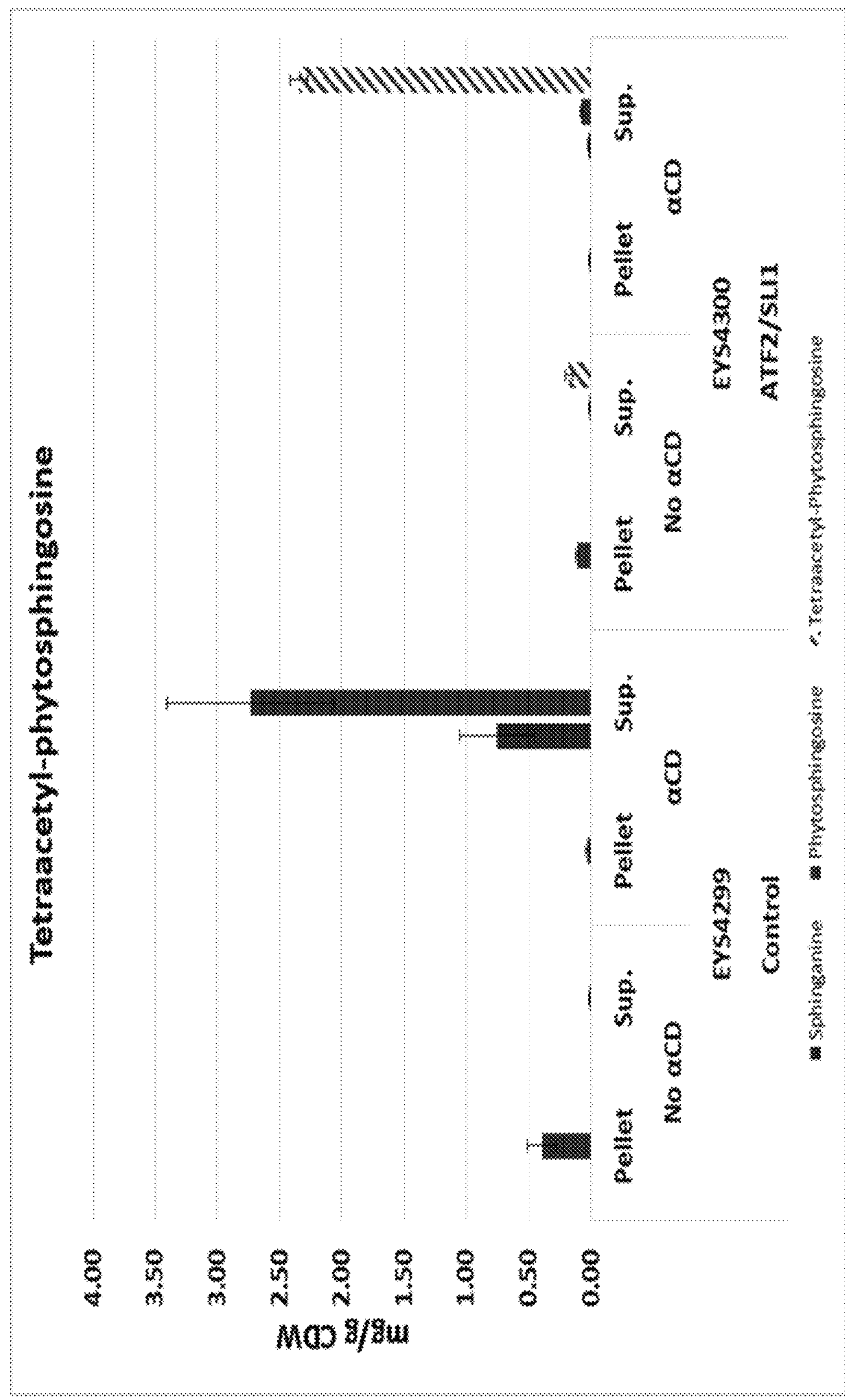
FIG. 3: The Figure shows data regarding excretion of sphingoid bases in shake flask cultures with or without α-cyclodextrin and with or without overexpression of *Wickerhamomyces ciferrii* acetyltransferase genes ATF2 and SLI1 in *S. cerevisiae*. Control strain EYS4299 and acetyltransferase genes expression strain EYS4300 were grown under standard conditions with or without α-cyclodextrin (αCD), pellets were extracted, and supernatants were analyzed directly. Sphinganine, phytosphingosine, and tetraacetylated-phytosphingosine were quantified. Mono- to triacetylated sphinganine and phytosphingosine were detected, but were not quantified.

Results are shown in FIG. 3. Upon expression of *Wickerhamomyces ciferrii* ATF2 and SLI1 genes, phytosphingosine was quantitatively converted to tetra-acetylated-phytosphingosine (i.e., TAPS). Addition of α-cyclodextrin resulted in increased acetylated long-chain base concentrations in the media. This demonstrates that cyclodextrin enhances the secretion of TAPS.

Example 6: Cyclodextrin Improves Excretion of Sphingoid Bases Produced in Different Yeast Strains in Shake Flask Cultures Stimulation of production of phytosphingosine and acetylated phytosphingosine and acetyl-phytosphingosine was evaluated in culture supernatants of two *S. cerevisiae* and two *Wickerhamomyces ciferrii* strains as indicated below:

EYS2958 (wild type strain)
EYS4423 (phytosphingosine producer strain)
EYS3062 (*Wickerhamomyces ciferrii*)
EYS3063 (*Wickerhamomyces sydowiorum*)

Figure 4:
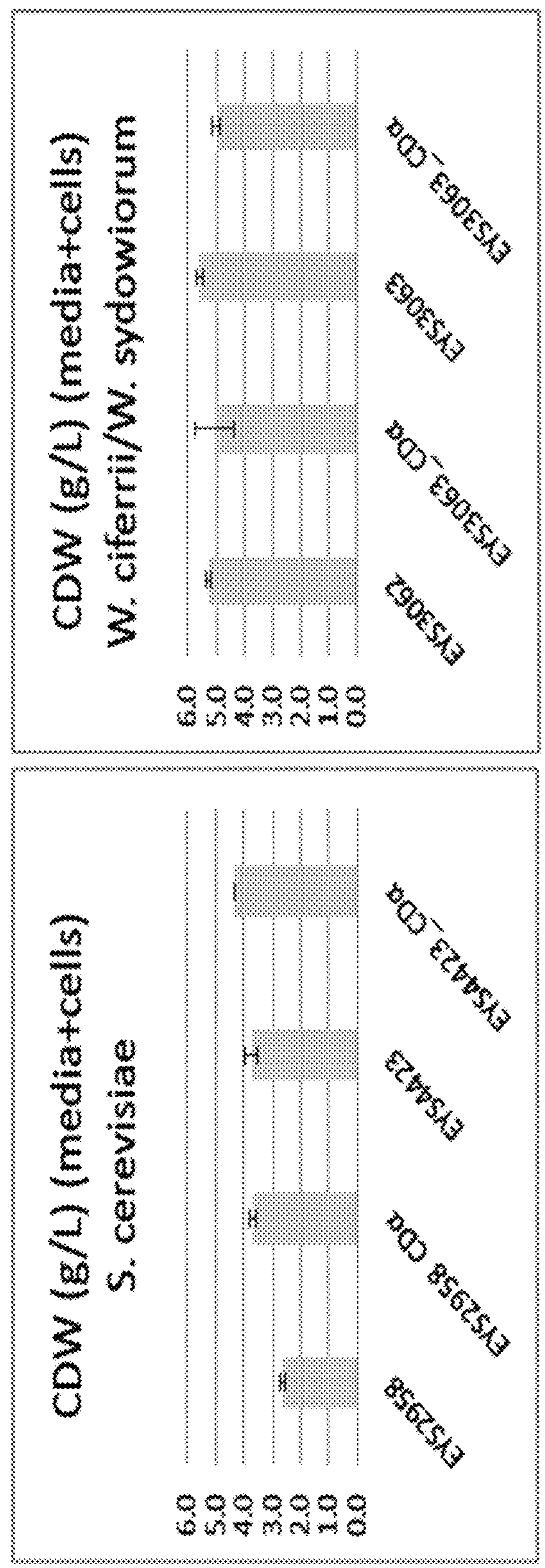
FIG. 4: The Figure shows data regarding Biomass in shake flask cultures. The left panel shows biomass production of *S. cerevisiae* strains EYS2958 (basic strain) and EYS4423 (Δcha1 Δlcb4 Δorm2 Δcka2 [ScLCB1 ScLCB2] [ScTSC10][PcSUR2]) in the presence or absence of 10 g/L α-cyclodextrin. The right panel shows biomass of *Wickerhamomyces ciferrii* (EYS3062) and *Wickerhamomyces sydowiorum* (EYS3063) strains.

Strain EYS2958 is the Applicant's nomenclature for the previously described strain BY4742 (ATCC 201389; EUROSCARF Y10000) and represents a wild type strain. Strain EYS4423 (Δcha1 Δlcb4 Δorm2 Δcka2 [ScLCB1 ScLCB2][ScTSC10][PcSUR2]) is a phytosphingosine producer strain, which was also described previously. Strain EYS3062 is a *Wickerhamomyces ciferrii* (*Pichia ciferrii*) strain (EXT. PRODUCER: ATCC, NOTES: *Wickerhamomyces ciferrii* Y-1031 (ATCC 14091)). Strain EYS3063 is a *Wickerhamomyces sydowiorum* (*Pichia sydowiorum*) strain (XT. PRODUCER: ATCC, NOTES: *Wickerhamomyces sydowiorum* Y-7130 (ATCC 58369)). All four different strains were grown in shake flask cultures in SC medium in presence or in absence of 10 g/L α-cyclodextrin for 48 h at 30° C., in duplicate. For strain EYS4423 histidine, leucine and uracil were not added to the SC medium. The amount of biomass is shown in FIG. 4. The broth (media+cells) was diluted in methanol and centrifuged prior to analysis for presence of phytosphingosine or mono-, di-, tri-, and tetra-acetylated phytosphingosine. LC-MS analysis was performed as described in Example 4 with the exception that samples were diluted 20-fold in methanol. Concentration of tetraacetyl-phytosphingosine (TAPS) was determined according to a calibration curve with purified TAPS in the matrix corresponding to the samples (for example medium containing cyclodextrin diluted in methanol). Monoacetyl-, diacetyl-, triacetyl-phytosphingosine peak areas were measured based on their respective extracted mass chromatograms. Due to an absence of standards, absolute quantification could not be made for mono-, di-, tri-acetylated phytosphingosine. However, tetra-acetylated phytosphingosine production could be quantified, owing to the presence of appropriate standards.

Figure 5:
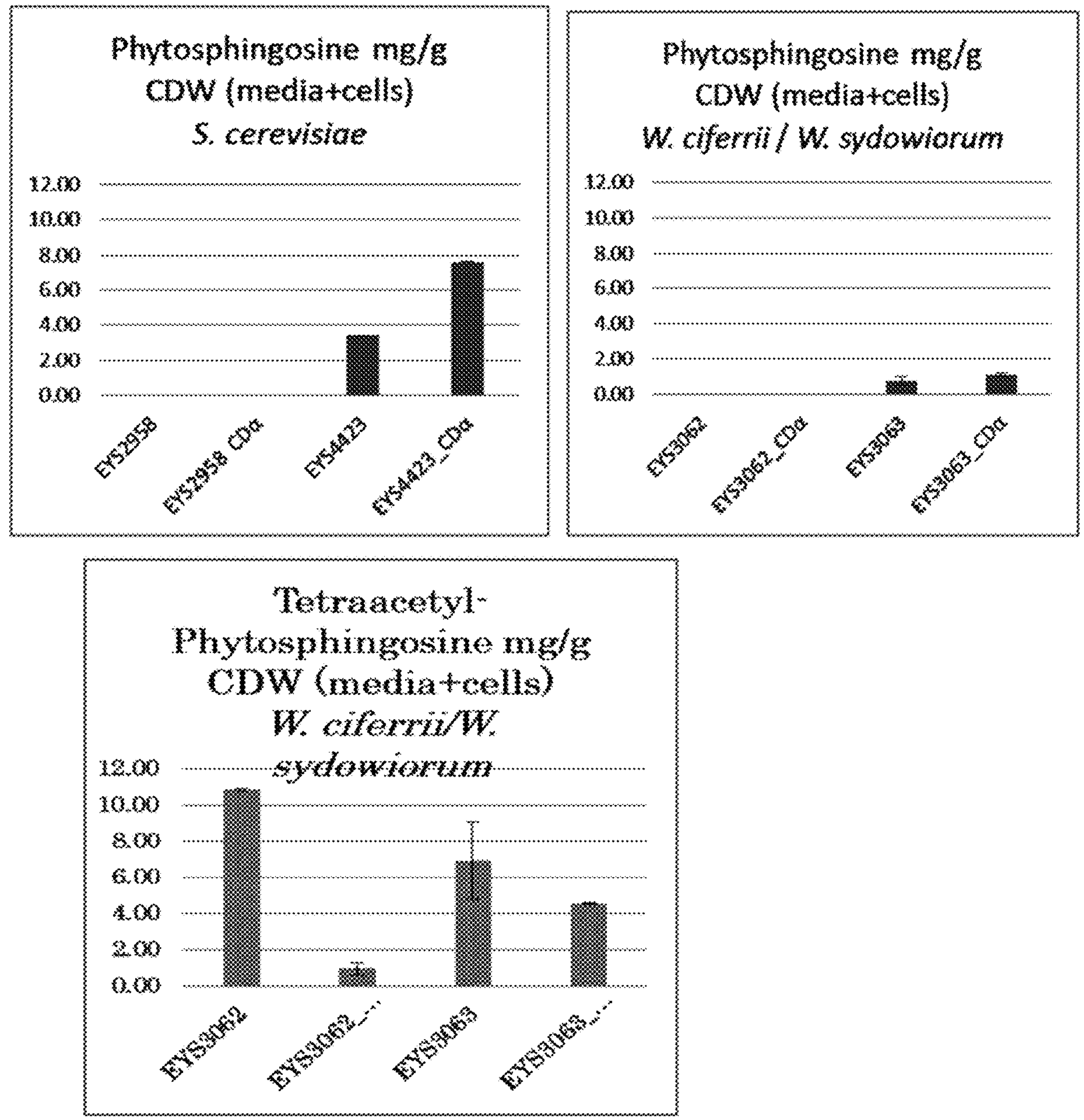
FIG. 5: The Figure shows data regarding long-chain base production in *S. cerevisiae, W. ciferrii*, and *W. sydowiorum* strains. Long-chain bases phytosphingosine and tetraacetylphytosphingosine (TAPS) in the supernatants of cultures with strains *S. cerevisiae* strains EYS2958 (basic strain), EYS4423 (Δcha1 Δlcb4 Δorm2Δcka2 [ScLCB1 ScLCB2] [ScTSC10][PcSUR2]), *Wickerhamomyces ciferrii* (EYS3062), and *Wickerhamomyces sydowiorum* (EYS3063) are presented in the graphs.

Results are shown in FIG. 5 and Table 3. The presence α-cyclodextrin increased production of phytosphingosine in the engineered strain EYS4423 (Δcha1 Δlcb4 Δorm2 Δcka2 [ScLCB1 ScLCB2][ScTSC10][PcSUR2]) by more than 2-fold (FIG. 5). On the contrary, tetra-acetylated phytosphingosine (TAPS) production in either of the *Wickerhamomyces* strains was reduced in the presence of α-cyclodextrin (FIG. 5, Table 3). However, production of the lesser acetylated forms—mono-, di-, tri-acetylated phytosphingosine—in either of the *Wickerhamomyces* strains was clearly increased in presence of α-cyclodextrin (FIG. 5, Table 3). This example shows that cyclodextrin improves the excretion of sphingoid bases in different yeast strains in shake flask cultures.

TABLE 3

Phytosphingosine species produced in *Wickerhamomyces ciferrii* and *Wickerhamomyces sydowiorum*.

| | Tetra-acetyl-PHS mg/g CDW | Tetra-acetyl-PHS mg/g CDW | Peak Area Triacetyl PHS | Peak Area Triacetyl PHS | Peak Area Diacetyl PHS | Peak Area Diacetyl-PHS | Peak Area mono-acetyl-PHS | Peak Area mono-acetyl-PHS |
|---|---|---|---|---|---|---|---|---|
| Cyclodextrin | − | + | − | + | − | + | − | + |
| *W. ciferrii* | 10.8 | 0.9 | 2011710 | 4323410 | 125430 | 312810 | 5880 | 28240 |
| *W. sydowiorum* | 6.9 | 4.5 | 3284160 | 3670530 | 252830 | 367450 | 21620 | 52370 |

For tetraacetyl-phytosphingosine, absolute concentrations in mg/g CDW are given.
For monoacetyl-, diacetyl-, triacetyl-phytosphingosine peak areas are reported.

Example 7: Cyclodextrin Improves Excretion of Sphingoid Bases Produced in *Wickerhamomyces ciferrii* in Bioreactor Fed-batch fermentation with *Wickerhamomyces ciferrii* strain EYS3062 was performed in SC media supplemented with or without 15 g/L α-cyclodextrin in batch and feed media at 30° C. Samples were taken at various time points during fermentation and analyzed by LC-MS for the presence of monoacetyl-, diacetyl-, triacetyl- and tetraacetyl-phytosphingosine. LC-MS analysis was performed as described in Example 4 except that samples were diluted 2000-fold in methanol. Concentration of tetraacetyl-phytosphingosine (TAPS) was determined according to a calibration curve with purified TAPS in the matrix corresponding to the samples (for example medium containing cyclodextrin diluted in methanol). Monoacetyl-, diacetyl-, triacetyl-phytosphingosine peak areas were measured on their respective extracted mass chromatograms.

Results are shown in Table 4. Cyclodextrin exposure resulted in increased production of the intermediates diacetyl- and triacetyl-phytosphingosine (Table 4). For triacetyl-phytosphingosine and diacetyl-phytosphingosine, chromatogram peak areas increased by 64% and 126%, respectively (Table 4). Addition of cyclodextrin to the medium decreased TAPS production by of 43% (Table 4). This decrease may be due to capturing of intermediates before being further metabolized to TAPS. Phytosphingosine and sphinganine were not found in these samples (data not shown). This example demonstrates that cyclodextrin enhances the excretion of sphingoid bases in *Wickerhamomyces ciferrii* in bioreactor.

TABLE 4

Analysis of *Wickerhamomyces ciferrii* fermentations in the presence or absence of α-cyclodextrin.

| Molecules | Tetra-acetyl PHS (mg/L) | Tetra-acetyl PHS (mg/L) | Peak area Triacetyl PHS | Peak area Triacetyl PHS | Peak area Diacetyl PHS | Peak area Diacetyl PHS | Peak area acetyl PHS | Peak area acetyl PHS |
|---|---|---|---|---|---|---|---|---|
| Cyclodextrin | − | + | − | + | − | + | − | + |
| 25.6 h | 235 | 0 | 13190 | 6075 | 366 | 1 | 0 | 0 |
| 27.6 h | 442 | 0 | 32094 | 21327 | 1 | 1 | 29 | 0 |
| 45 h | 1124 | 0 | 52199 | 56337 | 2687 | 2584 | 62 | 0 |
| 47.1 h | 1251 | 0 | 57284 | 73690 | 3097 | 6156 | 111 | 0 |
| 49.9 h | 1332 | 694 | 49776 | 95277 | 1 | 7861 | 219 | 0 |
| 51.8 h | 1414 | 800 | 65261 | 107192 | 4061 | 9198 | 114 | 0 |

Total broth, which included biomass and supernatant, was analyzed. Absolute quantification is shown for tetraacetyl-phytosphingosine. Peak area numbers are given for tri-, di-, and monoacetyl-phytosphingosine (PHS).

Example 8: Cyclodextrin Improves the Excretion of Phytoceramide and Glycosyl-Phytoceramide Strains BY4742 (wt), EYS4022 (cha1Δ ypc1Δ lcb4Δ LAG1 LAC1 LIP1), and EYS4798 (cha1Δ ypc1Δ lcb4Δ LAG1 LAC1 LIP1 and *Xenopus laevis* UGT21-M expressed from plasmid pEVE4782) were grown in shake flask cultures in selective SC medium with 200 g/l methyl-β-cyclodextrin for 48 h at 30° C. Supernatants were analyzed by LC-MS for the presence of phytoceramide and glucosyl-phytoceramide. LC-MS analysis was performed using Waters Ultra Performance Liquid Chromatography (UPLC) coupled with a Bruker Micro Q-TOF II mass spectrometer. Typically 5 μl samples were injected into an Acquity BEH UPLC C8 2.1×100 mm 1.7 am column (Waters). 2 mM ammonium formate in water with 0.2% formic acid (mobile phase A) and a mixture of acetonitrile and methanol 1:1 containing 1 mM ammonium formate and 0.2% formic acid (mobile phase B) were used as mobile phases. The gradient was from 50% mobile phase B to 85% mobile phase B in 1 minute and then went to 100% B in 3 minutes. Mobile phase B was kept at 100% for 3 minutes followed by a reconditioning step of 50% mobile phase B during 2 minutes. The column temperature was kept at 50° C. and the flow was 0.4 ml/min. The mass spectrometry analysis was performed in electrospray positive mode with a capillary voltage of 4.5 kV, a source temperature of 180° C. and nebulizer pressure of 1.6 bar. The mass spectrum was acquired from a mass-to-charge ratio (m/z) of 100-1400. Concentration of phytosphingosine, C24-phytoceramide and glycosyl-C26-phytoceramide were determined according to the calibration curve of phytosphingosine standard (Santa Cruz Biotechnology), C24-phytoceramide standard (Avanti Polar Lipids Inc.) and α-Galactosyl-C26-phytoceramide (Larodan Fine Chemicals AB) in a matrix corresponding to the samples (for example medium containing cyclodextrin diluted in methanol). Concentration of C26-phytoceramide was estimated using C24-phytosphingosine calibration curve.

Figure 6:
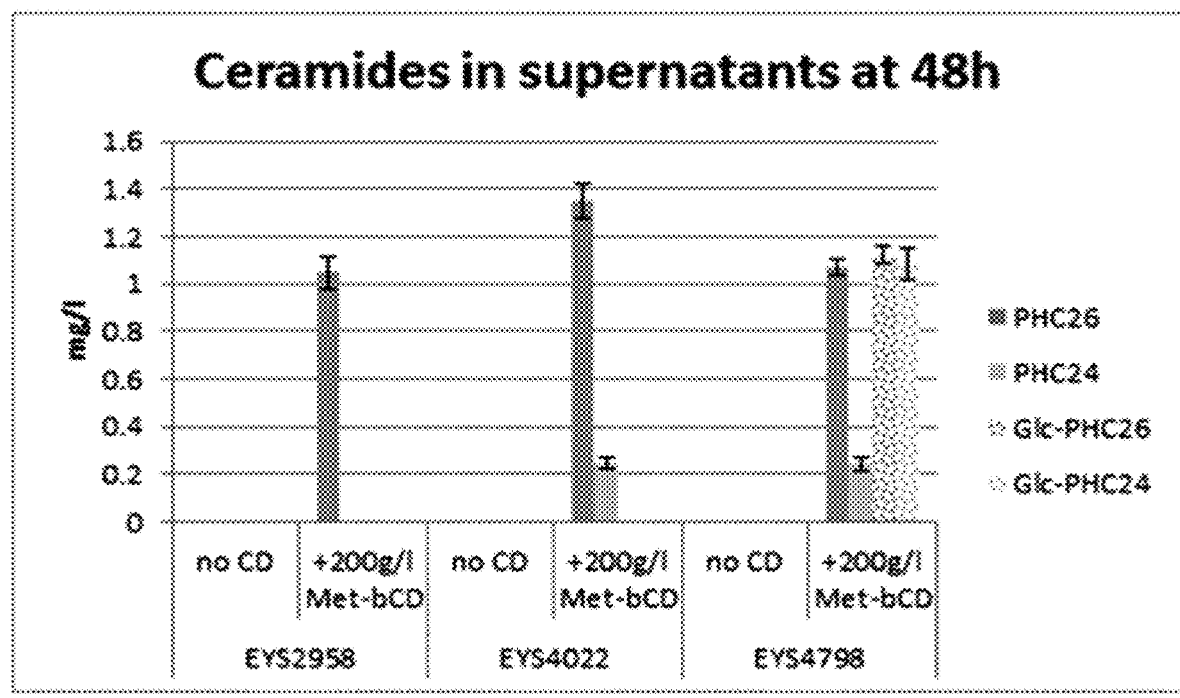
FIG. 6: The Figure shows data regarding Ceramide and PHS amounts in supernatants. EYS2958 (basic strain), EYS4022 (cha1Δ ypc1Δ lcb4Δ LAG1 LAC1 LIP1), and EYS4798 (cha1Δ ypc1Δ lcb4Δ LAG1 LAC1 LIP1 [*Xenopus laevis* UGT21-M]) were grown for 48 h in SC medium containing 200 g/l methyl-β-cyclodextrin (Met-bCD). The ceramide content of the supernatants was quantified by LC/MS according to a calibration curve established in SC medium containing 200 g/l methyl-β-cyclodextrin.

Results are shown in FIG. 6. Up to 2.5 mg/l phytoceramide was detected in the supernatants of EYS4022 cultures (FIG. 6). Glycosylated phytoceramide was detected in the supernatants of strain EYS4798 (FIG. 6). These studies demonstrate that cyclodextrin improves the excretion of both phytoceramide and glycosyl-phytoceramide.

Materials

Materials used in the Examples are shown in Tables 5-11.

TABLE 5

Primer sequences

| Target Gene | Forward primer # | Forward Primer Sequence | SEQ ID | Reverse Primer # | Reverse primer Sequence | SEQ ID |
|---|---|---|---|---|---|---|
| LCB4 | EV4024 | AAGTCTAGCAGCGAAAAGTACGC GAAGAATCTACTATAGATAATGC CAGCTGAAGCTTCGTACGC | 45 | EV4025 | TTTTACAAAAAAATCATTTTTGA AGGAAAATATAACGTTAATCTAG CATAGGCCACTAGTGGATCTG | 46 |
| LCB5 | EV4030 | AAACCACAAATAGTGTAAGATTT AAACAGTAAGCCAAAAGAGATGC CAGCTGAAGCTTCGTACGC | 47 | EV4031 | TTGATTAATTGTTCAGTACGAAG GAAAAGATTAAGTAAAGTGTCAG CATAGGCCACTAGTGGATCTG | 48 |
| YCP1 | EV4018 | TAAATAAAAGCAGAAATCTTTAT TTAAGAAAATAGAAGATTGATGC CAGCTGAAGCTTCGTACGC | 49 | EV4019 | AAATATGCCTATACATTATGAAT ATATATTATGCTATAATTATTAG CATAGGCCACTAGTGGATCTG | 50 |
| CHA1 | EV3782 | TAAGTGCTGGATAGACAAGAGAC AGGAAAATTAACCAGCGAGATGC CAGCTGAAGCTTCGTACGC | 51 | EV3783 | TCAAGGGCAAATTGATGCTTCAA CGAAAAAGTTATTGGATTTTCAG CATAGGCCACTAGTGGATCTG | 52 |
| ORM2 | EV4215 | AAGACTATACCATTATAAAAACG CATAAGAAACAGTTTCATCATGC CAGCTGAAGCTTCGTACGC | 53 | EV4216 | ATATATATATATATATACATATA TGCGTATAGGCAGAGCCAACTAG CATAGGCCACTAGTGGATCTG | 54 |
| CKA2 | EV4740 | AAATAGAAGGAACAATAAACCTA AAAGAATAGAAGAAACAGAATGC CAGCTGAAGCTTCGTACGCTGC | 55 | EV4741 | TGGTGGAAAAAGAATTGCCTTGC TAAGAGTATTGTTGTCCAATTAC CGCATAGGCCACTAGTGGATCTG | 56 |

TABLE 6

| Plasmid sequences | |
|---|---|
| Plasmid | SEQ ID |
| pEVE698 | 57 |
| pEVE73 | 58 |
| pEVE2785 | 59 |
| pEVE2120 | 60 |
| pEVE3908 | 61 |
| pEVE3910 | 62 |
| pEVE3105 | 63 |
| pEVE2932 | 64 |
| pEVE4321 | 65 |
| pEVE2152 | 66 |
| pEVE2159 | 67 |
| pEVE4782 | 68 |
| pEVE0078 | 69 |

TABLE 7

| Promoter sequences | |
|---|---|
| Promoter | SEQ ID |
| GPD1 | 70 |
| PGK1 | 71 |
| TEF1 | 80 |
| KEX2 | 81 |

TABLE 8

| Terminator sequences | |
|---|---|
| Terminator | SEQ ID |
| CYC1 | 72 |
| ADH2 | 73 |
| ADH1 | 82 |
| ENO2 | 83 |

TABLE 9

| Additional sequences | | |
|---|---|---|
| LoxP | Sequence | SEQ ID |
| loxP used | ATAACTTCGTATA GCATACAT TATACGAAGTTAT | 74 |
| loxP consensus | ATAACTTCGTATA NNNTANNN TATACGAAGTTAT | 75 |

TABLE 10

| Gene deletion constructs | |
|---|---|
| Deletion construct | SEQ ID |
| CHA1 | 76 |
| LCB4 | 77 |
| ORM2 | 78 |
| CKA2 | 79 |

TABLE 11

| Complete SC mixture | |
|---|---|
| Component | Concentration mg/l |
| Adenine | 18 |
| L-Alanine | 76 |
| L-Arginine HCl | 76 |
| L-Asparagine | 76 |
| Aspartic Acid | 76 |
| L-Cysteine | 76 |
| L-Glutamine | 76 |
| L-Glutamic Acid | 76 |
| Glycine | 76 |
| L-Histidine | 76 |
| myo-Inositol | 76 |
| L-Isoleucine | 76 |
| L-Leucine | 380 |
| L-Lysine | 76 |
| L-Methionine | 76 |
| para-Aminobenzoic Acid | 8 |
| L-Phenylalanine | 76 |
| L-Proline | 76 |
| L-Serine | 76 |
| L-Threonine | 76 |
| L-Tryptophan | 76 |
| L-Tyrosine | 76 |
| Uracil | 76 |
| L-Valine | 76 |

INDUSTRIAL APPLICABILITY

According to the present invention, production of an objective substance such as sphingoid bases and sphingolipids by yeast can be improved, and an objective substance can be efficiently produced.

EXPLANATION OF SEQUENCE LISTING

SEQ ID NO: 1, Nucleotide sequence of LCB1 gene of *Saccharomyces cerevisiae*

SEQ ID NO: 2, Amino acid sequence of Lcb1 protein of *Saccharomyces cerevisiae*

SEQ ID NO: 3, Nucleotide sequence of LCB2 gene of *Saccharomyces cerevisiae*

SEQ ID NO: 4, Amino acid sequence of Lcb2 protein of *Saccharomyces cerevisiae*

SEQ ID NO: 5, Nucleotide sequence of TSC10 gene of *Saccharomyces cerevisiae*

SEQ ID NO: 6, Amino acid sequence of Tsc10 protein of *Saccharomyces cerevisiae*

SEQ ID NO: 7, Nucleotide sequence of SUR2 gene of *Saccharomyces cerevisiae*

SEQ ID NO: 8, Amino acid sequence of Sur2 protein of *Saccharomyces cerevisiae*

SEQ ID NO: 9, Nucleotide sequence of SLI1 gene of *Saccharomyces cerevisiae*

SEQ ID NO: 10, Amino acid sequence of Sli1 protein of *Saccharomyces cerevisiae*

SEQ ID NO: 11, Nucleotide sequence of ATF2 gene of *Saccharomyces cerevisiae*

SEQ ID NO: 12, Amino acid sequence of Atf2 protein of *Saccharomyces cerevisiae*

SEQ ID NO: 13, Nucleotide sequence of LAG1 gene of *Saccharomyces cerevisiae*

SEQ ID NO: 14, Amino acid sequence of Lag1 protein of *Saccharomyces cerevisiae*

SEQ ID NO: 15, Nucleotide sequence of LAC1 gene of *Saccharomyces cerevisiae*

SEQ ID NO: 16, Amino acid sequence of Lac1 protein of *Saccharomyces cerevisiae*

SEQ ID NO: 17, Nucleotide sequence of LIP1 gene of *Saccharomyces cerevisiae*

SEQ ID NO: 18, Amino acid sequence of Lip1 protein of *Saccharomyces cerevisiae*

SEQ ID NO: 19, Nucleotide sequence of ugcg-a gene of *Xenopus laevis* (mRNA)

SEQ ID NO: 20, Amino acid sequence of Ugcg-a protein of *Xenopus laevis*

SEQ ID NO: 21, Nucleotide sequence of ugcg-b gene of *Xenopus laevis* (mRNA)

SEQ ID NO: 22, Amino acid sequence of Ugcg-b protein of *Xenopus laevis*

SEQ ID NO: 23, Nucleotide sequence of LCB4 gene of *Saccharomyces cerevisiae*

SEQ ID NO: 24, Amino acid sequence of Lcb4 protein of *Saccharomyces cerevisiae*

SEQ ID NO: 25, Nucleotide sequence of LCB5 gene of *Saccharomyces cerevisiae*

SEQ ID NO: 26, Amino acid sequence of Lcb5 protein of *Saccharomyces cerevisiae*

SEQ ID NO: 27, Nucleotide sequence of ELO3 gene of *Saccharomyces cerevisiae*

SEQ ID NO: 28, Amino acid sequence of Elo3 protein of *Saccharomyces cerevisiae*

SEQ ID NO: 29, Nucleotide sequence of CKA2 gene of *Saccharomyces cerevisiae*

SEQ ID NO: 30, Amino acid sequence of Cka2 protein of *Saccharomyces cerevisiae*

SEQ ID NO: 31, Nucleotide sequence of ORM2 gene of *Saccharomyces cerevisiae*

SEQ ID NO: 32, Amino acid sequence of Orm2 protein of *Saccharomyces cerevisiae*

SEQ ID NO: 33, Nucleotide sequence of CHA1 gene of *Saccharomyces cerevisiae*

SEQ ID NO: 34, Amino acid sequence of Cha1 protein of *Saccharomyces cerevisiae*

SEQ ID NO: 35, Nucleotide sequence of YPC1 gene of *Saccharomyces cerevisiae*

SEQ ID NO: 36, Amino acid sequence of Ypc1 protein of *Saccharomyces cerevisiae*

SEQ ID NO: 37, Nucleotide sequence of SUR2 gene of *Pichia ciferrii*

SEQ ID NO: 38, Amino acid sequence of Sur2 protein of *Pichia ciferrii*

SEQ ID NO: 39, Nucleotide sequence of SLI1 gene of *Pichia ciferrii* (partial)

SEQ ID NO: 40, Nucleotide sequence of SLI1 gene of *Pichia ciferrii*, optimized for *S. cerevisiae* codon usage SEQ ID NO: 41, Amino acid sequence of Sli1 protein of *Pichia ciferrii*

SEQ ID NO: 42, Nucleotide sequence of ATF2 gene of *Pichia ciferrii*

SEQ ID NO: 43, Nucleotide sequence of ATF2 gene of *Pichia ciferrii*, optimized for *S. cerevisiae* codon usage SEQ ID NO: 44, Amino acid sequence of Atf2 protein of *Pichia ciferrii*

SEQ ID NOS: 45-56, Primers

SEQ ID NOS: 57-69, Plasmids

SEQ ID NOS: 70, 71, Promoters

SEQ ID NOS: 72, 73, Terminators

SEQ ID NOS: 74, 75, LoxP sequences

SEQ ID NOS: 76-79, Gene deletion constructs

SEQ ID NOS: 80, 81, Promoters

SEQ ID NOS: 82, 83, Terminators

We claim:

1. A method for producing an objective substance, the method comprising:

cultivating yeast having an ability to produce the objective substance in a culture medium containing an additive that is able to associate with, bind to, solubilize, and/or capture the objective substance; and collecting the objective substance from cells of the yeast and/or the culture medium, wherein the objective substance is selected from the group consisting of sphingoid bases and sphingolipids, and wherein the additive is cyclodextrin, and wherein the amount produced of the objective substance by the yeast is increased in the presence of the additive as compared with in the absence of the additive.

2. The method according to claim 1, wherein the cyclodextrin is selected from the group consisting of alpha-cyclodextrin, beta-cyclodextrin, gamma-cyclodextrin, and derivatives thereof.

3. The method according to claim 2, wherein the derivatives are selected from the group consisting of methyl-alpha-cyclodextrin, methyl-beta-cyclodextrin, hydroxypropyl-alpha-cyclodextrin, and hydroxypropyl-beta-cyclodextrin.

4. The method according to claim 1, wherein the objective substance is selected from the group consisting of phytosphingosine (PHS), sphingosine, 6-hydroxysphingosine, sphinganine (DHS), tetraacetylphytosphingosine (TAPS), triacetylphytosphingosine, diacetylphytosphingosine, phytoceramides, dihydroceramides, 6-hydroxyceramides, and glucosylceramides.

5. The method according to claim 1, wherein the objective substance is selected from the group consisting of phytosphingosine (PHS), sphinganine (DHS), tetraacetylphytosphingosine (TAPS), phytoceramides, and glucosylceramides.

6. The method according to claim 5, wherein the phytosphingosine is selected from the group consisting of C16 PHS, C18 PHS, C20 PHS, C18:1 PHS, C20:1 PHS, 4-(hydroxymethyl)-2-methyl-6-tetradecanyl-1,3-oxazinan-5-ol, and 4-(hydroxymethyl)-2-methyl-6-hexadecanyl-1,3 -oxazinan-5-ol.

7. The method according to claim 1, wherein the yeast has been modified so that the expression and/or activity or activities of one or more proteins selected from proteins encoded by LCB1, LCB2, TSC10, SUR2, SLI1, ATF2, LAG1, LAC1, LIP1, and UGCG genes are increased.

8. The method according to claim 7, wherein the activity or activities of the one or more proteins are increased by increasing the expression of the respective genes encoding the one or more proteins.

9. The method according to claim 1, wherein the yeast has been modified so that the expression and/or activity or activities of one or more proteins selected from proteins encoded by LCB4, LCB5, ELO3, CKA2, ORM2, CHA1, and YPC1 genes are reduced by attenuating the expression of the respective genes encoding the one or more proteins, or by disrupting the respective genes encoding the one or more proteins.

10. The method according to claim 1, wherein the yeast belongs to the genus *Saccharomyces* or *Pichia*.

11. The method according to claim 1, wherein the yeast is *Saccharomyces cerevisiae* or *Pichia ciferrii* (*Wickerhamomyces ciferrii*).

* * * * *